United States Patent
Holmes

(10) Patent No.: US 12,227,580 B2
(45) Date of Patent: *Feb. 18, 2025

(54) ANTIGEN BINDING MOLECULES THAT BIND LIGHT

(71) Applicant: CENTESSA PHARMACEUTICALS (UK) LIMITED, Altrincham (GB)

(72) Inventor: Steve Holmes, Altrincham (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 276 days.

This patent is subject to a terminal disclaimer.

(21) Appl. No.: 17/660,382

(22) Filed: Apr. 22, 2022

(65) Prior Publication Data

US 2023/0035798 A1 Feb. 2, 2023

Related U.S. Application Data

(62) Division of application No. 16/256,688, filed on Jan. 24, 2019, now Pat. No. 11,312,781.

(60) Provisional application No. 62/621,346, filed on Jan. 24, 2018.

(51) Int. Cl.
C07K 16/28 (2006.01)
A61K 39/00 (2006.01)

(52) U.S. Cl.
CPC .. *C07K 16/2875* (2013.01); *A61K 39/001136* (2018.08); *A61K 2039/505* (2013.01); *C07K 2317/51* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,635,743 B1 | 10/2003 | Ebner et al. | |
| 6,998,108 B1 | 2/2006 | Ware | |
| 7,575,745 B2 | 8/2009 | Ware | |
| 7,964,190 B2 | 6/2011 | Ebner et al. | |
| 8,058,402 B2 | 11/2011 | Granger et al. | |
| 8,461,307 B2 | 6/2013 | Granger et al. | |
| 8,524,869 B2 | 9/2013 | Smith et al. | |
| 8,734,795 B2 | 5/2014 | Wang et al. | |
| 8,974,787 B2 | 3/2015 | Granger et al. | |
| 9,771,419 B2 | 9/2017 | Granger et al. | |
| 2003/0104477 A1 | 6/2003 | Buechler et al. | |
| 2013/0345406 A1 | 12/2013 | Van De Winkel et al. | |
| 2015/0118222 A1 | 4/2015 | Levy et al. | |
| 2016/0214954 A1 | 7/2016 | O'Neill et al. | |
| 2017/0029521 A1 | 2/2017 | Van De Winkel et al. | |
| 2017/0051351 A1 | 2/2017 | Hakonarson et al. | |
| 2017/0051352 A1 | 2/2017 | Hakonarson et al. | |
| 2017/0058037 A1 | 3/2017 | Croft et al. | |
| 2017/0165230 A1 | 6/2017 | Rudd et al. | |
| 2017/0232104 A1 | 8/2017 | Schnieders et al. | |
| 2018/0016345 A1 | 1/2018 | Croft et al. | |

FOREIGN PATENT DOCUMENTS

| | | | |
|---|---|---|---|
| EP | 1336619 A2 | 8/2003 | |
| EP | 1274840 B1 | 6/2007 | |
| EP | 1674575 B1 | 10/2010 | |
| EP | 1003782 B1 | 1/2011 | |
| EP | 2292663 B1 | 10/2013 | |
| EP | 2666787 A1 | 11/2013 | |
| EP | 2411412 B1 | 5/2015 | |
| EP | 3041831 A1 | 7/2016 | |
| EP | 3060251 A1 | 8/2016 | |
| EP | 2484696 B1 | 8/2017 | |
| EP | 3337465 A1 | 6/2018 | |
| EP | 3337509 A1 | 6/2018 | |
| EP | 2830658 B1 | 10/2018 | |
| EP | 3431104 A1 | 1/2019 | |
| JP | 2012507299 A | 3/2012 | |
| WO | WO2003089575 A2 | 10/2003 | |
| WO | WO2008027338 A2 | 3/2008 | |
| WO | WO2008083169 A2 | 7/2008 | |
| WO | WO2009039310 A2 | 3/2009 | |
| WO | WO2010111180 A1 | 9/2010 | |
| WO | WO2013148686 A2 | 3/2013 | |
| WO | WO2013148350 A2 | 10/2013 | |
| WO | WO2015035212 A1 | 3/2015 | |
| WO | WO2015061752 A1 | 4/2015 | |
| WO | WO2015107331 A2 | 7/2015 | |
| WO | WO2015155738 A2 | 10/2015 | |
| WO | WO2016127059 A2 | 8/2016 | |
| WO | WO2017035010 A1 | 3/2017 | |
| WO | WO2017035017 A1 | 3/2017 | |

OTHER PUBLICATIONS

International Search Report mailed Aug. 2, 2018 in connection with International Application No. PCT/GB2018/050203 (7 pgs.).
Search Report under Section 17 for GB Application No. GB1701194.1 dated Nov. 15, 2017 (2 pgs.).
P. Pitaksajjakul et al., "Fab MAbs specific to HA of influenza virus with H5N1 neutralizing activity selected from Immunized chicken phage library", Biochemical and Biophysical Research Communications, 395 (2010) 496-501 (6 pgs.).
Ware, Carl F., "Targeting lymphocyte activation through the lymphotoxin and LIGHT pathways", Immunol Rev. Jun. 2008; 223: 186-201 (29 pgs.).
Wu, H., et al., "Humanization of a Murine Monoclonal Antibody by Simultaneous Optimization of Framework and CDR Residues". J. Mol. Biol. (1999) 294, 151-162 (12 pgs.).

(Continued)

*Primary Examiner* — Daniel C Gamett
(74) *Attorney, Agent, or Firm* — Wilson Sonsini Goodrich & Rosati

(57) ABSTRACT

The present invention relates to antigen binding molecules, including antibodies, fragments, and variants thereof, that bind to the TNF-related cytokine LIGHT (TNFSF14). The present invention also relates to methods of use of such antigen binding molecules in treating and/or preventing inflammatory disorders and immune disorders.

24 Claims, 16 Drawing Sheets

Specification includes a Sequence Listing.

(56) References Cited

OTHER PUBLICATIONS

Yang, J., et al.(2011) Therapeutic Potential and Challenges of Targeting Receptor Tyrosine Kinase ROR1 with Monoclonal Antibodies in B-Cell Malignancies. PLoS ONE 6(6): e21018. doi:10.1371/journal.pone.0021018.
Casset et al. ((2003) BBRC 307, 198-205 (Year: 2003).
Padlan et al. (PNAS 1989, 86:5938-5942) (Year: 1989).
Amminmaki et al. (JBC 2001,276:36687-36694) (Year: 2001).
Ward et al. (Nature 341 :544-546 ( 1989)) (Year: 1989).
Smith-Gill et al. (J. Immunol. 139:4135-4144 (1987)) (Year: 1987).
Kumar et al. (J. Biol. Chem. 275:35129-35136 (2000)) (Year: 2000).
Lloyd et al. Protein Engineering, Design & Selection 2009, 22: 159-168 (Year: 2009).
Chen, Yvonne et al. Selection and Analysis of an Optimized Anti-VEGF Antibody: Crystal Structure of an Affinity-matured Fab in Complex With Antigen. Journal of Molecular Biology 293(4):865-881 (1999).
De Pascalis, Roberto et al. Grafting of "Abbreviated" Complementarity-Determining Regions Containing Specificity-Determining Residues Essential for Ligand Contact to Engineer a Less Immunogenic Humanized Monoclonal Antibody. The Journal of Immunology 169(6):3076-3084 (2002).
Maccallum, Robert M et al. Antibody-Antigen Interactions: Contact Analysis And Binding Site Topography. Journal of Molecular Biology 262(5):732-745 (1996).
Piche-Nicholas, Nicole M. et al. Changes In Complementarity-Determining Regions Significantly Alter IgG Binding To The Neonatal Fc Receptor (FcRn) And Pharmacokinetics. Monoclonal Antibodies 10(1):81-94 (2018).
Rudikoff, Stuart et al. Single Amino Acid Substitution Altering Antigen-binding Specificity. PNAS USA 79(6):1979-1983 (1982).
Schroeder, Harry W et al. Structure and Function of Immunoglobulins. Journal of Allergy and Clinical Immunology 125(2 Suppl 2):S41-S52 (2010).
U.S. Appl. No. 16/256,688 Notice of Allowance dated Dec. 22, 2021.
U.S. Appl. No. 16/256,688 Office Action dated Jun. 7, 2021.
U.S. Appl. No. 16/480,367 Final Office Action dated Mar. 23, 2023.
U.S. Appl. No. 16/480,367 Non-Final Office Action dated Jul. 8, 2022.
U.S. Appl. No. 16/480,367 Notice of Allowance dated Jul. 3, 2023.
Vajdos, et al. Comprehensive functional maps of the antigen-binding site of an anti-ErbB2 antibody obtained with shotgun scanning mutagenesis. Journal of Molecular Biology 320(2):415-428 (2002).

Figure 3

| Domain Type | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 3B04 VH | Q | V | Q | L | Q | Q | P | G | A | E | L | V | R | P | G | A | S | V | T | L | S | C | K | A | S | G | Y | T | F | T | D | Y | E | M | H | W | V | K | Q | T | P | V | H | G |
| 3D12 VH | Q | V | Q | L | Q | Q | P | G | A | E | L | V | R | P | G | A | S | V | T | L | S | C | K | A | S | D | Y | T | F | T | D | S | E | I | H | W | V | K | Q | T | P | V | H | G |
| 2E08 VH | Q | V | Q | L | Q | Q | P | S | A | E | L | V | R | P | G | V | S | V | K | L | S | C | K | G | S | G | Y | T | F | T | D | Y | A | L | H | W | V | K | Q | S | H | A | K | T |
| 3C10 VH | E | V | Q | M | Q | Q | S | G | A | E | L | V | R | P | G | A | S | V | T | L | S | C | K | A | S | G | Y | T | F | T | D | S | E | I | H | W | V | K | Q | T | P | V | H | G |
| 3A07 VH | Q | V | Q | L | Q | Q | P | G | A | E | L | V | R | P | G | A | S | V | T | L | S | C | K | A | S | G | Y | T | F | T | D | S | E | I | H | W | V | K | Q | T | P | V | H | G |
| 3E09 VH | E | V | Q | L | Q | E | S | G | G | G | L | V | K | P | G | G | S | L | K | L | S | C | E | A | S | G | F | T | F | S | D | Y | Y | M | Y | W | V | R | Q | T | P | E | K | R |
| 2B11 VH | E | V | Q | L | V | E | S | G | G | E | L | V | K | P | G | V | S | V | K | L | S | C | K | G | S | G | Y | T | F | T | D | Y | A | I | H | W | V | K | Q | S | H | A | K | S |

| Domain Type | 45 | 46 | 47 | 48 | 49 | 50 | 51 | 52 | 52A | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 3B04 VH | L | E | W | I | G | E | I | D | P | E | T | G | G | T | A | Y | S | Q | K | F | K | G | K | A | T | L | T | A | D | K | S | S | S | T | A | Y | M | E | F | R | S | L | T | S |
| 3D12 VH | L | E | W | I | G | E | I | D | P | E | T | G | G | T | A | Y | N | Q | K | F | K | G | K | A | T | L | T | A | D | K | S | S | S | T | A | Y | M | E | L | R | S | L | T | S |
| 2E08 VH | L | E | W | I | G | V | I | S | T | Y | Y | G | D | A | S | Y | N | Q | K | F | K | G | K | A | T | M | T | V | D | K | S | S | S | T | A | Y | M | E | L | A | R | L | T | S |
| 3C10 VH | L | E | W | I | G | E | I | D | P | E | T | G | G | T | A | Y | N | Q | K | F | K | G | K | A | T | L | T | A | D | K | S | S | S | T | A | Y | M | E | L | R | S | L | T | S |
| 3A07 VH | L | E | W | I | G | E | I | D | P | E | T | G | G | T | A | Y | A | Q | K | F | K | G | K | A | T | L | T | A | D | K | S | S | S | T | A | Y | M | E | L | R | S | L | T | S |
| 3E09 VH | L | E | W | V | A | A | I | S | G | G | G | G | I | P | Y | Y | A | D | T | V | K | G | R | F | T | I | S | R | D | N | A | K | N | I | L | Y | L | Q | M | S | N | L | K | S |
| 2B11 VH | L | E | W | I | G | V | I | S | T | Y | Y | G | D | A | S | Y | N | Q | K | F | K | G | K | A | T | M | T | V | D | K | S | S | S | T | A | Y | M | E | L | A | R | L | T | S |

| Domain Type | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 |
|---|---|---|---|---|---|---|---|---|---|---|---|---|---|---|---|---|---|---|---|---|---|---|---|---|---|---|---|---|---|---|---|---|---|---|
| 3B04 VH | E | D | S | A | V | Y | Y | C | S | R | E | T | D | Y | F | F | D | Y | W | G | Q | G | T | T | L | T | V | S | S |  |  |  |  |  |
| 3D12 VH | E | D | S | A | V | Y | Y | C | S | R | E | T | D | Y | F | F | D | Y | W | G | Q | G | T | T | L | T | V | S | S |  |  |  |  |  |
| 2E08 VH | D | D | S | A | I | Y | Y | C | A | R | S | R | G | E | Y | G | Y | D | A | M | D | Y | W | G | Q | G | T | S | S |  | T | V | S | S |
| 3C10 VH | E | D | S | A | V | Y | Y | C | S | R | E | T | D | Y | F | F | D | Y | W | G | Q | G | T | T | L | T | V | S | S |  |  |  |  |  |
| 3A07 VH | E | D | S | A | V | Y | Y | C | S | R | E | T | D | Y | F | F | D | Y | W | G | Q | G | T | L | V | T | V | S | S |  |  |  |  |  |
| 3E09 VH | E | D | T | A | M | Y | Y | C | A | R | G | T | G | D | G | F | A | Y | W | G | Q | G | T | L | V | T | V | S | S |  |  |  |  |  |
| 2B11 VH | E | D | S | A | I | Y | Y | C | A | R | S | R | G | E | Y | G | Y | D | A | M | D | Y | W | G | Q | G | T | S | S |  | T | V | S | S |

Figure 4.

Positions 1–44:

| Domain Type | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 3B04 VK | D | I | Q | M | T | Q | T | P | A | S | L | S | A | S | V | G | E | T | V | T | I | T | C | G | A | S | E | N | I | Y | G | A | L | N | W | Y | Q | R | K | Q | G | K | S | P |
| 3D12 VK | D | I | Q | M | T | Q | T | P | A | S | L | S | A | S | V | G | E | T | V | T | I | T | C | G | A | S | E | N | I | Y | G | A | L | N | W | Y | Q | R | K | Q | G | K | S | P |
| 2E08 VK | D | I | V | L | T | Q | S | P | A | S | L | A | V | S | L | G | Q | R | A | T | I | S | C | K | A | S | Q | S | V | D | Y | D | G | D | S | Y | M | N | W | Y | Q | Q | K | P |
| 3C10 VK | D | V | V | M | T | Q | T | P | A | - | M | S | A | S | P | G | E | K | V | T | M | T | C | S | A | S | S | S | V | S | Y | M | Y | W | Y | Q | Q | K | P | G | S | S | P | R |
| 3A07 VK | E | N | V | L | T | Q | S | P | A | - | M | S | A | S | P | G | E | K | V | T | M | T | C | R | A | S | S | S | V | S | Y | M | H | W | Y | Q | Q | K | P | G | S | S | P | R |
| 3E09 VK | D | I | V | L | T | Q | S | P | A | S | L | A | V | S | L | G | Q | R | A | T | I | S | C | R | A | S | E | S | V | D | S | Y | G | N | S | F | M | H | W | Y | Q | Q | K | P |
| 2B11 VK | D | I | V | L | T | Q | S | P | A | S | L | A | V | S | L | G | Q | R | A | T | I | S | C | R | A | S | E | S | V | D | S | Y | G | N | S | F | M | H | W | Y | D | D | V | P |

Positions 45–84:

| Domain Type | 45 | 46 | 47 | 48 | 49 | 50 | 51 | 52 | 52A | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 3B04 VK | Q | L | L | I | - | Y | G | A | T | N | L | A | D | G | M | S | R | F | S | G | S | G | S | G | R | Q | Y | S | L | K | - | S | S | L | H | P | D | D | F | A | T | Y | Y | C |
| 3D12 VK | Q | L | L | I | - | Y | G | A | T | N | L | A | D | G | M | S | R | F | S | G | S | G | S | G | R | Q | Y | S | L | K | - | S | S | L | H | P | D | D | V | A | T | Y | Y | C |
| 2E08 VK | G | Q | P | P | - | - | - | - | - | - | A | S | N | L | E | S | G | - | P | A | R | F | S | G | S | G | S | G | T | D | F | T | L | N | - | H | P | V | E | E | E | D | A | A |
| 3C10 VK | G | L | L | I | Y | D | T | S | N | - | L | A | S | G | V | R | F | S | G | S | G | S | G | T | S | Y | S | L | T | - | - | S | R | M | E | A | E | D | A | A | T | Y | Y | A |
| 3A07 VK | G | L | L | I | Y | D | T | S | N | - | L | A | S | G | V | R | F | S | G | S | G | S | G | T | S | Y | S | L | T | - | - | S | R | M | E | A | E | D | A | A | T | Y | Y | A |
| 3E09 VK | G | Q | P | P | K | L | L | - | - | - | L | A | S | N | L | E | S | G | V | P | A | R | F | S | G | S | G | S | G | T | D | F | T | L | - | D | P | V | E | A | T | Y | Y | C |
| 2B11 VK | G | Q | P | P | K | L | L | - | - | - | R | A | S | N | L | E | S | G | V | P | A | R | F | S | G | S | G | S | G | T | D | F | T | L | - | N | P | V | E | A | T | Y | Y | C |

Positions 85–107:

| Domain Type | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|
| 3B04 VK | Q | N | V | L | T | T | P | W | T | F | G | G | G | T | K | L | E | I | K |  |  |  |  |
| 3D12 VK | Q | N | V | L | T | T | P | W | T | F | G | G | G | T | K | L | E | I | K |  |  |  |  |
| 2E08 VK | T | Y | Y | C | Q | Q | S | N | E | D | P | L | T | F | G | A | G | T | K | L | E | L | K |
| 3C10 VK | Q | W | S | S | Y | P | L | T | F | G | A | G | T | K | L | E | L | K |  |  |  |  |  |
| 3A07 VK | Q | W | S | S | Y | P | L | T | F | G | S | G | T | K | L | E | I | K |  |  |  |  |  |
| 3E09 VK | T | Y | Y | C | Q | Q | N | N | E | D | P | Y | T | F | G | G | G | T | K | L | E | I | K |
| 2B11 VK | T | Y | Y | C | Q | Q | S | N | E | D | P | Y | T | F | G | G | G | T | K | L | E | I | K |

Figure 5.

Light chain sequences

>3B04_VL
DIQMTQTPASLSAVGETVTITCGASENIYGALNWYQRKQGKSPQLLIYGATNLADGMSSRFSGSGSGRQYSLKISSLHPDFATYYCQNVLTTPWTFGGGTKLEIKR

>3B04_VL_1
DIQMTQSPSSLSASVGDRVTITCGASENIYGALNWYQRKQGKAPQLLIYGATNLADGVSSRFSGSGSGRDYTLTISSLQPEDFATYYCQNVLTTPWTFGQGTKLEIKR

>3B04_VL_2
DIQMTQSPSSLSASVGDRVTITCGASENIYGALNWYQRKQGKAPKLLIYGATNLADGVPSRFSGSGSGRDYTLTISSLQPEDFATYYCQNVLTTPWTFGQGTKLEIKR

>3B04_VL_3
DIQMTQSPSSLSASVGDRVTITCGASENIYGALNWYQQKPGKAPKLLIYGATNLADGVPSRFSGSGSGRDYTLTISSLQPEDFATYYCQNVLTTPWTFGQGTKLEIKR

>3B04_VL_4
DIQMTQSPSSLSASVGDRVTITCRASENIYGALNWYQQKPGKAPKLLIYGATNLAEGVPSRFSGSGSGRDYTLTISSLQPEDFATYYCQNVLTTPWTFGQGTKLEIKR

Heavy chain sequences

>3B04_VH
QVQLQQPGAELVRPGASVTLSCKASGYTFTDYEMHWVKQTPVHGLEWIGEIDPETGDTAYSQKFKGKATLTADKSSSTAYMEFRSLTSEDSAVYYCSRETDYFFDYWGQGTLVTVSS

>3B04_VH_1
QVQLVQSGAEVKKPGASVKVSCKASGYTFTDYEMHWVRQAPGQGLEWIGEIDPETGDTAYSQKFKGRATLTADKSTSTAYMEFSSLRSEDTAVYYCSRETDYFFDYWGQGTLVTVSS

>3B04_VH_2
QVQLVQSGAEVKKPGASVKVSCKASGYTFTDYEMHWVRQAPGQGLEWIGEIDPETGDTAYSQKFQGGRVTLTADKSTSTAYMEFSSLRSEDTAVYYCSRETDYFFDYWGQGTLVTVSS

>3B04_VH_3
QVQLVQSGAEVKKPGASVKVSCKASGYTFTDYEMHWVRQAPGQGLEWMGEIDPETGDTAYAQKFQGGRVTLTADKSTSTAYMEFSSLRSEDTAVYYCSRETDYFFDYWGQGTLVTVSS

>3B04_VH_4
QVQLVQSGAEVKKPGASVKVSCKASGYTFTDYEMHWVRQAPGQGLEWMGEIDPETGDTAYAQKFQGGRVTLTADKSTSTAYMELSSLRSEDTAVYYCSRETDYFFDYWGQGTLVTVSS

Figure 6.

Light chain sequences

>3D12_VL
DIQMTQSPASLSASVGETVTITCGASENIYGALNWYQRKQGKSPQLLIYGATNLADGMSSRFSGSGSGRQYSLKISSLHPDVATYYCQNVLSTPWTFGGGTKLEIKR

>3D12_VL_1
DIQMTQSPSSLSASVGDRVTITCGASENIYGALNWYQRKQGKAPQLLIYGATNLADGVSSRFSGSGSGRDYTLTISSLQPEDVATYYCQNVLSTPWTFGQGTKLEIKR

>3D12_VL_2
DIQMTQSPSSLSASVGDRVTITCGASENIYGALNWYQRKQGKAPKLLIYGATNLADGVPSRFSGSGSGRDYTLTISSLQPEDVATYYCQNVLSTPWTFGQGTKLEIKR

>3D12_VL_3
DIQMTQSPSSLSASVGDRVTITCGASENIYGALNWYQQKPGKAPKLLIYGATNLADGVPSRFSGSGSGRDYTLTISSLQPEDVATYYCQNVLSTPWTFGQGTKLEIKR

>3D12_VL_4
DIQMTQSPSSLSASVGDRVTITCRASENIYGALNWYQQKPGKAPKLLIYGATNLAEGVPSRFSGSGSGRDYTLTISSLQPEDVATYYCQNVLSTPWTFGQGTKLEIKR

Heavy chain sequences

>3D12_VH
QVQLQQPGAELVRPGASVTLSCKASDYTFTDSEIHWVKQTPVHGLEWIGEIDPETGTAYNQKFKGKATLTADKSSSTAYMELRSLTSEDSAVYYCSRETDYFFDYWGQGTLLTVSS

>3D12_VH_1
QVQLVQSGAEVKKPGASVKVSCKASDYTFTDSEIHWVRQAPGQGLEWIGEIDPETGTAYNQKFKGRATLTADKSTSTAYMELSSLRSEDTAVYYCSRETDYFFDYWGQGTLVTVSS

>3D12_VH_2
QVQLVQSGAEVKKPGASVKVSCKASDYTFTDSEIHWVRQAPGQGLEWIGEIDPETGTAYNQKFQGRATLTADKSTSTAYMELSSLRSEDTAVYYCSRETDYFFDYWGQGTLVTVSS

>3D12_VH_3
QVQLVQSGAEVKKPGASVKVSCKASDYTFTDSEIHWVRQAPGQGLEWMGEIDPETGTAYAQKFQGRVTLTADKSTSTAYMELSSLRSEDTAVYYCSRETDYFFDYWGQGTLVTVSS

>3D12_VH_4
QVQLVQSGAEVKKPGASVKVSCKASGYTFTDSEMHWVRQAPGQGLEWMGEIDPETGTAYAQKFQGRVTLTADKSTSTAYMELSSLRSEDTAVYYCSRETDYFFDYWGQGTLVTVSS

Figure 7.
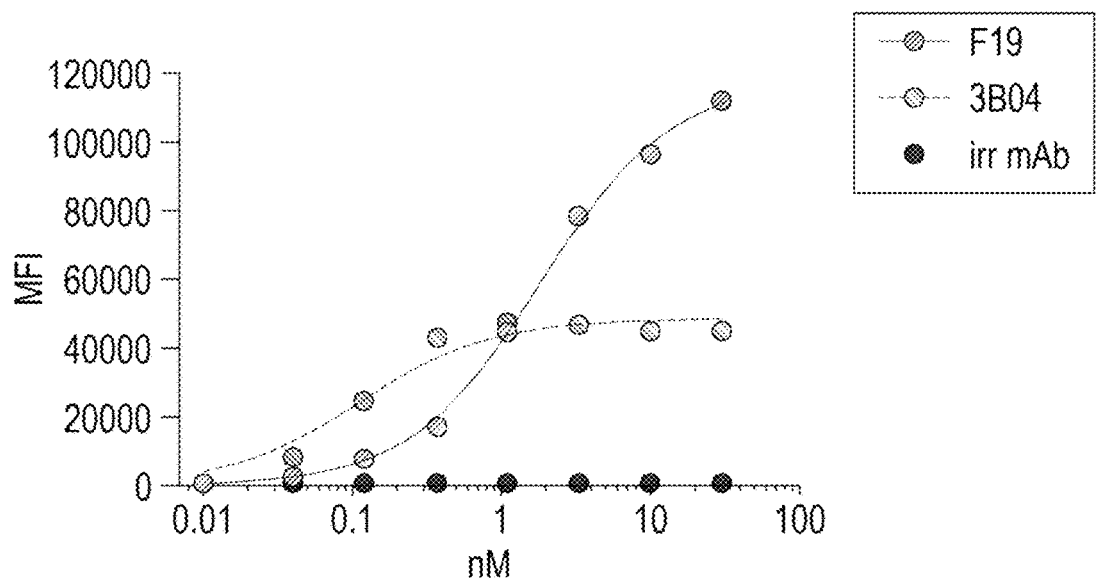
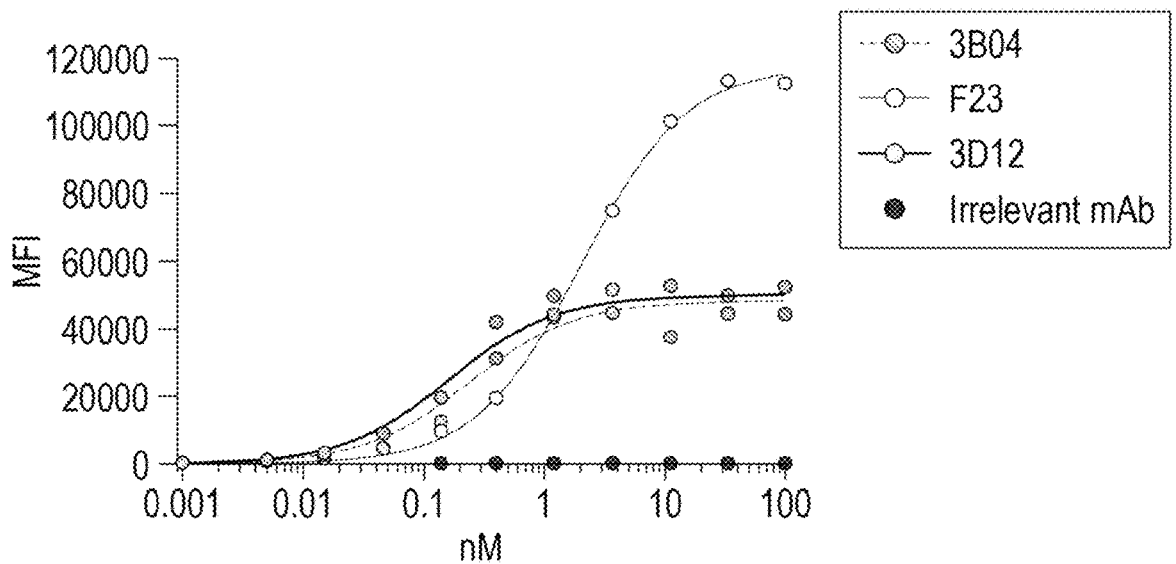

Figure 12.

Light chain sequences

>3B04_VL
DIQMTQTPASLSASVGETVTITCGASENIYGALNWYQRKQGKSPQLLIYGATNLADGMSSRFSGSGSGRQYSLKISSLHPDDFATYYCQNVLTTPWTFGGGTKLEIKR

>3B04_VL_1
DIQMTQSPSSLSASVGDRVTITCGASENIYGALNWYQRKQGKAPQLLIYGATNLADGVSSRFSGSGSGRDYTLTISSLQPEDFATYYCQNVLTTPWTFGQGTKLEIKR

>3B04_VL_2
DIQMTQSPSSLSASVGDRVTITCGASENIYGALNWYQRKQGKAPKLLIYGATNLADGVPSRFSGSGSGRDYTLTISSLQPEDFATYYCQNVLTTPWTFGQGTKLEIKR

>3B04_VL_3
DIQMTQSPSSLSASVGDRVTITCGASENIYGALNWYQQKPGKAPKLLIYGATNLADGVPSRFSGSGSGRDYTLTISSLQPEDFATYYCQNVLTTPWTFGQGTKLEIKR

>3B04_VL_4
DIQMTQSPSSLSASVGDRVTITCRASENIYGALNWYQQKPGKAPKLLIYGATNLAEGVPSRFSGSGSGRDYTLTISSLQPEDFATYYCQNVLTTPWTFGQGTKLEIKR

Heavy chain sequences

>3B04_VH
QVQLQQPGAELVRPGASVTLSCKASGYTFTDYEMHWVKQTPVHGLEWIGEIDPETGDTAYSQKFKGKATLTADKSSSTAYMEFRSLTSEDSAVYYCSRETDYFFDYWGQGTTLTVSS

>3B04_VH_1
QVQLVQSGAEVKKPGASVKVSCKASGYTFTDYEMHWVRQAPGQGLEWIGEIDPETGDTAYSQKFKGRATLTADKSTSTAYMEFSSLRSEDTAVYYCSRETDYFFDYWGQGTLVTVSS

>3B04_VH_2
QVQLVQSGAEVKKPGASVKVSCKASGYTFTDYEMHWVRQAPGQGLEWIGEIDPETGDTAYSQKFKGRATLTADKSTSTAYMEFSSLRSEDTAVYYCSRETDYFFDYWGQGTLVTVSS

>3B04_VH_3
QVQLVQSGAEVKKPGASVKVSCKASGYTFTDYEMHWVRQAPGQGLEWMGEIDPETGDTAYAQKFQGRVTLTADKSTSTAYMEFSSLRSEDTAVYYCSRETDYFFDYWGQGTLVTVSS

>3B04_VH_4
QVQLVQSGAEVKKPGASVKVSCKASGYTFTDYEMHWVRQAPGQGLEWMGEIDPETGDTAYAQKFQGRVTLTADKSTSTAYMELSSLRSEDTAVYYCSRETDYFFDYWGQGTLVTVSS

Figure 13.

Light chain sequences

>3D12_VL
DIQMTQSPASLSASVGETVTITCGASENIYGALNWYQRKQGKSPQLLIYGATNLADGMSSRFSGSGSGRQYSLKISSLHPDVATYYCQNVLSTPWTFGGGTKLEIKR

>3D12_VL_1
DIQMTQSPSSLSASVGDRVTITCGASENIYGALNWYQRKQGKAPQLLIYGATNLADGVSSRFSGSGSGRDYTLTISSLQPEDVATYYCQNVLSTPWTFGQGTKLEIKR

>3D12_VL_2
DIQMTQSPSSLSASVGDRVTITCGASENIYGALNWYQRKQGKAPKLLIYGATNLADGVPSRFSGSGSGRDYTLTISSLQPEDVATYYCQNVLSTPWTFGQGTKLEIKR

>3D12_VL_3
DIQMTQSPSSLSASVGDRVTITCGASENIYGALNWYQQKPGKAPKLLIYGATNLADGVPSRFSGSGSGRDYTLTISSLQPEDVATYYCQNVLSTPWTFGQGTKLEIKR

>3D12_VL_4
DIQMTQSPSSLSASVGDRVTITCRASENIYGALNWYQQKPGKAPKLLIYGATNLAEGVPSRFSGSGSGRDYTLTISSLQPEDVATYYCQNVLSTPWTFGQGTKLEIKR

Heavy chain sequences

>3D12_VH
QVQLQQPGAELVRPGASVTLSCKASDYTFTDSEIHWVKQTPVHGLEWIGEIDPETGGTAYNQKFKGKATLTADKSSSTAYMELRSLTSEDSAVYYCSRETDYFFDYWGQGTLVTVSS

>3D12_VH_1
QVQLVQSGAEVKKPGASVKVSCKASDYTFTDSEIHWVRQAPGQGLEWIGEIDPETGGTAYNQKFKGRATLTADKSTSTAYMELSSLRSEDTAVYYCSRETDYFFDYWGQGTLVTVSS

>3D12_VH_2
QVQLVQSGAEVKKPGASVKVSCKASDYTFTDSEIHWVRQAPGQGLEWIGEIDPETGGTAYNQKFKGRVTLTADKSTSTAYMELSSLRSEDTAVYYCSRETDYFFDYWGQGTLVTVSS

>3D12_VH_3
QVQLVQSGAEVKKPGASVKVSCKASDYTFTDSEIHWVRQAPGQGLEWMGEIDPETGGTAYAQKFQGRVTLTADKSTSTAYMELSSLRSEDTAVYYCSRETDYFFDYWGQGTLVTVSS

>3D12_VH_4
QVQLVQSGAEVKKPGASVKVSCKASGYTFTDSEMHWVRQAPGQGLEWMGEIDPETGGTAYAQKFQGRVTLTADKSTSTAYMELSSLRSEDTAVYYCSRETDYFFDYWGQGTLVTVSS

ANTIGEN BINDING MOLECULES THAT BIND LIGHT

STATEMENT OF RELATED APPLICATIONS

This application is a divisional of U.S. application Ser. No. 16/256,688, filed on Jan. 24, 2019, which claims priority to U.S. Provisional Application No. 62/621,346, filed on Jan. 24, 2018, which are herein incorporated by reference in their entireties.

FIELD OF THE INVENTION

The present invention relates antigen binding molecules, particularly antibodies, fragments and variants thereof, that bind to the TNF-related cytokine LIGHT (TNFSF14), competing with LIGHT binding to cellular receptors Herpes virus entry mediator (HVEM) and lymphotoxin beta receptor, and the use of said antigen binding molecules in treating and/or preventing inflammatory disorders and immune disorders.

BACKGROUND TO THE INVENTION

LIGHT, (lymphotoxin-like, exhibits inducible expression and competes with HSV glycoprotein D for HVEM, a receptor expressed by T lymphocytes), also known as TNFSF14 or CD258 is upregulated on activated T cells. LIGHT is not expressed on naïve T cells but is upregulated upon activation, appearing within 4 hours, peaking by 12-24 hours and disappearing by 48 hours on T cells ("Mechanisms regulating expression of the tumor necrosis factor-related LIGHT gene. Role of calcium-signaling pathway in the transcriptional control", Castellano R et al. J Biol Chem. 2002 Nov. 8; 277:42841-51). LIGHT is also expressed by immature dendritic cells, NK cells and monocytes ("Lymphotoxin/light, lymphoid microenvironments and autoimmune disease". Gommerman J L et al. Nat Rev Immunol 2003, 3:642-655; "LIGHT, a TNF-like molecule, costimulates T cell proliferation and is required for dendritic cell-mediated allogeneic T cell response". Tamada K et al. J Immunol 2000, 164:4105-4110). LIGHT is a ligand for three TNFSF receptors: herpes virus entry mediator (HVEM), mainly expressed by T cells ("Reciprocal Expression of the TNF Family Receptor Herpes Virus Entry Mediator and Its Ligand LIGHT on Activated T Cells: LIGHT Down-Regulates Its Own Receptor". Morel Y. et al. J. Immunol. 2001, 167:2479-2486); lymphotoxin β receptor (LTBR), expressed by stromal and non-lymphoid hematopoietic cells ("LIGHT, a novel ligand for lymphotoxin beta receptor and TR2/HVEM induces apoptosis and suppresses in vivo tumor formation via gene transfer". Zhai Y et al. J. Clin. Invest. 1998, 102:1142-1151); and the soluble protein decoy receptor 3 (DcR3/TNFRSF6B).

LIGHT was first identified to have a co-stimulatory role for HVEM when it was shown to promote T cell proliferation and IFNγ production, and blockade of LIGHT on DCs inhibited allogeneic T cell responses ("LIGHT, a TNF-like molecule, costimulates T cell proliferation and is required for dendritic cell-mediated allogeneic T cell response" Tamada K. et al. J Immunol 2000, 164:4105-4110; "Antibodies to TR2 ("herpesvirus entry mediator), a new member of the TNF receptor superfamily, block T cell proliferation, expression of activation markers, and production of cytokines". Harrop et al. J Immunol 1998, 161:1786-1794). LIGHT-HVEM interactions have also been shown to promote activation and effector function of NK cells, neutrophils and monocytes ("LIGHT enhances the bactericidal activity of human monocytes and neutrophils via HVEM" Heo S K et al. J Leukocyte Biol 2006, 79:330-338; "HVEM signaling in monocytes is mediated by intracellular calcium mobilization" Heo S K et al. J Immunol 2007, 179:6305-6310).

Although LTβR is mainly expressed on non-hematopoietic cells such as stromal cells, LIGHT-LTβR mediated signaling has recently been shown to be involved in DC activation and expansion ("Stimulating lymphotoxin beta receptor on the dendritic cells is critical for their homeostasis and expansion". Wang Y G et al. J Immunol 2007, 175:6997-7002). LTβR signaling is also crucial for the development of secondary lymphoid structures ("Modulating the intestinal immune system: the role of lymphotoxin and GALT organs". Spahn T W et al. Gut 2004, 53:456-465) and deletion of both LTP and LIGHT in mice led to the absence of all secondary lymphoid structures ("Targeted disruption of LIGHT causes defects in costimulatory T cell activation and reveals cooperation with lymphotoxin beta in mesenteric lymph node genesis". Scheu, S. et al. J Exp Med 2002, 195:1613-1624).

LIGHT has been implicated in the processes of chronic inflammatory autoimmune diseases ("LIGHT, a new member of the TNF superfamily, and lymphotoxin alpha are ligands for herpesvirus entry mediator", Mauri D N et al. Immunity. 1998 January; 8(1):21-30) and recent evidence indicates LIGHT contributes to early onset inflammatory bowel disease.

Inflammatory bowel disease (IBD), is a group of inflammatory conditions of the colon and small intestine. The major types of IBD are Crohn's disease (CD) and ulcerative colitis (UC). Accounting for far fewer cases are other forms of IBD, such as: collagenous colitis, lymphocytic colitis, ischemic colitis, diversion colitis, Behcet's disease, and indeterminate colitis.

The main difference between CD and UC is the location and nature of the inflammatory changes. CD can affect any part of the gastrointestinal tract, from mouth to anus, although a majority of the cases start in the terminal ileum. UC, in contrast, is restricted to the colon and the rectum. In addition, CD and UC present with extra-intestinal manifestations, such as liver problems, arthritis, skin manifestations, and eye problems, in different proportions.

Although very different diseases, both CD and UC may present with any of the following symptoms: abdominal pain, vomiting, diarrhoea, rectal bleeding, severe internal cramps/muscle spasms in the region of the pelvis, weight loss, and various associated complaints or diseases such as arthritis, pyoderma gangrenosum, and primary sclerosing cholangitis. Diagnosis is generally by colonoscopy with biopsy of pathological lesions. While IBD can limit a person's quality of life because of pain, vomiting, diarrhoea, and other socially unacceptable symptoms, it is rarely fatal on its own. The treatment of IBD places considerable demands on the healthcare system and is associated with increased healthcare costs. Optimal treatment of IBD depends on its form. For example, mesalazine is more useful in UC than in CD. Generally, depending on the level of severity, IBD may require immunosuppression with drugs, such as prednisone, azathioprine (Imuran), methotrexate, or 6-mercaptopurine. Often, steroids are used to control disease flares. Recently, protein based therapeutics have been used, such as antibodies that neutralise TNF (TNF inhibitors). However, only a third of patients with IBD respond well to TNF inhibitors, and a third show no response at all. Severe cases of IBD may require surgery, such as bowel resection, strictureplasty, or a temporary or permanent colostomy or ileostomy.

Usually treatment is started by administering drugs with broad anti-inflammatory effects, such as prednisone. If the inflammation is successfully controlled, the patient is usually switched to a lighter drug to keep the disease in remission, such as Asacol, a mesalazine. If unsuccessful, a combination of the aforementioned immunosuppression drugs with a mesalazine (which may also have an anti-inflammatory effect) may or may not be administered, depending on the patient. The goal of treatment is toward achieving remission, after which the patient is usually switched to a lighter drug with fewer potential side effects. Every so often, however, an acute resurgence of the original symptoms may appear; which is known as a "flare-up". Depending on the circumstances, it may go away on its own or require medication. The time between flare-ups may be anywhere from weeks to years, and varies wildly between patients and therapies.

Therefore, there is a pressing need in the art for improved treatment regimens that are more consistently effective in treating IBD, and which are non-immunogenic and safe for use in humans.

New experimental approaches are being investigated. Mice treated with an inhibitory LTβR-Fc fusion protein reduced the inflammatory symptoms in the CD4+ CD45RBhigh T cell transfer model of colitis, a CD4+ T cell-mediated pathology (Gastroenterology. 1998 December; 115(6):1464-75, "Both the lymphotoxin and tumor necrosis factor pathways are involved in experimental murine models of colitis", Mackay F et al.). Constitutive transgenic T cell specific expression of LIGHT also has been shown to lead to severe intestinal inflammation with autoimmune-like pathology resembling human IBD ("The critical role of LIGHT in promoting intestinal inflammation and Crohn's disease", Wang J et al. J Immunol. 2005 Jun. 15; 174:8173-82; "Constitutive expression of LIGHT on T cells leads to lymphocyte activation, inflammation, and tissue destruction", Shaikh R B et al J Immunol. 2001, 167:6330-7; "The critical role of LIGHT, a TNF family member, in T cell development", Wang J et al. J Immunol. 2001, 167:5099-105; "Dysregulated LIGHT expression on T cells mediates intestinal inflammation and contributes to IgA nephropathy", Wang J et al. J Clin Invest. 2004, 113:826-35). LIGHT-expressing lymphocytes can induce IBD-like symptoms (e.g., cytokine profiles of human Crohn's disease, fissuring ulcers, ileitis, and increases in colonic IFN-γ and TNF) when mesenteric lymph node cells from LIGHT transgenic animals are transferred to RAG−/− mice ("The critical role of LIGHT in promoting intestinal inflammation and Crohn's disease", Wang J et al. J Immunol. 2005; 174:8173-82). In human disease, increases of LIGHT expression were observed in patients with active Crohn's disease (Cohavy et al 2005 supra; Wang et al 2005 supra; Wang et al 2004 supra; "LIGHT expression by mucosal T cells may regulate IFN-gamma expression in the intestine", Cohavy O et al. J Immunol. 2004, 173:251-8). LIGHT has also been demonstrated to be elevated in gut T cells of IBD patients (Cohavy et al 2004 supra). Genetic evidence also supports a role for LIGHT in IBD ("Genomic characterization of LIGHT reveals linkage to an immune response locus on chromosome 19p13.3 and distinct isoforms generated by alternate splicing or proteolysis", Granger S W et al. J Immunol. 2001, 167:5122-8). Genomic characterization of LIGHT also reveals linkage to an immune response locus on chromosome 19p13.3 and distinct isoforms generated by alternate splicing or proteolysis; ("Genomewide search in Canadian families with inflammatory bowel disease reveals two novel susceptibility loci", Rioux J D et al. Rioux et al. Am J Hum Genet. 2000, 66:1863-70; "Inflammatory bowel disease is linked to 19p13 and associated with ICAM-12", Low J H et al. Inflamm Bowel Dis. 2004, 10:173-81; "The genetics of inflammatory bowel disease", Bonen D K, Cho J H Gastroenterology 2003, 124:521-36). In addition, defective variants in DcR3 have a role in the pathogenesis of some cases of IBD and it has been suggested that interventions targeting this group of tumor necrosis factor-family members may benefit patients with IBD ("Targeted resequencing identifies defective variants of decoy receptor 3 in pediatric-onset inflammatory bowel disease", Cardinale C J et al. Genes Immun. 2013, 14:447-52).

Human LIGHT (LIGHT) has also been implicated in graft-versus-host disease (GvHD). For example, LIGHT has been shown to provide potent costimulatory activity for T cells, enhancing proliferation and the production of Th1 cytokines independent of the B7-CD28 pathway (see, e.g., Tamada et al 2000 supra). Blocking of LIGHT-HVEM costimulation by either anti-HVEM monoclonal antibodies, or HVEM-lg, inhibits allogeneic T cell responses (see, e.g., Tamada et al 2000 supra; Harrop J A et al. 1998 supra). Furthermore, in vivo administration of LTβR-lg or murine anti-LIGHT antibodies inhibits anti-host cytotoxic T lymphocyte (CTL) responses in a murine acute GvHD model ("Modulation of T-cell-mediated immunity in tumor and graft-versus-host disease models through the LIGHT costimulatory pathway", Tamada K et al. Nat Med. 2000, 6:283-9).

Much of the action that directs the proinflammatory and inhibitory signaling by HVEM is controlled at the cell surface. These distinct signaling outcomes stem from three key biophysical parameters: the specific pairing of ligand and receptor, the form of the ligand in soluble or membrane-anchored positions, and the cis or trans context of ligand-receptor engagement. The specificity of the ligand and receptor provides the primary mechanism that directs inflammatory and inhibitory signaling. HVEM plays dual roles as both receptor and ligand since BTLA (B and T lymphocyte attenuator) and LIGHT engage distinct sites on HVEM, which is itself an activating ligand for BTLA. The ectodomain of HVEM contains four repeats of a cysteine-rich domain, the signature motif of the TNFR superfamily ("The molecular architecture of the TNF superfamily", Bodmer J L et al. Trends Biochem Sci. 2002; 27:19-26). The BTLA binding site is located in the first cysteine-rich domain at the N-terminus of HVEM, whereas homology modeling indicates LIGHT binds in the second and third domains, but on the opposite face of HVEM ("Attenuating lymphocyte activity: the crystal structure of the BTLA-HVEM complex", Compaan D M et al. J Biol Chem. 2005; 280:39553-39561). LIGHT, a type II transmembrane protein, can be proteolyzed releasing a soluble, bioactive form ("Genomic Characterization of LIGHT Reveals Linkage to an Immune Response Locus on Chromosome 19p13.3 and Distinct Isoforms Generated by Alternate Splicing or Proteolysis", Granger et al. J Immunol. 2001; 167:5122-5128). Soluble LIGHT binds HVEM with high affinity, but does not compete with BTLA, allowing both ligands to simultaneously occupy HVEM. In fact, soluble LIGHT and LTα enhance the binding of BTLA to HVEM, implicating the formation of a trimolecular complex ("Evolutionarily divergent herpesviruses modulate T cell activation by targeting the herpesvirus entry mediator cosignaling pathway", Cheung T C et al. Proc Natl Acad Sci USA. 2005; 102:

13218-13223). In striking contrast, the membrane form of LIGHT interferes with HVEM-BTLA binding, by an uncompetitive mechanism, presumably steric hindrance due to proximity of the membrane.

Trans Signaling

Based on the conservation seen in several TNF ligand-receptor crystal structures, the stereoconformation of membrane LIGHT must be in trans (in an adjacent cell membrane) to engage HVEM and activate signaling. BTLA forms dimers in the membrane of viable cells as revealed by flow cytometric-based FRET system. The dimeric conformation of BTLA suggested a mechanism for clustering HVEM and this mechanism was confirmed in experiments demonstrating that BTLA induces activation of HVEM as either a membrane protein or engineered as a soluble dimeric fusion protein with Fe of IgG ("TNF SUPERFAMILY NETWORKS: Bidirectional and Interference Pathways of the Herpesvirus Entry Mediator (TNFSF14)", Ware C F and Sedy J Curr Opin Immunol. 2011, 23: 627-631).

Despite the location of the binding regions on the opposite sides of HVEM, both LIGHT and BTLA induce the canonical NFκB RelA pathway through a TRAF2-dependent mechanism, indicating signaling outcome is qualitatively the same for both ligands ("Unconventional ligand activation of herpesvirus entry mediator signals cell survival", Cheung T C et al. Proc Natl Acad Sci USA. 2009; 106:6244-6249). This result suggests both ligands provide HVEM with sufficient conformational reorganization to initiate the TRAF2 E3 ligase pathway that activates NFκB. HVEM does not recruit TRAF3 into its signaling complex as do other TNFR such as the LTβR, and thus the signaling activity of HVEM is limited to the activation NFκB RelA.

The Cis and Trans of HVEM

Coexpression of HVEM and BTLA in T cells creates an intrinsic mechanism that interferes with the ability of LIGHT and the other ligands to access and activate HVEM ("T cell intrinsic heterodimeric complexes between HVEM and BTLA determine receptivity to the surrounding microenvironment", Cheung T C et al. J Immunol. 2009; 183:7286-7296). Previous studies had largely assumed that the behaviour of the soluble form of LIGHT was representative of its membrane bound form. This assumption is indeed the case in the ability of soluble LIGHT to activate the LTβR or HVEM in epithelia cells. However, a distinction between soluble and membrane LIGHT emerged in studies of T cells, which in contrast to epithelia cells, coexpress HVEM with its inhibitory receptor BTLA. T cells derived from human blood and naïve mouse spleens constitutively coexpress HVEM and BTLA. HVEM and BTLA are expressed independently of each other as shown in mice genetically deficient in either gene. Together the HVEM-BTLA cis complex is stable and expressed at the cell surface, although no signaling activity is associated with HVEM. The formation of the cis complex required only HVEM to bind the ectodomain of BTLA and mutations that affect BTLA binding to HVEM in trans, also impacted binding in cis, indicating the HVEM-BTLA cis complex occupies the same binding sites as in trans. Indeed, cells coexpressing HVEM and BTLA are unable to bind HVEM or BTLA-Fc, which provided a method to quantify the HVEM and BTLA on the cell surface of T cells at a ratio of 1:1 with >85% of the molecules in the cis complex. Importantly, the addition of soluble LIGHT or LTα failed to activate HVEM as detected by induction of NFκB, although binding of LIGHT was detectable as expected, and in cells expressing HVEM alone, these ligands were fully functional. BTLA or CD160 in either soluble or membrane positions also failed to activate HVEM in cells expressing the cis complex. Thus, BTLA functions as an inhibitor when coexpressed with HVEM ("TNF SUPERFAMILY NETWORKS: Bidirectional and Interference Pathways of the Herpesvirus Entry Mediator (TNFSF14)", Ware C F and Sedy J Curr Opin Immunol. 2011, 23:627-631).

The membrane form of LIGHT is the only cellular ligand capable of activating HVEM within the cis complex with BTLA. However, this activation is reduced compared to membrane LIGHT activation of HVEM in the absence of BTLA. The presence of antibodies to BTLA that disrupt the cis-complex synergizes with LIGHT to activate HVEM, which suggests the disassociation of HVEM from BTLA is a key biophysical feature of membrane LIGHT's ability to activate HVEM. Together, these results indicate that membrane LIGHT has four distinct signaling functions: activation of HVEM, disruption of HVEM-BTLA cis complex, activation of the LTβR, and in soluble form enhancing HVEM-BTLA complex formation i.e. soluble LIGHT is anti-inflammatory ("Targeting lymphocyte activation through the lymphotoxin and LIGHT pathways", Ware C F Immunol Rev. 2008; 223:186-201).

SUMMARY OF THE INVENTION

The present inventors have identified antigen binding molecules that specifically bind LIGHT, in particular membrane LIGHT. The antigen binding molecules of the invention bind membrane LIGHT with a higher affinity than soluble LIGHT. The antigen binding molecules of the invention also preferentially bind trimers of LIGHT in a ratio of 1 antigen binding molecule to 1 LIGHT trimer.

In a first aspect of the invention there is provided an antigen binding molecule or fragment or variant thereof comprising a heavy chain variable region comprising a VHCDR3 and/or a light chain variable region comprising a VLCDR3, wherein the antigen binding molecule binds to LIGHT.

In a second aspect of the invention there is provided an antigen binding molecule or fragment or variant thereof comprising a heavy chain variable region and/or a light chain variable region, each comprising 3 CDR regions, wherein the antigen binding molecule binds to LIGHT.

In a third aspect of the invention, there are provided antigen binding molecules, wherein the antigen binding molecule is an antibody that specifically binds to LIGHT and is selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16. The present invention also provides fragments and variants derived from said antibodies.

In a fourth aspect of the invention there is provided an antigen binding molecule or fragment or variant thereof, that binds to LIGHT and competes for binding to LIGHT with an antigen binding molecule of the first, second or third aspect of the invention.

In a fifth aspect of the invention, there is provided an antigen binding molecule that specifically binds to an epitope of LIGHT that is bound by an antigen binding molecule of the first, second or third aspect of the invention.

In a sixth aspect of the invention, there is provided an antigen binding molecule that specifically binds to an epitope of LIGHT wherein the epitope comprises the amino acids GRATSSSRVW (SEQ ID NO: 124).

In a seventh aspect of the invention, there is provided an antigen binding molecule that specifically binds to a timer of LIGHT molecules in a ratio of 1 antigen binding molecule to 1 LIGHT trimer.

In an eight aspect of the invention, there is provided an antigen binding molecule that specifically binds to LIGHT and inhibits the binding of LIGHT to an antigen binding molecule of the first, second or third aspect of the invention.

In a ninth aspect of the invention, there is provided an anti-LIGHT antigen binding molecule comprising 1 to 10, 1 to 5 or 1 to 2 amino acid substitutions from the antigen binding molecule of the first, second or third aspect of the invention. In a further aspect of the invention, there is provided an anti-LIGHT antigen binding molecule, wherein the anti-LIGHT antigen binding molecule is a humanised derivative of an anti-LIGHT antigen binding molecule of the invention.

In a further aspect of the invention, there is provided an affinity matured mutant of an antigen binding molecule or antibody of the invention.

In a still further aspect of the invention, there is provided an anti-LIGHT antigen binding molecule or an affinity matured mutant thereof, wherein the antigen binding molecule or an affinity matured mutant has $K_D$ value for membrane LIGHT of less than about 1 nM and a $K_D$ value for soluble LIGHT of more than about 1 nM, in particular an anti-LIGHT antigen binding molecule or an affinity matured mutant thereof, that has $K_D$ value for membrane LIGHT of less than about 1 nM and a $K_D$ value for soluble LIGHT of more than about 5 nM, and preferably an anti-LIGHT antigen binding molecule or an affinity matured mutant thereof, that has $K_D$ value for membrane LIGHT of less than of less than about 0.5 nM and a $K_D$ value for soluble LIGHT of more than about 10 nM, or a $K_D$ value for membrane LIGHT of less than about 0.1 nM and a $K_D$ value for soluble LIGHT of more than about 10 nM.

In another aspect of the invention, there is provided an anti-LIGHT antibody that inhibits the binding of membrane LIGHT to HVEM and/or LTβR or the binding of LIGHT expressing cells to HVEM and/or LTβR and optionally partially inhibits the binding of membrane LIGHT to decoy receptor 3 or cells expressing membrane LIGHT to decoy receptor 3.

In a further aspect of the invention, a pharmaceutical composition comprising an antigen binding molecule of the invention, or a fragment or variant thereof, is provided.

In a still further aspect of the invention there is provided the antigen binding molecules or pharmaceutical compositions of the invention for use in medicine.

In another aspect, there is provided the antigen binding molecules or pharmaceutical compositions of the invention for use in preventing and/or treating an inflammatory disorder or disease.

In another aspect, there is provided the use of antigen binding molecules or pharmaceutical compositions of the invention for the manufacture of a medicament for use in treatment of an inflammatory disorder or disease.

In a further aspect, there is provided a method of treating or preventing an inflammatory disorder or disease in a subject in need thereof, comprising administering to the subject a therapeutically effective amount of an antigen binding molecule or pharmaceutical composition of the invention.

Also provided are nucleic acids encoding the antigen binding molecules of the invention, vectors comprising the nucleic acids, and host cells, as well as kits, methods of inhibiting the binding of LIGHT protein to HVEM and/or LTβR or the binding of LIGHT expressing cells to HVEM and/or LTβR, methods of producing cell that expresses an anti-LIGHT antigen binding molecule, comprising transfecting said cell with a plasmid or vector of the invention, and methods for the production on an anti-LIGHT antigen binding molecule, comprising culturing a host cell of the invention in a cell culture medium under conditions to express the encoding nucleic acid sequence of the plasmid or vector inside the cell.

BRIEF DESCRIPTION OF FIGURES

FIG. 3 shows the amino acid sequences of seven murine monoclonal anti-LIGHT heavy chain variable regions. The CDRs (CDR1, CDR2 and CDR3) of each heavy chain variable region are highlighted (Kabat).

FIG. 4 shows amino acid sequences of seven murine monoclonal anti-LIGHT antibodies light chain variable regions. The CDRs (CDR1, CDR2 and CDR3) of each light chain variable region are highlighted (Kabat).

FIG. 5 shows the amino acid sequences of variable heavy and light humanised and deimmunised chains derived from 3B04 parent antibody. The CDRs (CDR1, CDR2 and CDR3) of each heavy and light chain variable region are highlighted (Kabat).

FIG. 6 shows the amino acid sequences of variable heavy and light humanised and deimmunised chains derived from 3D12 parent antibody. The CDRs (CDR1, CDR2 and CDR3) of each heavy and light chain variable region are highlighted (Kabat).

FIG. 7 shows the binding of anti-membrane LIGHT mAbs 3B04 and 3D12 in comparison to other anti-LIGHT (membrane and soluble) mAbs to stably transfected LIGHT EL4 cells. For comparison mAb F19 and mAb F23 from EP2292663 is included.

FIG. 12 shows the amino acid sequences of variable heavy and light humanised and deimmunised chains derived from 3B04 parent antibody. The CDRs (CDR1, CDR2 and CDR3) of each heavy and light chain variable region are highlighted (Chothia).

FIG. 13 shows the amino acid sequences of variable heavy and light humanised and deimmunised chains derived from 3D12 parent antibody. The CDRs (CDR1, CDR2 and CDR3) of each heavy and light chain variable region are highlighted (Chothia).

DETAILED DESCRIPTION

Figure 1A:
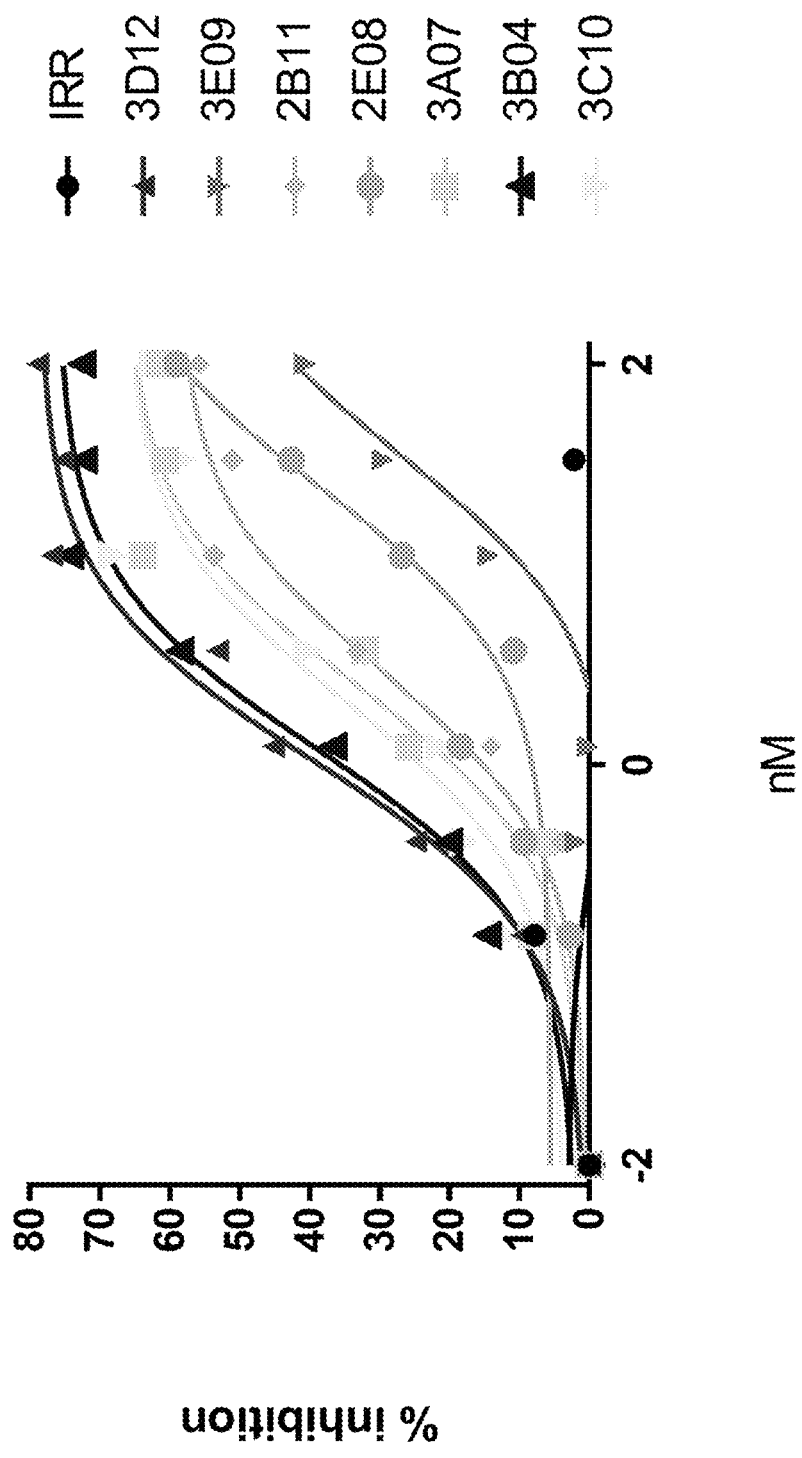
FIGS. 1A and 1B show a competition assay for the anti-membrane LIGHT mAbs 3D12, 3B04, 3E09, 2B11, 2E08, 3A07 and 3C10 inhibition against biotinylated HVEM-Fc (FIG. 1A) or biotinylated LTβR-Fc (FIG. 1B) binding to membrane LIGHT (HEK293FF human-LIGHT cells). IRR is a negative control anti-HEL mAb.

As used herein, an "antigen binding molecule" is a member of a pair of molecules which have binding specificity for one another. The members of an antigen binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of antigen binding pairs are antigen-antibody, biotin-avidin, hormone-hormone receptor, receptor-ligand and enzyme-substrate. The present invention is generally concerned with antigen-antibody type interactions. The antigen binding molecule used in the present invention binds with greater affinity to LIGHT, hLIGHT, membrane LIGHT, an epitope of LIGHT or an epitope of hLIGHT than to other molecules, i.e. it binds specifically to LIGHT, hLIGHT, membrane LIGHT, an epitope of LIGHT or an epitope of hLIGHT. The binding affinity of the antigen binding molecule to LIGHT, hLIGHT, membrane LIGHT, an epitope of LIGHT or an epitope of hLIGHT can be measured using the dissociation constant ($K_D$). The binding affinity of the antigen binding molecule to LIGHT, hLIGHT, membrane LIGHT, an epitope of LIGHT or an epitope of hLIGHT can also be measured using the association constant ($K_a$). The $K_D$ value of the antigen binding molecule for the epitope of hLIGHT described herein will be lower than the $K_D$ value of the antigen binding molecule for an alternative epitope of LIGHT or a non-LIGHT epitope.

Antigen binding molecules which bind to LIGHT, hLIGHT and/or membrane LIGHT include anti-LIGHT antibodies. The antigen binding molecule used in the present invention is typically an antibody.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. Antibodies may be polyclonal or monoclonal. These can be derived from natural sources, or they may be partly or wholly synthetically produced. Antibodies are polypeptides that typically contain two identical heavy chains and two identical light chains, which are smaller than the heavy chains. In mammals there are two types of light chain, which are called lambda (λ) and kappa (κ). Each of the heavy chains and each of the light chains are composed of a variable region and a constant region. The heavy chain variable region is referred to as the VH region and the light chain variable region is referred to as the VL region. For kappa light chains, the VL region can also be referred to as the VK region. Each of the variable regions of the heavy and light chains comprise three complementarity determining regions (CDRs), CDR1, CDR2 and CDR3. These are named VLCDR1, VLCDR2, VLCDR3, VHCDR1, VHCDR2 and VHCDR3 respectively. Examples of antibodies are the immunoglobulin isotypes (e.g., IgG, IgE, IgM, IgD and IgA) and their isotypic subclasses; fragments which comprise an antigen binding domain, such as Fab, F(ab')2, Fv, scFv, dAb, Fd; and diabodies.

Fragments of Antibodies and Antigen Binding Molecules

The antigen binding molecule of the invention can be a fragment of an antibody, specifically an antigen binding fragment of an antibody. The antigen binding fragments comprise one or more antigen binding regions. It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., Proc. Natl. Acad. Sci. USA 90: 6444-6448 (1993)). Typically, the fragment is a Fab, F(ab')2 or Fv fragment or an scFv molecule.

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, Current Opinion Biotechnol. 4:446-449 (1993)), e.g. prepared chemically or from hybrid hybridomas, or may be any of the bispecific antibody fragments mentioned below. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991).

Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Identity and Homology

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptides or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100). Generally, references to % identity herein refer to % identity along the entire length of the molecule, unless the context specifies or implies otherwise.

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Typically, the amino acid sequence of the CDRs of the antigen binding molecules provided in the invention have at least 70% identity, for example using the default parameters of the BLAST computer program (Atschul et al., J. Mol. Biol. 215, 403-410 (1990)) provided by HGMP (Human Genome Mapping Project), at the amino acid level, to the amino acid sequences of the CDRs described below. More typically, the CDR sequence has at least 75%, 80%, 85%, 90%, 91%, 92%, 93%, 94%, 95%, 96%, 97%, 98% or at least 99% identity, at the amino acid level, to the sequences shown below. Typically, each of the CDR sequences of the antigen binding molecule used in the invention has this level of identity to the amino acid sequences of the CDRs set out below. Alternatively, any 1, 2, 3, 4 or 5 of the CDRs of the antigen binding molecule used in the invention has this level of identity to the amino acid sequences of the CDRs set out below.

The amino acid sequence of the VH and VL regions of the antigen binding molecules provided in the invention have at least 70% identity, for example using the default parameters of the BLAST computer program (Atschul et al., J. Mol. Biol. 215, 403-410 (1990)) provided by HGMP (Human Genome Mapping Project), at the amino acid level, to the amino acid sequences of the VH and VL regions described below. More typically, the VH and VL regions have at least 75%, 80%, 85%, 90%, 91%, 92%, 93%, 94%, 95%, 96%, 97%, 98% or at least 99% identity, at the amino acid level, to the sequences shown below. Typically, each of the VH and VL regions of the antigen binding molecule used in the invention has this level of identity to the amino acid sequences of the VH and VL regions set out below. Alternatively, only one of the VH and VL regions of the antigen binding molecule used in the invention has this level of identity to the amino acid sequences of the VH and VL regions set out below.

Identity, as used herein, is used interchangeable with "homology" and "similarity". References to particular % identities apply equally to % homology and % similarity. Homology and similarity may be determined using appropriate algorithms, such as FASTA, BLAST and Gapped BLAST. Software for performing these analyses are publicly available.

Variants

The present invention also extends to variants of peptide sequences referred to below. As used herein the term "variant" relates to proteins that have a similar amino acid sequence and/or that retain the same function. For instance, the term "variant" encompasses proteins or polypeptides which include one or more amino acid additions, deletions, substitutions or the like. An example of a variant of the present invention is a protein comprising a peptide as defined below, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Using the three letter and one letter codes the amino acids may be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

Amino acid deletions or insertions can also be made relative to the amino acid sequence for the fusion protein referred to below. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

In some embodiments, the following amino acids can be exchange for each other for conservative amino acid substitutions:

| Class | Exchangeable amino acids |
| --- | --- |
| Aliphatic | Glycine, Alanine, Valine, Leucine, Isoleucine |
| Hydroxyl or Sulfur/Selenium-containing | Serine, Cysteine, Threonine, Methionine |
| Aromatic | Phenylalanine, Tyrosine, Tryptophan |
| Basic | Histidine, Lysine, Arginine |
| Acidic and their Amide | Aspartate, Glutamate, Asparagine, Glutamine |

Amino acid changes relative to the sequence given below can be made using any suitable technique e.g. by using site-directed mutagenesis or solid state synthesis.

It should be appreciated that amino acid substitutions or insertions within the scope of the present invention can be made using naturally occurring or non-naturally occurring amino acids.

Whether or not natural or synthetic amino acids are used, it is preferred that only L-amino acids are present.

In one embodiment of the invention there is provided antigen binding molecule, or antigen binding fragment thereof, of the invention comprising between 1 and 10, preferably between 1 and 5, amino acid substitutions in the antibody binding domain or antigen binding domains. For example, in one embodiment of the invention, there is provided an anti-LIGHT antibody or antigen binding fragment thereof, wherein the anti-LIGHT antibody antigen binding fragment thereof comprises the 6 CDR regions of an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, wherein the antigen binding molecule has between 1 and 10 amino acid substitutions across all of its CDR regions, preferably between 1 and 5 amino acid substitutions.

In a further embodiment of the invention, there is provided an anti-LIGHT antigen binding molecule or antigen binding fragment thereof, wherein the anti-LIGHT antibody antigen binding fragment thereof comprises the VH and VL sequences of an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, wherein the antigen binding molecule has between 1 and 10 amino acid substitutions across its VH and VL sequences, preferably between 1 and 5 amino acid substitutions. In a still further embodiment of the invention, there is provided an anti-LIGHT antibody, wherein the anti-LIGHT antibody is an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, wherein the antibody has between 1 and 10 amino acid substitutions, preferably between 1 and 5 amino acid substitutions.

In some embodiments, the one or more amino acid substitutions are in the CDR region or regions. In other embodiments, the one or more amino acid substitutions are in the framework regions, i.e. in the variable heavy and light chains but not in the CDR region or regions. In other embodiments, the one or more amino acid substitutions may be at any position in the variable heavy and/or variable light regions.

Other variants that are within the scope of the present invention include antigen binding molecules of the invention that are modified to have increased affinity for LIGHT, preferably membrane LIGHT. In one embodiment, the antigen binding molecule of the invention is an affinity-matured antibody. In one embodiment, the antigen binding molecules of the invention are humanised affinity-matured antibodies.

Any known methods can be used to increase the affinity of the antigen binding molecules of the invention to generate affinity-matured antibodies or humanised affinity-matured antibodies with an increased affinity for LIGHT, preferably membrane LIGHT.

There are therefore provided antigen binding molecules that are affinity matured mutants or variants of the antigen binding molecules of the invention. For example, in one embodiment there is provided an affinity-matured variant of an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16. Generally, the affinity matured mutants have a higher affinity for LIGHT (in particular human LIGHT) than the parent antibody (the antibody from which the mutant is derived). Also provided by the present invention are antigen binding molecules and antibodies obtainable or obtained by affinity maturation of an antigen binding molecule or antibody of the invention.

The antigen binding molecule of the invention is typically an antibody, more typically a monoclonal antibody. In a preferred embodiment, the monoclonal antibody of the present invention is a humanised antibody. In some embodiments, the antibody is a fully-human monoclonal antibody, in which the human constant region is employed.

Methods for the production of monoclonal antibodies are well known to the skilled person, for examples as described in Frenzel et al., "Expression of Recombinant Antibodies", *Front Immunol,* 2013, 4:217, the contents of which is hereby incorporated by reference.

The monoclonal antibodies of the present invention can be humanised by modifying the amino acid sequence of the antibody. Methods to reduce the immunogenicity of the antigen binding molecules of the invention include CDR grafting on to a suitable antibody framework scaffold or variable surface residues remodelling, e.g. by site-directed mutagenesis or other commonly used molecular biological techniques (Roguska et al *Protein Eng.* 9 895-904 (1996)).

Other methods applicable can include the identification of potential T-cell epitopes within the molecule, and the subsequent removal of these e.g. by site-directed mutagenesis (deimmunisation). Humanisation of the antigen binding molecule may be desired where the molecule is to be used as a therapeutic agent. Humanisation of the CDR regions or of the surrounding framework sequence can be carried out as desired.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced.

In one embodiment, the heavy chain variable region and/or the light chain variable region are at least 85% humanised, at least 90% humanized, at least 95% humanized, at least 96% humanized, at least 97% humanized, at least 98% humanized or at least 99% humanized. In some embodiments, the antibodies are conservatively humanised, for example to retain better antigen binding. In such conservatively humanised antibodies, fewer antibody substations may be made, compared to humanised antibodies.

For example, in one embodiment, the light variable region may be humanised but may retain Arg38, Gln40, Gln45 and Ser59 and the heavy variable region may be humanised but may retain Ile48, Asn61, Lys65 and Ala68. In another embodiment, the light variable region may be humanised but may retain Arg38 and Gln40 and the heavy variable region may be humanised but may retain Ile48 and Asn61.

The antigen binding molecules of the invention are, in some embodiment, deimmunised, for example using methods described in Jones et al., "Deimmunization of monoclonal antibodies", *Methods Mol Biol,* 2009, 525:405-23, the contents of which are hereby incorporated by reference. Deimmunisation removes T-cell epitopes from the sequences using a combined immunological and molecular biology technique.

In some embodiments of the invention, there is therefore provided a deimmunised anti-LIGHT antigen binding molecule or antigen binding fragment thereof, wherein the anti-LIGHT antigen binding molecule or antigen binding fragment thereof comprises deimmunised variants of the 6 CDR regions of an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16. In a further embodiment of the invention, there is provided a deimmunised anti-LIGHT antigen binding molecule or antigen binding fragment thereof, wherein the anti-LIGHT antigen binding molecule or antigen binding fragment thereof comprises deimmunised variants of the VH and/or VL sequences from an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

In a still further embodiment of the invention, there is provided a deimmunised anti-LIGHT antibody, wherein the anti-LIGHT antibody is a deimmunised variant of an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

The antigen binding molecules and antigen binding fragments thereof are based on 7 parental antibodies 3B04, 3D12, 2E08, 3C10, 3A07, 3E09 and 2B11. In addition to the parental antibodies, the invention is particularly concerned with humanised and deimmunised derivatives of the parental antibodies, including 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, however humanised and deimmunised derivatives of the remaining 5 parental antibodies are also provided. The invention is also based on antibody-fragments comprising one more antigen binding domains from the parental or humanised/deimmunised antibodies of the invention, as well as further variants such as antigen binding domains containing 1 or more conservative amino acid substitutions (such as between 1 and 10, or preferably 1 and 5 substitutions) and affinity matured variants of the antigen binding molecules of the invention. All of the antigen binding molecules of the invention specifically bind LIGHT.

The antigen binding molecules of the invention, in particular antibodies, may be of any suitable type, including IgA, IgD, IgE, IgG, IgM and IgY, although IgG may be preferred. IgG4 backbones may be most preferred. In relevant embodiments, the constant region of the antibodies of the invention may be modified for advantageous effect, for example to increase stability and reduce Fe gamma receptor interaction. Such modifications include S241P and L248E substitutions in the Fe region. Other suitable modifications are known to the skilled person.

As summary of the antibodies provided by the present invention is provided below. Antigen binding variants, derivatives and fragments thereof are also provided as part of the present invention:

TABLE 1

Summary of parental mouse antibodies and conservatively humanised, humanised and deimmunised versions of two parental antibodies

| Antibody | SEQ ID NOs | | | | | | | |
|---|---|---|---|---|---|---|---|---|
| | VL | VLCDR1 | VLCDR2 | VLCDR3 | VH | VHCDR1 | VHCDR2 | VHCDR3 |
| Parental 3B04 | 1 | 2 | 3 | 4 | 5 | 6 | 7 | 8 |
| 3B04_var1 | 9 | 10 | 11 | 12 | 13 | 14 | 15 | 16 |
| 3B04_var2 | 9 | 10 | 11 | 12 | 21 | 22 | 23 | 24 |
| 3B04_var3 | 9 | 10 | 11 | 12 | 29 | 30 | 31 | 32 |
| 3B04_var4 | 9 | 10 | 11 | 12 | 37 | 38 | 39 | 40 |
| 3B04_var5 | 17 | 18 | 19 | 20 | 13 | 14 | 15 | 16 |
| 3B04_var6 | 17 | 18 | 19 | 20 | 21 | 22 | 23 | 24 |
| 3B04_var7 | 17 | 18 | 19 | 20 | 29 | 30 | 31 | 32 |
| 3B04_var8 | 17 | 18 | 19 | 20 | 37 | 38 | 39 | 40 |
| 3B04_var9 | 25 | 26 | 27 | 28 | 13 | 14 | 15 | 16 |
| 3B04_var10 | 25 | 26 | 27 | 28 | 21 | 22 | 23 | 24 |
| 3B04_var11 | 25 | 26 | 27 | 28 | 29 | 30 | 31 | 32 |
| 3B04_var12 | 25 | 26 | 27 | 28 | 37 | 38 | 39 | 40 |
| 3B04_var13 | 33 | 34 | 35 | 36 | 13 | 14 | 15 | 16 |
| 3B04_var14 | 33 | 34 | 35 | 36 | 21 | 22 | 23 | 24 |
| 3B04_var15 | 33 | 34 | 35 | 36 | 29 | 30 | 31 | 32 |
| 3B04_var16 | 33 | 34 | 35 | 36 | 37 | 38 | 39 | 40 |
| Parental 3D12 | 41 | 42 | 43 | 44 | 45 | 46 | 47 | 48 |
| 3D12_var1 | 49 | 50 | 51 | 52 | 53 | 54 | 55 | 56 |
| 3D12_var2 | 49 | 50 | 51 | 52 | 61 | 62 | 63 | 64 |
| 3D12_var3 | 49 | 50 | 51 | 52 | 69 | 70 | 71 | 72 |
| 3D12_var4 | 49 | 50 | 51 | 52 | 77 | 78 | 79 | 80 |
| 3D12_var5 | 57 | 58 | 59 | 60 | 53 | 54 | 55 | 56 |
| 3D12_var6 | 57 | 58 | 59 | 60 | 61 | 62 | 63 | 64 |
| 3D12_var7 | 57 | 58 | 59 | 60 | 69 | 70 | 71 | 72 |
| 3D12_var8 | 57 | 58 | 59 | 60 | 77 | 78 | 79 | 80 |
| 3D12_var9 | 65 | 66 | 67 | 68 | 53 | 54 | 55 | 56 |
| 3D12_var10 | 65 | 66 | 67 | 68 | 61 | 62 | 63 | 64 |
| 3D12_var11 | 65 | 66 | 67 | 68 | 69 | 70 | 71 | 72 |
| 3D12_var12 | 65 | 66 | 67 | 68 | 77 | 78 | 79 | 80 |
| 3D12_var13 | 73 | 74 | 75 | 76 | 53 | 54 | 55 | 56 |
| 3D12_var14 | 73 | 74 | 75 | 76 | 61 | 62 | 63 | 64 |
| 3D12_var15 | 73 | 74 | 75 | 76 | 69 | 70 | 71 | 72 |
| 3D12_var16 | 73 | 74 | 75 | 76 | 77 | 78 | 79 | 80 |
| Parental 2E08 | 81 | 82 | 83 | 84 | 85 | 86 | 87 | 88 |

TABLE 1-continued

Summary of parental mouse antibodies and conservatively humanised, humanised and deimmunised versions of two parental antibodies

| | SEQ ID NOs | | | | | | | |
|---|---|---|---|---|---|---|---|---|
| Antibody | VL | VLCDR1 | VLCDR2 | VLCDR3 | VH | VHCDR1 | VHCDR2 | VHCDR3 |
| Parental 3C10 | 89 | 90 | 91 | 92 | 93 | 94 | 95 | 96 |
| Parental 3A07 | 97 | 98 | 99 | 100 | 101 | 102 | 103 | 104 |
| Parental 3E09 | 105 | 106 | 107 | 108 | 109 | 110 | 111 | 112 |
| Parental 2B11 | 113 | 114 | 115 | 116 | 117 | 118 | 119 | 120 |

TABLE 2

3B04 humanisation and de-immunisation.

| | | | SEQ ID NOs | | | |
|---|---|---|---|---|---|---|
| Chain | Chain Name | Chain | CDR1 | CDR2 | CDR3 | Description |
| L | 3B04_VL | 1 | 2 | 3 | 4 | Parental light chain variable region |
| L | 3B04_VL_1 | 9 | 10 | 11 | 12 | Conservatively humanised chain retaining L:Arg38, L:Gln40, L:Gln45, L:Ser59. |
| L | 3B04_VL_2 | 17 | 18 | 19 | 20 | Conservatively humanised chain retaining L:Arg38 and L:Gln40. |
| L | 3B04_VL_3 | 25 | 26 | 27 | 28 | Humanised chain. |
| L | 3B04_VL_4 | 33 | 34 | 35 | 36 | Deimmunised chain with substitutions L:G24R and L:D55E. |
| H | 3B04_VH | 5 | 6 | 7 | 8 | Parental heavy chain variable region |
| H | 3B04_VH_1 | 13 | 14 | 15 | 16 | Conservatively humanised chain retaining H:Ile48, H:Ser61, H:Lys65, H:Ala68. |
| H | 3B04_VH_2 | 21 | 22 | 23 | 24 | Conservatively humanised chain retaining H:Ile48 and H:Ser61. |
| H | 3B04_VH_3 | 29 | 30 | 31 | 32 | Humanised chain. |
| H | 3B04_VH_4 | 37 | 38 | 39 | 40 | Deimmunised chain with substitution H:F83L. |

TABLE 3

3D12 humanisation and de-immunisation.

| | | | SEQ ID NOs | | | |
|---|---|---|---|---|---|---|
| Chain | Chain Name | Chain | CDR1 | CDR2 | CDR3 | Description |
| L | 3D12_VL | 41 | 42 | 43 | 44 | Parental light chain variable region |
| L | 3D12_VL_1 | 49 | 50 | 51 | 52 | Conservatively humanised chain retaining L:Arg38, L:Gln40, L:Gln45, L:Ser59. |
| L | 3D12_VL_2 | 57 | 58 | 59 | 60 | Conservatively humanised chain retaining L:Arg38 and L:Gln40. |
| L | 3D12_VL_3 | 65 | 66 | 67 | 68 | Humanised chain. |
| L | 3D12_VL_4 | 73 | 74 | 75 | 76 | Deimmunised chain with substitutions L:G24R and L:D56E. |
| H | 3D12_VH | 45 | 46 | 47 | 48 | Parental heavy chain variable region |
| H | 3D12_VH_1 | 53 | 54 | 55 | 56 | Conservatively humanised chain retaining H:Ile48, H:Asn61, H:Lys65, H:Ala68. |
| H | 3D12_VH_2 | 61 | 62 | 63 | 64 | Conservatively humanised chain retaining H:Ile48 and H:Asn61. |
| H | 3D12_VH_3 | 69 | 70 | 71 | 72 | Humanised chain. |
| H | 3D12_VH_4 | 77 | 78 | 79 | 80 | Deimmunised chain with substitutions H:D26G and H:I34M. |

TABLE 4

Combination of humanised/deimmunised heavy and light chain variable regions produces 16 antibodies derived from the 3B04 parent antibody

| Variant Name | Light chain | SEQ ID No. | Heavy chain | SEQ ID No. |
|---|---|---|---|---|
| 3B04 | 3B04_VL | 1 | 3B04_VH | 5 |
| 3B04_var1 | 3B04_VL_1 | 9 | 3B04_VH_1 | 13 |
| 3B04_var2 | 3B04_VL_1 | 9 | 3B04_VH_2 | 21 |
| 3B04_var3 | 3B04_VL_1 | 9 | 3B04_VH_3 | 29 |
| 3B04_var4 | 3B04_VL_1 | 9 | 3B04_VH_4 | 37 |
| 3B04_var5 | 3B04_VL_2 | 17 | 3B04_VH_1 | 13 |
| 3B04_var6 | 3B04_VL_2 | 17 | 3B04_VH_2 | 21 |
| 3B04_var7 | 3B04_VL_2 | 17 | 3B04_VH_3 | 29 |
| 3B04_var8 | 3B04_VL_2 | 17 | 3B04_VH_4 | 37 |
| 3B04_var9 | 3B04_VL_3 | 25 | 3B04_VH_1 | 13 |
| 3B04_var10 | 3B04_VL_3 | 25 | 3B04_VH_2 | 21 |
| 3B04_var11 | 3B04_VL_3 | 25 | 3B04_VH_3 | 29 |
| 3B04_var12 | 3B04_VL_3 | 25 | 3B04_VH_4 | 37 |
| 3B04_var13 | 3B04_VL_4 | 33 | 3B04_VH_1 | 13 |
| 3B04_var14 | 3B04_VL_4 | 33 | 3B04_VH_2 | 21 |
| 3B04_var15 | 3B04_VL_4 | 33 | 3B04_VH_3 | 29 |
| 3B04_var16 | 3B04_VL_4 | 33 | 3B04_VH_4 | 37 |

TABLE 5

Combination of humanised/deimmunised heavy and light chain variable regions produces 16 antibodies derived from 3D12 parent antibody

| Variant Name | Light chain | SEQ ID No. | Heavy chain | SEQ ID No. |
|---|---|---|---|---|
| 3D12 | 3D12_VL | 41 | 3D12_VH | 45 |
| 3D12_var1 | 3D12_VL_1 | 49 | 3D12_VH_1 | 53 |
| 3D12_var2 | 3D12_VL_1 | 49 | 3D12_VH_2 | 61 |
| 3D12_var3 | 3D12_VL_1 | 49 | 3D12_VH_3 | 69 |
| 3D12_var4 | 3D12_VL_1 | 49 | 3D12_VH_4 | 77 |
| 3D12_var5 | 3D12_VL_2 | 57 | 3D12_VH_1 | 53 |
| 3D12_var6 | 3D12_VL_2 | 57 | 3D12_VH_2 | 61 |
| 3D12_var7 | 3D12_VL_2 | 57 | 3D12_VH_3 | 69 |
| 3D12_var8 | 3D12_VL_2 | 57 | 3D12_VH_4 | 77 |
| 3D12_var9 | 3D12_VL_3 | 65 | 3D12_VH_1 | 53 |
| 3D12_var10 | 3D12_VL_3 | 65 | 3D12_VH_2 | 61 |
| 3D12_var11 | 3D12_VL_3 | 65 | 3D12_VH_3 | 69 |
| 3D12_var12 | 3D12_VL_3 | 65 | 3D12_VH_4 | 77 |
| 3D12_var13 | 3D12_VL_4 | 73 | 3D12_VH_1 | 53 |
| 3D12_var14 | 3D12_VL_4 | 73 | 3D12_VH_2 | 61 |
| 3D12_var15 | 3D12_VL_4 | 73 | 3D12_VH_3 | 69 |
| 3D12_var16 | 3D12_VL_4 | 73 | 3D12_VH_4 | 77 |

The various embodiments of the invention are now discussed in more detail.

Antigen Binding Molecules Comprising a VHCDR3 and/or a VLCDR3 Region

3B04

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 8) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLTTPWT (SEQ ID NO: 4). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 8) and/or a light chain variable region comprising an amino acid sequence having at least 90% identity to the amino acid sequence QNVLTTPWT (SEQ ID NO: 4).

In one embodiment, an antigen binding molecule, for example an antibody, fragment or variant thereof is provided comprising a heavy chain variable region comprising the amino acid sequence ETDYFFDY (SEQ ID NO: 8) and/or a light chain variable region comprising the amino acid sequence QNVLTTPWT (SEQ ID NO: 4). In a particular embodiment, the antigen binding molecule is an antibody or fragment or variant thereof, wherein the VHCDR3 region of said antibody or fragment or variant thereof is ETDYFFDY (SEQ ID NO: 8) and/or the VLCDR3 region of said antibody or fragment or variant thereof is QNVLTTPWT (SEQ ID NO: 4).

3D12

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 48) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLSTPWT (SEQ ID NO: 44). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 48) and/or a light chain variable region comprising an amino acid sequence having at least 90% identity to the amino acid sequence QNVLSTPWT (SEQ ID NO: 44).

In one embodiment, an antigen binding molecule, for example an antibody, fragment or variant thereof is provided comprising a heavy chain variable region comprising the amino acid sequence ETDYFFDY (SEQ ID NO: 48) and/or a light chain variable region comprising the amino acid sequence QNVLSTPWT (SEQ ID NO: 44). In a particular embodiment, the antigen binding molecule is an antibody or fragment or variant thereof, wherein the VHCDR3 region of said antibody or fragment or variant thereof is ETDYFFDY (SEQ ID NO: 48) and/or the VLCDR3 region of said antibody or fragment or variant thereof is QNVLSTPWT (SEQ ID NO: 44).

2E08

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence SRGEYGNYDAMDY (SEQ ID NO: 88) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQSNEDPLT (SEQ ID NO: 84). In one embodiment, an antigen binding molecule, for example an antibody, fragment or variant thereof is provided comprising a heavy chain variable region comprising an amino acid sequence having at least 90% identity to the amino acid sequence SRGEYGNYDAMDY (SEQ ID NO: 88) and/or a light chain variable region comprising an amino acid sequence having at least 90% identity to the amino acid sequence QQSNEDPLT (SEQ ID NO: 15).

In one embodiment, an antigen binding molecule, for example an antibody, fragment or variant thereof is provided comprising a heavy chain variable region comprising the amino acid sequence SRGEYGNYDAMDY (SEQ ID NO: 88) and/or a light chain variable region comprising the amino acid sequence QQSNEDPLT (SEQ ID NO: 84). In a particular embodiment, the antigen binding molecule is an antibody or fragment or variant thereof, wherein the VHCDR3 region of said antibody or fragment or variant thereof is SRGEYGNYDAMDY (SEQ ID NO: 88) and/or the VLCDR3 region of said antibody or fragment or variant thereof is QQSNEDPLT (SEQ ID NO: 84).

3C10

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 96) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQWSSYPLT (SEQ ID NO: 92). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 96) and/or a light chain variable region comprising an amino acid sequence having at least 90% identity to the amino acid sequence QQWSSYPLT (SEQ ID NO: 92).

In one embodiment, an antigen binding molecule, for example an antibody, fragment or variant thereof is provided comprising a heavy chain variable region comprising the amino acid sequence ETDYFFDY (SEQ ID NO: 96) and/or a light chain variable region comprising the amino acid sequence QQWSSYPLT (SEQ ID NO: 92). In a particular embodiment, the antigen binding molecule is an antibody or fragment or variant thereof, wherein the VHCDR3 region of said antibody or fragment or variant thereof is ETDYFFDY (SEQ ID NO: 96) and/or the VLCDR3 region of said antibody or fragment or variant thereof is QQWSSYPLT (SEQ ID NO: 92).

3A07

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 104) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQWSSYPLT (SEQ ID NO: 100). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 104) and/or a light chain variable region comprising an amino acid sequence having at least 90% identity to the amino acid sequence QQWSSYPLT (SEQ ID NO: 100).

In one embodiment, an antigen binding molecule, for example an antibody, fragment or variant thereof is provided comprising a heavy chain variable region comprising the amino acid sequence ETDYFFDY (SEQ ID NO: 104) and/or a light chain variable region comprising the amino acid sequence QQWSSYPLT (SEQ ID NO: 100). In a particular embodiment, the antigen binding molecule is an antibody or fragment or variant thereof, wherein the VHCDR3 region of said antibody or fragment or variant thereof is ETDYFFDY (SEQ ID NO: 104) and/or the VLCDR3 region of said antibody or fragment or variant thereof is QQWSSYPLT (SEQ ID NO: 100).

3E09

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence GTGDGFAY (SEQ ID NO: 112) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQNNEDPYT (SEQ ID NO: 108). In one embodiment, an antigen binding molecule, for example an antibody, fragment or variant thereof is provided comprising a heavy chain variable region comprising an amino acid sequence having at least 90% identity to the amino acid sequence GTGDGFAY (SEQ ID NO: 112) and/or a light chain variable region comprising an amino acid sequence having at least 90% identity to the amino acid sequence QQNNEDPYT (SEQ ID NO: 108).

In one embodiment, an antigen binding molecule, for example an antibody, fragment or variant thereof is provided comprising a heavy chain variable region comprising the amino acid sequence GTGDGFAY (SEQ ID NO: 112) and/or a light chain variable region comprising the amino acid sequence QQNNEDPYT (SEQ ID NO: 108). In a particular embodiment, the antigen binding molecule is an antibody or fragment or variant thereof, wherein the VHCDR3 region of said antibody or fragment or variant thereof is GTGDGFAY (SEQ ID NO: 112) and/or the VLCDR3 region of said antibody or fragment or variant thereof is QQNNEDPYT (SEQ ID NO: 108).

2B11

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence SRGEYGNYDAMDY (SEQ ID NO: 120) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQSNEDPYT (SEQ ID NO: 116).

In one embodiment, an antigen binding molecule, for example an antibody, fragment or variant thereof is provided comprising a heavy chain variable region comprising an amino acid sequence having at least 90% identity to the amino acid sequence SRGEYGNYDAMDY sequence (SEQ ID NO: 120) and/or a light chain variable region comprising an amino acid sequence having at least 90% identity to the amino acid sequence QQSNEDPYT (SEQ ID NO: 116).

In one embodiment, an antigen binding molecule, for example an antibody, fragment or variant thereof is provided comprising a heavy chain variable region comprising the amino acid sequence SRGEYGNYDAMDY sequence (SEQ ID NO: 120) and/or a light chain variable region comprising the amino acid sequence QQSNEDPYT (SEQ ID NO: 116). In a particular embodiment, the antigen binding molecule is an antibody or fragment or variant thereof, wherein the VHCDR3 region of said antibody or fragment or variant thereof is SRGEYGNYDAMDY sequence (SEQ ID NO:

120) and/or the VLCDR3 region of said antibody or fragment or variant thereof is QQSNEDPYT (SEQ ID NO: 116).

3B04 Variants

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 16) and/or a light chain variable region comprising the amino acid sequence having at least 70%, 75%, 80%, 85%, 90%, 91%, 92%, 93%, 94%, 95%, 96%, 97%, 98% or 99% identity to the amino acid sequence QNVLTTPWT (SEQ ID NO: 12). In one embodiment, the heavy chain variable region comprises an amino acid sequence having at least 90% identity to the amino acid sequence ETDYFFDY (SEQ ID NO: 16) and/or the light chain variable region comprises an amino acid sequence having at least 90% identity to the amino acid sequence QNVLTTPWT (SEQ ID NO: 12).

In one embodiment, an antibody, fragment or variant thereof is provided comprising a heavy chain variable region comprising the amino acid sequence ETDYFFDY (SEQ ID NO: 16) and/or a light chain variable region comprising the amino acid sequence QNVLTTPWT (SEQ ID NO: 12). In a particular embodiment, an antibody, fragment or variant thereof is provided, wherein the VHCDR3 region of said antibody or fragment or variant thereof is ETDYFFDY (SEQ ID NO: 16) and/or the VLCDR3 region of said antibody or fragment or variant thereof is QNVLTTPWT (SEQ ID NO: 12).

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 24) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLTTPWT (SEQ ID NO: 20). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 24) and/or a light chain variable region comprising an amino acid sequence having at least 90% identity to the amino acid sequence QNVLTTPWT (SEQ ID NO: 20).

In one embodiment, an antibody, fragment or variant thereof is provided comprising a heavy chain variable region comprising the amino acid sequence ETDYFFDY (SEQ ID NO: 24) and/or a light chain variable region comprising the amino acid sequence QNVLTTPWT (SEQ ID NO: 20). In a particular embodiment, an antibody, fragment or variant thereof is provided, wherein the VHCDR3 region of said antibody or fragment or variant thereof is ETDYFFDY (SEQ ID NO: 24) and/or the VLCDR3 region of said antibody or fragment or variant thereof is QNVLTTPWT (SEQ ID NO: 20).

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 32) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLTTPWT (SEQ ID NO: 28). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 32) and/or a light chain variable region comprising an amino acid sequence having at least 90% identity to the amino acid sequence QNVLTTPWT (SEQ ID NO: 28).

In one embodiment, an antibody, fragment or variant thereof is provided comprising a heavy chain variable region comprising the amino acid sequence ETDYFFDY (SEQ ID NO: 32) and/or comprising a light chain variable region comprising the amino acid sequence QNVLTTPWT (SEQ ID NO: 28). In a particular embodiment, an antibody, fragment or variant thereof is provided, wherein the VHCDR3 region of said antibody or fragment or variant thereof is ETDYFFDY (SEQ ID NO: 32) and/or the VLCDR3 region of said antibody or fragment or variant thereof is QNVLTTPWT (SEQ ID NO: 28).

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 40) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLTTPWT (SEQ ID NO: 36). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 40) and/or a light chain variable region comprising an amino acid sequence having at least 90% identity to the amino acid sequence QNVLTTPWT (SEQ ID NO: 36).

In one embodiment, an antibody, fragment or variant thereof is provided comprising a heavy chain variable region comprising the amino acid sequence ETDYFFDY (SEQ ID NO: 40) and/or a light chain variable region comprising the amino acid sequence QNVLTTPWT (SEQ ID NO: 36). In a particular embodiment, an antibody, fragment or variant thereof is provided, wherein the VHCDR3 region of said antibody or fragment or variant thereof is ETDYFFDY (SEQ ID NO: 40) and/or the VLCDR3 region of said antibody or fragment or variant thereof is QNVLTTPWT (SEQ ID NO: 36).

3D12 Variants

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 56) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLSTPWT (SEQ ID NO: 52). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 56) and/or a light chain variable region comprising an amino acid sequence having at least 90% identity to the amino acid sequence QNVLSTPWT (SEQ ID NO: 52).

In one embodiment, an antibody, fragment or variant thereof is provided comprising a heavy chain variable region comprising an amino acid sequence ETDYFFDY (SEQ ID NO: 56) and/or a light chain variable region comprising the amino acid sequence QNVLSTPWT (SEQ ID NO: 52). In a particular embodiment, an antibody, fragment or variant thereof is provided, wherein the VHCDR3 region of said antibody or fragment or variant thereof is ETDYFFDY (SEQ ID NO: 56) and/or the VLCDR3 region of said antibody or fragment or variant thereof is QNVLSTPWT (SEQ ID NO: 52).

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 64) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLSTPWT (SEQ ID NO: 60). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 64) and/or a light chain variable region comprising an amino acid sequence having at least 90% identity to the amino acid sequence QNVLSTPWT (SEQ ID NO: 60).

In one embodiment, an antibody, fragment or variant thereof is provided comprising a heavy chain variable region comprising the amino acid sequence ETDYFFDY (SEQ ID NO: 64) and/or a light chain variable region comprising the amino acid sequence QNVLSTPWT (SEQ ID NO: 60). In a particular embodiment, an antibody, fragment or variant thereof is provided, wherein the VHCDR3 region of said antibody or fragment or variant thereof is ETDYFFDY (SEQ ID NO: 64) and/or the VLCDR3 region of said antibody or fragment or variant thereof is QNVLSTPWT (SEQ ID NO: 60).

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 72) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLSTPWT (SEQ ID NO: 68). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 72) and/or a light chain variable region comprising an amino acid sequence having at least 90% identity to the amino acid sequence QNVLSTPWT (SEQ ID NO: 68).

In one embodiment, an antibody, fragment or variant thereof is provided comprising a heavy chain variable region comprising the amino acid sequence ETDYFFDY (SEQ ID NO: 72) and/or a light chain variable region comprising the amino acid sequence QNVLSTPWT (SEQ ID NO: 68). In a particular embodiment, an antibody, fragment or variant thereof is provided, wherein the VHCDR3 region of said antibody or fragment or variant thereof is ETDYFFDY (SEQ ID NO: 72) and/or the VLCDR3 region of said antibody or fragment or variant thereof is QNVLSTPWT (SEQ ID NO: 68).

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence ETDYFFDY (SEQ ID NO: 80) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QNVLSTPWT (SEQ ID NO: 76). In one embodiment, an antigen binding molecule, for example an antibody, fragment or variant thereof is provided comprising a heavy chain variable region comprising an amino acid sequence having at least 90% identity to the amino acid sequence ETDYFFDY (SEQ ID NO: 180) and/or comprising a light chain variable region comprising an amino acid sequence having at least 90% identity to the amino acid sequence QNVLSTPWT (SEQ ID NO: 76).

In one embodiment, an antibody, fragment or variant thereof is provided comprising a heavy chain variable region comprising the amino acid sequence ETDYFFDY (SEQ ID NO: 80) and/or a light chain variable region comprising the amino acid sequence QNVLSTPWT (SEQ ID NO: 76). In a particular embodiment, an antibody, fragment or variant thereof is provided, wherein the VHCDR3 region of said antibody or fragment or variant thereof is ETDYFFDY (SEQ ID NO: 80) and/or the VLCDR3 region of said antibody or fragment or variant thereof is QNVLSTPWT (SEQ ID NO: 76).

Heavy and/or Light Chain CDRs

3B04

In one embodiment, an antibody, fragment or variant thereof, is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFKG (SEQ ID NO: 7), a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 8); and/or
- a light chain variable region comprising a VLCDR1 comprising the at least 70%, 75%, 80%, 85%, 90%, 91%, 92%, 93%, 94%, 95%, 96%, 97%, 98% or 99% identity to amino acid sequence GASENIYGALN (SEQ ID NO: 2), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 4).

In one embodiment, an antibody, fragment or variant thereof, is provided comprising:
- a heavy chain variable region comprising a VHCDR1 comprising at least 90% identity to the amino acid sequence DYEMH (SEQ ID NO: 6), a VHCDR2 comprising at least 90% identity to the amino acid sequence EIDPETGDTAYSQKFKG (SEQ ID NO: 7), a VHCDR3 comprising at least 90% identity to the amino acid sequence ETDYFFDY (SEQ ID NO: 8); and/or
a light chain variable region comprising a VLCDR1 comprising the at least 90% identity to amino acid sequence GASENIYGALN (SEQ ID NO: 2), a VLCDR2 comprising at least 90% identity to the amino acid sequence GATNLAD (SEQ ID NO: 3) and a VLCDR3 comprising at least 90% identity to the amino acid sequence QNVLTTPWT (SEQ ID NO: 4).

In one embodiment, an antibody, fragment or variant thereof, is provided comprising:
a heavy chain variable region comprising a VHCDR1 comprising the amino acid sequence DYEMH (SEQ ID NO: 6), a VHCDR2 comprising the amino acid sequence EIDPETGDTAYSQKFKG (SEQ ID NO: 7), a VHCDR3 comprising the amino acid sequence ETDYFFDY (SEQ ID NO: 8); and/or
a light chain variable region comprising a VLCDR1 comprising the amino acid sequence GASENIYGALN (SEQ ID NO: 2), a VLCDR2 comprising the amino acid sequence GATNLAD (SEQ ID NO: 3) and a VLCDR3 comprising the amino acid sequence QNVLTTPWT (SEQ ID NO: 4).

3D12

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 46), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFKG (SEQ ID NO: 47), a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 48); and/or
a light chain variable region comprising at least 70%, 75%, 80%, 85%, 90%, 91%, 92%, 93%, 94%, 95%, 96%, 97%, 98% or 99% identity to a VLCDR1 comprising the amino acid sequence GASENIYGALN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 44).

In one embodiment, an antibody, fragment or variant thereof, is provided comprising:
a heavy chain variable region comprising a VHCDR1 comprising at least 90% identity to the amino acid sequence DSEIH (SEQ ID NO: 46), a VHCDR2 comprising at least 90% identity to the amino acid sequence EIDPETGGTAYNQKFKG (SEQ ID NO: 47), a VHCDR3 comprising at least 90% identity to the amino acid sequence ETDYFFDY (SEQ ID NO: 48); and/or
a light chain variable region comprising at least 90% identity to a VLCDR1 comprising the amino acid sequence GASENIYGALN (SEQ ID NO: 42), a VLCDR2 comprising at least 90% identity to the amino acid sequence GATNLAD (SEQ ID NO: 43) and a VLCDR3 comprising at least 90% identity to the amino acid sequence QNVLSTPWT (SEQ ID NO: 44).

In one embodiment, an antibody, fragment or variant thereof, is provided comprising:
a heavy chain variable region comprising a VHCDR1 comprising the amino acid sequence DSEIH (SEQ ID NO: 46), a VHCDR2 comprising the amino acid sequence EIDPETGGTAYNQKFKG (SEQ ID NO: 47), a VHCDR3 comprising the amino acid sequence ETDYFFDY (SEQ ID NO: 48); and/or
a light chain variable region comprising a VLCDR1 comprising the amino acid sequence GASENIYGALN (SEQ ID NO: 42), a VLCDR2 comprising the amino acid sequence GATNLAD (SEQ ID NO: 43) and a VLCDR3 comprising the amino acid sequence QNVLSTPWT (SEQ ID NO: 44).

2E08

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYAIH (SEQ ID NO: 86), a VHCDR2 comprising at least 70%, 75%, 80%, 85%, 90%, 91%, 92%, 93%, 94%, 95%, 96%, 97%, 98% or 99% identity to the amino acid sequence VISTYYGDASYNQKFKG (SEQ ID NO: 87), a VHCDR3 comprising at least 70%, 75%, 80%, 85%, 90%, 91%, 92%, 93%, 94%, 95%, 96%, 97%, 98% or 99% identity to the amino acid SRGEYGNYDAMDY sequence (SEQ ID NO: 88); and/or
a light chain variable region comprising a VLCDR1 comprising at least 70%, 75%, 80%, 85%, 90%, 91%, 92%, 93%, 94%, 95%, 96%, 97%, 98% or 99% identity to the amino acid sequence KASQSVDYDGDSYMN (SEQ ID NO: 82), a VLCDR2 comprising at least 70%, 75%, 80%, 85%, 90%, 91%, 92%, 93%, 94%, 95%, 96%, 97%, 98% or 99% identity to the amino acid sequence AASNLES (SEQ ID NO: 83) and a VLCDR3 comprising at least 70%, 75%, 80%, 85%, 90%, 91%, 92%, 93%, 94%, 95%, 96%, 97%, 98% or 99% identity to the amino acid sequence QQSNEDPLT (SEQ ID NO: 84).

In one embodiment, an antibody, fragment or variant thereof, is provided comprising:
a heavy chain variable region comprising a VHCDR1 comprising at least 90% identity to the amino acid sequence DYAIH (SEQ ID NO: 86), a VHCDR2 comprising at least 90% identity to the amino acid sequence VISTYYGDASYNQKFKG (SEQ ID NO: 87), a VHCDR3 comprising at least 90% identity to the amino acid SRGEYGNYDAMDY sequence (SEQ ID NO: 88); and/or
a light chain variable region comprising at least 90% identity to the amino acid sequence KASQSVDYDGDSYMN (SEQ ID NO: 82), a VLCDR2 comprising at least 90% identity to the amino acid sequence AASNLES (SEQ ID NO: 83) and a VLCDR3 comprising at least 790% identity to the amino acid sequence QQSNEDPLT (SEQ ID NO: 84).

In one embodiment, an antibody, fragment or variant thereof, is provided comprising:
a heavy chain variable region comprising a VHCDR1 comprising the amino acid sequence DYAIH (SEQ ID NO: 86), a VHCDR2 comprising the amino acid sequence VISTYYGDASYNQKFKG (SEQ ID NO:

87), a VHCDR3 comprising the amino acid SRGEYG-NYDAMDY sequence (SEQ ID NO: 88); and/or
a light chain variable region comprising a VLCDR1 comprising the amino acid sequence KASQSVDYDGDSYMN (SEQ ID NO: 82), a VLCDR2 comprising the amino acid sequence AASNLES (SEQ ID NO: 83) and a VLCDR3 comprising the amino acid sequence QQSNEDPLT (SEQ ID NO: 84).

3C10

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 94), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFKG (SEQ ID NO: 95), a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 96); and/or
a light chain variable region comprising a VLCDR1 comprising at least 70%, 75%, 80%, 85%, 90%, 91%, 92%, 93%, 94%, 95%, 96%, 97%, 98% or 99% identity to the amino acid sequence SASSSVSYMY (SEQ ID NO: 90), a VLCDR2 comprising at least 70%, 75%, 80%, 85%, 90%, 91%, 92%, 93%, 94%, 95%, 96%, 97%, 98% or 99% identity to the amino acid sequence DTSNLAS (SEQ ID NO: 91) and a VLCDR3 comprising at least 70%, 75%, 80%, 85%, 90%, 91%, 92%, 93%, 94%, 95%, 96%, 97%, 98% or 99% identity to the amino acid sequence QQWSSYPLT (SEQ ID NO: 92).

In one embodiment, an antibody, fragment or variant thereof, is provided comprising:
a heavy chain variable region comprising a VHCDR1 comprising at least 90% identity to the amino acid sequence DSEIH (SEQ ID NO: 94), a VHCDR2 comprising at least 90% identity to the amino acid sequence EIDPETGGTAYNQKFKG (SEQ ID NO: 95), a VHCDR3 comprising at least 90% identity to the amino acid sequence ETDYFFDY (SEQ ID NO: 96); and/or
a light chain variable region comprising a VLCDR1 comprising at least 90% identity to the amino acid sequence SASSSVSYMY (SEQ ID NO: 90), a VLCDR2 comprising at least 90% identity to the amino acid sequence DTSNLAS (SEQ ID NO: 91) and a VLCDR3 comprising at least 90% identity to the amino acid sequence QQWSSYPLT (SEQ ID NO: 92).

In one embodiment, an antibody, fragment or variant thereof, is provided comprising:
a heavy chain variable region comprising a VHCDR1 comprising the amino acid sequence DSEIH (SEQ ID NO: 94), a VHCDR2 comprising the amino acid sequence EIDPETGGTAYNQKFKG (SEQ ID NO: 95), a VHCDR3 comprising the amino acid sequence ETDYFFDY (SEQ ID NO: 96); and/or
a light chain variable region comprising a VLCDR1 comprising the amino acid sequence SASSSVSYMY (SEQ ID NO: 90), a VLCDR2 comprising the amino acid sequence DTSNLAS (SEQ ID NO: 91) and a VLCDR3 comprising the amino acid sequence QQWSSYPLT (SEQ ID NO: 92).

3A07

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 102), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFKG (SEQ ID NO: 103), a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 104); and/or
a light chain variable region comprising a VLCDR1 comprising at least 70%, 75%, 80%, 85%, 90%, 91%, 92%, 93%, 94%, 95%, 96%, 97%, 98% or 99% identity to the amino acid sequence SASSSVSYMY (SEQ ID NO: 98), a VLCDR2 comprising at least 70%, 75%, 80%, 85%, 90%, 91%, 92%, 93%, 94%, 95%, 96%, 97%, 98% or 99% identity to the amino acid sequence DTSNLAS (SEQ ID NO: 99) and a VLCDR3 comprising at least 70%, 75%, 80%, 85%, 90%, 91%, 92%, 93%, 94%, 95%, 96%, 97%, 98% or 99% identity to the amino acid sequence QQWSSYPLT (SEQ ID NO: 100).

In one embodiment, an antibody, fragment or variant thereof, is provided comprising:
a heavy chain variable region comprising a VHCDR1 comprising at least 90% identity to the amino acid sequence DSEIH (SEQ ID NO: 102), a VHCDR2 comprising at least 90% identity to the amino acid sequence EIDPETGGTAYNQKFKG (SEQ ID NO: 103), a VHCDR3 comprising at least 90% identity to the amino acid sequence ETDYFFDY (SEQ ID NO: 104); and/or
a light chain variable region comprising a VLCDR1 comprising at least 90% identity to the amino acid sequence SASSSVSYMY (SEQ ID NO: 98), a VLCDR2 comprising at least 90% identity to the amino acid sequence DTSNLAS (SEQ ID NO: 99) and a VLCDR3 comprising at least 90% identity to the amino acid sequence QQWSSYPLT (SEQ ID NO: 100).

In one embodiment, an antibody, fragment or variant thereof, is provided comprising:
a heavy chain variable region comprising a VHCDR1 comprising the amino acid sequence DSEIH (SEQ ID NO: 102), a VHCDR2 comprising the amino acid sequence EIDPETGGTAYNQKFKG (SEQ ID NO: 103), a VHCDR3 comprising the amino acid sequence ETDYFFDY (SEQ ID NO: 104); and/or
a light chain variable region comprising a VLCDR1 comprising the amino acid sequence SASSSVSYMY (SEQ ID NO: 98), a VLCDR2 comprising the amino acid sequence DTSNLAS (SEQ ID NO: 99) and a VLCDR3 comprising the amino acid sequence QQWSSYPLT (SEQ ID NO: 100).

3E09

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYYMY (SEQ ID NO: 110), a VHCDR2 comprising at least 70%, 75%, 80%, 85%, 90%, 91%, 92%, 93%, 94%, 95%, 96%, 97%, 98% or 99% identity to the amino acid sequence AIGDGGIYTYYADTVKG (SEQ ID NO: 111), a VHCDR3 comprising at least 70%, 75%, 80%, 85%, 90%, 91%, 92%, 93%, 94%, 95%, 96%, 97%, 98% or 99% identity to the amino acid sequence GTGDGFAY (SEQ ID NO: 112); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASESVDSYGNSFMH (SEQ ID NO: 106), a VLCDR2 comprising at least 70%, 75%, 80%, 85%, 90%, 91%, 92%, 93%, 94%, 95%, 96%, 97%, 98% or 99% identity to the amino acid sequence LASNLES (SEQ ID NO: 107) and a VLCDR3 comprising at least 70%, 75%, 80%, 85%, 90%, 91%, 92%, 93%, 94%, 95%, 96%, 97%, 98% or 99% identity to the amino acid sequence QQNNEDPYT (SEQ ID NO: 108).

In one embodiment, an antibody, fragment or variant thereof, is provided comprising:
a heavy chain variable region comprising a VHCDR1 comprising at least 90% identity to the amino acid sequence DYYMY (SEQ ID NO: 110), a VHCDR2 comprising at least 90% identity to the amino acid sequence AIGDGGIYTYYADTVKG (SEQ ID NO: 111), a VHCDR3 comprising at least 90% identity to the amino acid sequence GTGDGFAY (SEQ ID NO: 112); and/or a light chain variable region comprising a VLCDR1 comprising at least 90% identity to the amino acid sequence RASESVDSYGNSFMH (SEQ ID NO: 106), a VLCDR2 comprising at least 90% identity to the amino acid sequence LASNLES (SEQ ID NO: 107) and a VLCDR3 comprising at least 90% identity to the amino acid sequence QQNNEDPYT (SEQ ID NO: 108).

In one embodiment, an antibody, fragment or variant thereof, is provided comprising:
a heavy chain variable region comprising a VHCDR1 comprising the amino acid sequence DYYMY (SEQ ID NO: 110), a VHCDR2 comprising the amino acid sequence AIGDGGIYTYYADTVKG (SEQ ID NO: 111), a VHCDR3 comprising the amino acid sequence GTGDGFAY (SEQ ID NO: 112); and/or a light chain variable region comprising a VLCDR1 comprising the amino acid sequence RASESVDSYG-NSFMH (SEQ ID NO: 106), a VLCDR2 comprising the amino acid sequence LASNLES (SEQ ID NO: 107) and a VLCDR3 comprising the amino acid sequence QQNNEDPYT (SEQ ID NO: 108).

2B11

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYAIH (SEQ ID NO: 118), a VHCDR2 comprising at least 70%, 75%, 80%, 85%, 90%, 91%, 92%, 93%, 94%, 95%, 96%, 97%, 98% or 99% identity to the amino acid sequence VISTYYG-DASYNQKFKG (SEQ ID NO: 119), a VHCDR3 comprising at least 70%, 75%, 80%, 85%, 90%, 91%, 92%, 93%, 94%, 95%, 96%, 97%, 98% or 99% identity to the amino acid sequence SRGEYGNYDAMDY (SEQ ID NO: 120); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASESVDSYGNSFMH (SEQ ID NO: 114), a VLCDR2 comprising at least 70%, 75%, 80%, 85%, 90%, 91%, 92%, 93%, 94%, 95%, 96%, 97%, 98% or 99% identity to the amino acid sequence RASNLES (SEQ ID NO: 115) and a VLCDR3 comprising at least 70%, 75%, 80%, 85%, 90%, 91%, 92%, 93%, 94%, 95%, 96%, 97%, 98% or 99% identity to the amino acid sequence QQSNEDPYT (SEQ ID NO: 116).

In one embodiment, an antibody, fragment or variant thereof, is provided comprising:
a heavy chain variable region comprising a VHCDR1 comprising at least 90% identity to the amino acid sequence DYAIH (SEQ ID NO: 118), a VHCDR2 comprising at least 90% identity to the amino acid sequence VISTYYGDASYNQKFKG (SEQ ID NO: 119), a VHCDR3 comprising at least 90% identity to the amino acid sequence SRGEYGNYDAMDY (SEQ ID NO: 120); and/or a light chain variable region comprising a VLCDR1 comprising at least 90% identity to the amino acid sequence RASESVDSYGNSFMH (SEQ ID NO: 114), a VLCDR2 comprising at least 90% identity to the amino acid sequence RASNLES (SEQ ID NO: 115) and a VLCDR3 comprising at least 90% identity to the amino acid sequence QQSNEDPYT (SEQ ID NO: 116).

In one embodiment, an antibody, fragment or variant thereof, is provided comprising:
a heavy chain variable region comprising a VHCDR1 comprising the amino acid sequence DYAIH (SEQ ID NO: 118), a VHCDR2 comprising the amino acid sequence VISTYYGDASYNQKFKG (SEQ ID NO: 119), a VHCDR3 comprising the amino acid sequence SRGEYGNYDAMDY (SEQ ID NO: 120); and/or a light chain variable region comprising a VLCDR1 comprising the amino acid sequence RASESVDSYG-NSFMH (SEQ ID NO: 114), a VLCDR2 comprising the amino acid sequence RASNLES (SEQ ID NO: 115) and a VLCDR3 comprising the amino acid sequence QQSNEDPYT (SEQ ID NO: 116).

3b04_var 1

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 14), a VHCDR2 comprising at least 70%, 75%, 80%, 85%, 90%, 91%, 92%, 93%, 94%, 95%, 96%, 97%, 98% or 99% identity to the amino acid sequence EIDPETGD-TAYSQKFKG (SEQ ID NO: 15) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 16); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 10), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 11) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 12).

In one embodiment, an antibody, fragment or variant thereof, is provided comprising:
  a heavy chain variable region comprising a VHCDR1 comprising at least 90% identity to the amino acid sequence DYEMH (SEQ ID NO: 14), a VHCDR2 comprising at least 90% identity to the amino acid sequence EIDPETGDTAYSQKFKG (SEQ ID NO: 15) and a VHCDR3 comprising at least 90% identity to the amino acid sequence ETDYFFDY (SEQ ID NO: 16); and/or
  a light chain variable region comprising a VLCDR1 comprising at least 90% identity to the amino acid sequence GASENIYGALN (SEQ ID NO: 10), a VLCDR2 comprising at least 90% identity to the amino acid sequence GATNLAD (SEQ ID NO: 11) and a VLCDR3 comprising at least 90% identity to the amino acid sequence QNVLTTPWT (SEQ ID NO: 12).

In one embodiment, an antibody, fragment or variant thereof, is provided comprising:
  a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and/or
  a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12).

3b04_var 2

In one embodiment, an antibody, fragment or variant thereof, is provided comprising:
  a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 22), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 23) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 24); and/or
  a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 10), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 11) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 12).

In one embodiment, an antibody, fragment or variant thereof, is provided comprising:
  a heavy chain variable region comprising a VHCDR1 comprising at least 90% identity to the amino acid sequence DYEMH (SEQ ID NO: 22), a VHCDR2 comprising at least 90% identity to the amino acid sequence EIDPETGDTAYSQKFQG (SEQ ID NO: 23) and a VHCDR3 comprising at least 90% identity to the amino acid sequence ETDYFFDY (SEQ ID NO: 24); and/or
  a light chain variable region comprising a VLCDR1 comprising at least 90% identity to the amino acid sequence GASENIYGALN (SEQ ID NO: 10), a VLCDR2 comprising at least 90% identity to the amino acid sequence GATNLAD (SEQ ID NO: 11) and a VLCDR3 comprising at least 90% identity to the amino acid sequence QNVLTTPWT (SEQ ID NO: 12).

In one embodiment, an antibody, fragment or variant thereof, is provided comprising:
  a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24)); and/or
  a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12).

3b04_var3

In one embodiment, an antibody, fragment or variant thereof, is provided comprising
  a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 30), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 31) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 32); and/or
  a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 10), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 11) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 12).

In one embodiment, an antibody, fragment or variant thereof, is provided comprising:
  a heavy chain variable region comprising a VHCDR1 comprising at least 90% identity to the amino acid sequence DYEMH (SEQ ID NO: 30), a VHCDR2 comprising at least 90% identity to the amino acid sequence EIDPETGDTAYSQKFQG (SEQ ID NO: 31) and a VHCDR3 comprising at least 90% identity to the amino acid sequence ETDYFFDY (SEQ ID NO: 32); and/or
  a light chain variable region comprising a VLCDR1 comprising at least 90% identity to the amino acid sequence GASENIYGALN (SEQ ID NO: 10), a VLCDR2 comprising at least 90% identity to the amino acid sequence GATNLAD (SEQ ID NO: 11) and a VLCDR3 comprising at least 90% identity to the amino acid sequence QNVLTTPWT (SEQ ID NO: 12).

In one embodiment, an antibody, fragment or variant thereof, is provided comprising
- a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and/or
- a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12).

3b04_var4

In one embodiment, an antibody, fragment or variant thereof, is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 38), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 39) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 40); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 10), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 11) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 12).

In one embodiment, an antibody, fragment or variant thereof, is provided comprising:
- a heavy chain variable region comprising a VHCDR1 comprising at least 90% identity to the amino acid sequence DYEMH (SEQ ID NO: 38), a VHCDR2 comprising at least 90% identity to the amino acid sequence EIDPETGDTAYSQKFQG (SEQ ID NO: 39) and a VHCDR3 comprising at least 90% identity to the amino acid sequence ETDYFFDY (SEQ ID NO: 40); and/or
- a light chain variable region comprising a VLCDR1 comprising at least 90% identity to the amino acid sequence GASENIYGALN (SEQ ID NO: 10), a VLCDR2 comprising at least 90% identity to the amino acid sequence GATNLAD (SEQ ID NO: 11) and a VLCDR3 comprising at least 90% identity to the amino acid sequence QNVLTTPWT (SEQ ID NO: 12).

In one embodiment, an antibody, fragment or variant thereof, is provided comprising:
- a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and/or
- a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12).

3b04_var5

In one embodiment, an antibody, fragment or variant thereof, is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 14), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFKG (SEQ ID NO: 15) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 16); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 18), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 19) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 20).

In one embodiment, an antibody, fragment or variant thereof, is provided comprising:
- a heavy chain variable region comprising a VHCDR1 comprising at least 90% identity to the amino acid sequence DYEMH (SEQ ID NO: 14), a VHCDR2 comprising at least 90% identity to the amino acid sequence EIDPETGDTAYSQKFKG (SEQ ID NO: 15) and a VHCDR3 comprising at least 90% identity to the amino acid sequence ETDYFFDY (SEQ ID NO: 16); and/or
- a light chain variable region comprising a VLCDR1 comprising at least 90% identity to the amino acid sequence GASENIYGALN (SEQ ID NO: 18), a VLCDR2 comprising at least 90% identity to the amino acid sequence GATNLAD (SEQ ID NO: 19) and a VLCDR3 comprising at least 90% identity to the amino acid sequence QNVLTTPWT (SEQ ID NO: 20).

In one embodiment, an antibody, fragment or variant thereof, is provided comprising:
- a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and/or
- a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20).

3b04_var6

In one embodiment, an antibody, fragment or variant thereof, is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 22), a VHCDR2 comprising at least 70%, 75%, 80%, 85%, 90%, 91%, 92%, 93%, 94%, 95%, 96%, 97%, 98% or 99% identity to the amino acid sequence EIDPETGD-TAYSQKFQG (SEQ ID NO: 23) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 24); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 18), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 19) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 20).

In one embodiment, an antibody, fragment or variant thereof, is provided comprising:
a heavy chain variable region comprising a VHCDR1 comprising at least 90% identity to the amino acid sequence DYEMH (SEQ ID NO: 22), a VHCDR2 comprising at least 90% identity to the amino acid sequence EIDPETGDTAYSQKFQG (SEQ ID NO: 23) and a VHCDR3 comprising at least 90% identity to the amino acid sequence ETDYFFDY (SEQ ID NO: 24); and/or a light chain variable region comprising a VLCDR1 comprising at least 90% identity to the amino acid sequence GASENIYGALN (SEQ ID NO: 18), a VLCDR2 comprising at least 90% identity to the amino acid sequence GATNLAD (SEQ ID NO: 19) and a VLCDR3 comprising at least 90% identity to the amino acid sequence QNVLTTPWT (SEQ ID NO: 20).

In one embodiment, an antibody, fragment or variant thereof, is provided comprising:
a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24) and/or a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20).

3b04_var 7

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 30), a VHCDR2 comprising at least 70%, 75%, 80%, 85%, 90%, 91%, 92%, 93%, 94%, 95%, 96%, 97%, 98% or 99% identity to the amino acid sequence EIDPETGD-TAYSQKFQG (SEQ ID NO: 31) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 32); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 18), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 19) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 20).

In one embodiment, an antibody, fragment or variant thereof, is provided comprising:
a heavy chain variable region comprising a VHCDR1 comprising at least 90% identity to the amino acid sequence DYEMH (SEQ ID NO: 30), a VHCDR2 comprising at least 90% identity to the amino acid sequence EIDPETGDTAYSQKFQG (SEQ ID NO: 31) and a VHCDR3 comprising at least 90% identity to the amino acid sequence ETDYFFDY (SEQ ID NO: 32); and/or a light chain variable region comprising a VLCDR1 comprising at least 90% identity to the amino acid sequence GASENIYGALN (SEQ ID NO: 18), a VLCDR2 comprising at least 90% identity to the amino acid sequence GATNLAD (SEQ ID NO: 19) and a VLCDR3 comprising at least 90% identity to the amino acid sequence QNVLTTPWT (SEQ ID NO: 20).

In one embodiment, an antibody, fragment or variant thereof, is provided comprising
a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and/or a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20).

3b04_var 8

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 38), a VHCDR2 comprising at least 70%, 75%, 80%, 85%, 90%, 91%, 92%, 93%, 94%, 95%, 96%, 97%, 98% or 99% identity to the amino acid sequence EIDPETGD-TAYSQKFQG (SEQ ID NO: 39) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 40); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 18), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 19) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 20).

In one embodiment, an antibody, fragment or variant thereof, is provided comprising:
  a heavy chain variable region comprising a VHCDR1 comprising at least 90% identity to the amino acid sequence DYEMH (SEQ ID NO: 38), a VHCDR2 comprising at least 90% identity to the amino acid sequence EIDPETGDTAYSQKFQG (SEQ ID NO: 39) and a VHCDR3 comprising at least 90% identity to the amino acid sequence ETDYFFDY (SEQ ID NO: 40); and/or
  a light chain variable region comprising a VLCDR1 comprising at least 90% identity to the amino acid sequence GASENIYGALN (SEQ ID NO: 18), a VLCDR2 comprising at least 90% identity to the amino acid sequence GATNLAD (SEQ ID NO: 19) and a VLCDR3 comprising at least 90% identity to the amino acid sequence QNVLTTPWT (SEQ ID NO: 20).

In one embodiment, an antibody, fragment or variant thereof, is provided comprising
  a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and/or
  a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20).

3b04_var 9

In one embodiment, an antibody, fragment or variant thereof, is provided comprising:
  a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 14), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFKG (SEQ ID NO: 15) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 16); and/or
  a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 26), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 27) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 28).

In one embodiment, an antibody, fragment or variant thereof, is provided comprising:
  a heavy chain variable region comprising a VHCDR1 comprising at least 90% identity to the amino acid sequence DYEMH (SEQ ID NO: 14), a VHCDR2 comprising at least 90% identity to the amino acid sequence EIDPETGDTAYSQKFKG (SEQ ID NO: 15) and a VHCDR3 comprising at least 90% identity to the amino acid sequence ETDYFFDY (SEQ ID NO: 16); and/or
  a light chain variable region comprising a VLCDR1 comprising at least 90% identity to the amino acid sequence GASENIYGALN (SEQ ID NO: 26), a VLCDR2 comprising at least 90%, 98% or 99% identity to the amino acid sequence GATNLAD (SEQ ID NO: 27) and a VLCDR3 comprising at least 90% identity to the amino acid sequence QNVLTTPWT (SEQ ID NO: 28).

In one embodiment, an antibody, fragment or variant thereof, is provided comprising:
  a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and/or
  a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28).

3b04_var10

In one embodiment, an antibody, fragment or variant thereof, is provided comprising:
  a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 22), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 23) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 24); and/or
  a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 26), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 27) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 28).

In one embodiment, an antibody, fragment or variant thereof, is provided comprising:
  a heavy chain variable region comprising a VHCDR1 comprising at least 90% identity to the amino acid sequence DYEMH (SEQ ID NO: 22), a VHCDR2 comprising at least 90% identity to the amino acid sequence EIDPETGDTAYSQKFQG (SEQ ID NO: 23) and a VHCDR3 comprising at least 90% identity to the amino acid sequence ETDYFFDY (SEQ ID NO: 24); and/or
  a light chain variable region comprising a VLCDR1 comprising at least 90% identity to the amino acid sequence GASENIYGALN (SEQ ID NO: 26), a VLCDR2 comprising at least 90% identity to the amino acid sequence GATNLAD (SEQ ID NO: 27) and a VLCDR3 comprising at least 90% identity to the amino acid sequence QNVLTTPWT (SEQ ID NO: 28).

In one embodiment, an antibody, fragment or variant thereof, is provided comprising:
- a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and/or
- a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28).

3b04_var 11

In one embodiment, an antibody, fragment or variant thereof, is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 30), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 31) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 32) and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 26), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 27) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 28).

In one embodiment, an antibody, fragment or variant thereof, is provided comprising:
- a heavy chain variable region comprising a VHCDR1 comprising at least 90% identity to the amino acid sequence DYEMH (SEQ ID NO: 30), a VHCDR2 comprising at least 90% identity to the amino acid sequence EIDPETGDTAYSQKFQG (SEQ ID NO: 31) and a VHCDR3 comprising at least 90% identity to the amino acid sequence ETDYFFDY (SEQ ID NO: 32); and/or
- a light chain variable region comprising a VLCDR1 comprising at least 90% identity to the amino acid sequence GASENIYGALN (SEQ ID NO: 26), a VLCDR2 comprising at least 90% identity to the amino acid sequence GATNLAD (SEQ ID NO: 27) and a VLCDR3 comprising at least 90% identity to the amino acid sequence QNVLTTPWT (SEQ ID NO: 28).

In one embodiment, an antibody, fragment or variant thereof, is provided comprising:
- a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and/or
- a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28).

3b04_var 12

In one embodiment, an antibody, fragment or variant thereof, is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 38), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 39) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 40) and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 26), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 27) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 28).

In one embodiment, an antibody, fragment or variant thereof, is provided comprising:
- a heavy chain variable region comprising a VHCDR1 comprising at least 90% identity to the amino acid sequence DYEMH (SEQ ID NO: 38), a VHCDR2 comprising at least 90% identity to the amino acid sequence EIDPETGDTAYSQKFQG (SEQ ID NO: 39) and a VHCDR3 comprising at least 90% identity to the amino acid sequence ETDYFFDY (SEQ ID NO: 40); and/or
- a light chain variable region comprising a VLCDR1 comprising at least 90% identity to the amino acid sequence GASENIYGALN (SEQ ID NO: 26), a VLCDR2 comprising at least 90% identity to the amino acid sequence GATNLAD (SEQ ID NO: 27) and a VLCDR3 comprising at least 90% identity to the amino acid sequence QNVLTTPWT (SEQ ID NO: 28).

In one embodiment, an antibody, fragment or variant thereof, is provided comprising
- a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and/or
- a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28).

3b04_var 13

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 14), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFKG (SEQ ID NO: 15) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 16); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 34), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 35) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 36).

In one embodiment, an antibody, fragment or variant thereof, is provided comprising:
  a heavy chain variable region comprising a VHCDR1 comprising at least 90% identity to the amino acid sequence DYEMH (SEQ ID NO: 14), a VHCDR2 comprising at least 90% identity to the amino acid sequence EIDPETGDTAYSQKFKG (SEQ ID NO: 15) and a VHCDR3 comprising at least 90% identity to the amino acid sequence ETDYFFDY (SEQ ID NO: 16); and/or
  a light chain variable region comprising a VLCDR1 comprising at least 90% identity to the amino acid sequence RASENIYGALN (SEQ ID NO: 34), a VLCDR2 comprising at least 90% identity to the amino acid sequence GATNLAE (SEQ ID NO: 35) and a VLCDR3 comprising at least 90% identity to the amino acid sequence QNVLTTPWT (SEQ ID NO: 36).

In one embodiment, an antibody, fragment or variant thereof, is provided comprising:
  a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and/or
  a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36).

3b04_var 14

In one embodiment, an antibody, fragment or variant thereof, is provided comprising:
  a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 22), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 23) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 24); and/or
  a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 34), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 35) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 36).

In one embodiment, an antibody, fragment or variant thereof, is provided comprising:
  a heavy chain variable region comprising a VHCDR1 comprising at least 90% identity to the amino acid sequence DYEMH (SEQ ID NO: 22), a VHCDR2 comprising at least 90% identity to the amino acid sequence EIDPETGDTAYSQKFQG (SEQ ID NO: 23) and a VHCDR3 comprising at least 90% identity to the amino acid sequence ETDYFFDY (SEQ ID NO: 24); and/or
  a light chain variable region comprising a VLCDR1 comprising at least 90% identity to the amino acid sequence RASENIYGALN (SEQ ID NO: 34), a VLCDR2 comprising at least 90% identity to the amino acid sequence GATNLAE (SEQ ID NO: 35) and a VLCDR3 comprising at least 90% identity to the amino acid sequence QNVLTTPWT (SEQ ID NO: 36).

In one embodiment, an antibody, fragment or variant thereof, is provided comprising:
  a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and/or
  a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36).

3b04_var15

In one embodiment, an antibody, fragment or variant thereof, is provided comprising:
  a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 30), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 31) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 32); and/or
  a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 34), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 35) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 36).

In one embodiment, an antibody, fragment or variant thereof, is provided comprising:
- a heavy chain variable region comprising a VHCDR1 comprising at least 90% identity to the amino acid sequence DYEMH (SEQ ID NO: 30), a VHCDR2 comprising at least 90% identity to the amino acid sequence EIDPETGDTAYSQKFQG (SEQ ID NO: 31) and a VHCDR3 comprising at least 90% identity to the amino acid sequence ETDYFFDY (SEQ ID NO: 32); and/or
- a light chain variable region comprising a VLCDR1 comprising at least 90% identity to the amino acid sequence RASENIYGALN (SEQ ID NO: 34), a VLCDR2 comprising at least 90% identity to the amino acid sequence GATNLAE (SEQ ID NO: 35) and a VLCDR3 comprising at least 90% identity to the amino acid sequence QNVLTTPWT (SEQ ID NO: 36).

In one embodiment, an antibody, fragment or variant thereof, is provided comprising
- a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and/or
- a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36).

3b04_var 16

In one embodiment, an antibody, fragment or variant thereof, is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYEMH (SEQ ID NO: 38), a VHCDR2 comprising at least 70%, 75%, 80%, 85%, 90%, 91%, 92%, 93%, 94%, 95%, 96%, 97%, 98% or 99% identity to the amino acid sequence EIDPETGDTAYSQKFQG (SEQ ID NO: 39) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 40); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 34), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 35) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 36).

In one embodiment, an antibody, fragment or variant thereof, is provided comprising:
- a heavy chain variable region comprising:
  a VHCDR1 comprising at least 90% identity to the amino acid sequence DYEMH (SEQ ID NO: 38), a VHCDR2 comprising at least 90% identity to the amino acid sequence EIDPETGDTAYSQKFQG (SEQ ID NO: 39) and a VHCDR3 comprising at least 90% identity to the amino acid sequence ETDYFFDY (SEQ ID NO: 40); and/or
- a light chain variable region comprising a VLCDR1 comprising at least 90% identity to the amino acid sequence RASENIYGALN (SEQ ID NO: 34), a VLCDR2 comprising at least 90% identity to the amino acid sequence GATNLAE (SEQ ID NO: 35) and a VLCDR3 comprising at least 90% identity to the amino acid sequence QNVLTTPWT (SEQ ID NO: 36).

In one embodiment, an antibody, fragment or variant thereof, is provided comprising:
- a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and/or
- a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36).

3d12_var 1

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 54), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFKG (SEQ ID NO: 55) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 56); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 50), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 51) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 52).

In one embodiment, an antibody, fragment or variant thereof is provided comprising:
- a heavy chain variable region comprising a VHCDR1 comprising at least 90% identity to the amino acid sequence DSEIH (SEQ ID NO: 54), a VHCDR2 comprising at least 90% identity to the amino acid sequence EIDPETGGTAYNQKFKG (SEQ ID NO: 55) and a VHCDR3 comprising at least 90% identity to the amino acid sequence ETDYFFDY (SEQ ID NO: 56); and/or
- a light chain variable region comprising a VLCDR1 comprising at least 90% identity to the amino acid sequence GASENIYGALN (SEQ ID NO: 50), a VLCDR2 comprising at least 90% identity to the amino acid sequence GATNLAD (SEQ ID NO: 51) and a VLCDR3 comprising at least 90% identity to the amino acid sequence QNVLSTPWT (SEQ ID NO: 52).

In one embodiment, an antibody, fragment or variant thereof is provided comprising:
- a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and/or
- a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52).

3d12 Heavy 2, Light 1 Var 2

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 62), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFQG (SEQ ID NO: 63) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 64); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 50), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 51) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 52).

In one embodiment, an antibody, fragment or variant thereof is provided comprising:
- a heavy chain variable region comprising a VHCDR1 comprising at least 90% identity to the amino acid sequence DSEIH (SEQ ID NO: 62), a VHCDR2 comprising at least 90% identity to the amino acid sequence EIDPETGGTAYNQKFQG (SEQ ID NO: 63) and a VHCDR3 comprising at least 90% identity to the amino acid sequence ETDYFFDY (SEQ ID NO: 64); and/or
- a light chain variable region comprising a VLCDR1 comprising at least 90% identity to the amino acid sequence GASENIYGALN (SEQ ID NO: 50), a VLCDR2 comprising at least 90% identity to the amino acid sequence GATNLAD (SEQ ID NO: 51) and a VLCDR3 comprising at least 90% identity to the amino acid sequence QNVLSTPWT (SEQ ID NO: 52).

In one embodiment, an antibody, fragment or variant thereof is provided comprising:
- a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and/or
- a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52).

3d12 Heavy 3, Light 1, Var 3

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 70), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 71) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 72); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 50), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 51) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 52).

In one embodiment, an antibody, fragment or variant thereof is provided comprising:
- a heavy chain variable region comprising a VHCDR1 comprising at least 90% identity to the amino acid sequence DSEIH (SEQ ID NO: 70), a VHCDR2 comprising at least 90% identity to the amino acid sequence EIDPETGGTAYAQKFQG (SEQ ID NO: 71) and a VHCDR3 comprising at least 90% identity to the amino acid sequence ETDYFFDY (SEQ ID NO: 72); and/or
- a light chain variable region comprising a VLCDR1 comprising at least 90% identity to the amino acid sequence GASENIYGALN (SEQ ID NO: 50), a VLCDR2 comprising at least 90% identity to the amino acid sequence GATNLAD (SEQ ID NO: 51) and a VLCDR3 comprising at least 90% identity to the amino acid sequence QNVLSTPWT (SEQ ID NO: 52).

In one embodiment, an antibody, fragment or variant thereof is provided comprising:
- a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and/or
- a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52).

3d12 Heavy 4, Light 1, Var 4

In one embodiment, an antibody, fragment or variant thereof is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEMH (SEQ ID NO: 78), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 79) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 80); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 50), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 51) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 52).

In one embodiment, an antibody, fragment or variant thereof is provided comprising:

a heavy chain variable region comprising a VHCDR1 comprising at least 90% identity to the amino acid sequence DSEMH (SEQ ID NO: 78), a VHCDR2 comprising at least 90% identity to the amino acid sequence EIDPETGGTAYAQKFQG (SEQ ID NO: 79) and a VHCDR3 comprising at least 90% identity to the amino acid sequence ETDYFFDY (SEQ ID NO: 80); and/or a light chain variable region comprising a VLCDR1 comprising at least 90% identity to the amino acid sequence GASENIYGALN (SEQ ID NO: 50), a VLCDR2 comprising at least 90% identity to the amino acid sequence GATNLAD (SEQ ID NO: 51) and a VLCDR3 comprising at least 90% identity to the amino acid sequence QNVLSTPWT (SEQ ID NO: 52).

In one embodiment, an antibody, fragment or variant thereof is provided comprising:

a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and/or a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52).

3d12, Heavy 1, Light 2, Var 5

In one embodiment, an antibody, fragment or variant thereof is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 54), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFKG (SEQ ID NO: 55) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 56); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 58), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 59) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 60).

In one embodiment, an antibody, fragment or variant thereof is provided comprising:

a heavy chain variable region comprising a VHCDR1 comprising at least 90% identity to the amino acid sequence DSEIH (SEQ ID NO: 54), a VHCDR2 comprising at least 90% identity to the amino acid sequence EIDPETGGTAYNQKFKG (SEQ ID NO: 55) and a VHCDR3 comprising at least 90% identity to the amino acid sequence ETDYFFDY (SEQ ID NO: 56); and/or a light chain variable region comprising a VLCDR1 comprising at least 90% identity to the amino acid sequence GASENIYGALN (SEQ ID NO: 58), a VLCDR2 comprising at least 90% identity to the amino acid sequence GATNLAD (SEQ ID NO: 59) and a VLCDR3 comprising at least 90% identity to the amino acid sequence QNVLSTPWT (SEQ ID NO: 60).

In one embodiment, an antibody, fragment or variant thereof is provided comprising:

a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and/or a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60).

3d12 Heavy 2, Light 2, Var 6

In one embodiment, an antibody, fragment or variant thereof is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 62), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFQG (SEQ ID NO: 63) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 64); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 58), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 59) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 60).

In one embodiment, an antibody, fragment or variant thereof is provided comprising:
- a heavy chain variable region comprising a VHCDR1 comprising at least 90% identity to the amino acid sequence DSEIH (SEQ ID NO: 62), a VHCDR2 comprising at least 90% identity to the amino acid sequence EIDPETGGTAYNQKFQG (SEQ ID NO: 63) and a VHCDR3 comprising at least 90% identity to the amino acid sequence ETDYFFDY (SEQ ID NO: 64); and/or
- a light chain variable region comprising a VLCDR1 comprising at least 90% identity to the amino acid sequence GASENIYGALN (SEQ ID NO: 58), a VLCDR2 comprising at least 90% identity to the amino acid sequence GATNLAD (SEQ ID NO: 59) and a VLCDR3 comprising at least 90% identity to the amino acid sequence QNVLSTPWT (SEQ ID NO: 60).

In one embodiment, an antibody, fragment or variant thereof is provided comprising:
- a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and/or
- a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60).

3d12, Heavy 3, Light 2, Var 7

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 70), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 71) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 72); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 58), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 59) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 60).

In one embodiment, an antibody, fragment or variant thereof is provided comprising:
- a heavy chain variable region comprising a VHCDR1 comprising at least 90% identity to the amino acid sequence DSEIH (SEQ ID NO: 70), a VHCDR2 comprising at least 90% identity to the amino acid sequence EIDPETGGTAYAQKFQG (SEQ ID NO: 71) and a VHCDR3 comprising at least 90% identity to the amino acid sequence ETDYFFDY (SEQ ID NO: 72); and/or
- a light chain variable region comprising a VLCDR1 comprising at least 90% identity to the amino acid sequence GASENIYGALN (SEQ ID NO: 58), a VLCDR2 comprising at least 90% identity to the amino acid sequence GATNLAD (SEQ ID NO: 59) and a VLCDR3 comprising at least 90% identity to the amino acid sequence QNVLSTPWT (SEQ ID NO: 60).

In one embodiment, an antibody, fragment or variant thereof is provided comprising:
- a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and/or
- a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60).

3d12 Heavy 4, Light 2, Var 8

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEMH (SEQ ID NO: 78), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 79) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 80); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 58), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 59) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 60).

In one embodiment, an antibody, fragment or variant thereof is provided comprising:
- a heavy chain variable region comprising a VHCDR1 comprising at least 90% identity to the amino acid sequence DSEMH (SEQ ID NO: 78), a VHCDR2 comprising at least 90% identity to the amino acid sequence EIDPETGGTAYAQKFQG (SEQ ID NO: 79) and a VHCDR3 comprising at least 90% identity to the amino acid sequence ETDYFFDY (SEQ ID NO: 80); and/or
- a light chain variable region comprising a VLCDR1 comprising at least 90% identity to the amino acid sequence GASENIYGALN (SEQ ID NO: 58), a VLCDR2 comprising at least 90% identity to the amino acid sequence GATNLAD (SEQ ID NO: 59) and a VLCDR3 comprising at least 90% identity to the amino acid sequence QNVLSTPWT (SEQ ID NO: 60).

In one embodiment, an antibody, fragment or variant thereof is provided comprising:
- a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and/or
- a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60). 3d12, heavy 1, light 3, var 9

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 54), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFKG (SEQ ID NO: 55) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 56); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 66), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 67) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 68).

In one embodiment, an antibody, fragment or variant thereof is provided comprising:
- a heavy chain variable region comprising a VHCDR1 comprising at least 90% identity to the amino acid sequence DSEIH (SEQ ID NO: 54), a VHCDR2 comprising at least 90% identity to the amino acid sequence EIDPETGGTAYNQKFKG (SEQ ID NO: 55) and a VHCDR3 comprising at least 90% identity to the amino acid sequence ETDYFFDY (SEQ ID NO: 56); and/or
- a light chain variable region comprising a VLCDR1 comprising at least 90% identity to the amino acid sequence GASENIYGALN (SEQ ID NO: 66), a VLCDR2 comprising at least 90% identity to the amino acid sequence GATNLAD (SEQ ID NO: 67) and a VLCDR3 comprising at least 90% identity to the amino acid sequence QNVLSTPWT (SEQ ID NO: 68).

In one embodiment, an antibody, fragment or variant thereof is provided comprising:
- a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3; and/or
- a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68).

3d12 Heavy 2, Light 3 Var 10

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 62), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFQG (SEQ ID NO: 63) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 64); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 66), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 67) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 68).

In one embodiment, an antibody, fragment or variant thereof is provided comprising:
- a heavy chain variable region comprising a VHCDR1 comprising at least 90% identity to the amino acid sequence DSEIH (SEQ ID NO: 62), a VHCDR2 comprising at least 90% identity to the amino acid sequence EIDPETGGTAYNQKFQG (SEQ ID NO: 63) and a VHCDR3 comprising at least 90% identity to the amino acid sequence ETDYFFDY (SEQ ID NO: 64); and/or
- a light chain variable region comprising a VLCDR1 comprising at least 90% identity to the amino acid sequence GASENIYGALN (SEQ ID NO: 66), a VLCDR2 comprising at least 90% identity to the amino acid sequence GATNLAD (SEQ ID NO: 67) and a VLCDR3 comprising at least 90% identity to the amino acid sequence QNVLSTPWT (SEQ ID NO: 68).

In one embodiment, an antibody, fragment or variant thereof is provided comprising:
- a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and/or
- a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68).

3d12, Heavy 3, Light 3, Var 11

In one embodiment, an antibody, fragment or variant thereof is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 70), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 71) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 72); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 66), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 67) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 68).

In one embodiment, an antibody, fragment or variant thereof is provided comprising:

a heavy chain variable region comprising a VHCDR1 comprising at least 90% identity to the amino acid sequence DSEIH (SEQ ID NO: 70), a VHCDR2 comprising at least 90% identity to the amino acid sequence EIDPETGGTAYAQKFQG (SEQ ID NO: 71) and a VHCDR3 comprising at least 90% identity to the amino acid sequence ETDYFFDY (SEQ ID NO: 72)' and/or a light chain variable region comprising a VLCDR1 comprising at least 90% identity to the amino acid sequence GASENIYGALN (SEQ ID NO: 66), a VLCDR2 comprising at least 90% identity to the amino acid sequence GATNLAD (SEQ ID NO: 67) and a VLCDR3 comprising at least 90% identity to the amino acid sequence QNVLSTPWT (SEQ ID NO: 68).

In one embodiment, an antibody, fragment or variant thereof is provided comprising:

a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and/or a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68).

3d12 Heavy 4, Light 3, Var 12

In one embodiment, an antibody, fragment or variant thereof is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEMH (SEQ ID NO: 78), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 79) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 80); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 66), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 67) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 68).

In one embodiment, an antibody, fragment or variant thereof is provided comprising:

a heavy chain variable region comprising a VHCDR1 comprising at least 90% identity to the amino acid sequence DSEMH (SEQ ID NO: 78), a VHCDR2 comprising at least 90% identity to the amino acid sequence EIDPETGGTAYAQKFQG (SEQ ID NO: 79) and a VHCDR3 comprising at least 90% identity to the amino acid sequence ETDYFFDY (SEQ ID NO: 80); and/or a light chain variable region comprising a VLCDR1 comprising at least 90% identity to the amino acid sequence GASENIYGALN (SEQ ID NO: 66), a VLCDR2 comprising at least 90% identity to the amino acid sequence GATNLAD (SEQ ID NO: 67) and a VLCDR3 comprising at least 90% identity to the amino acid sequence QNVLSTPWT (SEQ ID NO: 68).

In one embodiment, an antibody, fragment or variant thereof is provided comprising:

a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and/or a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68).

3d12, Heavy 1, Light 4, Var 13

In one embodiment, an antibody, fragment or variant thereof is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 54), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFKG (SEQ ID NO: 55) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 56); and/or a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 74), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 75) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 76).

In one embodiment, an antibody, fragment or variant thereof is provided comprising:
- a heavy chain variable region comprising a VHCDR1 comprising at least 90% identity to the amino acid sequence DSEIH (SEQ ID NO: 54), a VHCDR2 comprising at least 90% identity to the amino acid sequence EIDPETGGTAYNQKFKG (SEQ ID NO: 55) and a VHCDR3 comprising at least 90% identity to the amino acid sequence ETDYFFDY (SEQ ID NO: 56); and/or
- a light chain variable region comprising a VLCDR1 comprising at least 90% identity to the amino acid sequence RASENIYGALN (SEQ ID NO: 74), a VLCDR2 comprising at least 90% identity to the amino acid sequence GATNLAE (SEQ ID NO: 75) and a VLCDR3 comprising at least 90% identity to the amino acid sequence QNVLSTPWT (SEQ ID NO: 76).

In one embodiment, an antibody, fragment or variant thereof is provided comprising:
- a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3; and/or
- a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76).

3d12 Heavy 2, Light 4, Var 14

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 62), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYNQKFQG (SEQ ID NO: 63) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 64); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 74), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 75) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 76).

In one embodiment, an antibody, fragment or variant thereof is provided comprising:
- a heavy chain variable region comprising a VHCDR1 comprising at least 90% identity to the amino acid sequence DSEIH (SEQ ID NO: 62), a VHCDR2 comprising at least 90% identity to the amino acid sequence EIDPETGGTAYNQKFQG (SEQ ID NO: 63) and a VHCDR3 comprising at least 90% identity to the amino acid sequence ETDYFFDY (SEQ ID NO: 64); and/or
- a light chain variable region comprising a VLCDR1 comprising at least 90% identity to the amino acid sequence RASENIYGALN (SEQ ID NO: 74), a VLCDR2 comprising at least 90% identity to the amino acid sequence GATNLAE (SEQ ID NO: 75) and a VLCDR3 comprising at least 90% identity to the amino acid sequence QNVLSTPWT (SEQ ID NO: 76).

In one embodiment, an antibody, fragment or variant thereof is provided comprising:
- a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and/or
- a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76).

3d12, Heavy 3, Light 4, Var 15

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEIH (SEQ ID NO: 70), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 71) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 72); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 74), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 75) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 76).

In one embodiment, an antibody, fragment or variant thereof is provided comprising:
- a heavy chain variable region comprising a VHCDR1 comprising at least 90% identity to the amino acid sequence DSEIH (SEQ ID NO: 70), a VHCDR2 comprising at least 90% identity to the amino acid sequence EIDPETGGTAYAQKFQG (SEQ ID NO: 71) and a VHCDR3 comprising at least 90% identity to the amino acid sequence ETDYFFDY (SEQ ID NO: 72); and/or
- a light chain variable region comprising a VLCDR1 comprising at least 90% identity to the amino acid sequence RASENIYGALN (SEQ ID NO: 74), a VLCDR2 comprising at least 90% identity to the amino acid sequence GATNLAE (SEQ ID NO: 75) and a VLCDR3 comprising at least 90% identity to the amino acid sequence QNVLSTPWT (SEQ ID NO: 76).

In one embodiment, an antibody, fragment or variant thereof is provided comprising:
- a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and/or
- a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76).

3d12 Heavy 4, Light 4, Var 16

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DSEMH (SEQ ID NO: 78), a VHCDR2 comprising at least 70%, 75%, 80%, 85%, 90%, 91%, 92%, 93%, 94%, 95%, 96%, 97%, 98% or 99% identity to the amino acid sequence EIDPETGGTAYAQKFQG (SEQ ID NO: 79) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 80); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence RASENIYGALN (SEQ ID NO: 74), a VLCDR2 comprising at least 70%, 75%, 80%, 85%, 90%, 91%, 92%, 93%, 94%, 95%, 96%, 97%, 98% or 99% identity to the amino acid sequence GATNLAE (SEQ ID NO: 75) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 76).

In one embodiment, an antibody, fragment or variant thereof is provided comprising:
- a heavy chain variable region comprising a VHCDR1 comprising at least 90% identity to the amino acid sequence DSEMH (SEQ ID NO: 78), a VHCDR2 comprising at least 90% identity to the amino acid sequence EIDPETGGTAYAQKFQG (SEQ ID NO: 79) and a VHCDR3 comprising at least 90% identity to the amino acid sequence ETDYFFDY (SEQ ID NO: 80); and/or
- a light chain variable region comprising a VLCDR1 comprising at least 90% identity to the amino acid sequence RASENIYGALN (SEQ ID NO: 74), a VLCDR2 comprising at least 90% identity to the amino acid sequence GATNLAE (SEQ ID NO: 75) and a VLCDR3 comprising at least 90% identity to the amino acid sequence QNVLSTPWT (SEQ ID NO: 76).

In one embodiment, an antibody, fragment or variant thereof is provided comprising:
- a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and/or
- a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76).

Heavy and/or Light Chain Variable Regions

In one embodiment, the invention provides an antigen binding molecules, in particular an antibody that binds to LIGHT, comprising a heavy chain variable region having at least 70%, 75%, 80%, 85%, 90%, 91%, 92%, 93%, 94%, 95%, 96%, 97%, 98% or 99% identity to an amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, SEQ ID NO: 77, SEQ ID NO: 85, SEQ ID NO: 93, SEQ ID NO: 101, SEQ ID NO: 109, SEQ ID NO: 117, and/or a light chain variable region having at least 70%, 75%, 80%, 85%, 90%, 91%, 92%, 93%, 94%, 95%, 96%, 97%, 98% or 99% identity to an amino acid sequence selected from the group consisting of consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, SEQ ID NO: 73, SEQ ID NO: 81, SEQ ID NO: 89, SEQ ID NO: 97, SEQ ID NO: 105, SEQ ID NO: 113.

In one embodiment, the antibody binds to LIGHT and comprises a heavy chain variable region having the amino acid sequence selected from the group consisting of SEQ ID NO: 5, SEQ ID NO: 45, SEQ ID NO: 85, SEQ ID NO: 93, SEQ ID NO: 101, SEQ ID NO: 109, SEQ ID NO: 117, and/or a light chain variable region having the amino acid sequence selected from the group consisting of SEQ ID NO: 1, SEQ ID NO: 41, SEQ ID NO: 81, SEQ ID NO: 89, SEQ ID NO: 97, SEQ ID NO: 105, SEQ ID NO: 113.

In one embodiment, an antigen binding molecule, for example an antibody, variant or fragment thereof is provided, wherein the antigen binding molecule comprises a heavy chain variable region and a light chain variable region selected from the group consisting of:
- (a) a VH comprising the amino acid sequence of SEQ ID NO: 5 and a VL comprising the amino acid sequence of SEQ ID NO: 1 (or comprising VH and VL sequences that are at least 90% identical to SEQ ID NO: 5 and SEQ ID NO: 1, respectively);
- (b) a VH comprising the amino acid sequence of SEQ ID NO: 45 and a VL comprising the amino acid sequence of SEQ ID NO: 41 (or comprising VH and VL sequences that are at least 90% identical to SEQ ID NO: 45 and SEQ ID NO: 41, respectively);
- (c) a VH comprising the amino acid sequence of SEQ ID NO: 85 and a VL comprising the amino acid sequence of SEQ ID NO: 81 (or comprising VH and VL sequences that are at least 90% identical to SEQ ID NO: 85 and SEQ ID NO: 81, respectively);
- (d) a VH comprising the amino acid sequence of SEQ ID NO: 93 and a VL comprising the amino acid sequence of SEQ ID NO: 89 (or comprising VH and VL sequences that are at least 90% identical to SEQ ID NO: 93 and SEQ ID NO: 89, respectively);
- (d) a VH comprising the amino acid sequence of SEQ ID NO: 101 and a VL comprising the amino acid sequence of SEQ ID NO: 97 (or comprising VH and VL sequences that are at least 90% identical to SEQ ID NO: 101 and SEQ ID NO: 97, respectively);
- (e) a VH comprising the amino acid sequence of SEQ ID NO: 109 and a VL comprising the amino acid sequence of SEQ ID NO: 105 (or comprising VH and VL sequences that are at least 90% identical to SEQ ID NO: 109 and SEQ ID NO: 105, respectively);
(f) a VH comprising the amino acid sequence of SEQ ID NO: 117 and a VL comprising the amino acid sequence of SEQ ID NO: 113 (or comprising VH and VL sequences that are at least 90% identical to SEQ ID NO: 117 and SEQ ID NO: 113, respectively);
(g) a VH comprising the amino acid sequence of SEQ ID NO: 13 and a VL comprising the amino acid sequence of SEQ ID NO: 9 (or comprising VH and VL sequences that are at least 90% identical to SEQ ID NO: 13 and SEQ ID NO: 9, respectively);
(h) a VH comprising the amino acid sequence of SEQ ID NO: 21 and a VL comprising the amino acid sequence of SEQ ID NO: 9 (or comprising VH and VL sequences that are at least 90% identical to SEQ ID NO: 21 and SEQ ID NO: 9, respectively);
(i) a VH comprising the amino acid sequence of SEQ ID NO: 29 and a VL comprising the amino acid sequence of SEQ ID NO: 9 (or comprising VH and VL sequences that are at least 90% identical to SEQ ID NO: 29 and SEQ ID NO: 9, respectively);
(j) a VH comprising the amino acid sequence of SEQ ID NO: 37 and a VL comprising the amino acid sequence of SEQ ID NO: 9 (or comprising VH and VL sequences that are at least 90% identical to SEQ ID NO: 37 and SEQ ID NO: 9, respectively);
(k) a VH comprising the amino acid sequence of SEQ ID NO: 13 and a VL comprising the amino acid sequence of SEQ ID NO: 17 (or comprising VH and VL sequences that are at least 90% identical to SEQ ID NO: 13 and SEQ ID NO: 17, respectively);
(l) a VH comprising the amino acid sequence of SEQ ID NO: 21 and a VL comprising the amino acid sequence of SEQ ID NO: 17 (or comprising VH and VL sequences that are at least 90% identical to SEQ ID NO: 21 and SEQ ID NO: 17, respectively);
(m) a VH comprising the amino acid sequence of SEQ ID NO: 37 and a VL comprising the amino acid sequence of SEQ ID NO: 17 (or comprising VH and VL sequences that are at least 90% identical to SEQ ID NO: 37 and SEQ ID NO: 17, respectively);
(n) a VH comprising the amino acid sequence of SEQ ID NO: 13 and a VL comprising the amino acid sequence of SEQ ID NO: 25 (or comprising VH and VL sequences that are at least 90% identical to SEQ ID NO: 13 and SEQ ID NO: 25, respectively);
(o) a VH comprising the amino acid sequence of SEQ ID NO: 21 and a VL comprising the amino acid sequence of SEQ ID NO: 25 (or comprising VH and VL sequences that are at least 90% identical to SEQ ID NO: 21 and SEQ ID NO: 25, respectively);
(p) a VH comprising the amino acid sequence of SEQ ID NO: 29 and a VL comprising the amino acid sequence of SEQ ID NO: 25 (or comprising VH and VL sequences that are at least 90% identical to SEQ ID NO: 37 and SEQ ID NO: 25, respectively);
(q) a VH comprising the amino acid sequence of SEQ ID NO: 29 and a VL comprising the amino acid sequence of SEQ ID NO: 25 (or comprising VH and VL sequences that are at least 90% identical to SEQ ID NO: 37 and SEQ ID NO: 25, respectively);
(r) a VH comprising the amino acid sequence of SEQ ID NO: 13 and a VL comprising the amino acid sequence of SEQ ID NO: 33 (or VH and VL sequences that are at least 90% identical to SEQ ID NO: 13 and SEQ ID NO: 33, respectively);
(s) a VH comprising the amino acid sequence of SEQ ID NO: 21 and a VL comprising the amino acid sequence of SEQ ID NO: 33 (or VH and VL sequences that are at least 90% identical to SEQ ID NO: 21 and SEQ ID NO: 33, respectively);
(t) a VH comprising the amino acid sequence of SEQ ID NO: 29 and a VL comprising the amino acid sequence of SEQ ID NO: 33 (or VH and VL sequences that are at least 90% identical to SEQ ID NO: 29 and SEQ ID NO: 33, respectively);
(u) a VH comprising the amino acid sequence of SEQ ID NO: 37 and a VL comprising the amino acid sequence of SEQ ID NO: 33 (VH and VL sequences that are at least 90% identical to SEQ ID NO: 37 and SEQ ID NO: 33, respectively);
(v) a VH comprising the amino acid sequence of SEQ ID NO: 53 and a VL comprising the amino acid sequence of SEQ ID NO: 49 (or VH and VL sequences that are at least 90% identical to SEQ ID NO: 53 and SEQ ID NO: 49, respectively);
(x) a VH comprising the amino acid sequence of SEQ ID NO: 61 and a VL comprising the amino acid sequence of SEQ ID NO: 49 (or VH and VL sequences that are at least 90% identical to SEQ ID NO: 61 and SEQ ID NO: 49, respectively);
(y) a VH comprising the amino acid sequence of SEQ ID NO: 69 and a VL comprising the amino acid sequence of SEQ ID NO: 49 (or VH and VL sequences that are at least 90% identical to SEQ ID NO: 69 and SEQ ID NO: 49, respectively);
(z) a VH comprising the amino acid sequence of SEQ ID NO: 77 and a VL comprising the amino acid sequence of SEQ ID NO: 49 (or VH and VL sequences that are at least 90% identical to SEQ ID NO: 77 and SEQ ID NO: 49, respectively);
(aa) a VH comprising the amino acid sequence of SEQ ID NO: 53 and a VL comprising the amino acid sequence of SEQ ID NO: 57 (or VH and VL sequences that are at least 90% identical to SEQ ID NO: 53 and SEQ ID NO: 57, respectively);
(ab) a VH comprising the amino acid sequence of SEQ ID NO: 61 and a VL comprising the amino acid sequence of SEQ ID NO: 57 (or VH and VL sequences that are at least 90% identical to SEQ ID NO: 61 and SEQ ID NO: 57, respectively);
(ac) a VH comprising the amino acid sequence of SEQ ID NO: 69 and a VL comprising the amino acid sequence of SEQ ID NO: 57 (or VH and VL sequences that are at least 90% identical to SEQ ID NO: 69 and SEQ ID NO: 57, respectively);
(ad) a VH comprising the amino acid sequence of SEQ ID NO: 77 and a VL comprising the amino acid sequence of SEQ ID NO: 57 (or VH and VL sequences that are at least 90% identical to SEQ ID NO: 77 and SEQ ID NO: 57, respectively);
(ae) a VH comprising the amino acid sequence of SEQ ID NO: 77 and a VL comprising the amino acid sequence of SEQ ID NO: 57 (or VH and VL sequences that are at least 90% identical to SEQ ID NO: 77 and SEQ ID NO: 57, respectively);
(af) a VH comprising the amino acid sequence of SEQ ID NO: 53 and a VL comprising the amino acid sequence of SEQ ID NO: 65 (or VH and VL sequences that are at least 90% identical to SEQ ID NO: 53 and SEQ ID NO: 65, respectively);
(ag) a VH comprising the amino acid sequence of SEQ ID NO: 61 and a VL comprising the amino acid sequence of SEQ ID NO: 65 (or VH and VL sequences that are at least 90% identical to SEQ ID NO: 61 and SEQ ID NO: 65, respectively);

(ah) a VH comprising the amino acid sequence of SEQ ID NO: 69 and a VL comprising the amino acid sequence of SEQ ID NO: 65 (or VH and VL sequences that are at least 90% identical to SEQ ID NO: 69 and SEQ ID NO: 65, respectively);

(ai) a VH comprising the amino acid sequence of SEQ ID NO: 77 and a VL comprising the amino acid sequence of SEQ ID NO: 65 (or VH and VL sequences that are at least 90% identical to SEQ ID NO: 77 and SEQ ID NO: 65, respectively);

(aj) a VH comprising the amino acid sequence of SEQ ID NO: 53 and a VL comprising the amino acid sequence of SEQ ID NO: 73 (or VH and VL sequences that are at least 90% identical to SEQ ID NO: 53 and SEQ ID NO: 73, respectively);

(ak) a VH comprising the amino acid sequence of SEQ ID NO: 61 and a VL comprising the amino acid sequence of SEQ ID NO: 73 (or VH and VL sequences that are at least 90% identical to SEQ ID NO: 61 and SEQ ID NO: 73, respectively);

(al) a VH comprising the amino acid sequence of SEQ ID NO: 69 and a VL comprising the amino acid sequence of SEQ ID NO: 73 (or VH and VL sequences that are at least 90% identical to SEQ ID NO: 69 and SEQ ID NO: 73, respectively); and (am) a VH comprising the amino acid sequence of SEQ ID NO: 77 and a VL comprising the amino acid sequence of SEQ ID NO: 73 (or VH and VL sequences that are at least 90% identical to SEQ ID NO: 77 and SEQ ID NO: 73, respectively).

Variants therefore are also provided, as discussed above, including humanised and affinity matured variants thereof, and variants having smaller or greater % identities or homologies, for example at least 70%, 75%, 80%, 85%, 90%, 91%, 92%, 93%, 94%, 95%, 96%, 97%, 98% or 99% identity or homology to the specified sequence(s). Variants having one or more amino acid substitutions are also provided.

CDR Definitions

The CDRs identified in the VH and VL sequences of the antibodies can be defined using the Kabat system or the Chothia system (Dondelinger M et al., Front Immunol. 2018 Oct. 16; 9:2278). The CDRs discussed above have been defined using the Kabat system (as shown in FIGS. 3 to 6). In some embodiments of the invention the CDRs of the VH and VL sequences disclosed herein are defined using the Kabat system. In some embodiments of the invention the CDRs of the VH and VL sequences disclosed herein are defined using the Chothia system (for example, as shown in FIGS. 12 and 13).

Using the Kabat system, the CDRs of the VH and VL sequences disclosed herein are defined as shown in Table 1 and in FIGS. 3 to 6. Furthermore, the specific sequences are disclosed in the relevant passages discussing each antibody or variant.

In an alternative embodiment, the CDRs can be defined using the Chothia system, for example as shown in FIGS. 12 and 13. If the Chothia system is used to define the CDRs then the VHCDR1 of 3B04 can be the amino acid sequence GYTFTDY (SEQ ID NO: 125). The VHCDR1 of variant 3B04 heavy chains 3B04_VH_1, 3B04_VH_2, 3B04_VH_3 and 3B04_VH_4 can also be the amino acid sequence GYTFTDY (SEQ ID NO: 125) when defined using the Chothia system.

If the Chothia system is used to define the CDRs then the VHCDR2 of 3B04 can be the amino acid sequence DPETGDTA (SEQ ID NO: 126). The VHCDR2 of variant 3B04 heavy chains 3B04_VH_1, 3B04_VH_2, 3B04_VH_3 and 3B04_VH_4 can also be the amino acid sequence DPETGDTA (SEQ ID NO: 126) when defined using the Chothia system.

If the Chothia system is used to define the CDRs then the VHCDR1 of 3D12 can be the amino acid sequence DYTFTDS (SEQ ID NO: 127). The VHCDR1 of variant 3D12 heavy chains 3D12_VH_1, 3D12_VH_2, 3D12_VH_3 and 3D12_VH_4 can also be the amino acid sequence DYTFTDS (SEQ ID NO: 127) when defined using the Chothia system.

If the Chothia system is used to define the CDRs then the VHCDR2 of 3D12 can be the amino acid sequence DPETGGTA (SEQ ID NO: 128). The VHCDR2 of variant 3D12 heavy chains 3D12_VH_1, 3D12_VH_2, 3D12_VH_3 and 3D12_VH_4 can also be the amino acid sequence DPETGGTA (SEQ ID NO: 128) when defined using the Chothia system.

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GYTFTDY (SEQ ID NO: 125), a VHCDR2 comprising at least 70%, 75%, 80%, 85%, 90%, 91%, 92%, 93%, 94%, 95%, 96%, 97%, 98% or 99% identity to the amino acid sequence DPETGDTA (SEQ ID NO: 126) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 8); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 2), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QNVLTTPWT (SEQ ID NO: 4).

In one embodiment, an antibody, fragment or variant thereof is provided comprising:
- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence DYTFTDS (SEQ ID NO: 127), a VHCDR2 comprising at least 70%, 75%, 80%, 85%, 90%, 91%, 92%, 93%, 94%, 95%, 96%, 97%, 98% or 99% identity to the amino acid sequence DPETGGTA (SEQ ID NO: 128) and a VHCDR3 comprising at least 70%, 75%, 80%, 85%, 90%, 91%, 92%, 93%, 94%, 95%, 96%, 97%, 98% or 99% identity to the amino acid sequence ETDYFFDY (SEQ ID NO: 48); and/or
- a light chain variable region comprising a VLCDR1 comprising at least 70%, 75%, 80%, 85%, 90%, 91%, 92%, 93%, 94%, 95%, 96%, 97%, 98% or 99% identity to the amino acid sequence GASENIYGALN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence GATNLAD (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QNVLSTPWT (SEQ ID NO: 44).

Variants having one or more amino acid substitutions in the specified CDRs are also provided.

Nucleic Acid Sequences Encoding Antigen Binding Molecules

In one aspect of the invention, there is provided nucleic acid sequences that encode the antigen binding molecules of the invention, including fragments and variants thereof.

In one embodiment, nucleic acid molecules encoding an antigen binding molecule that binds to LIGHT comprising a heavy chain variable region having at least 70%, 75%, 80%, 85%, 90%, 91%, 92%, 93%, 94%, 95%, 96%, 97%, 98% or 99% identity to an amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, SEQ ID NO: 77, SEQ ID NO: 85, SEQ ID NO: 93, SEQ ID NO: 101, SEQ ID NO: 109, and SEQ ID NO: 117, and/or a light chain variable region having at least 70%, 75%, 80%, 85%, 90%, 91%, 92%, 93%, 94%, 95%, 96%, 97%, 98% or 99% identity to an amino acid sequence selected from the group consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, SEQ ID NO: 73, SEQ ID NO: 81, SEQ ID NO: 89, SEQ ID NO: 97, SEQ ID NO: 105, and SEQ ID NO: 113 are provided.

In one embodiment, nucleic acid molecules encoding an antibody that binds to LIGHT comprising a heavy chain variable region having an amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, SEQ ID NO: 77, SEQ ID NO: 85, SEQ ID NO: 93, SEQ ID NO: 101, SEQ ID NO: 109, and SEQ ID NO: 117, and/or a light chain variable region having an amino acid sequence selected from the group consisting of consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, SEQ ID NO: 73, SEQ ID NO: 81, SEQ ID NO: 89, SEQ ID NO: 97, SEQ ID NO: 105, and SEQ ID NO: 113 are provided.

The invention also provides an anti-light antigen binding molecule having the following CDRH and CDRL sequences:

| Light | CDR1 | $X_1$ASENIYGALN |
|---|---|---|
|  | CDR2 | GATNLAD$X_2$ |
|  | CDR3 | QNVLSTPWT |
| Heavy | CDR1 | D$X_3$E$X_4$H |
|  | CDR2 | EIDPETG$X_6$TAYX$_7$QKF$X_8$G |
|  | CDR3 | ETDYFFDY | wherein each of $X_1$ to $X_8$ are any amino acid, preferably any naturally occurring amino acid. In preferred embodiments, each of $X_1$ to $X_8$ are selected from the group consisting of G, R, D, E, Y, S, M, I, A, N, K and Q. In a more preferred embodiment:

$X_1$ G or R or a conservative amino acid substitution thereof;

$X_2$ is D or E or a conservative amino acid substitution thereof;

$X_3$ is Y or S or a conservative amino acid substitution thereof;

$X_4$ is M or I or a conservative amino acid substitution thereof;

$X_6$ is D or G or a conservative amino acid substitution thereof;

$X_7$ is S, A or N or a conservative amino acid substitution thereof; and $X_8$ is K or Q or a conservative amino acid substitution thereof.

Also provided are nucleic acid molecules that encode an amino acid sequence according to any one of SEQ ID NOs 1 to 120

Also provided are plasmid and vectors comprising a nucleic acid sequence encoding an antigen binding molecule of the invention. The nucleic acids may be incorporated into a plasmid or vector for expression, in particular in a eukaryotic expression system, more specifically, mammalian cell lines. Accordingly, also provided are host cells transfected with a plasmid or vector of the invention, such as NS0 muine myeloma cells or CHO cells.

Also provided is a method for the production on an anti-LIGHT antigen binding molecule, comprising culturing a host cell of the invention in a cell culture medium under conditions to express the encoding nucleic acid sequence of the plasmid or vector inside the cell. The method may further comprise obtaining the anti-LIGHT antigen binding molecule from the cell culture supernatant. Further, there is provided a method of producing cell that expresses an anti-LIGHT antigen binding molecule, comprising transfecting said cell with a plasmid or vector of the invention. Said cells can then be cultured for the production of the antigen binding molecule.

Antigens

The antigen binding molecules of the invention bind specifically to LIGHT, in particular human LIGHT, or hLIGHT. Most preferably, the antigen binding molecules of the invention specifically bind to membrane-bound human LIGHT.

The antigen binding molecules of the invention generally do not bind to mouse LIGHT.

LIGHT is also known as tumor necrosis factor superfamily member 14 (TNFSF14), LTg, CD258 and HVEML. It is recognized by herpesvirus entry mediator (HVEM or TNFRSF14), as well as LTβR and decoy receptor 3. Some of the antigen binding molecules of the invention are therefore able to disrupt the interaction between LIGHT and, for example, HVEM and LTβR. The antigen binding molecules of the invention may also partially inhibit the binding of LIGHT, in particular membrane LIGHT to decoy receptor 3.

LIGHT protein may function as a costimulatory factor for the activation of lymphoid cells and as a deterrent to infection by herpesvirus. This protein has been shown to stimulate the proliferation of T cells, and trigger apoptosis of various tumor cells. This protein is also reported to prevent tumor necrosis factor alpha mediated apoptosis in primary hepatocytes.

At least two alternatively spliced transcript variant encoding distinct isoforms have been reported: a 204 amino acid splice variant (NCBI reference sequence NM_172014.3/XM_005259670) and a 240 amino acid splice variant (NCBI reference sequence NM_003807.4). The 240 amino acid splice variant is preferred as an antigen for the binding molecules of the invention, although they may recognise both.

Polymorphic variants of LIGHT are also known, including E214K and S32L. The antigen binding molecules of the invention may bind to one or both variants, as well as to the 214E and 32S variants of LIGHT.

The amino acid sequences of three human LIGHT variants to which the antigen binding molecules of the invention bind are provided below.

```
Human LIGHT-214E
Amino Acid Sequence
                                       (SEQ ID NO: 121)
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEEVVVRVLDERLVRLRDGTRSYFGAFMV

Human LIGHT-214K
Amino Acid Sequence
                                       (SEQ ID NO: 122)
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEKVVVRVLDERLVRLRDGTRSYFGAFMV

Human LIGHT-32L
                                       (SEQ ID NO: 123)
MEESVVRPSVFVVDGQTDIPFTRLGRSHRRQLCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEEVVVRVLDERLVRLRDGTRSYFGAFMV
```

In vivo, LIGHT protein may be membrane-bound (i.e. full-length LIGHT) or it may be soluble. The present inventors have surprisingly found that the antigen binding molecules of the present invention bind with greater affinity to membrane LIGHT (i.e. full-length LIGHT) than soluble LIGHT. The antigen binding molecules therefore recognise and can target cells that express membrane LIGHT.

Membrane LIGHT refers to membrane-bound LIGHT protein. In particular, the antigen binding molecules of the invention (especially 3B04 and 3D12 and antibody fragments and variants thereof) have less than 10, less than 50 or less than 100-fold cross-reactivity to soluble LIGHT (for example amino acid residues 74 to 240 and/or 64 to 240 of full-length LIGHT) compared to membrane LIGHT. This relative binding affinity for membrane LIGHT versus soluble LIGHT is significant, since soluble LIGHT is considered to have an anti-inflammatory effect, whereas membrane LIGHT is considered to have a proinflammatory effect in vivo. Therefore, the antigen binding molecules of the invention are particularly useful as potential anti-inflammatory agents. For example, cross-reactivity or differences in binding preference can be measured by determining the binding of the antigen binding molecules of the invention to 500 pg/ml of soluble LIGHT in a NF-kB luciferase reporter assay using HeLa—NF-kB reporter cells. More specifically, the assay may comprise the steps of incubating 500 pg/ml of soluble LIGHT with up to 1 ug/ml of test antigen binding molecule for 20 min at 4° C., followed by incubation of 100 µl of the LIGHT/antibody solution with the cells at 37° C. for 24 hours.

The antigen binding molecules of the invention that bind membrane LIGHT will also therefore bind to cells that express LIGHT. Accordingly, the present invention also provides a binding molecule having the formula TM-Ln-AM, wherein TM is a targeting moiety and is an antigen binding molecule of the invention, L is a linker, n is a number between 0 and 1 (so a linker may or may not be present), and AM is an active moiety. The antigen binding molecules of the invention can be used to target the active moieties to cells expressing membrane-LIGHT. Suitable linkers include a hydrazine group, a polypeptide, a disulfide group, and a thioether group, and the linker may be cleavable by enzyme action. Suitable active moieties include pharmaceutically active components, such as anti-inflammatory agents, immunosuppressants or other such components that are suitable or desirable for use in combination with the antigen binding molecules of the invention. Suitable such agents are also discussed elsewhere.

In one embodiment, the antigen binding molecules of the present invention have a $K_D$ value for membrane LIGHT of less than about 5 nM. In a preferred embodiment, the antigen binding molecules of the present invention have a $K_D$ value for membrane LIGHT of less than about 1 nM. In a more preferred embodiment, the antigen binding molecules of the present invention have a $K_D$ value for membrane LIGHT of less than about 0.5 nM. The term $K_D$ is well known to the skilled person and refers to an equilibrium dissociation constant that measures the strength of the binding interaction between an antibody and antigen. The $K_D$ can be measured according to any suitable means. For example, a suitable assay may be a flow-cytometry assay comprising incubating EL4-LIGHT cells with test antigen binding molecule at a concentration of up to 70 µg/mL for 30 to 40 minutes at 4° C.

In some embodiments of the invention, the antigen binding molecules of the present invention have a $K_D$ value for soluble LIGHT of more than about 1 nM. In a more preferred embodiment, the antigen binding molecules of the present invention have a $K_D$ value for soluble LIGHT of more than about 5 nM. In a more preferred embodiment, the antigen binding molecules of the present invention have a $K_D$ value for soluble LIGHT of more than about 10 nM.

In particular embodiments of the invention, the antigen binding molecules have a $K_D$ value for membrane LIGHT of less than about 1 nM and a $K_D$ value for soluble LIGHT of more than about 1 nM. In a preferred embodiment, the antigen binding molecules have a $K_D$ value for membrane LIGHT of less than about 1 nM and a $K_D$ value for soluble LIGHT of more than about 5 nM. In a most preferred embodiment, the antigen binding molecules have a $K_D$ value for membrane LIGHT of less than about 0.5 nM and a $K_D$ value for soluble LIGHT of more than about 10 nM, or a $K_D$ value for membrane LIGHT about 0.1 nM and a $K_D$ value for soluble LIGHT of more than about 10 nM.

In some embodiments of the invention, the inventors have discovered the antigen binding molecules decrease the secretion of IL-8. In further embodiments of the invention, the binding of DcR3 (decoy receptor 3) to LIGHT, in particular membrane light, is partially inhibited by the antigen binding molecules of the invention. Notably, unlike some antibodies of the prior art (such as F19), the antigen binding molecules of the invention do not show complete inhibition of DcR3 binding to LIGHT.

Alternatively, the antigen binding molecules of the invention inhibit the binding of LIGHT to DcR3 (or cells expression LIGHT to DcR3) by up to about 45%, or up to about 35%, as measured using a competition binding assay of anti-membrane LIGHT antibodies with His tagged DcR3 (DcR3-His). Such a competition binding assay may be as follows: percent inhibition of LIGHT binding to DcR3 as measured using flow cytometry analysis of EL4-LIGHT cells preincubated with a test antigen binding molecule at a concentration of up to 100 nM for 15 min at 4° C. followed by incubation with 1 nM histidine-tagged DcR3 for 30 min at 4° C., and as compared to anti-hen egg lysozyme (HEL) antibody as a control.

The present inventors have also found that the antigen binding molecules of the invention inhibit the binding of membrane LIGHT expressing cells to HVEM and/or LTβR. In some embodiments, the antigen binding molecules of the invention inhibit the binding by at least about 25%, at least about 50% or preferably at least about 75%. In some embodiments, binding is completely inhibited. The IC50 for inhibition of binding to HVEM may be less than about 50 nM, or less than 30 mM, or between about 0.1 nM and about 30 nM, or between about 0.1 nM and 5 nM, for example as measured in EL4 cells. The IC50 for inhibition of binding to LTβR may be less than about 50 nM, or between about 0.1 and about 40 nM, for example as measured in EL4 cells. A suitable assay for measuring IC50 using EL4-LIGHT cells may be as follows: 50 µl of test antigen binding molecule up to 300 nM is incubated with EL4-LIGHT cells for 30 min at 4° C., followed by 50 µl of labelled test ligand (HVEM or LTBR), for example at a concentration of two times the EC50 for the test ligand binding to LIGHT, for 90 minutes at 4° C., as compared to anti-HEL mAb as a control.

The IC50 for inhibition of IL-8 secretion may be less than about 50 nM, or between about 0.05 nM and about 2.5 nM, for example as measured in inhibition of IL-8 secretion from HT-29 cells stimulated by membrane LIGHT expressed in EL4-NC-LIGHT cells. For example, a suitable assay can be incubation of up to 100 nM test antigen binding molecule with EL4-NC-LIGHT cells for 15 min at 37° C., followed by incubation with HT-29 cells for 2 hours at 37° C. and 5% $CO_2$, compared to HT29 cells alone as a control.

In one aspect, an anti-LIGHT antigen binding molecule, for example an antibody, fragment or variant thereof is provided, wherein the antigen binding molecule competes for binding to LIGHT with an antigen binding molecule of the invention as defined above.

For example, in one embodiment the invention provides an antigen binding molecule (preferably an antibody) wherein the antigen binding molecule specifically binds to LIGHT, in particular membrane LIGHT, and competes for binding to (membrane) LIGHT with an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16. Antigen binding molecules that compete with the fragments and variants thereof for binding to membrane LIGHT are also provided (for example antigen binding molecules comprising the 6 CDR regions or the VH and VL sequences of the above antibodies, as well as other variants).

To determine if a test antigen binding molecule can compete for binding to the same epitope as the epitope bound by the antibodies of the present invention, a cross-blocking assay e.g., a competitive ELISA assay can be performed. In an exemplary competitive ELISA assay, LIGHT-coated wells of a microtiter plate, or LIGHT-coated sepharose beads, are pre-incubated with or without candidate competing antibody and then a biotin-labelled anti-LIGHT antibody of the invention is added. The amount of labelled anti-LIGHT antibody bound to the LIGHT antigen in the wells or on the beads can be measured using avidin peroxidase conjugate and appropriate substrate.

Alternatively, the anti-LIGHT antibody can be labelled, e.g., with a radioactive or fluorescent label or some other detectable and measurable label. The amount of labelled anti-LIGHT antibody that binds to the antigen will have an inverse correlation to the ability of the candidate competing antibody (test antigen binding molecule) to compete for binding to the same epitope on the antigen, i.e., the greater the affinity of the test antigen binding molecule for the same epitope, the less labelled anti-LIGHT antibody will be bound to the antigen-coated wells.

A candidate competing antibody is considered an antibody that binds substantially to the same epitope or that competes for binding to the same epitope as an anti-LIGHT antibody of the invention if the candidate competing antibody can block binding of the anti-LIGHT antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

In one embodiment of the invention, there is provided an anti-LIGHT antigen binding molecule, for example an antibody, fragment or variant thereof, wherein the antigen binding molecule competes for binding to LIGHT with an antigen binding molecule of the invention as defined above, wherein the competing antibody can block binding of the anti-LIGHT antibody of the invention by at least 50% as measured in a competitive ELISA assay.

There is also provided an antigen binding molecule that specifically binds to membrane LIGHT and inhibits the binding of membrane LIGHT to an antigen binding molecule of the invention.

For example, in one embodiment, the antigen binding molecule (preferably an antibody) specifically binds to membrane LIGHT and inhibits the binding of membrane LIGHT to an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16. Antigen binding molecules that specifically bind to membrane LIGHT and inhibit the binding of membrane LIGHT to fragments and variants thereof are also provided (for example antigen binding molecules comprising the 6 CDR regions or the VH and VL sequences of the above antibodies, as well as other variants).

There is also provided an antigen binding molecule that specifically binds to an epitope of LIGHT that is bound by an antigen binding molecule of the invention.

For example, in one embodiment the invention provides an antigen binding molecule (preferably an antibody) wherein the antigen binding molecule specifically binds to an epitope of LIGHT that is bound by an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16. Antigen binding molecules that specifically bind to an epitope of LIGHT that is bound by fragments and variants thereof are also provided (for example antigen binding molecules comprising the 6 CDR regions or the VH and VL sequences of the above antibodies, as well as other variants).

In one aspect, there is also provided an antigen binding molecule that specifically binds to an epitope of LIGHT that is different to the DcR3 binding region (i.e. amino acids 170 to 178 of human LIGHT).

For example, in one embodiment the invention provides an antigen binding molecule that specifically binds to an epitope of human LIGHT wherein the epitope comprises one or more amino acid residues comprised in the amino acid stretch GRATSSSRVW (SEQ ID NO: 124). In one embodiment, the invention provides an antigen binding molecule that specifically binds to an epitope of human LIGHT wherein the epitope comprises the amino acid sequence GRATSSSRVW (SEQ ID NO: 124). The epitope GRATSSSRVW may be of particular relevance to anti-LIGHT antigen binding molecules that preferentially bind the membrane form of LIGHT (i.e. LIGHT in its trimeric form). Epitopes may be determined by any suitable method known in the art, for example an alanine scanning method.

In one embodiment, there is provided an antigen binding molecule that specifically binds to an epitope of human LIGHT wherein the epitope comprises one or more amino acid residues comprised in the amino acid stretch of amino acids 188 to 197 of SEQ ID NO: 121, 122 or 123 (GRATSSSRVW).

In one embodiment the invention provides an antigen binding molecule that specifically binds to an epitope of human LIGHT wherein the epitope comprises one or more amino acid residues comprised in the amino acid stretch GRATSSSRVW (SEQ ID NO: 124) and wherein the antigen binding molecule is selected from 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, or a fragment or variant thereof.

In one embodiment, the invention provides an antigen binding molecule that specifically binds to an epitope of human LIGHT wherein the epitope comprises the amino acids GRATSSSRVW (SEQ ID NO: 124) and wherein the antigen binding molecule is selected from 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, or fragments or variants thereof.

In one embodiment, an antigen binding molecule that specifically binds human LIGHT is provided wherein the epitope bound by the antigen-binding molecule comprises GRATSSSRVW (SEQ ID NO: 124) and wherein the antigen binding molecule is 3B04_var16, or a variant or fragment thereof. In one embodiment, an antigen binding molecule that specifically binds human LIGHT is provided wherein the epitope bound by the antigen-binding molecule comprises GRATSSSRVW (SEQ ID NO: 124) and wherein the antigen binding molecule is 3B04, or a variant or fragment thereof. In one embodiment, an antigen binding molecule that specifically binds human LIGHT is provided wherein the epitope bound by the antigen-binding molecule comprises GRATSSSRVW (SEQ ID NO: 124) and wherein the antigen binding molecule is 3D12, or a variant or fragment thereof.

In contrast to known antibodies to LIGHT which may bind native trimeric LIGHT in a ratio of three antibodies bound to one native LIGHT trimer (3:1 ratio of antibody molecule to LIGHT trimer), the antigen binding molecules of the present invention have a binding ratio of 1:1, i.e. one antigen binding molecule of the present invention binds to one native LIGHT trimer. In one embodiment, an antigen binding molecule that specifically binds human LIGHT is provided wherein the ratio of binding of the antigen binding molecule to human LIGHT trimer is 1:1.

In one embodiment, an antigen binding molecule that specifically binds human LIGHT is provided wherein the antigen-binding molecule binds to a trimer of human LIGHT in a ratio of 1:1 and wherein the antigen binding molecule is selected from 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, or a fragment or variant thereof.

In one embodiment, an antigen binding molecule that specifically binds human LIGHT is provided wherein the antigen-binding molecule binds to a trimer of human LIGHT in a ratio of 1:1 and wherein the antigen binding molecule is 3B04_var16, or a variant or fragment thereof. In one embodiment, an antigen binding molecule that specifically binds human LIGHT is provided wherein the antigen-binding molecule binds to a trimer of human LIGHT in a ratio of 1:1 and wherein the antigen binding molecule is 3B04, or a variant or fragment thereof. In one embodiment, an antigen binding molecule that specifically binds human LIGHT is provided wherein the antigen-binding molecule binds to a trimer of human LIGHT in a ratio of 1:1 and wherein the antigen binding molecule is 3D12, or a variant or fragment thereof.

In one embodiment, there is provided an antigen binding molecule that specifically binds to an epitope of human LIGHT wherein the antigen-binding molecule binds to a trimer of human LIGHT in a ratio of 1:1 and wherein the epitope bound by the antigen-binding molecule comprises GRATSSSRVW (SEQ ID NO: 124).

In one embodiment, there is provided an antigen binding molecule that specifically binds to human LIGHT wherein the antigen binding molecule has a higher affinity for membrane-bound LIGHT compared to soluble LIGHT (for example at least a 50-times preference for membrane LIGHT) and wherein the epitope bound by the antigen-binding molecule comprises GRATSSSRVW (SEQ ID NO: 124).

In one embodiment, there is provided an antigen binding molecule that specifically binds to human LIGHT wherein the antigen-binding molecule binds to a trimer of human LIGHT in a ratio of 1:1 and wherein the antigen binding molecule has a higher affinity for membrane-bound LIGHT compared to soluble LIGHT (for example at least a 50-times preference for membrane LIGHT).

In one embodiment, there is provided an antigen binding molecule that specifically binds to an epitope of human LIGHT;
  wherein the antigen-binding molecule binds to a trimer of human LIGHT in a ratio of 1:1 (for example at least a 50-times preference for membrane LIGHT); and
  wherein the antigen binding molecule has a higher affinity for membrane-bound LIGHT compared to soluble LIGHT;
  and wherein the epitope bound by the antigen-binding molecule comprises GRATSSSRVW (SEQ ID NO: 124).

Compositions

In one aspect of the invention, a pharmaceutical composition comprising an antigen binding molecule of the invention is provided.

The compositions of the invention can be formulated for use by any convenient route. The pharmaceutical composition of the invention will normally include a pharmaceutically acceptable carrier, excipient, diluent, adjuvant, vehicle, buffer or stabiliser in addition to an antigen binding molecule of the invention. Such carriers include, but are not limited to, saline, buffered saline, dextrose, liposomes, water, glycerol, polyethylene glycol, ethanol and combinations thereof.

The pharmaceutical composition may be in any suitable form depending upon the desired method of administering it to a patient.

The pharmaceutical compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will of course depend on the condition being treated, the route of administration and the age, weight and condition of the patient and will be at the doctor's discretion.

The pharmaceutical compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. IV administration may be preferred. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical compositions of the invention can also contain one or more other therapeutically active agents in addition to the molecule of the present invention.

In some embodiments, the formulation of the active drug concentrate can comprise a pharmaceutically acceptable tonicity agent, a buffering agent, and a pharmaceutically acceptable surfactant.

Alternatively, the formulation can comprise the active ingredient plus sodium phosphate, monobasic, sodium phosphate dibasic, sodium chloride, polysorbate 80 or polysorbate 20 (surfactant to minimise risk of agitation-induced aggregation) and water (USP/Ph.Eur), optionally with a pH adjusted to about 6.0 to 7.0, e.g. around 6.5.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

Methods of Treatment

The antigen binding molecules of the invention are useful in preventing and/or treating LIGHT-mediated disorders or diseases, in particular inflammatory disorders or diseases. This aspect of the invention therefore also includes a method for the treatment of a LIGHT-mediated disorder or disease (such as an inflammatory disorder or disease) in a subject, comprising administering to the subject an antigen binding molecule of the invention. The invention therefore also extends to the use of an antigen binding molecule of the invention in the manufacture of a medicament for use in the treatment and/or prevention of a LIGHT-mediate disorder or disease (such as an inflammatory disorder or disease), and use of the antigen binding molecules of the invention in prevention and/or treatment of such conditions.

The method of treatment can be of a human or an animal subject and the invention extends equally to uses in both human and/or veterinary medicine. The antigen binding molecule of the invention is preferably administered to an individual in a "therapeutically effective amount", this being sufficient to show benefit to the individual. As used herein, "treatment" includes any regime that can benefit a human or non-human animal, preferably a mammal. The treatment may be in respect of an existing condition or may be prophylactic (preventative treatment).

In one embodiment, the antigen binding molecules of the invention are for use in inflammation, inflammatory disorders including autoimmune diseases. In a preferred embodiment, the antigen binding molecules of the invention are for use in treating inflammatory bowel disease. As used herein "inflammatory bowel disease" (IBD) relates to inflammatory conditions of the colon and small intestine. These include ankylosing spondylitis, atopic dermatitis, coeliac disease, inflammatory bowel disease (IBD), Crohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), chronic heart failure, chronic obstructive pulmonary disease, kidney disease, septic shock, ulcerative colitis, fibrosis (i.e. fibrotic disease), multiple sclerosis, Sjogren's syndrome, lupus, airway inflammation, liver disease, hepatitis, coeliac disease, dermatitis, eosinophilia and primary biliary cirrhosis. Of particular interest is the treatment of inflammatory bowel disease such as ulcerative colitis and Crohn's disease.

Depending on the condition being treated, the antigen binding molecules of the invention may be used in combination with other pharmaceutically active components for simultaneous, separate or sequential use. For example, when treating an inflammatory disease or disorder, the antigen binding molecules of the invention may be used in combination with anti-inflammatory agents. Suitable anti-inflammatory agents include non-steroidal anti-inflammatory drugs (NSAIDS) and steroids. NSAIDS may be preferred, including but not limited to salicylates (such as aspirin (acetylsalicylic acid), diflunisal, salicylic acid, salsalate), propionic acid derivatives (ibuprofen, dexibuprofen, naproxen), acetic acid derivatives (indomethacin, diclofenac), enolic acid derivatives, anthranilic acid derivatives (fenamates), selective COX-2 inhibitors, and sulfonanilides.

When treating an immune-mediate disorder or disease, immunosuppressants may be used, for example glucocorticoids, cytostatics (such as alkylating agents, antimetabolites, methotrexate, azathioprine, mercaptopurine, or cytotoxic antibiotics). Of particular relevance to GvHD are glucocorticoids, such as cortisol, cortisone, prednisone, prednisolone, methylprednisolone, dexamethasone, betamethasone, triamcinolone, beclomethasone, fludrocortisone, deoxycorticosterone and aldosterone).

Further additional components that are desirable to use in combination with the antigen binding molecules of the invention include TNF-inhibitors, IL-12 inhibitors, IL-23 inhibitors and α4β7 integrin inhibitors. The inhibitors may themselves be antigen binding molecules, such as antibodies and preferably monoclonal antibodies.

Suitable TNF inhibitors include infliximab (Remicade), adalimumab (Humira), certolizumab pegol (Cimzia), and golimumab (Simponi). Suitable IL-12 and IL-23 inhibitors include ustekinumab (Stelara), which is an inhibitor of both. Suitable α4β7 integrin inhibitors include vedolizumab (Entyvio).

The pharmaceutical compositions of the invention may be formulated to include one or more additional pharmaceutically active components, such as those listed above. The antigen binding molecules of the invention may be provided as part of a kit. Such kits may include instructions for use and/or additional pharmaceutically active components. The antigen binding molecules may and the additional pharmaceutically active components may be disposed separately within the kit, or in some embodiments the antigen binding molecules may and the additional pharmaceutically active components may be formulated together.

In one embodiment of the invention there is provided an antibody, in particular a monoclonal antibody, that specifically binds to LIGHT. The antibody is selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16. The antibodies are of use in the treatment of inflammatory diseases, including IBD.

In one embodiment, the invention provides an antigen binding molecule that specifically binds to an epitope of human LIGHT, wherein the antigen binding molecule is selected from 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, or fragments or variants thereof, for use in the treatment of ankylosing spondylitis, atopic dermatitis, coeliac disease, inflammatory bowel disease (IBD), Crohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), chronic heart failure, chronic obstructive pulmonary disease, kidney disease, septic shock, ulcerative colitis, fibrotic disease, multiple sclerosis, Sjogren's syndrome, lupus, airway inflammation, liver disease, hepatitis, coeliac disease, dermatitis, eosinophilia and primary biliary cirrhosis.

In one embodiment, the invention provides an antigen binding molecule that specifically binds to an epitope of human LIGHT, wherein the antigen binding molecule is selected from 3B04, 3D12, and 3B04_var16, or fragments or variants thereof, for use in the treatment of inflammatory bowel disease. In one embodiment, the antigen binding molecule is 3B04_var16.

In one embodiment, the invention provides an antigen binding molecule that specifically binds to an epitope of human LIGHT, wherein the antigen binding molecule is selected from 3B04, 3D12, and 3B04_var16, or fragments or variants thereof, for use in the treatment of Crohn's disease. In one embodiment, the antigen binding molecule is 3B04_var16.

In one embodiment, the invention provides an antigen binding molecule that specifically binds to an epitope of human LIGHT, wherein the antigen binding molecule is selected from 3B04, 3D12, and 3B04_var16, or fragments or variants thereof, for use in the treatment of ulcerative colitis. In one embodiment, the antigen binding molecule is 3B04_var16.

This aspect of the invention therefore also extends to a method of treatment of inflammatory bowel disorders, comprising administration to the subject an antigen-binding molecule of the invention. In one embodiment, the inflammatory bowel disease may be Crohn's disease. In one embodiment, the inflammatory bowel disease may be ulcerative colitis. In an alternative embodiment, the invention may be seen as providing the use of an antigen binding molecule of the invention in the preparation of a medicament for the treatment of inflammatory bowel disorders. In one embodiment, the inflammatory bowel disease may be Crohn's disease. In one embodiment, the inflammatory bowel disease may be ulcerative colitis.

The present invention will now be further described with reference to a number of specific examples, which are presented for illustrated purposes and are not to be construed as limiting on the scope of the invention.

EXAMPLES

Antigen Preparation, Immunization Procedures, RNA Extraction and Fab Generation

The following example provides a detailed description of the generation and identification of a panel of anti-human membrane LIGHT Fabs. An immune-tolerizing protocol was employed to generate anti-human membrane LIGHT Fabs using a modified immunization procedure that included sequential injections of human soluble recombinant human LIGHT (amino acids 74-240), cyclophosphamide, and a recombinant cell line expressing LIGHT. This protocol effectively amplified clones with reactivity toward membrane LIGHT epitopes. The method employed is similar to the protocols described in Salata R A et al. (Application of an immune-tolerizing procedure to generate monoclonal antibodies specific to an alternate protein isoform of bovine growth hormone. Anal Biochem. 1992 Nov. 15; 207(1):142-9) and Chin N W et al. (A novel monoclonal antibody to cytokeratin 18 with reactivity toward lung squamous cell carcinomas and adenocarcinomas of various sites. Am J Pathol. 1992 May; 140(5):1061-9).

Cloning and Expression of Recombinant Human LIGHT (214E) and Cynomolgus LIGHT cDNA encoding the full length human LIGHT (214E allele) and for the cynomolgus (*Macaca fascicularis*) LIGHT protein were cloned into the pCDNA3.1(+) expression vector via KpnI/NotI.

0.5-5.0+06 cells of CHO-K1 cells (ATCC® CCL-61TM) and of HEK293FF cells (Invitrogen, R79007) were transfected with 30 micrograms of the human or cynomolgus monkey LIGHT constructs using Lipofectamine 2000 transfection reagent (Invitrogen, 11668019) according to the manufacturer's instruction. 24 hours after, transfected and non-transfected cells were assayed for cell surface expression of human and cynomolgus monkey LIGHT by flow cytometry assay using a mouse anti-LIGHT antibody (R&D Systems, MAB664) followed by a goat anti-mouse APC conjugated antibody (BD Biosciences, 550826). Results showed that 26% and 50% of CHO-K1 and HEK293FF cells transfected with the human construct respectively showed expression of LIGHT protein. In the case of cells transfected with the cynomolgus construct, 36% and 53% of transfected CHO-K1 and HEK293FF cells respectively showed expression of LIGHT protein. No LIGHT expression was detected in any of the non-transfected cell lines.

Immunization Procedure

Balb/c mice were immunized i.p. with 10 ug of recombinant human soluble LIGHT protein (R&D Systems, 664-LI-025) in Sigma adjuvant system (SAF, Sigma-Aldrich, 56322-1VL) every 2 weeks for a total of 3 injections. Cyclophosphamide monohydrate (Sigma cat. no. C0768) was injected i.p., 0.1 ml/mice (20 mg/ml in PBS) at 15 min, 1 and 2 days after the soluble LIGHT. This procedure was repeated two times at two week intervals. On day 42 200 µl of CHO-LIGHT cells ($6 \times 10^6$) in SAF was injected i.p. into each mouse and repeated on day 56 and day 70. On day 87 CHO-LIGHT cells ($6 \times 10^6$) were injected i.v. and the spleens harvested on day 91.

Determination of Serum Titers by FACS Using HEK293FF Human LIGHT Cells $2 \times 10^5$ WT HEK293FF cells, HEK293FF-human LIGHT cells or HEK293FF-cynomolgus LIGHT cells in 100 µl FACS buffer (1×PBS+0.5% Hi-FBS) were distributed to a 96 well U-bottom plate (Greiner) and stained with a reference antibody, (Human LIGHT/TNFSF14 MAb664, R&D Systems), or incubated with a titration of mouse serum previously prepared, diluted in FACS buffer, for 60 min at 4° C. After incubation, cells plus serum samples were washed 3 times with FACS Buffer and incubated with 50 µl of secondary goat anti-mouse APC conjugated antibody at 1:500 dilution (BD Biosciences, 550826) for 30 min at 4° C. and protected from the light. After incubation cells were washed 3 times in FACS buffer and then resuspended in 100 µl FACS buffer. Positive APC signal intensity (geomean and percent binding) was measured by flow cytometry using a FACS Accuri C6 instrument, in the FL4 channel.

RNA Extraction, and Fab Generation

For each immunized mouse, a cell suspension was prepared from half a spleen by mechanical and thermal treatment using DNAse/RNAse free tissue grinder and TRIzol reagent (AMBION, cat. nr. 15596026). RNA extraction from the cell suspension was performed using the Direct-zol RNA MiniPrep Kit (Zymo Research, cat. nr. R2050) according to manufacturer's specifications. Purity and integrity of extracted RNA was confirmed by measuring optical density at 260 and 280 nm and by visual analysis in a 1% agarose/TAE gel of bands corresponding to 28S and 18S rRNA.

Fab Library Construction

Amplification of antibody genes from immune repertoires. From the extracted RNA, cDNA was synthesized by RT-PCR using the SuperScript III First Strand Synthesis System (Invitrogen, cat. nr. 18080-051). The genes codifying for the variable domain of the heavy chain (VH), the first constant domain of IgG1 heavy chain and a portion of the hinge (CH1-Hinge), the variable domain (Vκ) and the constant domain (Cκ) of the antibody kappa light chain were PCR amplified from the cDNA using the Expand High Fidelity System (Roche, cat. nr. 4738268001). The primers used in these PCR reactions were designed to anneal in the mouse Hinge and in the 3' of Cκ region as well as in the 5' of framework one region of different mouse V genes. Nested PCR were performed using the previous amplification products as template and the same primers as used above tagged with the restriction sites needed for further cloning into a phagemid.

Per mouse the genes codifying for the VH1, CH1 and a small portion of hinge and the genes codifying for Vκ and Cκ were cloned separately into a phagemid and transformed into E. coli TG1 cells leading to heavy chain and light chain sub-libraries.

The final Fab library was constructed by cloning the VHCH1-Hinge inserts obtained by digesting the heavy chain sub-library DNA into the phagemid vector containing the light chain sub-library and by transforming E. coli TG1 cells. In total four Fab phage display libraries, where the phage particles express Fabs as a fusion protein with a C-terminal His6-c-myc tag and with the Gene-III protein, were generated with size varying from 4.0E+08 to 8.8E+09 cfu's.

Periplasmic Extract Screening in HEK293FF Human LIGHT Cells

Periplasmic extracts (P.E.) were diluted 1:5 in FACS Buffer (1×PBS+0.5% Hi-FBS) and incubated with mouse anti-c-myc at 1:1000 dilution (Gentaur CMYC-9E10, 0.5 mg/ml) in a final volume of 100 µl, 30 min at RT on a plate shaker. 2,0E+05 HEK293FF Human LIGHT transfected cells were incubated with 100 µl of mix P.E. and mouse anti-c-myc for 60 min at 4° C. on a plate shaker. Cells were then washed 3 times with FACS Buffer and stained with 50 µl of goat anti-mouse APC at 1:500 dilution for 30 min at 4° C. on a plate shaker. At the end cells were washed 3 times with FACS Buffer, resuspended in 100 µl FACS buffer and positive binders read in the FL4 channel by flow cytometry using a FACS Accuri C6 instrument.

Competition Assay for Selection of Specific Fab Clones in HEK293FF Human LIGHT Cells Purified Fabs of each of the 8 positive screened clones (EC50 concentrations) were incubated with and without 1 µg Soluble LIGHT Protein 30 min at RT. After incubation 100 µl mix of Fabs plus Soluble LIGHT protein were incubated with 2,0E+05 HEK293FF Human LIGHT cells 60 minutes at 4° C. on a plate shaker. Cells were washed 3 times with FACS Buffer and stained with 50 µl of goat anti-mouse APC at 1:500 dilution for 30 min at 4° C. on a plate shaker. At last cells were washed 3 times with FACS Buffer and positive binders read in the FL4 channel by flow cytometry using a FACS Accuri C6 instrument.

Selections and Screening of LIGHT Specific Fabs

Phage expressing Fabs were produced according to standard protocols using VCSM13 helper phage, precipitated in PEG/NaCl and used in two consecutive rounds of panning on cells expressing human LIGHT were performed. Transfected HEK293FF and CHO-K1 cells were used in the first and the second round respectively. Phage were incubated with cells in solution for one hour at 4° C. and then washed several times with 10% FBS/PBS. Bound phages were retrieved using trypsin at room temperature. Protease activity was immediately neutralized by protease inhibitor AEBSF. All phage outputs were infected into logarithmically grown E. coli TG1 cells and production of soluble Fabs in individual E. coli cells induced by isopropyl 1-thio-β-D-galactopyranoside. Bacteria periplasmic extracts containing soluble Fab (P.E.s) were extracted by a freeze/thaw cycle, bacteria were pelleted and frozen at −20° C. for overnight and then thawed at room temperature and resuspended in PBS. The supernatants containing the soluble Fab (P.E.) were collected after 30 min shaking at room temperature and centrifugation. A total of 380 P.E.s containing soluble Fabs were tested in FACs for binding to human LIGHT transfected and non-transfected HEK293FF cells. Binding of soluble Fabs was assessed by detecting the associated c-myc tag using an anti-myc antibody (Gentaur, cat. nr. 04-CMYC-9E10) and a goat anti-mouse APC conjugated antibody (BD Biosciences, cat. nr. 550826). Results were analyzed by looking to percentage of positive cells (%) and mean intensity Fluorescence levels (MFI) in the FL4-A channel detector of a flow cytometer (Accuri C6, BD Biosciences) A total of 70 clones showed binding to transfected cells, with one clone also showing binding to non-transfected cells.

Neutralization Assay for Selection of Specific P.E. Clones in HEK293FF Human LIGHT Cells HEK293FF Human LIGHT transfected cells were incubated 120 min 4° C. on a plate shaker with: 50 µl of P.E. from the selected clones (1:5) previously incubated with mouse anti-c-myc (1:1000) 30 min at RT on a plate shaker and 50 µl of LTβR-Fc ligand (15 nM-EC50; R&D Systems cat. no. 356-HV-100) or 50 µl HVEM-Fc (45 nM-EC50; R&D Systems cat. no. 629-LR-100). Cells were washed 3 times with FACS buffer and stained with 50 µl of goat anti-mouse APC at 1:500 dilution for 30 min at 4° C. on a plate shaker. At the end cells were washed 3 times with FACS Buffer and positive binders read in the FL4 channel by flow cytometry using a FACS Accuri C6 instrument. As control, cells were incubated only with ligands and detected using 50 µl of goat anti-Human IgG FITC (Sigma Cat. No. F9512-2ML, 1:1500) (FL1 channel). From the 69 positive binders in the primary screen 24 neutralizing Fabs were selected by the inventors that inhibited both LTβR-Fc and HVEM-Fc binding to LIGHT expressed on HEK293FF cells.

Competition Assay with Soluble LIGHT and Cynomolgus Monkey Cross Reactivity

P.E. of the 69 clones showing specific binding to human LIGHT expressing HEK293FF cells were re-tested for binding to the same cells in the presence and absence of soluble LIGHT protein (R&D Systems, cat. no. 664-LI0252). The amount of soluble LIGHT to be used in the competition assay (10 µg/ml), was determined by testing different amounts of soluble LIGHT that could block the binding of anti-LIGHT antibody (R&D Systems, cat. no. MAB664) to cells. The P.E.s from the 69 clones, were pre-incubated with mouse anti-c-myc antibody (Gentaur, cat. no. 04-CMYC- 9E10), in the presence or absence of 10 µg/ml of LIGHT protein and then added to human LIGHT HEK293FF transfected cells. For determination of specific membrane LIGHT binders, the ratio of the % of binding and MFI values of the P.E in the presence or absence of soluble LIGHT, was calculated, with the clones presenting values above 0.70 being consider as membrane LIGHT specific binders.

A total of 24 membrane LIGHT specific binder clones were identified. These clones were also tested for binding HEK293FF cells transfected with cynomolgus monkey LIGHT construct. As a result, seven anti-LIGHT Fabs were classified as human/cynomolgus cross-reactive.

Generation of Chimeric mAbs

Synthetic genes codifying for the variable domains of seven anti-LIGHT mouse Fabs plus of an irrelevant Fab were recloned into mammalian expression vectors comprising the human IgG4 HC (with S-to-P conversion at position 214 to prevent IgG4 switching and L-to-E conversion at position 248 to ablate residual Fc receptor binding activity) and human CL domains. Co-transfection of heavy and light chain containing vector in a mammalian expression system was performed, followed by protein A-based purification of the chimera IgG, quantification and QC on denaturing and non-denaturing PAGE. Nu-Page analysis confirm the purity and the presence of a 150 KDa band for non-reducing conditions and two bands (50 and 25 KDa) under reducing conditions.

Equilibrium Binding of Anti-LIGHT IgG4 to LIGHT on EL4 Cells.

Stably transduced LIGHT expressing EL4 cells (mouse lymphoma cell line; EL4-LIGHT; Cheung et al. J. Immunol. 2009; 183:7286-7296) were used for the flow cytometry-based binding analysis. EL4-LIGHT cells ($0.25 \times 10^6$ per well) that had been washed in were incubated with anti-LIGHT IgG4 clones (0.002-100 nM) for 30 min at 4° C. The cells were washed and anti-human IgG-APC conjugate (diluted 1:500, Biolegend cat. No. 409306) was used for detecting anti-LIGHT IgG bound on EL4-LIGHT cells.

Inhibition of HVEM and LTBR Binding to EL4-LIGHT Cells by Anti-Membrane LIGHT mAbs Biotin-LTβR-Fc and biotin-HVEM-Fc were prepared using a kit purchased from ThermoFisher (EZ-Link NHS-LC-Biotin; cat. no. 21336) according to the manufacturer's instructions. The binding competition assay with anti-membrane LIGHT antibodies in EL4-LIGHT cells was as follows: 50 µl/well of the antibodies 3D12, 3B04, 3E09, 2B11, 2E08, 3A07, 3C10; (3-fold dilutions 300 nM to 0,005 nM) were added to EL4-LIGHT cells ($0.25 \times 10^6$) and incubated for 30 min at 4° C. and then 50 µl/well of each ligand (biotin-LTβR-Fc or biotin-HVEM-Fc) at two times the EC50 concentration was added to EL4-LIGHT cells alone or plus antibodies, and incubated for 90 min at 4° C. The diluent used was FACS buffer. The cells were washed 3 times with FACS buffer and biotin-LTβR-Fc and biotin-HVEM-Fc binding detection to cells was performed with streptavidin-APC (1:400; BioLegend cat. No. 405207) for 30 min at 4° C. and fluorescence read in the RL-1 channel. The anti-HEL mAb 2A11 was utilised as a background control.

Inhibition of IL-8 Secretion from HT-29 Cells by Anti-Membrane LIGHT mAbs

CHO K1-LIGHT Cell Assay

HT29 cells (American Type Culture Collection, ATCC #HTB-38) were maintained in McCoys 5a medium (GIBCO)+10% v/v FBS (GIBCO). Cells were split between 1:4 and 1:12 from 100% confluency for routine culture. 100 µl $0.03 \times 10^6$ transiently transfected LIGHT CHO K1 cells were incubated with anti-membrane LIGHT antibodies (or a negative control anti-HEL, hen egg lysosome antibody) for 30 min at 37° C. in cell culture media and then added to 100 µl $1 \times 10^5$ HT29 cells and incubated for 6 hours at 37° C. in the $CO_2$ cell incubator chamber. Supernatant was recovered and IL-8 levels determined using a human IL-8 Duo-set ELISA Kit (R&D Systems). A negative control of HT29 cells was included as well as positive controls of HT-29 cells plus TNFα (10 ng/ml) or LTα1β2 (0.5 µg/ml).

EL4-NC-LIGHT Cell Assay

HT29 cells (American Type Culture Collection, ATCC #HTB-38) were maintained in McCoys 5a medium (GIBCO)+10% v/v FBS (GIBCO). Cells were split between 1:4 and 1:12 from 100% confluency for routine culture. 100 µl $1 \times 10^5$ HT-29 cells were incubated overnight in a humidified atmosphere chamber at 37° C. with 5% $CO_2$ in media.

EL4-NC-LIGHT cells (prepared as EL4-LIGHT cells except using stably transfected LIGHT without residues 81-84 to limit LIGHT cleavage) are centrifuged and washed with culture medium then resuspended in cell culture medium, to a final concentration of $2.5 \times 10^6$ cells/ml and 100 µl ($2.5 \times 10^5$ cells/well) is preincubated with 100 µl/well of the anti-LIGHT antibodies, in a round bottom 96 well plate, for 15 min at 37° C. The culture medium from the 96-well plate containing HT-29 seeded cells is aspirated and the anti-LIGHT antibodies plus EL4-NC-LIGHT cells, (in a total volume of 200 µl) is added to the HT29-cells and incubated for 2 hours in the cell culture incubator with humidified atmosphere at 37° C. and 5% $CO_2$. The supernatant is recovered and IL-8 levels determined using a human IL-8 Duo-set ELISA Kit (R&D Systems). A negative control of HT29 cells was included as well as positive controls of HT-29 cells plus TNFα (10 ng/ml) or LTα1β2 (0.5 µg/ml).

Competition Binding of Anti-Membrane LIGHT Antibodies with DcR3

DcR3 (TNFRSF6B) is a decoy receptor that competes with receptors for ligand binding. DcR3 can bind and neutralise LIGHT with high affinity and TL1A and FasL with lower affinity (Zhan C et al. Structure. 2011, 19:162-71 "Decoy strategies: the structure of TL1A:DcR3 complex"). Stably transduced LIGHT-expressing EL4 cells (mouse lymphoma cell line; EL4-LIGHT) were used for the flow cytometry-based competition-binding analysis.

Assay with DcR3-His Tagged

EL4-LIGHT cells ($0.25 \times 10^6$) were preincubated with anti-membrane LIGHT mAbs (0-300 nM) for 15 min at 4° C. followed by incubation with DcR3-His tagged (1 nM, Creative BioMart; ref: TNFRSF6B-552H, lot: 962512) for 30 min at 4° C. The samples were then incubated with mouse anti-histag antibody (diluted 1:500, Biolegend, cat. no. 652502) for 30 minutes at 4° C., followed by incubation with anti-mouse APC (dil 1:500, BDBiosciences, cat. no. 550826) for 30 minutes at 4° C. The tubes were washed three times after each of the detection antibody stages and flow cytometry analysis was performed. Specific mean fluorescence intensity (MFI) obtained from the binding of DcR3-His to LIGHT on EL4 cells were used to determine the levels of competition binding.

Human Peripheral Blood Mononuclear Cells (PBMC) Antigen Specific Recall Response In Vitro In order to test the efficacy of anti-LIGHT mAbs on stimulated PBMC a recall antigen CMV (cytomegalovirus) lysate was utilised to stimulate PBMC from human CMV-positive donors (ImmunXperts, Belgium). 200 000 cells per well in RPMI (Thermofisher cat. no. 11875) plus 10% FBS (GIBCO) was added to CMV lysate (Serion immunologics cat. no. BA109VS, final concentration 10 ug/ml) with test mAbs in a volume of 200 ul. After a 5 day incubation at 37 C and 5% CO2 the media was recovered by centrifugation and assayed for cytokines by Luminex immunoassay (ThermoFisher).

LIGHT Expression on Th17 Cells

CD4 T cells were negatively isolated from two PBMC donors using a kit from Stem cell technologies (cat. no. 19052). The CD T cells were stimulated with anti-CD3/anti-CD28 Dynabeads according to the manufacturer's instructions (ThermoFisher cat. no. 1161D) at 100,000 CD4 cells per well in RPMI (Thermofisher) cat. no. 11875) plus 10% FBS (GIBCO) with the following polarizing cocktail of cytokines (Miltenyi biotec) (TGF-β, 5 ng/mL), IL-6 (20 ng/mL), IL-23 (20 ng/mL), and IL-1β (10 ng/mL) to induce Th17 cells. After 3 days' incubation at 37 C and 5% CO2 the cells were centrifuged at 300 g for 10 minutes and the cell culture supernatant was discarded. Cells were then washed with DPBS (ThermoFisher cat. no. A1285801) and a viability stain, Zombie NIR (BioLegend cat. no. 423106), was added to the cells and incubated for 15 min at RT. The cells were then washed with DPBS/0.1% BSA and blocked with FcR blocking reagent (BD Bioscience) for 5 minutes. Antibodies were added to the cells in DPBS/0.1% BSA and cells were incubated for 30 minutes at 4 C. The stained cells were washed with DPBS/0.1% BSA, centrifuged at 300 g for 10 minutes then resuspended in 150 μl of DPBS/0.1% BSA for flow cytometry acquisition. The following antibodies were used for cell staining as per the manufacturer's instructions: anti-CCR7 (BD Bioscience 562555); anti-CCR6 (BioLegend 353422); anti-CD45A (BD Biosciences 564552); anti-CD4 (BioLend 344624); anti-CD294 (BioLegend 350105); anti-CXCR5 (BioLegend 356924); anti-CCR4 (BioLegend 359408) and anti-CD3 (BioLegend 300324).

Measurement of Antibody Affinity to Soluble and Membrane LIGHT

The term "surface plasmon resonance", as used herein, refers to an optical phenomenon that allows for the analysis of real-time biospecific interactions by detection of alterations in protein concentrations within a biosensor matrix, for example using the BIAcore system (GE Healthcare). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

Soluble LIGHT

Real-time binding interactions between captured antibody (chimeric anti-membrane LIGHT monoclonal antibody) captured on a biosensor matrix via goat anti-human Fc IgG and recombinant soluble LIGHT were measured by surface plasmon resonance (SPR) using the BIAcore system (GE Healthcare) according to manufacturer's instructions and standard procedures. Briefly, soluble LIGHT was diluted in HBS running buffer (GE Healthcare) and aliquots were injected through the immobilized protein matrices at a flow rate of 30 μl/mm. BIAevaluation software was used to calculate association rate (ka), dissociation rate (kd) and affinity ($K_D$).

Epitope Mapping

Native Mass Spectrometry Methods

The LIGHT protein (R&D Systems 664-LI-025) was solubilised in PBS buffer at a final concentration of 4 μM, whereas the mAbs were maintained at 20 μM in PBS. The samples were buffer exchanged into ammonium acetate pH 7.4 at different concentrations via a column with a cut-off of 40 kDa prior to mass spectrometry optimisation. Up to six desalting stages were performed for the LIGHT protein and antibodies, whereas the optimal ammonium acetate concentration was found to be 200 mM. Samples were stored at 4° C. and were used within one week. The antibodies were diluted to 1 μM prior to MSanalysis. For complex formation the LIGHT protein was incubated with each antibody separately in 1:5 ratio on ice and native mass measurements were performed 30 min after incubation.

Nano electrospray ionization measurements were performed using a Q Exactive hybrid quadrupole-Orbitrap mass spectrometer (Thermo Fisher Scientific) modified for the transmission and detection of high m/z ions. The samples were electrosprayed from gold-coated capillaries at high cone and capillary voltage and high temperature, resulting to partial dissociation of native oligomers. Elevated pressure was applied in the front optics and mass spectra were recorded at optimized collision energy. High resolution measurements were performed at a resolution of 35000 whereas low resolved spectra were obtained at a resolution of 2000. Data were analysed with Xcaliber software and deconvoluted manually.

Hydrogen-Deuterium Exchange (HDX) Mass Spectrometry

The LIGHT protein (R&D Systems 664-LI-025) was solubilised in PBS buffer at a final concentration of 8 μM, whereas the antibodies were maintained at 20 μM in PBS. For complex formation the LIGHT protein was incubated with each antibody separately in 1:5 ratio on ice and HDX measurements were performed 30 min after incubation. All data were recorded on a waters Synapt G2Si equipped with a HDX platform. The loading of each sample was performed manually in order to maintain the samples at low temperature, which was found to be critical for protein stability. The deuterium labelling was performed by adding 5 μL of sample to 65 μL of deuterated PBS buffer and left to equilibrate at 4 time points, 20 s, 60s, 300s and 1800s. Subsequently each sample was quenched with 50 μL of 2M guanidinium chloride in at pH 2. The samples were passed through a pepsin column for 5 min to digest the protein and peptides were separated using a reverse phase chromatography. Data were analysed with DynamX software. Peptides were selected with a maximum length of 15 amino acids and a 5 ppm mass accuracy error. These filter settings resulted in 48 unique peptides for the LIGHT protein. The analysis was repeated 3 times for each mAb.

Alanine Scanning of Membrane LIGHT

A useful method for identification of certain residues or regions within LIGHT that are the epitope of the antibodies is called "alanine scanning mutagenesis" as described by Cunningham and Wells in *Science*, 244:1081-1085 (1989). Here, a residue or group of target residues are identified and replaced by a neutral amino acid (most preferably alanine) to affect the interaction of the amino acids with the antibody. Those amino acid locations demonstrating functional sensitivity to the substitutions are then identified.

The full length LIGHT gene was synthesized by GeneArt (ThermoFisher Scientific) and cloned into the mammalian expression vector pcDNA 3.1(+). The following Ala mutations were introduced into the LIGHT gene: 30 single amino acid alanine substitutions from F57A to E86A; 2 single amino acid alanine substitutions; G188A, R189A; one serine substitution, A190S; 17 single amino acid alanine substitutions; T191A to V207A and 10 four amino acid alanine substitutions, 60-63, 64-67, 68-71, 72-75, 76-79, 80-83, 84-87, 88-91, 92-95 and 96-99. Constructs were reconstituted according to manufacture instructions, using DEPC-treated and sterile filtered water. Competent TOP10 *E. coli* cells were transformed with 100 ng of each construct and a single colony from each construct was picked and used to inoculate 10 ml of LB/carb100/glu2% medium and grown overnight at 37° C., 200 rpm. The extraction of the construct DNA was performed using the Qiagen QIAprep Spin Miniprep Kit (250) and the concentration was determined by measuring the O.D. at 260 nm in a spectrophotometer.

HEK293FF cells were cultured in Freestyle™293 expression medium (ThermoFisher scientific cat. no. 12338018) supplemented with 2 mM L-Glutamine. The day of transfection the cells were seeded in a 24-well plate at $0.6 \times 10^6$ cells/well. Lipofectamine 2000 (ThermoFisher scientific), 3 µl, was mixed with 50 µl OptiMEM medium (GIBCO) and then added to 50 µl Opti-MEM medium containing 3 ug plasmid DNA and incubated for 20 min at RT to form DNA-Lipofectamine 2000 complexes which were then added to the HEK293FF cells and incubated at 37° C., 5% $CO_2$ for 24 hours. For each construct, in duplicate, $0.60 \times 10^6$ cells/well were used in a 96 well round bottom plate. Cells were centrifuged for 3 minutes at 300×g at 4° C., the supernatant discarded and the cells washed with 150 µl FACS buffer (0.5% FBS in phosphate buffered saline). This process was repeated 3 times. For each construct, $1 \times 10^6$ cells/well were incubated with anti-LIGHT antibodies at the EC50 concentration and with positive controls of anti-LIGHT mAb MAB664 (R&D Systems), mAb F19 (EP2292663) or LTBR-Fc (R&D Systems), in a final volume of 50 µl/well for 30 min at 4° C., with shaking. The wells were washed 3 times as above and 50 µl/well of goat anti-human IgG FITC (1:1500 dilution in FACS buffer, SIGMA F9512-2ML) or goat anti-mouse APC (1/500 dilution in FACS buffer, BDBioscience 550826), as appropriate, was added to the wells and incubated for 30 min at 4° C. protected from the light, with shaking. The cells were then washed as above, resuspended in 100 µl of FACS buffer and binding of the antibodies to the constructs was measured using flow cytometry and a total of 10,000 cells were acquired for each sample. Controls of buffer and secondary antibody only as well as HEK293FF non transfected cells were also used.

Assessment of mAb 3B04 Variant 16 In Vivo Efficacy in the Dextran Sulfate Sodium (DSS)-Induced Acute Colitis in Humanized Mice The experiments were carried out with the NOD/Shi-scid/IL-2Rγnull immunodeficient mouse strain (NOG) engrafted with CD34+ hematopoietic stem cells isolated from human cord blood as described in Manfroi B et al. (Cancer Res. 2017; 77:1097-1107). The reconstitution of the human immune system in the mice occurred for at least 14 weeks, and hu-mice were used that had at least 25% human CD45+/total CD45 cells. Female hu-NOG mice were randomised into 3 groups (n=10) taking into account the humanization rate and the CD34+ cell donors. All animal studies described in this study have been reviewed and approved by the local ethic committee (CELEAG). Mice were allowed to acclimate to the experimental environment for 5 days prior to the beginning of the experiment. The DSS was administrated for 7 days, from day 2 to 8. The DSS (3%) was added to the drinking water (ad libitum) and freshly renewed every two days.

All treatments started before the DSS-induced colitis. 3B04 variant 16 (5 mg/kg) and the isotype control and anti-TNF (Humira) antibodies (10 mg/kg) were administrated i.p. on days 0, 3, 6, 9. The experiment was terminated on day 12. The following parameters were recorded daily for 12 days: body weight in grams (g); diarrhea and stool consistency; bleeding and mortality. The global clinical score was calculated as follows:

| Clinical signs | Description | Score |
|---|---|---|
| Diarrhea or stool consistency | Normal stool | 0 |
| | Softer stool | 1 |
| | Unformed stool | 2 |
| | Watery stool | 3 (severe) |
| | | 4 (very severe) |
| Bleeding | None | 0 |
| | Weak appearance of blood | 1 |
| | Visual blood in stool | 2 |
| | Fresh rectal bleeding | 3 (severe) |
| | | 4 (very severe) |
| Body weight loss | <2% | 0 |
| | 2% < X > 5% | 1 |
| | 5% < X > 10% | 2 |
| | 10% < X > 15% | 3 |
| | 15% < X > 20% | 4 |
| | 20% < X > 25% | 5 |
| | 25% < X > 30% | 6 |
| | X > 35% | 7 |

The maximum cumulative global clinical score is 15 and an animal was sacrificed if the weight loss was >35%.

Results

In order to produce an immune response biased towards to the membrane form of LIGHT mice were first tolerised with immunization to soluble LIGHT then followed by an immunization regime with LIGHT expressed on CHO cells. All 4 of the mice raised anti-LIGHT specific antibodies, with a range in human LIGHT and cynomolgus LIGHT specific IgG titers measured by FACS analysis of 1/4000 to 1/39000. Fab libraries were then produced from all 4 spleens. A total of 380 soluble Fabs were tested for specific binding to membrane LIGHT expressed on HEK293 cells. Of these, 69 Fabs were selected for testing in neutralization assays with HVEM-Fe and LT3R. 24 neutralizing Fabs were selected that inhibited both receptors binding to LIGHT expressed on HEK293FF cells. These 24 clones were then tested for cross-reactivity to cynomolgus membrane LIGHT and reactivity to soluble LIGHT. Seven anti-membrane Fabs were isolated that had the desired properties of selectivity to membrane LIGHT, neutralize HVEM and LTBR binding to membrane LIGHT and were cynomolgus membrane LIGHT cross-reactive. These Fabs were converted into chimeric IgG4 mAbs for further testing.

In order to compare the cross-reactivity of the mAbs to both human and cynomolgus LIGHT, transiently transfected human or cynomolgus LIGHT-HEK293FF cells were utilised in which approximately 50% of the cells expressed LIGHT and bound mAb was detected with goat anti-human IgG FITC. The EC50 of each mAb is depicted in Table 6 after correction for background binding to untransfected cells. (Note that when the relationship between receptor occupancy and response is linear, EC50 may be equivalent or substantially equivalent to KD).

TABLE 6

Cross reactivity of the mAbs to human and cynomolgus membrane LIGHT.

| | mAb | | | | | | |
|---|---|---|---|---|---|---|---|
| | 2E08 | 3A07 | 3B04 | 3C10 | 3D12 | 3E09 | 2B11 |
| Cynomolgus LIGHT EC50 nM | 0.3 | 7.6 | 0.1 | 10.3 | 0.3 | 0.7 | 0.02 |
| Human LIGHT EC50 nM | 0.3 | 0.1 | 0.2 | 0.2 | 0.2 | 1.3 | 0.4 |

The seven anti-membrane LIGHT mAbs were shown to bind to the stable human LIGHT expressing cell line EL4-LIGHT, but not to the parental EL4 cells. The EC50 of the 7 mAbs were calculated from binding to EL4-LIGHT cells (Table 7) which represents a more accurate comparison of the EC50's than utilising transiently transfected LIGHT cells. The binding of 6 of these anti-LIGHT antibodies reached saturation and the functional equilibrium binding affinity of each antibody was determined by titrating the amount of antibody needed to label EL4-LIGHT cells. Non-linear regression analysis was performed to determine the functional binding affinity measurement or EC50 for each mAb. A range of functional affinities was observed.

TABLE 7

EC50 calculations of the 7 lead mAbs binding to LIGHT stably expressed on EL4 cells.

| | mAb | | | | | | |
|---|---|---|---|---|---|---|---|
| | 2E08 | 3A07 | 3B04 | 3C10 | 3D12 | 3E09 | 2B11 |
| Human membrane LIGHT EC50, nM | 1.8 | 0.14 | 0.15 | 0.16 | 0.2 | 8.1 | 0.3 |

The specificity of two lead anti-membrane LIGHT mAbs to soluble LIGHT was determined by BIAcore analysis and compared to the $K_D$ calculated from the EC50 values in Table 7 (results in Table 9). In brief, mAbs 3D12, 3B04 were compared to a mAb that binds both soluble and membrane LIGHT, F19, (F19 IgG4 mAb from EP2292663). An irrelevant anti-HEL mAb, 2A11, was used as a negative control. The mAbs were captured on an anti-human Fc mAb coated chip and soluble LIGHT was passed over the surface and the kinetic parameters were calculated using BIAcore 3000 software. The soluble LIGHT preparations used were amino acids 74-240 LIGHT (R&D Systems, 664-LI-025) and 64-240 LIGHT (Abcam, ab82123). The results are depicted in Table 8.

TABLE 8

Kinetic constants of mAbs binding to soluble LIGHT from BIAcore analysis

| | mAb | | | | | |
|---|---|---|---|---|---|---|
| | 74-240 LIGHT Ka (1/Ms) | 74-240 LIGHT Kd (1/s) | 74-240 LIGHT $K_D$ (nM) | 64-240 LIGHT Ka (1/Ms) | 64-240 LIGHT Kd (1/s) | 64-240 LIGHT $K_D$ (nM) |
| F19 | $7.06E \times 10^4$ | $8.8 \times 10^{-4}$ | 5.4 | $1.34 \times 10^5$ | $3.12 \times 10^{-4}$ | 2.3 |
| 3B04 | $2.22 \times 10^5$ | $3.48 \times 10^{-3}$ | 15.7 | $2.51 \times 10^5$ | $3.45 \times 10^{-3}$ | 13.8 |
| 3D12 | $1.68 \times 10^5$ | $2.35 \times 10^{-3}$ | 14.0 | $2.19 \times 10^5$ | $2.34 \times 10^{-3}$ | 10.7 |

As can be seen from Table 9 the F19 mAb binds soluble and membrane LIGHT to an equal extent, (this mAb was raised by immunisation with soluble LIGHT), with a $K_D$ of 2.3-5.4 nM. The lead mAbs of this invention preferentially bind membrane LIGHT with at least a 50-100 fold specificity.

TABLE 9

$K_D$ comparison of mAbs binding to membrane LIGHT

| mAb | Soluble LIGHT 74-240 $K_D$ (nM) | Soluble LIGHT 64-240 $K_D$ (nM) | Membrane LIGHT $K_D$ (nM) |
|---|---|---|---|
| F19 | 5.4 | 2.3 | 2.9 |
| 3B04 | 15.7 | 13.8 | 0.15 |
| 3D12 | 14.0 | 10.7 | 0.2 |

The specificity of further anti-membrane LIGHT mAbs to soluble LIGHT was determined by using the same BIAcore analysis discussed above which was used to generate the data in Table 9. In brief, mAbs 3B04, 3D12, 3A07, 3C10 and 2B11 were compared to various prior art antibodies, (F19 and F23 IgG4 mAbs from EP2292663 and 1C02, 13H04 and 31A10 mAbs from WO2015/107331). As can be seen from Table 10, several mAbs of this invention preferentially bind membrane LIGHT with at least a 50-fold specificity.

TABLE 10

Further $K_D$ comparison of mAbs binding to membrane LIGHT

| Antibody | Soluble LIGHT 74-240 $K_D$ (nM) | Membrane LIGHT $K_D$ (nM) | Membrane:soluble LIGHT affinity ratio |
|---|---|---|---|
| 3B04 | 11.1 | 0.21 | 52.86 |
| 3D12 | 3.6 | 0.19 | 18.95 |
| 3A07 | 15.8 | 0.15 | 105.33 |
| 3C10 | 11 | 0.18 | 61.11 |
| 2B11 | 16 | 0.34 | 47.06 |
| 1C02 | <0.01 | 10.81 | — |
| 13H04 | <0.01 | 6.30 | — |
| 31A10 | <0.01 | 3.05 | — |
| F23 | 0.1 | 2.04 | 0.05 |
| F19 | 0.8 | 4.05 | 0.20 |

Figure 1B:
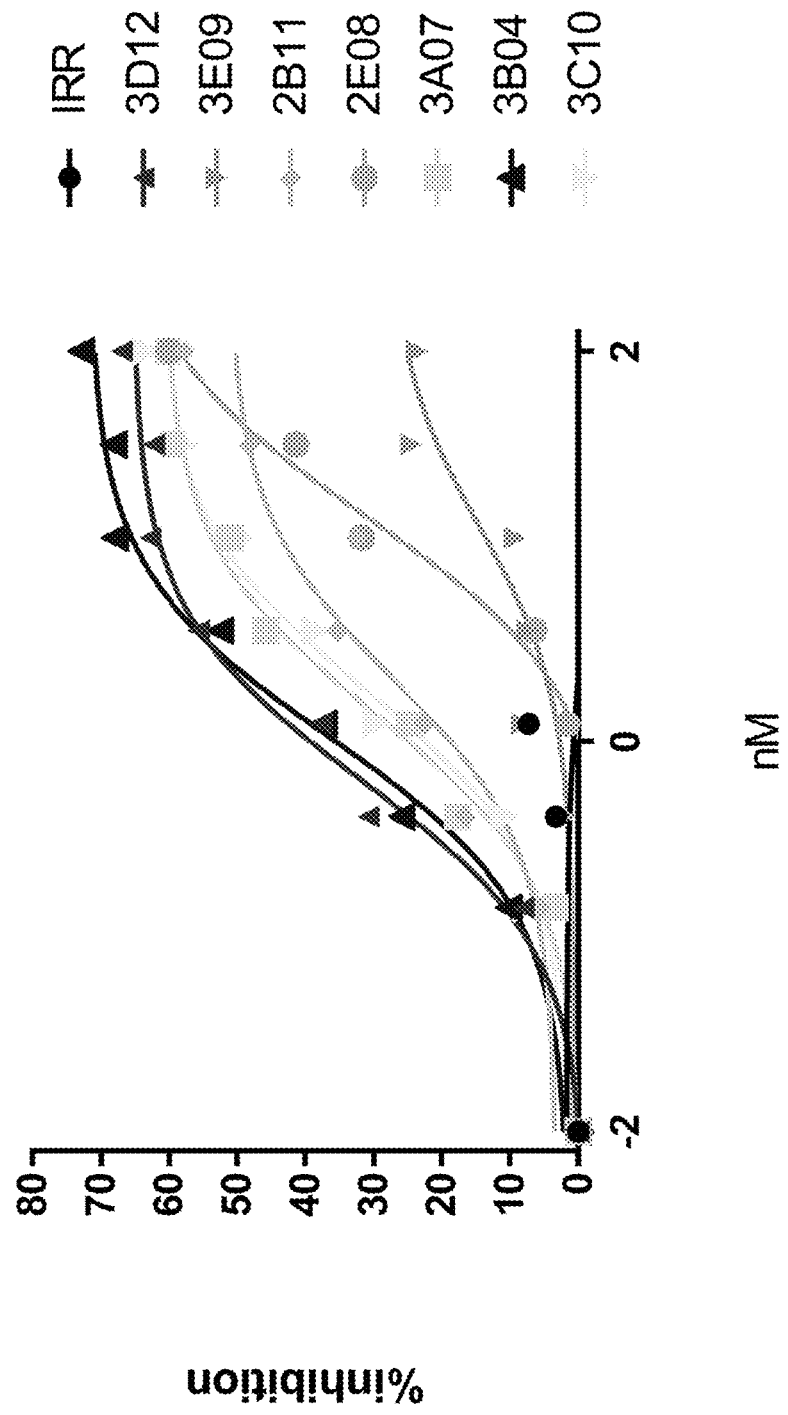

The ability of the 7 chimeric mAbs to block biotin-HVEM:Fc and biotin-LTβR:Fc fusion proteins to cell surface expressed LIGHT using a flow cytometric based assay is shown in FIGS. 1A and 1B respectively. In these experiments, graded amounts of each antibody were added to the HEK293FF cells transiently transfected with LIGHT with a 50% saturating amount of the receptor fusion protein. As shown, each of the antibodies blocked either receptor fusion protein from binding LIGHT, in contrast to the irrelevant antibody control which had no effect on either Fc-receptor fusion protein binding. In each experiment, all antibodies blocked receptor binding in a dose dependent manner enabling analysis by non-linear regression to determine the IC50 dose as shown in Table 11A.

TABLE 11A

IC50 dose for mAb inhibition of HVEM and LTβR binding to membrane LIGHT transiently expressed on HEK293FF cells.

| | mAb | | | | | | |
|---|---|---|---|---|---|---|---|
| | 2E08 | 3A07 | 3B04 | 3C10 | 3D12 | 3E09 | 2B11 |
| Inhibition HVEM binding to membrane LIGHT, IC50 nM | 23.8 | 2.5 | 1.2 | 2.1 | 1.0 | 36.6 | 2.9 |
| Inhibition LTβR binding to membrane LIGHT, IC50 nM | 14.4 | 1.4 | 1.1 | 1.9 | 0.6 | 12.0 | 2.1 |

The above experiment was repeated utilising LIGHT stably expressed on EL4-cells and the results depicted in Table 11B.

TABLE 11B

IC50 dose for inhibition of HVEM and LTβR binding to membrane LIGHT stably expressed in EL4-LIGHT cells.

| | mAb | | | | | | |
|---|---|---|---|---|---|---|---|
| | 2E08 | 3A07 | 3B04 | 3C10 | 3D12 | 3E09 | 2B11 |
| Inhibition HVEM binding to membrane LIGHT, IC50 nM | 4.3 | 0.32 | 0.13 | 0.8 | 0.16 | 24.1 | 0.34 |
| Inhibition LTβR binding to membrane LIGHT, IC50 nM | 5.7 | 0.35 | 0.19 | 0.86 | 0.19 | 38.0 | 0.36 |

When LIGHT is transiently expressed on HEK293FF cells approximately 50% of the cells express LIGHT leading to potential variability and inaccuracy in calculating the IC50. Table 11B reflects the IC50 values in stably expressed EL4-LIGHT cells and correlates with the EC50 values calculated in the same cells (Table 7). (As the competition cell based assays and EC50 determination are performed at 4° C. membrane LIGHT is stable and no soluble LIGHT is released due to cleavage from endogenous proteases).

Figure 2:
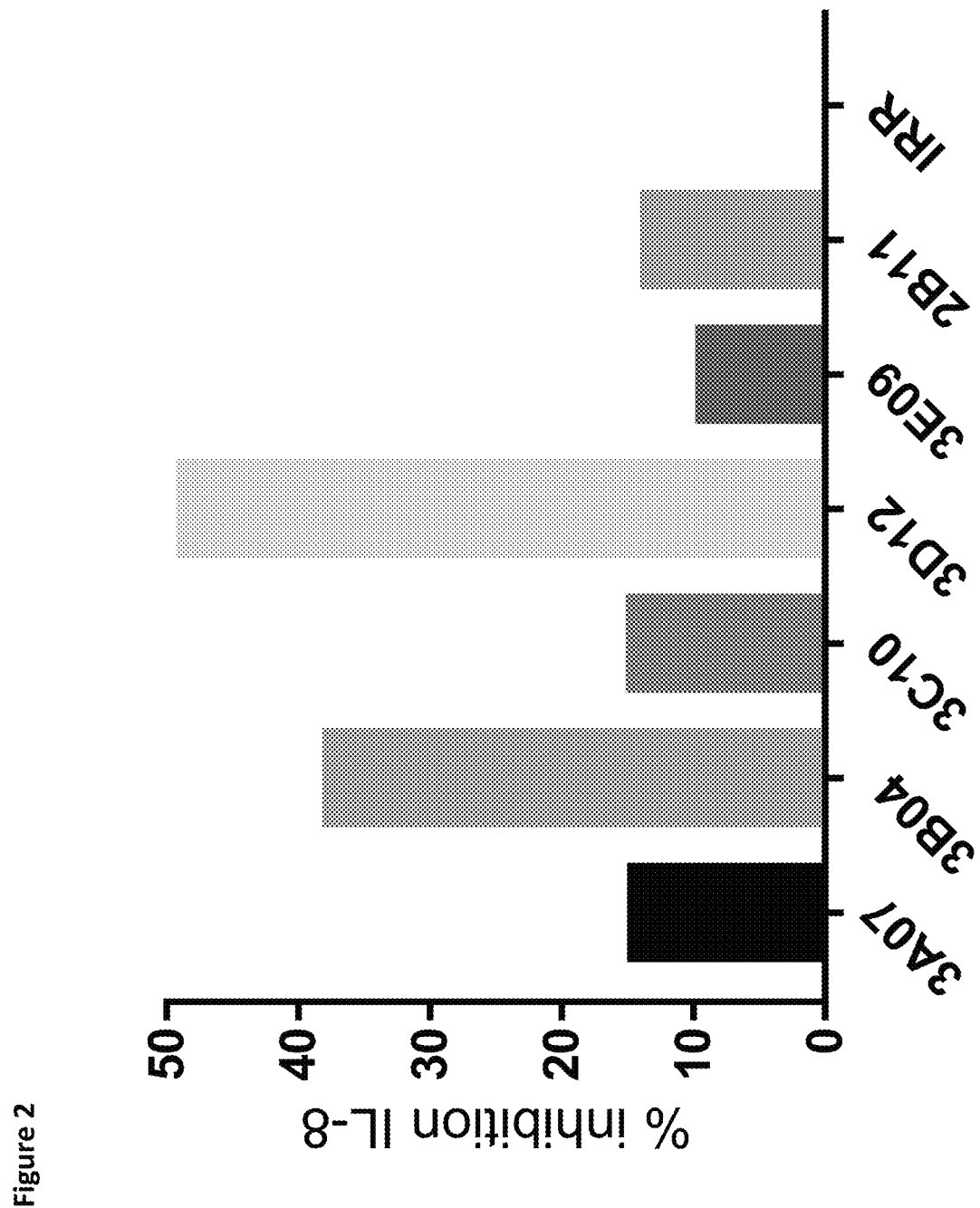
FIG. 2 shows the inhibition of IL-8 secretion from HT-29 cells stimulated by stably transfected EL4-LIGHT cells by the lead anti-membrane LIGHT mAbs. IRR is a negative control anti-HEL mAb.

To directly determine that the antagonistic anti-membrane LIGHT antibodies of the invention block membrane LIGHT-mediated stimulation, an assay to measure membrane LIGHT-mediated signaling in vitro was established. The cell line HT29, which expresses both LTβR and HVEM, was treated with a fixed number of CHO K1 cells expressing LIGHT and the growth media was analysed for the presence of secreted IL-8 over a 6h time-course. TNF was used as a positive control for IL-8 induction through the TNF receptors, while lymphotoxin was used as a positive control for signaling through the LTβR. The levels of IL-8 produced by contacting the cells with LIGHT were equivalent to those produced by TNF or lymphotoxin. As can be seen in FIG. 2 all the mAbs tested at a single concentration of 10 nM inhibited IL-8 secretion.

It was discovered that CHO K1-LIGHT cells during a 6-hour culture period at 37° C. can produce soluble LIGHT through endogenous enzymatic clipping of membrane LIGHT. In this situation both membrane LIGHT and soluble LIGHT are competing for HVEM and LTBR expressed on the HT-29 cells in this assay. Since the mAbs of this invention selectively inhibit only membrane LIGHT then only a partial inhibition would be observed, as is evident in FIG. 2. In order to overcome this limitation EL4-NC-LIGHT cells were prepared that are more resistant to endogenous enzymatic cleavage of membrane LIGHT. Utilising a two-hour incubation of EL4-NC-LIGHT cells at 37° C. revealed that no soluble LIGHT was detected during this period. Therefore, incubating EL4-NC-LIGHT cells and HT-29 cells in the presence of the mAbs of this invention for 2h at 37° C. will result in detecting only inhibition of the membrane form of LIGHT signaling. The IC50 of the mAbs are shown in Table 12 utilising EL4-NC-LIGHT cells.

TABLE 12

IC50 dose for mAb inhibition of IL-8 secretion from HT-29 cells stimulated by membrane LIGHT stably expressed in EL4-NC-LIGHT cells

| | mAb | | | | | | |
|---|---|---|---|---|---|---|---|
| | 2E08 | 3A07 | 3B04 | 3C10 | 3D12 | 3E09 | 2B11 |
| Inhibition IL-8 secretion from HT-29 cells by membrane LIGHT (EL4-NC-LIGHT cells), IC50 nM | 1.8 | 2.0 | 0.2 | 1.9 | 0.1 | ND | 0.6 |

The IC50 values for the mAbs of this invention inhibiting membrane LIGHT stimulation of HVEM and LTBR signaling (IL-8 release) present in HT-29 cells are again closely correlated with the EC50 (Table 7) and IC50 inhibition of LTBR/HVEM binding to EL4-LIGHT cells (Table 11B).

This cellular response assay is used to measure membrane LIGHT signaling and assess the capacity of antibodies of the present disclosure to block membrane LIGHT-mediated signaling events in vitro. It is believed that signaling initiated by cell surface LIGHT binding to its cognate receptors on other cells may be critical for exerting observed T cell co-stimulatory activity through HVEM interactions or increased IL-8 production through LTβR expressed on cells of stromal or epithelial origin in the gut, spleen or lymph nodes.

The IL-8 release assay was also used to compare the bioactivity of the anti-membrane LIGHT mAbs of this invention (Table 13A) with mAbs that neutralise both membrane and soluble LIGHT (Table 13B). In this assay 5 ng/ml of LIGHT (R&D systems cat. no. 664-LI-025) was used to test the cross-reactivity to soluble LIGHT and EL4-NC-LIGHT cells the cross-reactivity to membrane LIGHT.

TABLE 13A

Assessment of the cross-reactivity of the anti-membrane LIGHT mAbs (3B04, 3D12, 2E08, 3A07, 3C10 and 2B11) with soluble LIGHT and membrane LIGHT measured by IL-8 release from HT-29 cells. EL4-NC-LIGHT cells or soluble LIGHT (5 ng/ml) were incubated with HT-29 cells in the presence of mAbs (0 to 30 nM) for 2 hours and the IL-8 released quantitated by ELISA.

| | 3B04 | 3D12 | 2E08 | 3A07 | 3C10 | 2B11 |
|---|---|---|---|---|---|---|
| IC50, nM membrane LIGHT | 0.15 | 0.1 | 1.8 | 2.0 | 1.9 | 0.55 |
| IC50, nM soluble LIGHT | 6.5 | 3.4 | >100 | >100 | >100 | 47 |
| Ratio membrane:soluble LIGHT bioactivity | 43 | 34 | >100 | >100 | >100 | 86 |

TABLE 13B

Assessment of the cross-reactivity of the anti-LIGHT mAbs 13H04 and 31A10 (IgG4 mAbs from patent WO2015107331), and anti-LIGHT mAbs F19 and F23 (IgG4 mAbs from patent EP2292663) with soluble LIGHT and membrane LIGHT measured by IL-8 release from HT-29 cells. EL4-NC-LIGHT cells or soluble LIGHT (5 ng/ml) were incubated with HT-29 cells in the presence of mAbs (0 to 30 nM) for 2 hours and the IL-8 released quantitated by ELISA.

|  | 13H04 | 31A10 | F19 | F23 |
|---|---|---|---|---|
| IC50, nM membrane LIGHT | 0.54 | 0.52 | 0.8 | 0.4 |
| IC50, nM soluble LIGHT | 0.5 | 0.4 | 0.8 | 0.4 |
| Ratio membrane:soluble LIGHT bioactivity | 0.9 | 0.7 | 1 | 1 |

The assay was regulated such that both soluble LIGHT and membrane LIGHT (EL4-NC-LIGHT cells) gave approximately the same level of IL-8 secretion from HT-29 cells in the bioassay. From Table 13A it can be observed that the anti-membrane LIGHT mAbs (3B04, 3D12, 2E08, 3A07, 3C10 and 2B11) have a far greater affinity to membrane LIGHT than soluble LIGHT (>30 fold) as measured by comparing the IC50's of inhibition. In complete contrast, mAbs that were raised or screened against soluble LIGHT have approximately equal affinity to both soluble and membrane LIGHT (Table 13B). It should be noted that the exact molar quantity of membrane LIGHT (EL4-NC-LIGHT cells) in contact with HT-29 cells in the assay cannot be accurately quantitated and that soluble LIGHT may not have a comparable bioactivity to membrane LIGHT, therefore, the exact molar amounts of membrane LIGHT and soluble LIGHT may not be equivalent in the assay. However, since the biological signal in the assay was similar for both membrane and soluble LIGHT there is a distinct difference that the mAbs of this invention to preferentially neutralize membrane LIGHT, whereas, mAbs generated to or screened against soluble LIGHT (Table 13B) have an equivalent bioactivity to membrane and soluble LIGHT.

In humans, LIGHT is neutralized by DcR3, a unique soluble member of the TNFR superfamily, which tightly binds LIGHT (both soluble and membrane forms) and inhibits its interactions with HVEM and LTβR. A major binding determinant for DcR3 neutralization is the region T170-E178 on LIGHT (Liu et al. Structure 2014: 9; 1252-1262). The mAbs of this invention (3B04, 3D12, 2E08, 3A07, 3C10, 2B11 and 3E09) only partially inhibit the natural soluble inhibitor of LIGHT, DcR3, from binding to membrane LIGHT at up to 100 nM (Table 14). In contrast the anti-LIGHT mAb F19, (from EP2292663) which binds both soluble LIGHT and membrane LIGHT equally well completely displaces DcR3 from binding to membrane LIGHT highlighting a surprising an important functional difference between the anti-membrane LIGHT mAbs of this invention and other neutralizing anti-LIGHT mAbs that have been raised against or screened against soluble LIGHT. The complete inhibition of DcR3 binding to LIGHT by mAb F19 indicates that mAb F19 has a similar or overlapping epitope with DcR3.

TABLE 14

Competition binding of the anti-membrane LIGHT mAbs 3B04, 3D12, 2E08, 3A07, 3C10, 2B11 and 3E09 against DcR3-His for binding to membrane LIGHT (EL4-LIGHT) cells. For comparison mAb F19 from EP2292663 is included. The results are expressed as a percentage of the average binding of the irrelevant (Irr, anti-HEL) mAb.

| DcR3-His, nM | 3B04 | 3D12 | 2E08 | 3A07 | 3C10 | 2B11 | 3E09 | Irr. mAb | F19 |
|---|---|---|---|---|---|---|---|---|---|
| 100 | 75.8 | 80.3 | 53.7 | 64.2 | 63.8 | 70.6 | 65.0 | 98.0 | 13.7 |
| 33.3 | 85.1 | 78.1 | 78.4 | 67.5 | 81.9 | 79.8 | 70.5 | 100.8 | 42.8 |
| 11.1 | 78.3 | 61.1 | 85.7 | 75.8 | 83.6 | 77.5 | 71.1 | 93.5 | 85.5 |
| 3.7 | 78.5 | 68.6 | 66.1 | 89.6 | 86.9 | 78.6 | 80.4 | 101.9 | 99.9 |
| 1.23 | 75.1 | 72.8 | 118.3 | 90.6 | 95.5 | 115.4 | 66.9 | 102.2 | 99.1 |
| 0.41 | 94.8 | 99.4 | 107.0 | 102.0 | 124.3 | 113.9 | 94.2 | 99.9 | 98.8 |

The implication of this result is twofold. Firstly, that mAbs of this invention only partially compete with the endogenous LIGHT inhibitor, DcR3, with membrane LIGHT. Secondly, DcR3 is a cell adhesion protein binding to cells through interacting with heparan sulphate proteoglycans (Y-C Chang et al. J. Immunol. 2006: 176; 173-180). Through this mechanism DcR3 could be a depot for soluble LIGHT released by protease cleavage from activated immune cells. mAbs or receptor fusions (LTBR-Ig) that bind soluble LIGHT could displace soluble LIGHT from DcR3 through competition binding. Indeed, increased levels of soluble LIGHT have been reported in studies in humans treated with LTBR-Ig (Bienkowska J et al. PLoS ONE 9: e112545) or an anti-LIGHT mAb (Zhang M et al. Clin Pharmacol Drug Dev. 2017; 6:292-301). Long term treatment with agents that bind soluble LIGHT and/or compete with DcR3 for soluble LIGHT maybe deleterious. mAbs of this invention, (3B04, 3D12, 2E08, 3A07, 3C10, 2B11 and 3E09) only partially inhibit membrane LIGHT from binding to DcR3 and in addition are >100 fold less specific to soluble LIGHT than membrane LIGHT and therefore would not be expected to displace soluble LIGHT from DcR3 in vivo.

Analysis of Humanized 3B04 and 3D12 IgG4 mAbs

The sequences of the humanized and deimmunised variants of mAbs 3B04 and 3D12 are depicted in FIGS. 5 and 6. All 16 variants of 3B04 and 3D12 were prepared as human IgG4 (S241P and L248E, Kabat) and tested in two assays; EC50 analysis of the mAbs binding to LIGHT stably expressed on EL4 cells and the IC50 calculation for mAb inhibition of IL-8 secretion from HT-29 cells stimulated by membrane LIGHT (EL4-NC-LIGHT cells). The results of the analysis are shown in Table 15.

TABLE 15

EC50 and IC50 values for the 16 humanized and deimmunised variants of 3B04 and 3D12 (IgG4) comprising the VH and VL sequences from FIGS. 5 and 6

|  | 3B04 chimeric | 3B04 VL1V H1 (var1) | 3B04 VL1V H2 (var2) | 3B04 VL1V H3 (var3) | 3B04 VL1V H4 (var4) | 3B04 VL2V H1 (var5) | 3B04 VL2V H2 (var6) | 3B04 VL2V H3 (var7) | 3B04 VL2V H4 (var8) |
|---|---|---|---|---|---|---|---|---|---|
| EC50, nM | 0.12 | 0.24 | 0.38 | 0.32 | 0.26 | 0.27 | 0.27 | 0.23 | 0.28 |
| IC50, nM | 0.05 | 0.05 | 0.06 | 0.04 | 0.04 | 0.04 | 0.08 | 0.05 | 0.05 |

|  | 3B04 VL3V H1 (var9) | 3B04 VL3V H2 (var10) | 3B04 VL3V H3 (var11) | 3B04 VL3V H4 (var12) | 3B04 VL4V H1 (var13) | 3B04 VL4V H2 (var14) | 3B04 VL4V H3 (var15) | 3B04 VL4V H4 (var16) |
|---|---|---|---|---|---|---|---|---|
| EC50, nM | 0.26 | 0.49 | 0.37 | 0.24 | 0.32 | 0.30 | 0.39 | 0.24 |
| IC50, nM | 0.09 | 0.04 | 0.06 | 0.07 | 0.04 | 0.05 | 0.10 | 0.10 |

|  | 3D12 chimeric | 3D12 VL1V H1 (var1) | 3D12 VL1V H2 (var2) | 3D12 VL1V H3 (var3) | 3D12 VL1V H4 (var4) | 3D12 VL2V H1 (var5) | 3D12 VL2V H2 (var6) | 3D12 VL2V H3 (var7) | 3D12 VL2V H4 (var8) |
|---|---|---|---|---|---|---|---|---|---|
| EC50, nM | 0.08 | 0.22 | 0.47 | 0.33 | 0.32 | 0.33 | 0.31 | 0.38 | 0.31 |
| IC50, nM | 0.32 | 0.33 | 0.74 | 0.53 | 0.66 | 0.59 | 0.47 | 0.54 | 0.67 |

|  | 3D12 VL3V H1 (var9) | 3D12 VL3V H2 (var10) | 3D12 VL3V H3 (var11) | 3D12 VL3V H4 (var12) | 3D12 VL4V H1 (var13) | 3D12 VL4V H2 (var14) | 3D12 VL4V H3 (var15) | 3D12 VL4V H4 (var16) |
|---|---|---|---|---|---|---|---|---|
| EC50, nM | 0.36 | 0.39 | 0.34 | 0.33 | 0.24 | 0.23 | 0.22 | 0.26 |
| IC50, nM | 0.71 | 0.44 | 0.55 | 0.58 | 0.45 | 0.45 | 0.38 | 0.52 |

All the 3B04 variants and all the 3D12 variants have similar activity in terms of EC50 binding to membrane LIGHT and IC50 for inhibition of membrane LIGHT stimulated IL-8 release from HT-29 cells. In addition, all 3B04 variants and all 3D12 variants have equivalent activity to the parent chimeric antibody (Table 14). Competition assays with the humanized mAbs for LTBR-Fc or HVEM-Fc binding to membrane LIGHT also gave similar inhibition for all variants of 3B04 and 3D12 and equivalent activity to the parent chimeric mAb.

Binding Ratio of mAbs Bound to LIGHT by Mass Spectrometry

Native mass spectroscopy was utilised to determine the ratio of mAb bound to native trimeric LIGHT. The measured mass of 3B04 (IgG4) was 147256±0.7 Da and the F19 anti-LIGHT mAb, (IgG4 mAb from EP2292663) was 147364±6.6 Da. Unlike the monoclonal antibodies the LIGHT protein was highly heterogeneous as expected, due to post-translational glycosylation. Two major populations of the light protein were recorded with measured masses of 68 kDa and 71 kDa. Both of these proteoforms are higher in mass than the theoretical trimeric mass of the protein, 62827.38 Da. The added mass values are 2000 Da and 3002 Da per monomer respectively are due to the different glycans. LIGHT was incubated with 1:5 molar ratio (protein:antibody) with each antibody to form LIGHT-antibody complexes. Incubation of LIGHT with the F19 mAb led to the formation of a large complex with a stoichiometry of one LIGHT protein and three F19 antibodies (504370±57 Da), indicating that the F19 mAb (which binds soluble and membrane LIGHT equally) binds to one copy of LIGHT in the trimer (i.e. 3:1 ratio). In the case of LIGHT binding with 3B04, the stoichiometry can be assigned to one antibody per one LIGHT protein (masses of 219630±221 Da and 216960±380 were recorded).

Binding Ratio of mAbs Bound to Membrane LIGHT by Flow Cytometry

FIG. 7 depicts the flow cytometry analysis of the anti-membrane LIGHT mAbs (3B04 and 3D12) binding to LIGHT stably expressed on EL4 cells. The maximum signal of the IgG4 mAbs 3B04 and 3D12 binding to membrane LIGHT is approximately 40000 MFI. In contrast anti-LIGHT mAbs F19 and F23 (IgG4 mAbs from EP2292663) gave a maximal signal of approximately 120000 MFI. The ratio of binding of mAb F19 and mAb F23 is approximately 3 times that of the anti-membrane LIGHT mAbs 3B04 and 3D12. This data demonstrates that mAbs 3B04 and 3D12 bind membrane LIGHT in a 1:1 ratio, which is in direct contrast to other anti-LIGHT mAbs that bind both membrane and soluble LIGHT which bind LIGHT in a 3:1 ratio. Other mAbs of this invention; 2E08, 3A07, 3C10, 3E09 and 2B11 also bind LIGHT in a 1:1 ratio when compared to mAbs F19 and F23 by flow cytometry.

Epitope Identification from Hydrogen Deuterium Exchange (HDX) HDX Mass Spectrometry HDX was used as a starting point to identify the epitope of antibody 3B04 binding to the LIGHT protein. A sequence coverage of 69.2% of the LIGHT protein was achieved and the regions that were not observed were due to the presence of a disulfate bond and glycosylation. The glycans were not removed from LIGHT in order to preserve the structure of the protein in a native state. The digestion of LIGHT resulted in a total of 50 peptides and 48 of these peptides were used for the analysis (covering residues 84-238 of LIGHT). The data in Table 16 is from four time points in triplicate and shows the results of of the 48 LIGHT peptides and the uptake of deuterium in the presence of mAb 3B04 and control mAb. Peptides 203-209 and 203-219 are shown demonstrating no significant difference in the uptake between 3B04 and the control mAb. The other 43 peptides also showed no difference in uptake of mAb 3B04 in presence or absence of deuterium (data not shown). By comparing mAb 3B04 binding to LIGHT and deuterated LIGHT it was observed that 3B04 resulted in a lower uptake especially at amino acid R195, V196 and W197. (Difference in uptake between 3B04 and control mAb, Table 16, values in bold). The epitope of mAb 3B04 defined by HDX is focused on residues 195-197 of soluble LIGHT. The results from HDX spectrometry were used as a guide to identify a region of interest that was subsequently analysed using alanine scanning.

binding between the above alanine substitution LIGHT constructs and WT LIGHT. This indicates that the epitope of mAbs 3B04 and 3D12 are not in the region of LIGHT amino acids 57-99. The 2 single amino acid alanine substitutions; G188A, R189A; one serine substitution, A190S and 17 single amino acid alanine substitutions; T191A to V207A resulted in the identification of the epitope recognised by the mAbs of this invention and the results are presented in Table 17. There was no difference in binding between the mAbs of this invention compared to the WT control utilising alanine substitutions in residues D199A to V207A and these results are not shown. In addition, LTBR-Fc showed no difference in binding to the amino acid substitutions G188A to V207A compared to WT LIGHT indicating that the amino acid substitutions did not impair LIGHT binding to its receptor LTBR. Those substitutions that showed a significant decrease in binding versus the WT control and highlighted in bold in Table 17. All of the mAbs of this invention show a similar profile in that their epitope is located at amino acids

TABLE 16

Average deuterium uptake of LIGHT peptides after incubation with mAB 3B04 (n = 3) and difference in uptake compared to the control mAB.

| Protein | Start | End | Sequence | SEQ ID NO. | Mass | Exposure (sec) | Uptake 3B04 | Uptake 3B04 STDev | Uptake control mAb | Difference uptake (3B04-control) |
|---|---|---|---|---|---|---|---|---|---|---|
| LIGHT | 194 | 202 | SRVWWDSSF | 129 | 1169.537 | 0.00 | 0 | 0 | 0 | 0 |
| LIGHT | 194 | 202 | SRVWWDSSF | 129 | 1169.537 | 0.33 | 0.744 | 0.016 | 1.041 | −0.296 |
| LIGHT | 194 | 202 | SRVWWDSSF | 129 | 1169.537 | 1.00 | 0.885 | 0.051 | 1.328 | −0.443 |
| LIGHT | 194 | 202 | SRVWWDSSF | 129 | 1169.537 | 5.00 | 1.159 | 0.023 | 1.564 | −0.405 |
| LIGHT | 194 | 202 | SRVWWDSSF | 129 | 1169.537 | 30.00 | 1.392 | 0.043 | 2.048 | −0.656 |
| LIGHT | 195 | 202 | RVWWDSSF | 130 | 1082.505 | 0.00 | 0 | 0 | 0 | 0 |
| LIGHT | 195 | 202 | RVWWDSSF | 130 | 1082.505 | 0.33 | 0.393 | 0.060 | 0.648 | −0.254 |
| LIGHT | 195 | 202 | RVWWDSSF | 130 | 1082.505 | 1.00 | 0.480 | 0.055 | 0.878 | −0.399 |
| LIGHT | 195 | 202 | RVWWDSSF | 130 | 1082.505 | 5.00 | 0.631 | 0.054 | 1.106 | −0.474 |
| LIGHT | 195 | 202 | RVWWDSSF | 130 | 1082.505 | 30.00 | 0.805 | 0.057 | 1.561 | −0.756 |
| LIGHT | 197 | 202 | WWDSSF | 131 | 827.3359 | 0.00 | 0 | 0 | 0 | 0 |
| LIGHT | 197 | 202 | WWDSSF | 131 | 827.3359 | 0.33 | 0.240 | 0.0111 | 0.427 | −0.187 |
| LIGHT | 197 | 202 | WWDSSF | 131 | 827.3359 | 1.00 | 0.336 | 0.016 | 0.605 | −0.269 |
| LIGHT | 197 | 202 | WWDSSF | 131 | 827.3359 | 5.00 | 0.501 | 0.0140 | 0.718 | −0.217 |
| LIGHT | 197 | 202 | WWDSSF | 131 | 827.3359 | 30.00 | 0.603 | 0.023 | 0.855 | −0.252 |
| LIGHT | 203 | 209 | LGGVVHL | 132 | 694.4246 | 0.00 | 0 | 0 | 0 | 0 |
| LIGHT | 203 | 209 | LGGVVHL | 132 | 694.4246 | 0.33 | 0.145 | 0.060 | 0.174 | −0.029 |
| LIGHT | 203 | 209 | LGGVVHL | 132 | 694.4246 | 1.00 | 0.147 | 0.060 | 0.174 | −0.027 |
| LIGHT | 203 | 209 | LGGVVHL | 132 | 694.4246 | 5.00 | 0.237 | 0.056 | 0.250 | −0.014 |
| LIGHT | 203 | 209 | LGGVVHL | 132 | 694.4246 | 30.00 | 0.384 | 0.048 | 0.436 | −0.052 |
| LIGHT | 203 | 214 | LGGVVHLEAGEE | 133 | 1209.611 | 0.00 | 0 | 0 | 0 | 0 |
| LIGHT | 203 | 214 | LGGVVHLEAGEE | 133 | 1209.611 | 0.33 | 0.202 | 0.0058 | 0.252 | −0.050 |
| LIGHT | 203 | 214 | LGGVVHLEAGEE | 133 | 1209.611 | 1.00 | 0.266 | 0.0415 | 0.299 | −0.033 |
| LIGHT | 203 | 214 | LGGVVHLEAGEE | 133 | 1209.611 | 5.00 | 0.399 | 0.0044 | 0.487 | −0.087 |
| LIGHT | 203 | 214 | LGGVVHLEAGEE | 133 | 1209.611 | 30.00 | 0.807 | 0.0048 | 0.880 | −0.081 |

Epitope Identification by Alanine Scanning Mutagenesis and Flow Cytometry

The results from HDX mass spectrometry assisted in designing peptides for alanine scanning mutagenesis that included the 195-197 epitope but also included peptides not covered by HDX (e.g. amino acids 188-193 of LIGHT). In addition, this methodology can be used to define the epitope in native membrane LIGHT.

Figure 8:
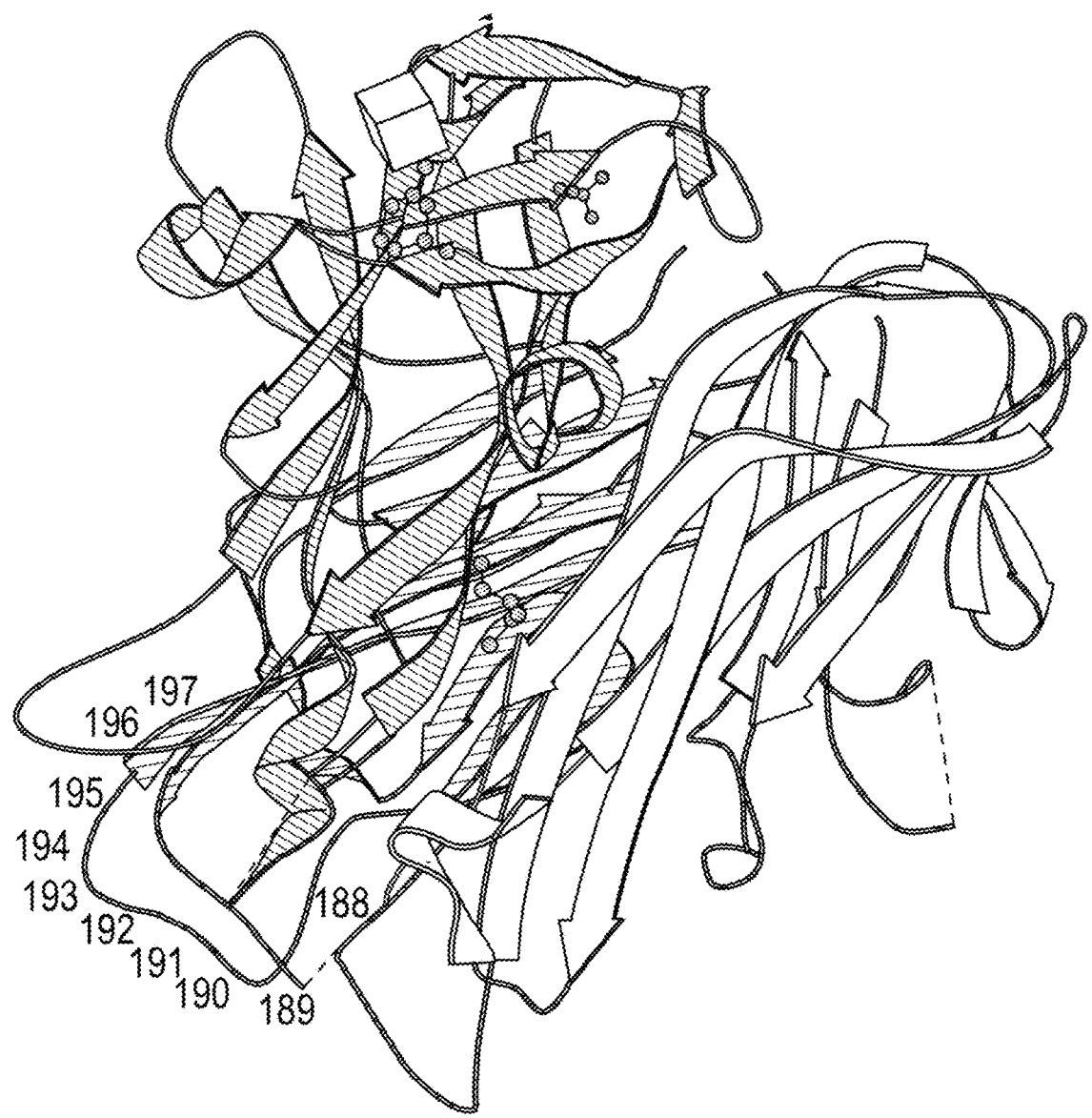
FIG. 8 shows a 3D visualisation of the crystal structure of LIGHT depicting the epitope location (aa 188-197) of mAbs 3B04, 3D12, 2E08, 3A07, 3C10, 2B11 and 3E09.

The results from introducing alanine mutations into full length LIGHT transfected into HEK293 cells revealed that the 30 single amino acid alanine substitutions from F57A to E86A and the 10 four amino acid alanine substitutions, 60-63, 64-67, 68-71, 72-75, 76-79, 80-83, 84-87, 88-91, 92-95 and 96-99 produced no difference in binding between mAbs 3B04 and 3D12 of this invention and the WT LIGHT control. In addition, LTBR-Fc also showed no difference in 188-197 of LIGHT. The conservative substitutions of A190S, S192A and V196A in LIGHT showed no difference in binding of the mAbs compared to the WT control. The epitope of the mAbs of this invention defined by alanine scanning mutagenesis are residues 188-197 of LIGHT. This is visually depicted in FIG. 8 utilising a 3D visualisation of the LIGHT trimer from the crystal structure of LIGHT from Liu et al. (Structure 22: 1252-62; 2014). This would result in the mAbs binding to the "tip" of the LIGHT trimer and explaining the 1:1 binding. The impact of this epitope would result in 33.3% less dosing of mAb 3B04 being required to neutralise membrane LIGHT compared to, for example, mAbs F19 and F23 (of EP2292663) which bind both soluble and membrane LIGHT equally and bind LIGHT in the ratio 3:1.

TABLE 17

Binding of mAbs 3B04, 3D12, 2E08, 3A07, 3C10, 2B11 and 3E09 to wild type (WT) membrane LIGHT and membrane LIGHT encompassing mutagenesis in residues G188A to W198A. Binding to WT LIGHT is depicted as 100% and binding to the other LIGHT constructs is shown as a percentage of the WT binding. Constructs in bold show a significant reduction in binding compared to the WT.

| aa mutation | SEQ ID NO. | 3B04 | 3D12 | 2E08 | 3A07 | 3D12 | 2B11 | 3E09 |
|---|---|---|---|---|---|---|---|---|
| WT | 134 | 100 | 100 | 100 | 100 | 100 | 100 | 100 |
| G188A | 135 | 6 | 20 | 44 | 5 | 3 | 3 | 35 |
| R189A | 136 | 0 | 1 | 2 | 0 | 0 | 0 | 1 |
| A190S | 137 | 68 | 82 | 93 | 47 | 40 | 52 | 97 |
| T191A | 138 | 2 | 8 | 22 | 4 | 3 | 1 | 88 |
| S192A | 139 | 88 | 84 | 122 | 41 | 35 | 96 | 50 |
| S193A | 140 | 0 | 0 | 0 | 0 | 0 | 0 | 0 |
| S194A | 141 | 0 | 2 | 3 | 1 | 0 | 0 | 1 |
| R195A | 142 | 1 | 25 | 43 | 15 | 6 | 78 | 1 |
| V196A | 143 | 80 | 70 | 99 | 77 | 78 | 73 | 34 |
| W197A | 144 | 0 | 1 | 0 | 1 | 0 | 0 | 1 |
| W198A | 145 | 81 | 83 | 83 | 82 | 86 | 77 | 48 |

In Vivo Efficacy of mAb 3B04_Var16

Figure 9:
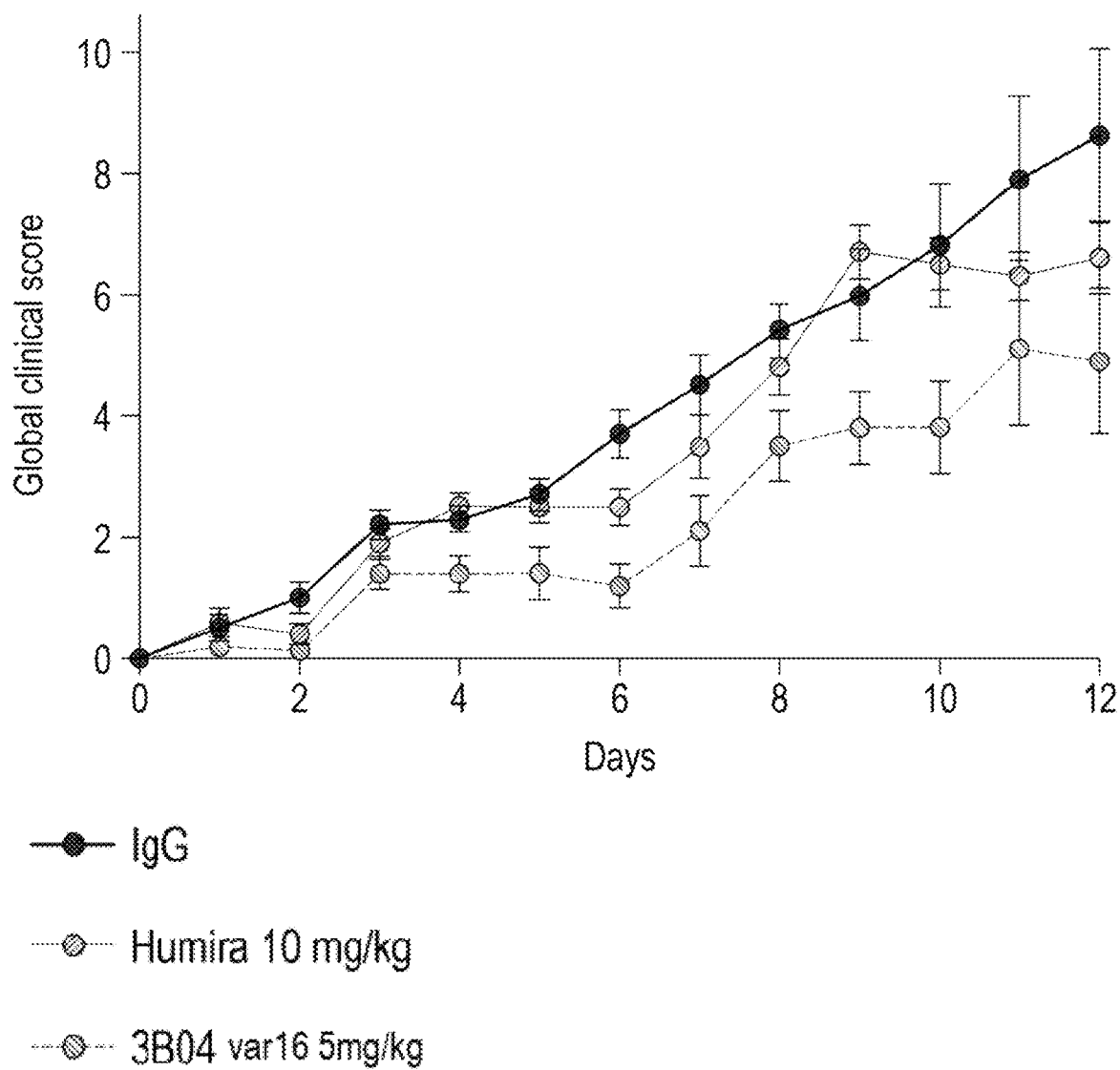
FIG. 9 shows the effect of anti-membrane LIGHT mAb 3B04 (variant 16) in an in vivo model of DSS-induced colitis in hu-NOG mice compared to a negative (IgG) and positive (humira, anti-TNF) controls.

The in vivo efficacy of the anti-membrane LIGHT mAb 3B04_var16 was tested in a DSS-induced colitis model in hu-NOG mice (FIG. 9). In this model the positive control, humira (anti-TNF), usually induces a significant drop in the global clinical score from days 9 to 11 compared to the IgG control. What was surprising, is that mAb 3B04_var16 induced a significant (p<0.05) decrease in global clinical score as early as day 2 in this model versus the IgG and humira controls. 3B04_var16 induced a fast, early onset of disease regression that was sustained throughout the experimental protocol. The effect of 3B04 var16 was significantly superior (p<0.05) to the anti-TNF positive control in this model as well. Administration of at least 3B04, 3D12, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16 is expected to result in a similarly significant (p<0.05) decrease in global clinical score in the DSS-induced colitis model in hu-NOG mice.

In Vitro Activity of mAb 3B04 Var16 on Primary Human PBMC

Figure 10A:
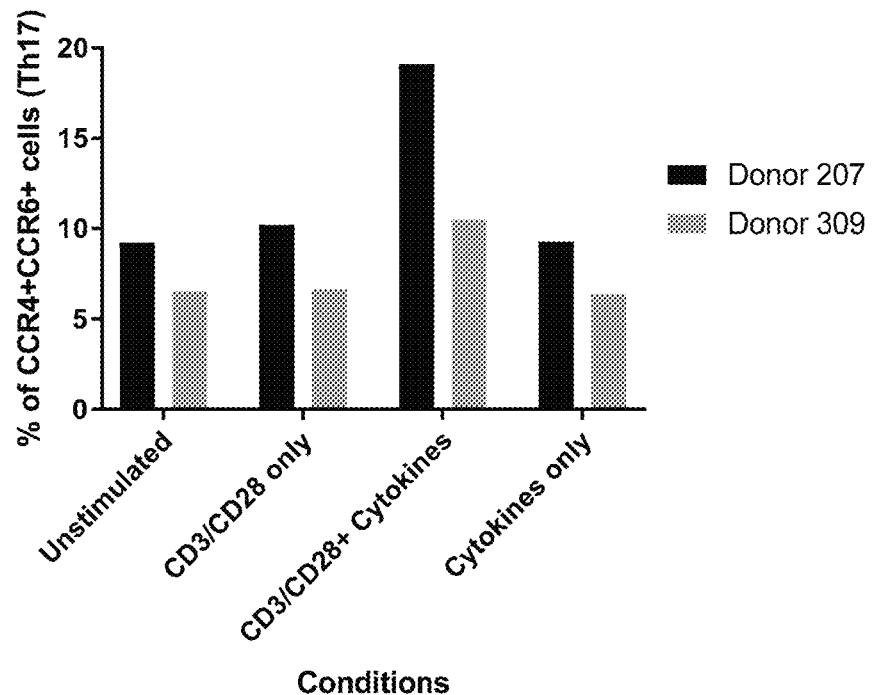
FIG. 10A shows the generation of human Th17 cells (CCR4+ CCR6+CD4 cells) under conditions of anti-CD3/CD28 stimulation, Th17 polarizing cytokines or the combination of both over a 3 day incubation.
Figure 10B:
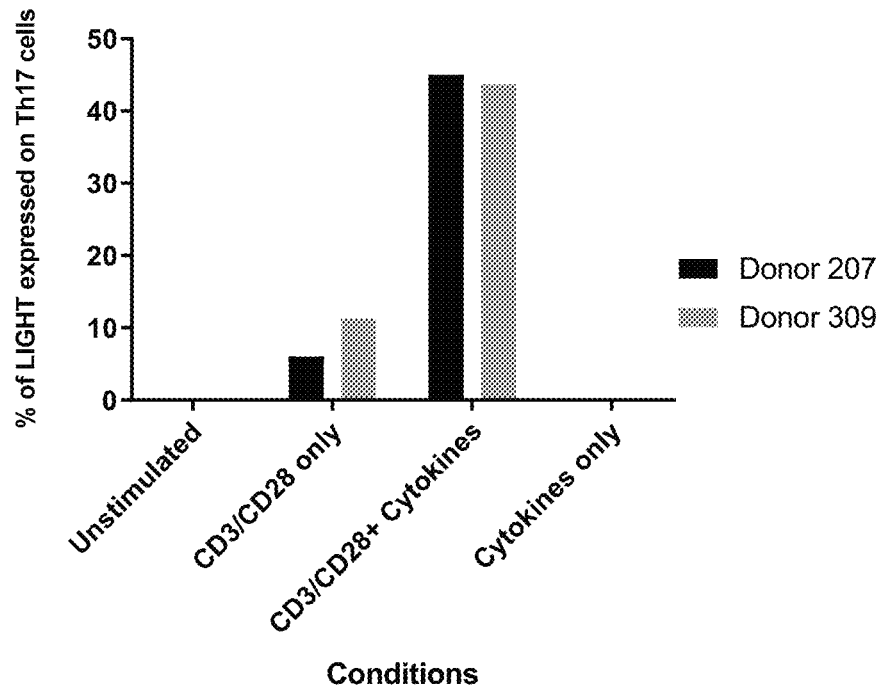
FIG. 10B shows the % of LIGHT expression on the Th17 cells generated from anti-CD3/CD28 stimulation, Th17 polarizing cytokines or the combination of both.
Figure 11A:
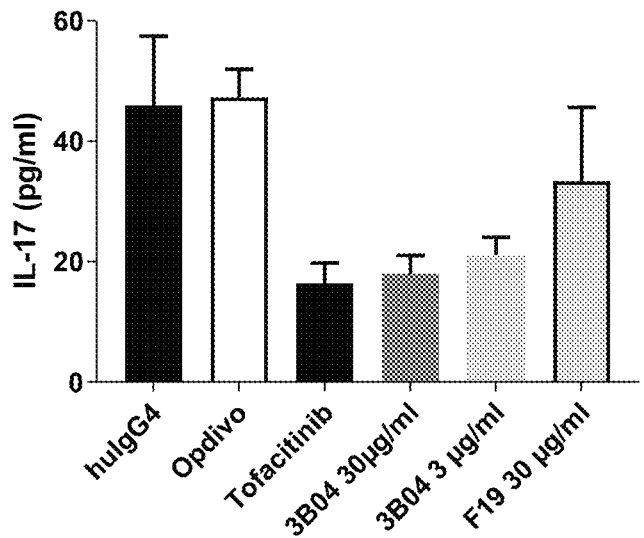
FIGS. 11A-11E shows the effect of anti-membrane LIGHT mAb 3B04 (var 16) on the inhibition of IL-17 (FIG. 11A), IFN gamma (FIG. 11B), TNF (FIG. 11C), IL-6 (FIG. 11D) and IL-12p70 (FIG. 11E) from CMV stimulation of human PBMC over a 5 day incubation. Two positive controls were used, Tofacitinib (1 uM) and Opdivo (10 ug/ml) and the control was human IgG4 at 10 ug/ml.
Figure 11B:
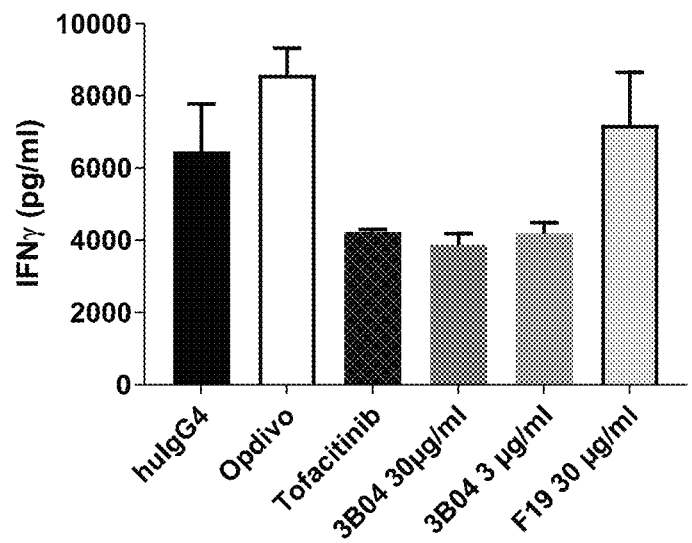
Figure 11C:
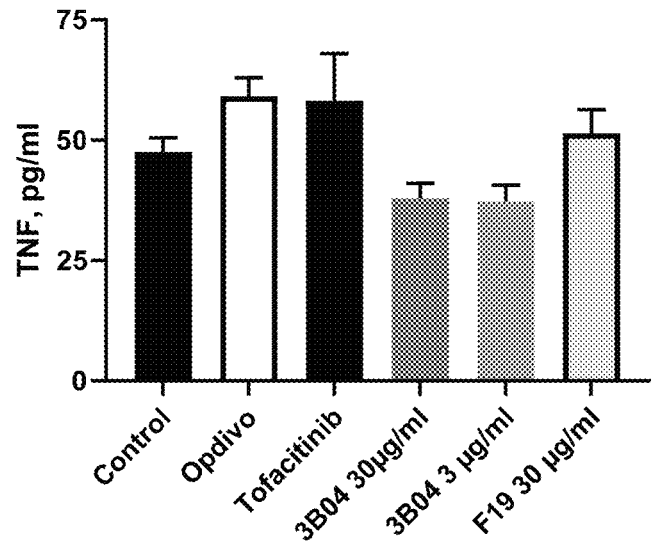
Figure 11D:
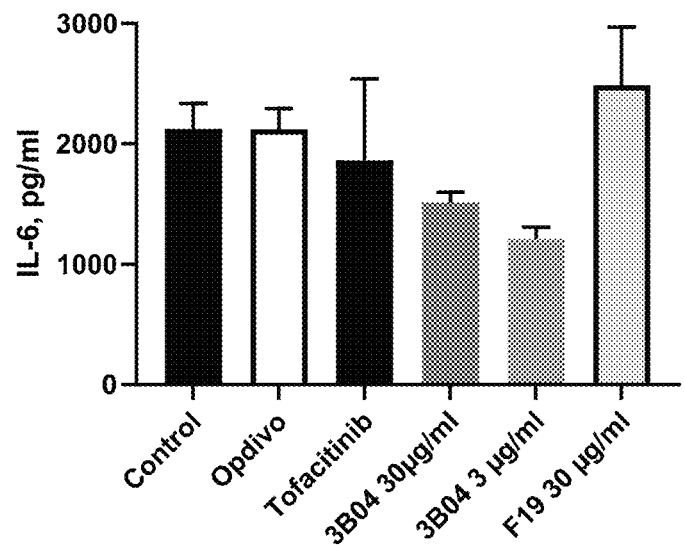
Figure 11E:
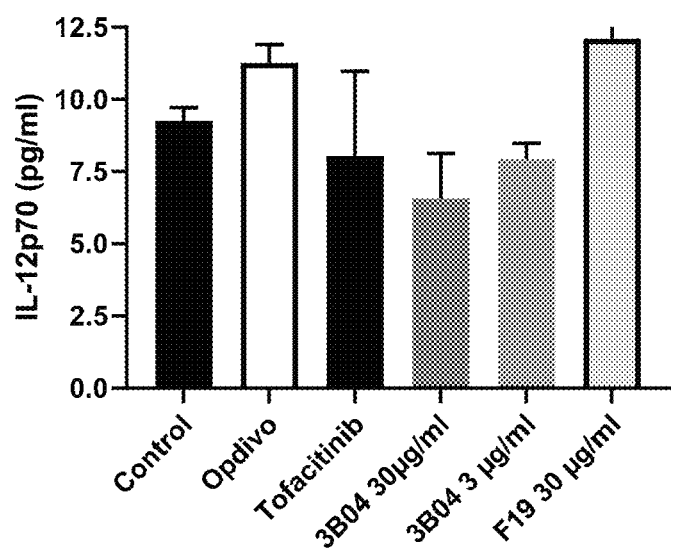

The spectrum of immune-mediated disease encompasses a wide variety of chronic inflammatory conditions such as IBD, comprised of Crohn's disease (CD) and ulcerative colitis (UC). Although the underlying initiators of the disease remain poorly understood, it is now clear that T cells are essential to the development and perpetuation of these diseases (Damsker et al. Ann N Y Acad Sci. 2010; 1183: 211-221). Since the initial description of functionally distinct T helper 1 (Th1) and Th2 CD4+ effector subsets, each with unique cytokine profiles (Mosmann et al. J Immunol. 1986; 136:2348-57), much work has focused on dissecting their roles in both health and disease. The emphasis has recently been focused to a new subset, the Th17 cell, so named due to its ability to secrete IL-17, which has emerged as a major factor in tissue-specific immune pathology. With respect to IBD, multiple CD-linked genetic susceptibility variants of IL23R have now been identified, as well as other genes of the Th17 pathway, including STAT3, RORc, IRF8, IL12b, ICOSLG and TNFSF15 (McGovern Gastroenterology. 2015; 149:1163-1176 and Duerr et al. Science. 2006; 314(5804):1461-3), which supports a hypothesis that IL-23-driven Th17 cells are mostly pathogenic in the development of CD. Th17 cells are also increased in CD and UC lesions as is increased expression of IL-17 and IL-23 (Kobayashi et al. Gut 2008; 57:1682-9; Fujino et al. Gut. 2003; 52:65-70; Cosmi et al. J Exp Med. 2008; 205:1903-16; Olsen et al. Cytokine. 2011; 56:633-40). For this reason, it was important to determine whether LIGHT is present on these inflammatory Th17 cells (identified as CCR6+CCR4+ CD4 cells). From FIG. 10A it can be seen that the Th17 combination cocktail (CD3/CD28 stimulation plus polarizing cytokines) is the most potent treatment to induce Th17 generation, a two-fold increase was generated with donor 207 and an increase of approximately 50% with donor 309. In this experiment LIGHT expression was induced by CD3/CD28 stimulation only (approximately 10%), and this expression was dramatically increased, approximately five-fold in the presence of the combination of CD3/CD28 stimulation and the polarizing cytokines on Th17 cells (FIG. 10B). The secretion of Th17 cytokines, IL-17 and IL-22, was also confirmed with the combination of CD3/CD28 stimulation and polarizing cytokines. It can be concluded that LIGHT is present on Th17 cells. In order to determine if 3B04 (variant 16) can inhibit cytokine production from PBMC a 5-day incubation of cells in the presence of the recall antigen, CMV, was utilised (FIG. 11A-E). It was found that 3B04 significantly (p<0.05) inhibited the inflammatory cytokines TNF, IL-17, IFN gamma, IL-6 and IL-12p70. It was surprising that the F19 mAb (from EP2292663) which recognises both membrane and soluble LIGHT equally had no activity in this human PBMC assay, demonstrating the importance of inhibiting only membrane LIGHT (with mAb 3B04) to significantly reduce inflammatory cytokine release. The positive controls of Tofacitinib (inhibited IL-17 and IFN gamma) and anti-PD-1 (Opdivo, increased IFN gamma) were also included.

Clauses

The present invention additionally provides the following embodiments, listed as numbered clauses, which may be combined with other features and aspects of the invention:
1. An anti-LIGHT antigen binding molecule comprising:
a VHCDR3 having at least 80% identity to the amino acid sequence of any one of SEQ ID NOs 8, 16, 24, 32, 40, 48, 56, 64, 72, 80, 88, 96, 104, 112 and 120; and/or a VLCDR3 having at least 80% identity to the amino acid sequence of any one of SEQ ID NOs 4, 12, 20, 28, 36, 44, 52, 60, 68, 76, 84, 92, 100, 108, and 116.

2. The anti-LIGHT antigen binding molecule of clause 1 comprising:
- a VHCDR3 having at least 85%, 90%, 91%, 92%, 93%, 94%, 95%, 96%, 97%, 98% or 99% identity to the amino acid sequence of any one of SEQ ID NOs 8, 16, 24, 32, 40, 48, 56, 64, 72, 80, 88, 96, 104, 112 and 120; and/or
- a VLCDR3 having at least 85%, 90%, 91%, 92%, 93%, 94%, 95%, 96%, 97%, 98% or 99% identity to the amino acid sequence of any one of SEQ ID NOs 4, 12, 20, 28, 36, 44, 52, 60, 68, 76, 84, 92, 100, 108, and 116.

3. The anti-LIGHT antigen binding molecule of clause 1 comprising:
- a VHCDR3 comprising the amino acid sequence of any one of SEQ ID NOs 8, 16, 24, 32, 40, 48, 56, 64, 72, 80, 88, 96, 104, 112 and 120; and/or
- a VLCDR3 comprising the amino acid sequence of any one of SEQ ID NOs 4, 12, 20, 28, 36, 44, 52, 60, 68, 76, 84, 92, 100, 108, and 116.

4. The anti-LIGHT antigen binding molecule of any one of clauses 1 to 3 comprising:
- a VHCDR1 having at least 80% identity to the amino acid sequence of any one of SEQ ID NOs 6, 14, 22, 30, 38, 46, 54, 62, 70, 78, 86, 94, 102, 110, 118;
- a VHCDR2 having at least 80% identity to the amino acid sequence of any one of SEQ ID NOs 7, 15, 23, 31, 39, 47, 55, 63, 71, 79, 87, 95, 103, 111, 119; and
- a VHCDR3 having at least 80% identity to the amino acid sequence of any one of SEQ ID NOs 8, 16, 24, 32, 40, 48, 56, 64, 72, 80, 88, 96, 104, 112 and 120; and/or
- a VLCDR1 having at least 80% identity to the amino acid sequence of any one of SEQ ID NOs 2, 10, 18, 26, 34, 42, 50, 58, 66, 74, 82, 90, 98, 106, 114;
- a VLCDR2 having at least 80% identity to the amino acid sequence of any one of SEQ ID NOs; 3, 11, 19, 27, 35, 43, 51, 59, 67, 75, 83, 91, 99, 107, 115; and
- a VLCDR3 having at least 80% identity to the amino acid sequence of any one of SEQ ID NOs 4, 12, 20, 28, 36, 44, 52, 60, 68, 76, 84, 92, 100, 108, and 116.

5. The anti-LIGHT antigen binding molecule of any one of clauses 1 to 4 comprising:
- a VHCDR1 having at least 85%, 90%, 91%, 92%, 93%, 94%, 95%, 96%, 97%, 98% or 99% identity to the amino acid sequence of any one of SEQ ID NOs 6, 14, 22, 30, 38, 46, 54, 62, 70, 78, 86, 94, 102, 110, 118;
- a VHCDR2 having at least 85%, 90%, 91%, 92%, 93%, 94%, 95%, 96%, 97%, 98% or 99% identity to the amino acid sequence of any one of SEQ ID NOs 7, 15, 23, 31, 39, 47, 55, 63, 71, 79, 87, 95, 103, 111, 119; and
- a VHCDR3 having at least 85%, 90%, 91%, 92%, 93%, 94%, 95%, 96%, 97%, 98% or 99% identity to the amino acid sequence of any one of SEQ ID NOs 8, 16, 24, 32, 40, 48, 56, 64, 72, 80, 88, 96, 104, 112 and 120; and/or
- a VLCDR1 having at least 85%, 90%, 91%, 92%, 93%, 94%, 95%, 96%, 97%, 98% or 99% identity to the amino acid sequence of any one of SEQ ID NOs 2, 10, 18, 26, 34, 42, 50, 58, 66, 74, 82, 90, 98, 106, 114;
- a VLCDR2 having at least 85%, 90%, 91%, 92%, 93%, 94%, 95%, 96%, 97%, 98% or 99% identity to the amino acid sequence of any one of SEQ ID NOs; 3, 11, 19, 27, 35, 43, 51, 59, 67, 75, 83, 91, 99, 107, 115; and
- a VLCDR3 having at least 85%, 90%, 91%, 92%, 93%, 94%, 95%, 96%, 97%, 98% or 99% identity to the amino acid sequence of any one of SEQ ID NOs 4, 12, 20, 28, 36, 44, 52, 60, 68, 76, 84, 92, 100, 108, and 116.

6. The anti-LIGHT antigen binding molecule of any one of clauses 1 to 5 comprising:
- a VHCDR1 comprising the amino acid sequence of any one of SEQ ID NOs 6, 14, 22, 30, 38, 46, 54, 62, 70, 78, 86, 94, 102, 110, 118;
- a VHCDR2 comprising the amino acid sequence of any one of SEQ ID NOs 7, 15, 23, 31, 39, 47, 55, 63, 71, 79, 87, 95, 103, 111, 119; and
- a VHCDR3 comprising the amino acid sequence of any one of SEQ ID NOs 8, 16, 24, 32, 40, 48, 56, 64, 72, 80, 88, 96, 104, 112 and 120;
and/or
- a VLCDR1 comprising the amino acid sequence of any one of SEQ ID NOs 2, 10, 18, 26, 34, 42, 50, 58, 66, 74, 82, 90, 98, 106, 114;
- a VLCDR2 comprising the amino acid sequence of any one of SEQ ID NOs; 3, 11, 19, 27, 35, 43, 51, 59, 67, 75, 83, 91, 99, 107, 115; and
- a VLCDR3 comprising the amino acid sequence of any one of SEQ ID NOs 4, 12, 20, 28, 36, 44, 52, 60, 68, 76, 84, 92, 100, 108, and 116.

7. The anti-LIGHT antigen binding molecule of any one of clauses 1 to 6 comprising:
- a heavy chain variable region having at least 80% identity to the amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, SEQ ID NO: 77, SEQ ID NO: 85, SEQ ID NO: 93, SEQ ID NO: 101, SEQ ID NO: 109, SEQ ID NO: 117;
and/or
- a light chain variable region having at least 80% identity to the amino acid sequence selected from the group consisting of consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, SEQ ID NO: 73, SEQ ID NO: 81, SEQ ID NO: 89, SEQ ID NO: 97, SEQ ID NO: 105, SEQ ID NO: 113.

8. The anti-LIGHT antigen binding molecule of any one of clauses 1 to 7 comprising:
a heavy chain variable region having at least 85%, 90%, 91%, 92%, 93%, 94%, 95%, 96%, 97%, 98% or 99% identity to the amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, SEQ ID NO: 77, SEQ ID NO: 85, SEQ ID NO: 93, SEQ ID NO: 101, SEQ ID NO: 109, SEQ ID NO: 117;
and/or
- a light chain variable region having at least 85%, 90%, 91%, 92%, 93%, 94%, 95%, 96%, 97%, 98% or 99% identity to the amino acid sequence selected from the group consisting of consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, SEQ ID NO: 73, SEQ ID NO: 81, SEQ ID NO: 89, SEQ ID NO: 97, SEQ ID NO: 105, SEQ ID NO: 113.

9. The anti-LIGHT antigen binding molecule of any one of clauses 1 to 8 comprising: a heavy chain variable region having an amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, SEQ ID NO:

77, SEQ ID NO: 85, SEQ ID NO: 93, SEQ ID NO: 101, SEQ ID NO: 109, SEQ ID NO: 117;

and/or a light chain variable region having an amino acid sequence selected from the group consisting of consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, SEQ ID NO: 73, SEQ ID NO: 81, SEQ ID NO: 89, SEQ ID NO: 97, SEQ ID NO: 105, SEQ ID NO: 113.

10. The anti-LIGHT antigen binding molecule of any preceding clause, wherein the antigen binding molecule is selected from the group consisting of:

(a) an anti-LIGHT antigen binding molecule comprising a heavy chain variable region comprising a VHCDR1 comprising the amino acid sequence DYEMH (SEQ ID NO: 6), a VHCDR2 comprising the amino acid sequence EIDPETGDTAYSQKFKG (SEQ ID NO: 7), a VHCDR3 comprising the amino acid sequence ETDYFFDY (SEQ ID NO: 8); and a light chain variable region comprising a VLCDR1 comprising the amino acid sequence GASENIYGALN (SEQ ID NO: 2), a VLCDR2 comprising the amino acid sequence GATNLAD (SEQ ID NO: 3) and a VLCDR3 comprising the amino acid sequence QNVLTTPWT (SEQ ID NO: 4);

or comprising VHCDR and VLCDR sequences that are at least 90%, at least 95%, at least 98% or at least 99% identical thereof;

(b) an anti-LIGHT antigen binding molecule comprising a heavy chain variable region comprising a VHCDR1 comprising the amino acid sequence DSEIH (SEQ ID NO: 46), a VHCDR2 comprising the amino acid sequence EIDPETGGTAYNQKFKG (SEQ ID NO: 47), a VHCDR3 comprising the amino acid sequence ETDYFFDY (SEQ ID NO: 48); and a light chain variable region comprising a VLCDR1 comprising the amino acid sequence GASENIYGALN (SEQ ID NO: 42), a VLCDR2 comprising the amino acid sequence GATNLAD (SEQ ID NO: 43) and a VLCDR3 comprising the amino acid sequence QNVLSTPWT (SEQ ID NO: 44);

or comprising VHCDR and VLCDR sequences that are at least 90%, at least 95%, at least 98% or at least 99% identical thereof;

(c) an anti-LIGHT antigen binding molecule comprising a heavy chain variable region comprising a VHCDR1 comprising the amino acid sequence DYAIH (SEQ ID NO: 86), a VHCDR2 comprising the amino acid sequence VISTYYGDASYNQKFKG (SEQ ID NO: 87), a VHCDR3 comprising the amino acid SRGEYGNYDAMDY sequence (SEQ ID NO: 88); and a light chain variable region comprising a VLCDR1 comprising the amino acid sequence KASQSVDYDGDSYMN (SEQ ID NO: 82), a VLCDR2 comprising the amino acid sequence AASNLES (SEQ ID NO: 83) and a VLCDR3 comprising the amino acid sequence QQSNEDPLT (SEQ ID NO: 84);

or comprising VHCDR and VLCDR sequences that are at least 90%, at least 95%, at least 98% or at least 99% identical thereof;

(d) an anti-LIGHT antigen binding molecule comprising a heavy chain variable region comprising a VHCDR1 comprising the amino acid sequence DSEIH (SEQ ID NO: 94), a VHCDR2 comprising the amino acid sequence EIDPETGGTAYNQKFKG (SEQ ID NO: 95), a VHCDR3 comprising the amino acid sequence ETDYFFDY (SEQ ID NO: 96); and a light chain variable region comprising a VLCDR1 comprising the amino acid sequence SASSSVSYMY (SEQ ID NO: 90), a VLCDR2 comprising the amino acid sequence DTSNLAS (SEQ ID NO: 91) and a VLCDR3 comprising the amino acid sequence QQWSSYPLT (SEQ ID NO: 92);

or comprising VHCDR and VLCDR sequences that are at least 90%, at least 95%, at least 98% or at least 99% identical thereof;

(e) an anti-LIGHT antigen binding molecule comprising heavy chain variable region comprising a VHCDR1 comprising the amino acid sequence DSEIH (SEQ ID NO: 102), a VHCDR2 comprising the amino acid sequence EIDPETGGTAYNQKFKG (SEQ ID NO: 103), a VHCDR3 comprising the amino acid sequence ETDYFFDY (SEQ ID NO: 104); and a light chain variable region comprising a VLCDR1 comprising the amino acid sequence SASSSVSYMY (SEQ ID NO: 98), a VLCDR2 comprising the amino acid sequence DTSNLAS (SEQ ID NO: 99) and a VLCDR3 comprising the amino acid sequence QQWSSYPLT (SEQ ID NO: 100);

or comprising VHCDR and VLCDR sequences that are at least 90%, at least 95%, at least 98% or at least 99% identical thereof;

(f) an anti-LIGHT antigen binding molecule comprising a heavy chain variable region comprising a VHCDR1 comprising the amino acid sequence DYYMY (SEQ ID NO: 110), a VHCDR2 comprising the amino acid sequence AIGDGGIYTYYADTVKG (SEQ ID NO: 111), a VHCDR3 comprising the amino acid sequence GTGDGFAY (SEQ ID NO: 112); and a light chain variable region comprising a VLCDR1 comprising the amino acid sequence RASESVDSYGNSFMH (SEQ ID NO: 106), a VLCDR2 comprising the amino acid sequence LASNLES (SEQ ID NO: 107) and a VLCDR3 comprising the amino acid sequence QQNNEDPYT (SEQ ID NO: 108);

or comprising VHCDR and VLCDR sequences that are at least 90%, at least 95%, at least 98% or at least 99% identical thereof; and (g) an anti-LIGHT antigen binding molecule comprising a heavy chain variable region comprising a VHCDR1 comprising the amino acid sequence DYAIH (SEQ ID NO: 118), a VHCDR2 comprising the amino acid sequence VISTYYGDASYNQKFKG (SEQ ID NO: 119), a VHCDR3 comprising the amino acid sequence SRGEYGNYDAMDY (SEQ ID NO: 120); and a light chain variable region comprising a VLCDR1 comprising the amino acid sequence RASESVDSYGNSFMH (SEQ ID NO: 114), a VLCDR2 comprising the amino acid sequence RASNLES (SEQ ID NO: 115) and a VLCDR3 comprising the amino acid sequence QQSNEDPYT (SEQ ID NO: 116);

or comprising VHCDR and VLCDR sequences that are at least 90%, at least 95%, at least 98% or at least 99% identical thereof.

11. The anti-LIGHT antigen binding molecule of any preceding clause, wherein the antigen binding molecule is selected from the group consisting of:

(a) an anti-LIGHT antigen binding molecule comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15)

and a VHCDR3 comprising the amino acid sequence ETDYFFDY (SEQ ID NO: 16); and
a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);
or comprising VHCDR and VLCDR sequences that are at least 90%, at least 95%, at least 98% or at least 99% identical thereof;
(b) an anti-LIGHT antigen binding molecule comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and
a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);
or comprising VHCDR and VLCDR sequences that are at least 90%, at least 95%, at least 98% or at least 99% identical thereof;
(c) an anti-LIGHT antigen binding molecule comprising a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and
a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);
or comprising VHCDR and VLCDR sequences that are at least 90%, at least 95%, at least 98% or at least 99% identical thereof;
(d) an anti-LIGHT antigen binding molecule comprising a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and
a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);
or comprising VHCDR and VLCDR sequences that are at least 90%, at least 95%, at least 98% or at least 99% identical thereof;
(e) an anti-LIGHT antigen binding molecule comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and
a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);
or comprising VHCDR and VLCDR sequences that are at least 90%, at least 95%, at least 98% or at least 99% identical thereof;
(f) an anti-LIGHT antigen binding molecule comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and
a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);
or comprising VHCDR and VLCDR sequences that are at least 90%, at least 95%, at least 98% or at least 99% identical thereof;
(g) an anti-LIGHT antigen binding molecule comprising a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and
a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);
or comprising VHCDR and VLCDR sequences that are at least 90%, at least 95%, at least 98% or at least 99% identical thereof;
(h) an anti-LIGHT antigen binding molecule comprising a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and
a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);
or comprising VHCDR and VLCDR sequences that are at least 90%, at least 95%, at least 98% or at least 99% identical thereof;
(i) an anti-LIGHT antigen binding molecule comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and
a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);
or comprising VHCDR and VLCDR sequences that are at least 90%, at least 95%, at least 98% or at least 99% identical thereof;

(j) an anti-LIGHT antigen binding molecule comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and
a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);
or comprising VHCDR and VLCDR sequences that are at least 90%, at least 95%, at least 98% or at least 99% identical thereof;

(k) an anti-LIGHT antigen binding molecule comprising a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and
a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);
or comprising VHCDR and VLCDR sequences that are at least 90%, at least 95%, at least 98% or at least 99% identical thereof;

(l) an anti-LIGHT antigen binding molecule comprising a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and
a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);
or comprising VHCDR and VLCDR sequences that are at least 90%, at least 95%, at least 98% or at least 99% identical thereof;

(m) an anti-LIGHT antigen binding molecule comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and
a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);
or comprising VHCDR and VLCDR sequences that are at least 90%, at least 95%, at least 98% or at least 99% identical thereof;

(n) an anti-LIGHT antigen binding molecule comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and
a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);
or comprising VHCDR and VLCDR sequences that are at least 90%, at least 95%, at least 98% or at least 99% identical thereof;

(o) an anti-LIGHT antigen binding molecule comprising a heavy chain variable region comprising a VHCDR1 comprising the amino acid sequence DYEMH (SEQ ID NO: 30), a VHCDR2 comprising the amino acid sequence EIDPETGDTAYSQKFQG (SEQ ID NO: 31) and a VHCDR3 comprising the amino acid sequence ETDYFFDY (SEQ ID NO: 32); and
a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);
or comprising VHCDR and VLCDR sequences that are at least 90%, at least 95%, at least 98% or at least 99% identical thereof; and (p) an anti-LIGHT antigen binding molecule comprising a heavy chain variable region comprising a VHCDR1 comprising the amino acid sequence DYEMH (SEQ ID NO: 38), a VHCDR2 comprising the amino acid sequence EIDPETGDTAYSQKFQG (SEQ ID NO: 39) and a VHCDR3 comprising the amino acid sequence ETDYFFDY (SEQ ID NO: 40); and
a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);
or comprising VHCDR and VLCDR sequences that are at least 90%, at least 95%, at least 98% or at least 99% identical thereof.

12. The anti-LIGHT antigen binding molecule of any preceding clause, wherein the antigen binding molecule is selected from the group consisting of:
(a) an anti-LIGHT antigen binding molecule comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and
GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);

or comprising VHCDR and VLCDR sequences that are at least 90%, at least 95%, at least 98% or at least 99% identical thereof;
(b) an anti-LIGHT antigen binding molecule comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and
GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);
or comprising VHCDR and VLCDR sequences that are at least 90%, at least 95%, at least 98% or at least 99% identical thereof;
(c) an anti-LIGHT antigen binding molecule comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and
a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);
or comprising VHCDR and VLCDR sequences that are at least 90%, at least 95%, at least 98% or at least 99% identical thereof;
(d) an anti-LIGHT antigen binding molecule comprising a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and
a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);
or comprising VHCDR and VLCDR sequences that are at least 90%, at least 95%, at least 98% or at least 99% identical thereof;
(e) an anti-LIGHT antigen binding molecule comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and
a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);
or comprising VHCDR and VLCDR sequences that are at least 90%, at least 95%, at least 98% or at least 99% identical thereof;
(f) an anti-LIGHT antigen binding molecule comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and
a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);
or comprising VHCDR and VLCDR sequences that are at least 90%, at least 95%, at least 98% or at least 99% identical thereof;
(g) an anti-LIGHT antigen binding molecule comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and
a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);
or comprising VHCDR and VLCDR sequences that are at least 90%, at least 95%, at least 98% or at least 99% identical thereof;
(h) an anti-LIGHT antigen binding molecule comprising a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and
a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);
or comprising VHCDR and VLCDR sequences that are at least 90%, at least 95%, at least 98% or at least 99% identical thereof;
(i) an anti-LIGHT antigen binding molecule comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3; and
a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);
or comprising VHCDR and VLCDR sequences that are at least 90%, at least 95%, at least 98% or at least 99% identical thereof;
(j) an anti-LIGHT antigen binding molecule comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63)

and a VHCDR3 comprising the amino acid sequence ETDYFFDY (SEQ ID NO: 64); and
a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);
or comprising VHCDR and VLCDR sequences that are at least 90%, at least 95%, at least 98% or at least 99% identical thereof;
(k) an anti-LIGHT antigen binding molecule comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and
a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);
or comprising VHCDR and VLCDR sequences that are at least 90%, at least 95%, at least 98% or at least 99% identical thereof;
(l) an anti-LIGHT antigen binding molecule comprising a heavy chain variable region comprising a VHCDR1 comprising the amino acid sequence DSEMIH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and
a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);
or comprising VHCDR and VLCDR sequences that are at least 90%, at least 95%, at least 98% or at least 99% identical thereof;
(m) an anti-LIGHT antigen binding molecule comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3; and
a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76);
or comprising VHCDR and VLCDR sequences that are at least 90%, at least 95%, at least 98% or at least 99% identical thereof;
(n) an anti-LIGHT antigen binding molecule comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and
a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76);
or comprising VHCDR and VLCDR sequences that are at least 90%, at least 95%, at least 98% or at least 99% identical thereof;
(o) an anti-LIGHT antigen binding molecule comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and
a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76); and
or comprising VHCDR and VLCDR sequences that are at least 90%, at least 95%, at least 98% or at least 99% identical thereof;
(p) an anti-LIGHT antigen binding molecule comprising a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and
a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76).

13. The anti-LIGHT antigen binding molecule of any preceding clause, wherein the antigen-binding molecule comprises a heavy chain variable region and a light chain variable region selected from the group consisting of:
(a) a VH comprising the amino acid sequence of SEQ ID NO: 5 and a VL comprising the amino acid sequence of SEQ ID NO: 1 or comprising VH and VL sequences that are at least 90%, at least 95%, at least 98% or at least 99% identical to SEQ ID NO: 5 and SEQ ID NO: 1, respectively;
(b) a VH comprising the amino acid sequence of SEQ ID NO: 45 and a VL comprising the amino acid sequence of SEQ ID NO: 41 or comprising VH and VL sequences that are at least 90%, at least 95%, at least 98% or at least 99% identical to SEQ ID NO: 45 and SEQ ID NO: 41, respectively;
(c) a VH comprising the amino acid sequence of SEQ ID NO: 85 and a VL comprising the amino acid sequence of SEQ ID NO: 81 or comprising VH and VL sequences that are at least 90%, at least 95%, at least 98% or at least 99% identical to SEQ ID NO: 85 and SEQ ID NO: 81, respectively;
(d) a VH comprising the amino acid sequence of SEQ ID NO: 93 and a VL comprising the amino acid sequence of SEQ ID NO: 89 or comprising VH and VL sequences that are at least 90%, at least 95%, at least 98% or at least 99% identical to SEQ ID NO: 93 and SEQ ID NO: 89, respectively;
(d) a VH comprising the amino acid sequence of SEQ ID NO: 101 and a VL comprising the amino acid sequence of SEQ ID NO: 97 or comprising VH and VL sequences that are at least 90%, at least 95%, at least 98% or at least 99% identical to SEQ ID NO: 101 and SEQ ID NO: 97, respectively;

(e) a VH comprising the amino acid sequence of SEQ ID NO: 109 and a VL comprising the amino acid sequence of SEQ ID NO: 105 or comprising VH and VL sequences that are at least 90%, at least 95%, at least 98% or at least 99% identical to SEQ ID NO: 109 and SEQ ID NO: 105, respectively;

(f) a VH comprising the amino acid sequence of SEQ ID NO: 117 and a VL comprising the amino acid sequence of SEQ ID NO: 113 or comprising VH and VL sequences that are at least 90%, at least 95%, at least 98% or at least 99% identical to SEQ ID NO: 117 and SEQ ID NO: 113, respectively;

14. The anti-LIGHT antigen binding molecule of any preceding clause, wherein the antigen-binding molecule comprises a heavy chain variable region and a light chain variable region selected from the group consisting of:

(a) a VH comprising the amino acid sequence of SEQ ID NO: 13 and a VL comprising the amino acid sequence of SEQ ID NO: 9 or comprising VH and VL sequences that are at least 90%, at least 95%, at least 98% or at least 99% identical to SEQ ID NO: 13 and SEQ ID NO: 9, respectively;

(b) a VH comprising the amino acid sequence of SEQ ID NO: 21 and a VL comprising the amino acid sequence of SEQ ID NO: 9 or comprising VH and VL sequences that are at least 90%, at least 95%, at least 98% or at least 99% identical to SEQ ID NO: 21 and SEQ ID NO: 9, respectively;

(c) a VH comprising the amino acid sequence of SEQ ID NO: 29 and a VL comprising the amino acid sequence of SEQ ID NO: 9 or comprising VH and VL sequences that are at least 90%, at least 95%, at least 98% or at least 99% identical to SEQ ID NO: 29 and SEQ ID NO: 9, respectively;

(d) a VH comprising the amino acid sequence of SEQ ID NO: 37 and a VL comprising the amino acid sequence of SEQ ID NO: 9 or comprising VH and VL sequences that are at least 90%, at least 95%, at least 98% or at least 99% identical to SEQ ID NO: 37 and SEQ ID NO: 9, respectively;

(e) a VH comprising the amino acid sequence of SEQ ID NO: 13 and a VL comprising the amino acid sequence of SEQ ID NO: 17 (or comprising VH and VL sequences that are at least 90%, at least 95%, at least 98% or at least 99% identical to SEQ ID NO: 13 and SEQ ID NO: 17, respectively);

(f) a VH comprising the amino acid sequence of SEQ ID NO: 21 and a VL comprising the amino acid sequence of SEQ ID NO: 17 or comprising VH and VL sequences that are at least 90%, at least 95%, at least 98% or at least 99% identical to SEQ ID NO: 21 and SEQ ID NO: 17, respectively;

(g) a VH comprising the amino acid sequence of SEQ ID NO: 37 and a VL comprising the amino acid sequence of SEQ ID NO: 17 or comprising VH and VL sequences that are at least 90%, at least 95%, at least 98% or at least 99% identical to SEQ ID NO: 37 and SEQ ID NO: 17, respectively;

(h) a VH comprising the amino acid sequence of SEQ ID NO: 13 and a VL comprising the amino acid sequence of SEQ ID NO: 25 or comprising VH and VL sequences that are at least 90%, at least 95%, at least 98% or at least 99% identical to SEQ ID NO: 13 and SEQ ID NO: 25, respectively;

(i) a VH comprising the amino acid sequence of SEQ ID NO: 21 and a VL comprising the amino acid sequence of SEQ ID NO: 25 or comprising VH and VL sequences that are at least 90%, at least 95%, at least 98% or at least 99% identical to SEQ ID NO: 21 and SEQ ID NO: 25, respectively;

(j) a VH comprising the amino acid sequence of SEQ ID NO: 29 and a VL comprising the amino acid sequence of SEQ ID NO: 25 or comprising VH and VL sequences that are at least 90%, at least 95%, at least 98% or at least 99% identical to SEQ ID NO: 37 and SEQ ID NO: 25, respectively;

(k) a VH comprising the amino acid sequence of SEQ ID NO: 29 and a VL comprising the amino acid sequence of SEQ ID NO: 25 or comprising VH and VL sequences that are at least 90%, at least 95%, at least 98% or at least 99% identical to SEQ ID NO: 37 and SEQ ID NO: 25, respectively;

(l) a VH comprising the amino acid sequence of SEQ ID NO: 13 and a VL comprising the amino acid sequence of SEQ ID NO: 33 or VH and VL sequences that are at least 90%, at least 95%, at least 98% or at least 99% identical to SEQ ID NO: 13 and SEQ ID NO: 33, respectively;

(m) a VH comprising the amino acid sequence of SEQ ID NO: 21 and a VL comprising the amino acid sequence of SEQ ID NO: 33 or VH and VL sequences that are at least 90%, at least 95%, at least 98% or at least 99% identical to SEQ ID NO: 21 and SEQ ID NO: 33, respectively;

(n) a VH comprising the amino acid sequence of SEQ ID NO: 29 and a VL comprising the amino acid sequence of SEQ ID NO: 33 or VH and VL sequences that are at least 90%, at least 95%, at least 98% or at least 99% identical to SEQ ID NO: 29 and SEQ ID NO: 33, respectively;

(o) a VH comprising the amino acid sequence of SEQ ID NO: 37 and a VL comprising the amino acid sequence of SEQ ID NO: 33 (VH and VL sequences that are at least 90%, at least 95%, at least 98% or at least 99% identical to SEQ ID NO: 37 and SEQ ID NO: 33, respectively;

15. The anti-LIGHT antigen binding molecule of any preceding clause, wherein the antigen-binding molecule comprises a heavy chain variable region and a light chain variable region selected from the group consisting of:

(a) a VH comprising the amino acid sequence of SEQ ID NO: 53 and a VL comprising the amino acid sequence of SEQ ID NO: 49 or VH and VL sequences that are at least 90%, at least 95%, at least 98% or at least 99% identical to SEQ ID NO: 53 and SEQ ID NO: 49, respectively;

(b) a VH comprising the amino acid sequence of SEQ ID NO: 61 and a VL comprising the amino acid sequence of SEQ ID NO: 49 or VH and VL sequences that are at least 90%, at least 95%, at least 98% or at least 99% identical to SEQ ID NO: 61 and SEQ ID NO: 49, respectively;

(c) a VH comprising the amino acid sequence of SEQ ID NO: 69 and a VL comprising the amino acid sequence of SEQ ID NO: 49 or VH and VL sequences that are at least 90%, at least 95%, at least 98% or at least 99% identical to SEQ ID NO: 69 and SEQ ID NO: 49, respectively;

(d) a VH comprising the amino acid sequence of SEQ ID NO: 77 and a VL comprising the amino acid sequence of SEQ ID NO: 49 or VH and VL sequences that are at least 90%, at least 95%, at least 98% or at least 99% identical to SEQ ID NO: 77 and SEQ ID NO: 49, respectively;

(e) a VH comprising the amino acid sequence of SEQ ID NO: 53 and a VL comprising the amino acid sequence of SEQ ID NO: 57 or VH and VL sequences that are at least 90%, at least 95%, at least 98% or at least 99% identical to SEQ ID NO: 53 and SEQ ID NO: 57, respectively;

(f) a VH comprising the amino acid sequence of SEQ ID NO: 61 and a VL comprising the amino acid sequence of SEQ ID NO: 57 or VH and VL sequences that are at least 90%, at least 95%, at least 98% or at least 99% identical to SEQ ID NO: 61 and SEQ ID NO: 57, respectively;

(g) a VH comprising the amino acid sequence of SEQ ID NO: 69 and a VL comprising the amino acid sequence of SEQ ID NO: 57 or VH and VL sequences that are at least 90%, at least 95%, at least 98% or at least 99% identical to SEQ ID NO: 69 and SEQ ID NO: 57, respectively;

(h) a VH comprising the amino acid sequence of SEQ ID NO: 77 and a VL comprising the amino acid sequence of SEQ ID NO: 57 or VH and VL sequences that are at least 90%, at least 95%, at least 98% or at least 99% identical to SEQ ID NO: 77 and SEQ ID NO: 57, respectively;

(i) a VH comprising the amino acid sequence of SEQ ID NO: 53 and a VL comprising the amino acid sequence of SEQ ID NO: 65 or VH and VL sequences that are at least 90%, at least 95%, at least 98% or at least 99% identical to SEQ ID NO: 53 and SEQ ID NO: 65, respectively;

(j) a VH comprising the amino acid sequence of SEQ ID NO: 69 and a VL comprising the amino acid sequence of SEQ ID NO: 65 or VH and VL sequences that are at least 90%, at least 95%, at least 98% or at least 99% identical to SEQ ID NO: 69 and SEQ ID NO: 65 respectively;

(k) a VH comprising the amino acid sequence of SEQ ID NO: 77 and a VL comprising the amino acid sequence of SEQ ID NO: 65 or VH and VL sequences that are at least 90%, at least 95%, at least 98% or at least 99% identical to SEQ ID NO: 77 and SEQ ID NO: 65, respectively;

(l) a VH comprising the amino acid sequence of SEQ ID NO: 53 and a VL comprising the amino acid sequence of SEQ ID NO: 73 or VH and VL sequences that are at least 90%, at least 95%, at least 98% or at least 99% identical to SEQ ID NO: 53 and SEQ ID NO: 73, respectively;

(m) a VH comprising the amino acid sequence of SEQ ID NO: 61 and a VL comprising the amino acid sequence of SEQ ID NO: 73 or VH and VL sequences that are at least 90%, at least 95%, at least 98% or at least 99% identical to SEQ ID NO: 61 and SEQ ID NO: 73, respectively;

(n) a VH comprising the amino acid sequence of SEQ ID NO: 69 and a VL comprising the amino acid sequence of SEQ ID NO: 73 or VH and VL sequences that are at least 90%, at least 95%, at least 98% or at least 99% identical to SEQ ID NO: 69 and SEQ ID NO: 73, respectively; and (o) a VH comprising the amino acid sequence of SEQ ID NO: 77 and a VL comprising the amino acid sequence of SEQ ID NO: 73 or VH and VL sequences that are at least 90%, at least 95%, at least 98% or at least 99% identical to SEQ ID NO: 77 and SEQ ID NO: 73, respectively.

16. The anti-LIGHT antigen binding molecule of any preceding clause wherein the anti-LIGHT antigen binding molecule is an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

17. The anti-LIGHT antigen binding molecule of clause 16, wherein the antibody comprises 1 to 10, 1 to 5 or 1 to 2 conservative amino acid substitutions across all 6 CDR regions.

18. The anti-LIGHT antigen binding molecule of clause 16, wherein the antibody comprises 1 to 10, 1 to 5 or 1 to 2 conservative amino acid substitutions in one or both of the variable heavy and light regions.

19. The anti-LIGHT antigen binding molecule of clause 16, wherein the antibody comprises 1 to 10, 1 to 5, or 1 to 2 conservative amino acid substitutions in the framework regions.

20. An antigen-binding molecule that specifically binds to LIGHT and inhibits the binding of LIGHT to an antigen-binding molecule of any one of clauses 1 to 19.

21. The antigen-binding molecule of clause 20 wherein the antigen-binding molecule specifically binds to LIGHT and inhibits the binding of LIGHT to an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

22. An antigen-binding molecule that specifically binds to an epitope of LIGHT that is bound by an antigen-binding molecule of any one of clauses 1 to 19.

23. The antigen-binding molecule of clause 22 wherein the antigen-binding molecule specifically binds to an epitope of LIGHT that is bound by an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

24. An antigen-binding molecule that specifically binds to an epitope of human LIGHT wherein the epitope comprises the amino acids GRATSSSRVW (SEQ ID NO: 124).

25. The antigen-binding molecule of clause 24 wherein the antigen binding molecule is selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, and fragments and variants thereof.

26. The antigen-binding molecule of clause 25 wherein the antigen-binding molecule is 3B04_var16.

27. An antigen-binding molecule that specifically binds to human LIGHT, wherein the antigen-binding molecule binds to a trimer of human LIGHT in a ratio of 1:1.

28. The antigen-binding molecule of clause 27 wherein the antigen-binding molecule is selected from 3B04, 3D12, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16, and fragments and variants thereof.

29. The antigen-binding molecule of clause 33 wherein the antigen-binding molecule is 3B04_var16. An antigen-binding molecule that specifically binds to LIGHT and competes with binding to LIGHT with an antigen-binding molecule of any one of clauses 1 to 19.

30. The antigen-binding molecule of clause 29 wherein the antigen-binding molecule specifically binds to LIGHT and competes with binding to LIGHT with an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

31. An anti-LIGHT antigen binding molecule according to any one of clauses 1 to 16, comprising 1 to 10 amino acid substitutions in the specified sequence or sequences.

32. The anti-LIGHT antigen binding molecule according to clause 31, comprising 1 to amino acid substitutions in the specified sequence or sequences.

33. The anti-LIGHT antigen binding molecule according to clause 31, comprising 1 to 2 amino acid substitutions in the specified sequence or sequences.

34. The anti-LIGHT antigen binding molecule according to any one of clauses 31 to 33, wherein the one or more amino acid substitutions are in the CDR region or CDR regions of the antigen binding molecule.

35. The anti-LIGHT antigen binding molecule according to any one of clauses 31 to 33, wherein the one or more amino acid substitutions are in one or both of the variable regions of the antigen binding molecule.

36. The anti-LIGHT antigen binding molecule according to any one of clauses 31 to 33, wherein the one or more amino acid substitutions are in the framework regions of the antigen binding molecule.

37. The anti-LIGHT antigen binding molecule according to any one of clauses 31 to 33, wherein the antigen-binding molecule is a variant derived from an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

38. The anti-LIGHT antigen binding molecule according to any one of clauses 17 to 19 or 31 to 33, wherein the amino acid substitutions are conservative amino acid substitutions.

39. The anti-LIGHT antigen binding molecule of any preceding clause wherein the antigen binding molecule is an antibody or fragment or derivative thereof.

40. The anti-LIGHT antigen binding molecule of clause 39, wherein the antibody fragment or derivative is Fab, F(ab')2, Fv, scFv, dAb, Fd, or a diabody.

41. The anti-LIGHT antibody of clause 39 wherein the antibody is a monoclonal antibody.

42. The anti-LIGHT antibody of clause 41 wherein the monoclonal antibody is humanised.

43. The anti-LIGHT antibody of clause 41 wherein the monoclonal antibody is deimmunised.

44. The anti-LIGHT antibody or antibody fragment of any one of clauses 39 to 43, wherein the antibody or antibody fragment is an IgA, IgD, IgE, IgG, IgM or IgY antibody or antibody fragment.

45. The anti-LIGHT antibody or antibody fragment of any one of clauses 39 to 44 wherein the antibody is an IgG antibody.

46. The anti-LIGHT antibody or antibody fragment of clause 45, wherein the IgG antibody or antibody fragment is an IgG4 antibody or antibody fragment.

47. An anti-LIGHT antigen binding molecule, wherein the anti-LIGHT antigen binding molecule is a humanised or deimmunised derivative of an anti-LIGHT antigen binding molecule of any one of clauses 1 to 19.

48. The anti-LIGHT antigen binding molecule according to clause 47, wherein the anti-LIGHT antigen binding molecule is a humanised or deimmunised derivative of an antibody selected from the group consisting of 2E08, 3A07, 3B04, 3C10, 3D12, 3E09 and 2B11.

49. An affinity matured mutant of an antigen-binding molecule or antibody according to any one of clauses 1 to 19.

50. The affinity matured mutant of clause 49, wherein the affinity matured mutant has a higher affinity for LIGHT compared to the parent antibody.

51. The affinity matured mutant of clause 49 or clause 50, wherein the affinity matured mutant is an affinity matured mutant derived from an antibody selected from the group consisting of 2E08, 3A07, 3B04, 3C10, 3D12, 3E09, 2B11, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

52. The antigen binding molecule or an affinity matured mutant of any preceding clause, wherein the antigen binding molecule or an affinity matured mutant specifically binds to human LIGHT.

53. The antigen binding molecule or an affinity matured mutant of any preceding clause, wherein the antigen binding molecule or an affinity matured mutant specifically binds to membrane-bound LIGHT.

54. The antigen binding molecule or an affinity matured mutant of any preceding clause, wherein the antigen binding molecule or an affinity matured mutant specifically binds to membrane-bound human LIGHT.

55. The antigen binding molecule or an affinity matured mutant of any preceding clause, wherein the antigen binding molecule or an affinity matured mutant has a higher affinity for membrane-bound LIGHT compared to soluble LIGHT.

56. The antigen binding molecule or an affinity matured mutant of clause 55, wherein the antigen binding molecule or an affinity matured mutant has at least about 10 times higher affinity for membrane-bound LIGHT compared to soluble LIGHT.

57. The antigen binding molecule or an affinity matured mutant of clause 55, wherein the antigen binding molecule or an affinity matured mutant has at least about 50 times higher affinity for membrane-bound LIGHT compared to soluble LIGHT.

58. The antigen binding molecule or an affinity matured mutant of clause 55, wherein the antigen binding molecule or an affinity matured mutant has at least about 100 times higher affinity for membrane-bound LIGHT compared to soluble LIGHT.

59. The antigen binding molecule or an affinity matured mutant of any preceding clause, wherein the antigen binding molecule or an affinity matured mutant has a $K_D$ value for membrane LIGHT of less than about 5 nM.

60. The antigen binding molecule or an affinity matured mutant of clause 59, wherein the antigen binding molecule or an affinity matured mutant has a $K_D$ value for membrane LIGHT of less than about 1 nM.

61. The antigen binding molecule or an affinity matured mutant of clause 59, wherein the antigen binding molecule or an affinity matured mutant has a $K_D$ value for membrane LIGHT of less than about 0.5 nM.

62. The antigen binding molecule or an affinity matured mutant of any preceding clause, wherein the antigen binding molecule or an affinity matured mutant has a $K_D$ value for soluble LIGHT of more than about 1 nM.

63. The antigen binding molecule or an affinity matured mutant of any preceding clause, wherein the antigen binding molecule or an affinity matured mutant has a $K_D$ value for soluble LIGHT of more than about 5 nM.

64. The antigen binding molecule or an affinity matured mutant of any preceding clause, wherein the antigen binding molecule or an affinity matured mutant has a $K_D$ value for soluble LIGHT of more than about 10 nM.

65. An anti-LIGHT antigen binding molecule or an affinity matured mutant thereof, wherein the antigen binding molecule or an affinity matured mutant has a $K_D$ value for membrane LIGHT of less than about 1 nM and a $K_D$ value for soluble LIGHT of more than about 1 nM.

66. An anti-LIGHT antigen binding molecule or an affinity matured mutant thereof, wherein the antigen binding molecule or an affinity matured mutant has a $K_D$ value for membrane LIGHT of less than about 1 nM and a $K_D$ value for soluble LIGHT of more than about 5 nM.

67. An anti-LIGHT antigen binding molecule or an affinity matured mutant thereof, wherein the antigen binding molecule or an affinity matured mutant has a $K_D$ value for membrane LIGHT of less than about 0.5 nM and a $K_D$ value for soluble LIGHT of more than about 10 nM, or a $K_D$ value for membrane LIGHT of less than about 0.1 nM and a $K_D$ value for soluble LIGHT of more than about 10 nM.

68. The antigen binding molecule or an affinity matured mutant of any preceding clause, wherein the antigen binding molecule or an affinity matured mutant inhibits the binding of membrane LIGHT to HVEM and/or LTβR or the binding of LIGHT expressing cells to HVEM and/or LTβR.

69. The antigen binding molecule or an affinity matured mutant of clause 68, wherein the antigen binding molecule or an affinity matured mutant inhibits the binding by at least 25%, at least 50% or at least 75%.

70. The antigen binding molecule or an affinity matured mutant of any preceding clause, wherein the antigen binding molecule or an affinity matured mutant partially inhibits the binding of membrane LIGHT to decoy receptor 3 or cells expressing membrane LIGHT to decoy receptor 3.

71. The antigen binding molecule or an affinity matured mutant of any preceding clause, wherein the antigen binding molecule or an affinity matured mutant decreases the secretion of IL-8 when administered in vivo or in vitro.

72. A pharmaceutical composition comprising an antigen binding molecule of any one of clauses 1 to 71 or an affinity matured mutant of any one of clauses 49 to 71.

73. A pharmaceutical composition of clause 72, further comprising another therapeutically active agent, or wherein the pharmaceutical composition is for use in combination with another therapeutically active agent.

74. The pharmaceutical composition of clause 73, wherein the other therapeutically active agent is an anti-inflammatory agent.

75. The pharmaceutical composition of clause 74, wherein the anti-inflammatory agent is an NSAID or a steroid.

76. The pharmaceutical composition of clause 75, wherein the NSAID is selected from the group consisting of salicylates (such as aspirin (acetylsalicylic acid), diflunisal, salicylic acid, salsalate), propionic acid derivatives (ibuprofen, dexibuprofen, naproxen), acetic acid derivatives (indomethacin, diclofenac), enolic acid derivatives, anthranilic acid derivatives (fenamates), selective COX-2 inhibitors, and sulfonanilides.

77. The pharmaceutical composition of clause 73, wherein the other therapeutically active agent is an immunosuppressant.

78. The pharmaceutical composition of clause 77, wherein the immunosuppressant is selected from the group consisting of glucocorticoids and cytostatics.

79. The pharmaceutical composition of clause 78, wherein the glucocorticoid is selected from the group consisting of cortisol, cortisone, prednisone, prednisolone, methylprednisolone, dexamethasone, betamethasone, triamcinolone, beclomethasone, fludrocortisone, deoxycorticosterone and aldosterone.

80. The pharmaceutical composition of clause 78, wherein the cytostatic is selected from the group consisting of an alkylating agent, an antimetabolite, methotrexate, azathioprine, mercaptopurine, and a cytotoxic antibiotic.

81. The pharmaceutical composition of clause 73, wherein the other pharmaceutically active agent is an inhibitor, wherein the inhibitor is selected from the group consisting of a TNF-inhibitor, an IL-12 inhibitor, an IL-23 inhibitor and an α4β7 integrin inhibitors.

82. The pharmaceutical composition of clause 81, wherein the inhibitor is a monoclonal antibody.

83. The pharmaceutical composition of clause 81, wherein the inhibitor is selected from the group consisting of infliximab (Remicade), adalimumab (Humira), certolizumab pegol (Cimzia), and golimumab (Simponi), ustekinumab (Stelara) and vedolizumab (Entyvio).

84. A kit comprising an antigen binding molecule of any one of clauses 1 to 66 or an affinity matured mutant of any one of clauses 49 to 71 or a pharmaceutical composition according to any one of clauses 72 to 83, and further comprising an additional therapeutically active agent.

85. The kit of clause 84, further comprising instructions for use.

86. The kit of clause 84 or clause 85, wherein the pharmaceutical components are disposed separately in the kit.

87. The kit of any preceding clause, wherein the additional therapeutically active agent is an anti-inflammatory agent, an immunosuppressant or an inhibitor.

88. The kit of clause 87, wherein the anti-inflammatory agent is an NSAID or a steroid.

89. The kit of clause 88, wherein the NSAID is selected from the group consisting of salicylates (such as aspirin (acetylsalicylic acid), diflunisal, salicylic acid, salsalate), propionic acid derivatives (ibuprofen, dexibuprofen, naproxen), acetic acid derivatives (indomethacin, diclofenac), enolic acid derivatives, anthranilic acid derivatives (fenamates), selective COX-2 inhibitors, and sulfonanilides.

90. The kit of clause 87, wherein the immunosuppressant is selected from the group consisting of glucocorticoids and cytostatics.

91. The kit of clause 90, wherein the glucocorticoid is selected from the group consisting of cortisol, cortisone, prednisone, prednisolone, methylprednisolone, dexamethasone, betamethasone, triamcinolone, beclomethasone, fludrocortisone, deoxycorticosterone and aldosterone.

92. The kit of clause 91, wherein the cytostatic is selected from the group consisting of an alkylating agent, an antimetabolite, methotrexate, azathioprine, mercaptopurine, and a cytotoxic antibiotic.

93. The kit of clause 87, wherein the additional therapeutically active agent is an inhibitor selected from the group consisting of a TNF-inhibitor, an IL-12 inhibitor, an IL-23 inhibitor and an α4β7 integrin inhibitor.

94. The kit of clause 87 or 93, wherein the inhibitor is a monoclonal antibody.

95. The kit of clause 94, wherein the inhibitor is selected from the group consisting of infliximab (Remicade), adalimumab (Humira), certolizumab pegol (Cimzia), and golimumab (Simponi) and etanercept (Enbrel), ustekinumab (Stelara) and vedolizumab (Entyvio).

96. The kit of any preceding clause, wherein the antigen binding molecule, affinity matured mutant or pharmaceutical composition and the additional therapeutically active agent are for separate, sequential or simultaneous administration.

97. An antigen binding molecule of any one of clauses 1 to 71, an affinity matured mutant of any one of clauses 49 to 71, or a pharmaceutical composition of any one of clauses 72 to 83, for use in medicine.

98. An antigen binding molecule of any one of clauses 1 to 71, an affinity matured mutant of any one of clauses 49 to 71, or a pharmaceutical composition of any one of clauses 72 to 83, for use in the treatment or prevention of an inflammatory disorder or disease or an autoimmune disorder or disease.

99. The antigen binding molecule, affinity matured mutant or pharmaceutical composition for use as in clause 98, wherein the inflammatory or autoimmune disorder or disease is selected from the group consisting of ankylosing spondylitis, atopic dermatitis, coeliac disease, inflammatory bowel disease (IBD), Crohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), chronic heart failure, chronic obstructive pulmonary disease, kidney disease, septic shock, ulcerative colitis, fibrosis, multiple sclerosis, Sjogren's syndrome, lupus, airway inflammation, liver disease, hepatitis, coeliac disease, dermatitis, eosinophilia and primary biliary cirrhosis.

100. The antigen binding molecule, affinity matured mutant or pharmaceutical composition for use as in clause 99, wherein the inflammatory disease is ulcerative colitis.

101. The antigen binding molecule, affinity matured mutant or pharmaceutical composition for use as in clause 100, wherein the inflammatory disease is Crohn's disease.

102. Use of an antigen binding molecule of any one of clauses 1 to 66 or an affinity matured mutant of any one of clauses 44 to 66 in the manufacture of a medicament for use in the treatment of an inflammatory disorder or disease or an autoimmune disorder or disease.

103. Use of an antigen binding molecule according to clause 102, wherein the inflammatory or autoimmune disorder or disease is selected from the group consisting of ankylosing spondylitis, atopic dermatitis, coeliac disease, inflammatory bowel disease (IBD), Crohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), chronic heart failure, chronic obstructive pulmonary disease, kidney disease, septic shock, ulcerative colitis, fibrosis, multiple sclerosis, Sjogren's syndrome, lupus, airway inflammation, liver disease, hepatitis, coeliac disease, dermatitis, eosinophilia and primary biliary cirrhosis.

104. Use of an antigen binding molecule according to clause 103 wherein the inflammatory disease is ulcerative colitis.

105. Use of an antigen binding molecule according to clause 103 wherein the inflammatory disease is Crohn's disease.

106. A method for the treatment or prevention of a LIGHT-mediated disease or disorder comprising administering to the subject an antigen binding molecule of any one of clauses 1 to 71 or an affinity matured mutant of any one of clauses 49 to 71 or a pharmaceutical composition according to any one of clauses 72 to 83.

107. The method of clause 106, wherein the LIGHT-mediated disease or disorder is an inflammatory disease or disorder or an immune disease or disorder.

108. The method of treatment of clause 107, wherein the inflammatory or autoimmune disorder or disease is selected from the group consisting of ankylosing spondylitis, atopic dermatitis, coeliac disease, inflammatory bowel disease (IBD), Crohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), chronic heart failure, chronic obstructive pulmonary disease, kidney disease, septic shock, ulcerative colitis, fibrosis, multiple sclerosis, Sjogren's syndrome, lupus, airway inflammation, liver disease, hepatitis, coeliac disease, dermatitis, eosinophilia and primary biliary cirrhosis.

109. The method of treatment of clause 108, wherein the inflammatory disease is ulcerative colitis.

110. The method of treatment of clause 108, wherein the inflammatory disease is Crohn's disease.

111. A method of inhibiting the binding of LIGHT protein to HVEM and/or LTβR or the binding of LIGHT expressing cells to HVEM and/or LTβR, comprising contacting the LIGHT protein or LIGHT expressing cell with an antigen-binding molecule according to any one of clauses 1 to 71 or affinity matured mutant according to any of clauses 49 to 71.

112. The method of clause 111, wherein the method is an in vitro method.

113. The method of clause 111, wherein the method is an in vivo method.

114. A nucleic acid encoding an antigen binding molecule of any one of clauses 1 to 71.

115. A plasmid comprising the nucleic acid of clause 114.

116. A vector comprising the nucleic acid of clause 114.

117. A host cell comprising a plasmid of vector according to clause 115 or clause 116.

118. A method of producing cell that expresses an anti-LIGHT antigen binding molecule, comprising transfecting said cell with a plasmid or vector according to clause 115 or clause 116.

119. A method for the production on an anti-LIGHT antigen binding molecule, comprising culturing a host cell according to clause 117 in a cell culture medium under conditions to express the encoding nucleic acid sequence of the plasmid or vector inside the cell.

120. The method of clause 119, further comprising obtaining the anti-LIGHT antigen binding molecule from the cell culture supernatant.

The invention claimed is:

1. A pharmaceutical composition for treatment of a LIGHT-mediated disease or disorder, the pharmaceutical composition comprising:

an anti-LIGHT antigen binding molecule, wherein the antigen binding molecule specifically binds to membrane-bound human LIGHT and has a higher affinity for membrane-bound human LIGHT compared to soluble human LIGHT, wherein the anti-LIGHT antigen binding molecule is selected from the group consisting of:

(a) an antibody comprising a heavy chain variable region comprising a VHCDR1 comprising the amino acid sequence DYEMH (SEQ ID NO: 38), a VHCDR2 comprising the amino acid sequence EIDPETGDTAYAQKFQG (SEQ ID NO: 147) and a VHCDR3 comprising the amino acid sequence ETDYFFDY (SEQ ID NO: 40); and a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);

(b) an antibody comprising a heavy chain variable region comprising a VHCDR1 comprising the amino acid sequence DYEMH (SEQ ID NO: 6), a VHCDR2 comprising the amino acid sequence EIDPETGDTAYSQKFKG (SEQ ID NO: 7), a VHCDR3 comprising the amino acid sequence ETDYFFDY (SEQ ID NO: 8); and a light chain variable region comprising a VLCDR1 comprising the amino acid sequence GASENIYGALN (SEQ ID NO: 2), a VLCDR2 comprising the amino acid sequence GATNLAD (SEQ ID NO: 3) and a VLCDR3 comprising the amino acid sequence QNVLTTPWT (SEQ ID NO: 4);

(c) an antibody comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);

(d) an antibody comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);

(e) an antibody comprising a heavy chain variable region comprising a VHCDR1 comprising the amino acid sequence DYEMH (SEQ ID NO: 30), a VHCDR2 comprising the amino acid sequence EIDPETGDTAYAQKFQG (SEQ ID NO: 146) and a VHCDR3 comprising the amino acid sequence ETDYFFDY (SEQ ID NO: 32); and a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);

(f) an antibody comprising a heavy chain variable region comprising a VHCDR1 comprising the amino acid sequence DYEMH (SEQ ID NO: 38), a VHCDR2 comprising the amino acid sequence EIDPETGDTAYAQKFQG (SEQ ID NO: 147) and a VHCDR3 comprising the amino acid sequence ETDYFFDY (SEQ ID NO: 40); and a light chain variable region comprising a VLCDR1 comprising the amino acid sequence GASENIYGALN (SEQ ID NO: 10), a VLCDR2 comprising the amino acid sequence GATNLAD (SEQ ID NO: 11) and a VLCDR3 comprising the amino acid sequence QNVLTTPWT (SEQ ID NO: 12);

(g) an antibody comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);

(h) an antibody comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);

(i) an antibody comprising a heavy chain variable region comprising a VHCDR1 comprising the amino acid sequence DYEMH (SEQ ID NO: 30), a VHCDR2 comprising the amino acid sequence EIDPETGDTAYAQKFQG (SEQ ID NO: 146) and a VHCDR3 comprising the amino acid sequence ETDYFFDY (SEQ ID NO: 32); and a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);

(j) an antibody comprising a heavy chain variable region comprising a VHCDR1 comprising the amino acid sequence DYEMH (SEQ ID NO: 38), a VHCDR2 comprising the amino acid sequence EIDPETGDTAYAQKFQG (SEQ ID NO: 147) and a VHCDR3 comprising the amino acid sequence ETDYFFDY (SEQ ID NO: 40); and a light chain variable region comprising a VLCDR1 comprising the amino acid sequence GASENIYGALN (SEQ ID NO: 18), a VLCDR2 comprising the amino acid sequence GATNLAD (SEQ ID NO: 19) and a VLCDR3 comprising the amino acid sequence QNVLTTPWT (SEQ ID NO: 20);

(k) an antibody comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);

(l) an antibody comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);

(m) an antibody comprising a heavy chain variable region comprising a VHCDR1 comprising the amino acid sequence DYEMH (SEQ ID NO: 30), a VHCDR2 comprising the amino acid sequence EIDPETGDTAYAQKFQG (SEQ ID NO: 146) and a VHCDR3 comprising the amino acid sequence ETDYFFDY (SEQ ID NO: 32); and a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);

(n) an antibody comprising a heavy chain variable region comprising a VHCDR1 comprising the amino acid sequence DYEMH (SEQ ID NO: 38), a VHCDR2 comprising the amino acid sequence EIDPETGDTAYAQKFQG (SEQ ID NO: 147) and a VHCDR3 comprising the amino acid sequence ETDYFFDY (SEQ ID NO: 40); and a light chain variable region comprising a VLCDR1 comprising the amino acid sequence GASENIYGALN (SEQ ID NO: 26), a VLCDR2 comprising the amino acid sequence GATNLAD (SEQ ID NO: 27) and a VLCDR3 comprising the amino acid sequence QNVLTTPWT (SEQ ID NO: 28);

(o) an antibody comprising a heavy chain variable region comprising a VHCDR1 comprising the amino acid sequence DYEMH (SEQ ID NO: 14), a VHCDR2 comprising the amino acid sequence EIDPETGDTAYSQKFKG (SEQ ID NO: 15) and a VHCDR3 comprising the amino acid sequence ETDYFFDY (SEQ ID NO: 16); and a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);

(p) an antibody comprising a heavy chain variable region comprising a VHCDR1 comprising the amino acid sequence DYEMH (SEQ ID NO: 22), a VHCDR2 comprising the amino acid sequence EIDPETGDTAYSQKFQG (SEQ ID NO: 23) and a VHCDR3 comprising the amino acid sequence ETDYFFDY (SEQ ID NO: 24); and a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);

(q) an antibody comprising a heavy chain variable region comprising a VHCDR1 comprising the amino acid sequence DYEMH (SEQ ID NO: 30), a VHCDR2 comprising the amino acid sequence EIDPETGDTAYAQKFQG (SEQ ID NO: 146) and a VHCDR3 comprising the amino acid sequence ETDYFFDY (SEQ ID NO: 32); and a light chain variable region comprising a VLCDR1 comprising the amino acid sequence RASENIYGALN (SEQ ID NO: 34), a VLCDR2 comprising the amino acid sequence GATNLAE (SEQ ID NO: 35) and a VLCDR3 comprising the amino acid sequence QNVLTTPWT (SEQ ID NO: 36);

(r) an antibody comprising a heavy chain variable region comprising a VHCDR1 comprising the amino acid sequence DSEIH (SEQ ID NO: 46), a VHCDR2 comprising the amino acid sequence EIDPETGGTAYNQKFKG (SEQ ID NO: 47), a VHCDR3 comprising the amino acid sequence ETDYFFDY (SEQ ID NO: 48); and a light chain variable region comprising a VLCDR1 comprising the amino acid sequence GASENIYGALN (SEQ ID NO: 42), a VLCDR2 comprising the amino acid sequence GATNLAD (SEQ ID NO: 43) and a VLCDR3 comprising the amino acid sequence QNVLSTPWT (SEQ ID NO: 44);

(s) an antibody comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);

(t) an antibody comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);

(u) an antibody comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);

(v) an antibody comprising a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and a light chain variable region comprising a VLCDR1 comprising the amino acid sequence GASENIYGALN (SEQ ID NO: 50), a VLCDR2 comprising the amino acid sequence GATNLAD (SEQ ID NO: 51) and a VLCDR3 comprising the amino acid sequence QNVLSTPWT (SEQ ID NO: 52);

(w) an antibody comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);

(x) an antibody comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);

(y) an antibody comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);

(z) an antibody comprising a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and a light chain variable region comprising a VLCDR1 comprising the amino acid sequence GASENIYGALN (SEQ ID NO: 58), a VLCDR2 comprising the amino acid sequence GATNLAD (SEQ ID NO: 59) and a VLCDR3 comprising the amino acid sequence QNVLSTPWT (SEQ ID NO: 60);

(aa) an antibody comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);

(ab) an antibody comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);

(ac) an antibody comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);

(ad) an antibody comprising a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and a light chain variable region comprising a VLCDR1 comprising the amino acid sequence GASENIYGALN (SEQ ID NO: 66), a VLCDR2 comprising the amino acid sequence GATNLAD (SEQ ID NO: 67) and a VLCDR3 comprising the amino acid sequence QNVLSTPWT (SEQ ID NO: 68);

(ae) an anti-LIGHT antigen binding molecule comprising a heavy chain variable region comprising a VHCDR1 comprising the amino acid sequence DSEIH (SEQ ID NO: 54), a VHCDR2 comprising the amino acid sequence EIDPETGGTAYNQKFKG (SEQ ID NO: 55) and a VHCDR3 comprising the amino acid sequence ETDYFFDY (SEQ ID NO: 56); and a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76);

(af) an antibody comprising a heavy chain variable region comprising a VHCDR1 comprising the amino acid sequence DSEIH (SEQ ID NO: 62), a VHCDR2 comprising the amino acid sequence EIDPETGGTAYNQKFQG (SEQ ID NO: 63) and a VHCDR3 comprising the amino acid sequence ETDYFFDY (SEQ ID NO: 64); and a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76);

(ag) an antibody comprising a heavy chain variable region comprising a VHCDR1 comprising the amino acid sequence DSEIH (SEQ ID NO: 70), a VHCDR2 comprising the amino acid sequence EIDPETGGTAYAQKFQG (SEQ ID NO: 71) and a VHCDR3 comprising the amino acid sequence ETDYFFDY (SEQ ID NO: 72); and a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76); and (ah) an antibody comprising a heavy chain variable region comprising a VHCDR1 comprising the amino acid sequence DSEMH (SEQ ID NO: 78), a VHCDR2 comprising the amino acid sequence EIDPETGGTAYAQKFQG (SEQ ID NO: 79) and a VHCDR3 comprising the amino acid sequence ETDYFFDY (SEQ ID NO: 80); and a light chain variable region comprising a VLCDR1 comprising the amino acid sequence RASENIYGALN (SEQ ID NO: 74), a VLCDR2 comprising the amino acid sequence GATNLAE (SEQ ID NO: 75) and a VLCDR3 comprising the amino acid sequence QNVLSTPWT (SEQ ID NO: 76).

2. The pharmaceutical composition for treatment of a LIGHT-mediated disease or disorder of claim 1, wherein the anti-LIGHT antigen binding molecule has from about 10 times to about 100 times higher affinity for membrane-bound human LIGHT compared to soluble human LIGHT.

3. The pharmaceutical composition for treatment of a LIGHT-mediated disease or disorder of claim 1, wherein the LIGHT-mediated disease or disorder is a chronic inflammatory autoimmune disease, an inflammatory disorder or disease, or an autoimmune disorder or disease.

4. The pharmaceutical composition for treatment of a LIGHT-mediated disease or disorder of claim 3, wherein the chronic inflammatory autoimmune disease, the inflammatory disorder or disease, or the autoimmune disorder or disease is inflammatory bowel disease (IBD).

5. The pharmaceutical composition for treatment of a LIGHT-mediated disease or disorder of claim 4, wherein the IBC is Crohn's disease (CD), ulcerative colitis (US), collagenous colitis, lymphocytic colitis, ischemic colitis, diversion colitis, Behcet's disease, and indeterminate colitis.

6. The pharmaceutical composition for treatment of a LIGHT-mediated disease or disorder of claim 1, wherein the anti-LIGHT antigen binding molecule comprises:
a heavy chain variable region having at least 80%, 85%, 90%, 91%, 92%, 93%, 94%, 95%, 96%, 97%, 98%, 99%, or 100% identity to the amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, and SEQ ID NO: 77; and/or a light chain variable region having at least 80%, 85%, 90%, 91%, 92%, 93%, 94%, 95%, 96%, 97%, 98%, 99%, or 100% identity to the amino acid sequence selected from the group consisting of consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, and SEQ ID NO: 73.

7. A method of treating a LIGHT-mediated disease or disorder in a subject in need thereof comprising administering to the subject a therapeutically effective amount of the pharmaceutical composition of claim 1.

8. A method of treating an inflammatory disorder or disease or an autoimmune disorder or disease in a subject in need thereof comprising administering to the subject a therapeutically effective amount of the pharmaceutical composition of claim 1.

9. A method of inhibiting interferon-gamma release by administering to a subject in need thereof a therapeutically effective amount of the pharmaceutical composition of claim 1.

10. A pharmaceutical composition for treatment of a LIGHT-mediated disease or disorder, the pharmaceutical composition comprising:
an anti-LIGHT antigen binding molecule, wherein the anti-LIGHT antigen binding molecule is an antibody that specifically binds to membrane-bound human LIGHT and is selected from the group consisting of: 3B04, 3D12, 3B04_var1, 3B04_var2, 3B04_var3, 3B04_var4, 3B04_var5, 3B04_var6, 3B04_var7, 3B04_var8, 3B04_var9, 3B04_var10, 3B04_var11, 3B04_var12, 3B04_var13, 3B04_var14, 3B04_var15, 3B04_var16, 3D12_var1, 3D12_var2, 3D12_var3, 3D12_var4, 3D12_var5, 3D12_var6, 3D12_var7, 3D12_var8, 3D12_var9, 3D12_var10, 3D12_var11, 3D12_var12, 3D12_var13, 3D12_var14, 3D12_var15 and 3D12_var16.

11. The pharmaceutical composition for treatment of a LIGHT-mediated disease or disorder of claim 10, wherein the anti-LIGHT antigen binding molecule has from about 10 times to about 100 times higher affinity for membrane-bound human LIGHT compared to soluble human LIGHT.

12. The pharmaceutical composition for treatment of a LIGHT-mediated disease or disorder of claim 10, wherein the LIGHT-mediated disease or disorder is a chronic inflammatory autoimmune disease, an inflammatory disorder or disease, or an autoimmune disorder or disease.

13. The pharmaceutical composition for treatment of a LIGHT-mediated disease or disorder of claim 12, wherein the chronic inflammatory autoimmune disease, the inflammatory disorder or disease, or the autoimmune disorder or disease is inflammatory bowel disease (IBD).

14. The pharmaceutical composition for treatment of a LIGHT-mediated disease or disorder of claim 13, wherein the IBC is Crohn's disease (CD), ulcerative colitis (US), collagenous colitis, lymphocytic colitis, ischemic colitis, diversion colitis, Behcet's disease, and indeterminate colitis.

15. A method of treating a LIGHT-mediated disease or disorder in a subject in need thereof comprising administering to the subject a therapeutically effective amount of the pharmaceutical composition of claim 10.

16. A method of treating an inflammatory disorder or disease or an autoimmune disorder or disease in a subject in need thereof comprising administering to the subject a therapeutically effective amount of the pharmaceutical composition of claim 10.

17. A method of inhibiting interferon-gamma release by administering to a subject in need thereof a therapeutically effective amount of the pharmaceutical composition of claim 10.

18. A nucleic acid encoding an anti-LIGHT antigen binding molecule comprising:
a heavy chain variable region having at least 80%, 85%, 90%, 91%, 92%, 93%, 94%, 95%, 96%, 97%, 98%, 99%, or 100% identity to the amino acid sequence selected from the group consisting of SEQ ID NO: 5, SEQ ID NO: 13, SEQ ID NO: 21, SEQ ID NO: 29, SEQ ID NO: 37, SEQ ID NO: 45, SEQ ID NO: 53, SEQ ID NO: 61, SEQ ID NO: 69, and SEQ ID NO: 77; and/or a light chain variable region having at least 80%, 85%, 90%, 91%, 92%, 93%, 94%, 95%, 96%, 97%, 98%, 99%, or 100% identity to the amino acid sequence selected from the group consisting of consisting SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 65, and SEQ ID NO: 73.

19. The nucleic acid of claim 18, wherein the anti-LIGHT antigen binding molecule is an antibody.

20. A plasmid comprising the nucleic acid of claim 18.

21. A vector comprising the nucleic acid of claim 18.

22. A method of producing an anti-LIGHT antigen binding molecule comprising:

transfecting a host cell using a vector comprising the nucleic acid of claim 18;

culturing the transfected host cell in a cell culture medium under conditions to express the anti-LIGHT antigen binding molecule encoded by the nucleic acid of claim 18.

23. The method of claim 22, further comprising obtaining the anti-LIGHT antigen binding molecule from supernatant of the cell culture medium.

24. The method of claim 22, further comprising obtaining the anti-LIGHT antigen binding molecule from supernatant of the cell culture medium.

* * * * *

SEQUENCE LISTING

```
<160> NUMBER OF SEQ ID NOS: 145

<210> SEQ ID NO 1
<211> LENGTH: 108
<212> TYPE: PRT
<213> ORGANISM: Homo sapiens

<400> SEQUENCE: 1

Asp Ile Gln Met Thr Gln Thr Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Phe Ala Thr Tyr Tyr Cys Gln Asn Val Leu Thr Thr Pro Trp
                85                  90                  95

Thr Phe Gly Gly Gly Thr Lys Leu Glu Ile Lys Arg
            100                 105

<210> SEQ ID NO 2
<211> LENGTH: 11
<212> TYPE: PRT
<213> ORGANISM: Homo sapiens

<400> SEQUENCE: 2

Gly Ala Ser Glu Asn Ile Tyr Gly Ala Leu Asn
1               5                   10

<210> SEQ ID NO 3
<211> LENGTH: 7
<212> TYPE: PRT
<213> ORGANISM: Homo sapiens

<400> SEQUENCE: 3

Gly Ala Thr Asn Leu Ala Asp
1               5

<210> SEQ ID NO 4
<211> LENGTH: 9
<212> TYPE: PRT
<213> ORGANISM: Homo sapiens

<400> SEQUENCE: 4

Gln Asn Val Leu Thr Thr Pro Trp Thr
1               5
```

<210> SEQ ID NO 5
<211> LENGTH: 117
<212> TYPE: PRT
<213> ORGANISM: Homo sapiens

<400> SEQUENCE: 5

Gln Val Gln Leu Gln Gln Pro Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Glu Ile Asp Pro Glu Thr Gly Asp Thr Ala Tyr Ser Gln Lys Phe
    50                  55                  60

Lys Gly Lys Ala Thr Leu Thr Ala Asp Lys Ser Ser Thr Ala Tyr
65                  70                  75                  80

Met Glu Phe Arg Ser Leu Thr Ser Glu Asp Ser Ala Val Tyr Tyr Cys
                85                  90                  95

Ser Arg Glu Thr Asp Tyr Phe Phe Asp Tyr Trp Gly Gln Gly Thr Thr
            100                 105                 110

Leu Thr Val Ser Ser
        115

<210> SEQ ID NO 6
<211> LENGTH: 5
<212> TYPE: PRT
<213> ORGANISM: Homo sapiens

<400> SEQUENCE: 6

Asp Tyr Glu Met His
1               5

<210> SEQ ID NO 7
<211> LENGTH: 17
<212> TYPE: PRT
<213> ORGANISM: Homo sapiens

<400> SEQUENCE: 7

Glu Ile Asp Pro Glu Thr Gly Asp Thr Ala Tyr Ser Gln Lys Phe Lys
1               5                   10                  15

Gly

<210> SEQ ID NO 8
<211> LENGTH: 8
<212> TYPE: PRT
<213> ORGANISM: Homo sapiens

<400> SEQUENCE: 8

Glu Thr Asp Tyr Phe Phe Asp Tyr
1               5

<210> SEQ ID NO 9
<211> LENGTH: 108
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala

```
                20                  25                  30
Leu Asn Trp Tyr Gln Arg Lys Gln Gly Lys Ala Pro Gln Leu Leu Ile
             35                  40                  45

Tyr Gly Ala Thr Asn Leu Ala Asp Gly Val Ser Ser Arg Phe Ser Gly
 50                  55                  60

Ser Gly Ser Gly Arg Asp Tyr Thr Leu Thr Ile Ser Ser Leu Gln Pro
 65                  70                  75                  80

Glu Asp Phe Ala Thr Tyr Tyr Cys Gln Asn Val Leu Thr Thr Pro Trp
             85                  90                  95

Thr Phe Gly Gln Gly Thr Lys Leu Glu Ile Lys Arg
            100                 105

<210> SEQ ID NO 10
<211> LENGTH: 11
<212> TYPE: PRT
<213> ORGANISM: Homo sapiens

<400> SEQUENCE: 10

Gly Ala Ser Glu Asn Ile Tyr Gly Ala Leu Asn
1               5                   10

<210> SEQ ID NO 11
<211> LENGTH: 7
<212> TYPE: PRT
<213> ORGANISM: Homo sapiens

<400> SEQUENCE: 11

Gly Ala Thr Asn Leu Ala Asp
1               5

<210> SEQ ID NO 12
<211> LENGTH: 9
<212> TYPE: PRT
<213> ORGANISM: Homo sapiens

<400> SEQUENCE: 12

Gln Asn Val Leu Thr Thr Pro Trp Thr
1               5

<210> SEQ ID NO 13
<211> LENGTH: 117
<212> TYPE: PRT
<213> ORGANISM: Homo sapiens

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
             20                  25                  30

Glu Met His Trp Val Arg Gln Ala Pro Gly Gln Gly Leu Glu Trp Ile
             35                  40                  45

Gly Glu Ile Asp Pro Glu Thr Gly Asp Thr Ala Tyr Ser Gln Lys Phe
 50                  55                  60

Lys Gly Arg Ala Thr Leu Thr Ala Asp Lys Ser Thr Ser Thr Ala Tyr
 65                  70                  75                  80

Met Glu Phe Ser Ser Leu Arg Ser Glu Asp Thr Ala Val Tyr Tyr Cys
             85                  90                  95

Ser Arg Glu Thr Asp Tyr Phe Asp Tyr Trp Gly Gln Gly Thr Leu
            100                 105                 110
```

```
Val Thr Val Ser Ser
        115

<210> SEQ ID NO 14
<211> LENGTH: 5
<212> TYPE: PRT
<213> ORGANISM: Homo sapiens

<400> SEQUENCE: 14

Asp Tyr Glu Met His
1               5

<210> SEQ ID NO 15
<211> LENGTH: 17
<212> TYPE: PRT
<213> ORGANISM: Homo sapiens

<400> SEQUENCE: 15

Glu Ile Asp Pro Glu Thr Gly Asp Thr Ala Tyr Ser Gln Lys Phe Lys
1               5                   10                  15

Gly

<210> SEQ ID NO 16
<211> LENGTH: 8
<212> TYPE: PRT
<213> ORGANISM: Homo sapiens

<400> SEQUENCE: 16

Glu Thr Asp Tyr Phe Phe Asp Tyr
1               5

<210> SEQ ID NO 17
<211> LENGTH: 108
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Gln Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Gln Asn Val Leu Thr Thr Pro Trp
                85                  90                  95

Thr Phe Gly Gln Gly Thr Lys Leu Glu Ile Lys Arg
            100                 105

<210> SEQ ID NO 18
<211> LENGTH: 11
<212> TYPE: PRT
<213> ORGANISM: Homo sapiens

<400> SEQUENCE: 18

Gly Ala Ser Glu Asn Ile Tyr Gly Ala Leu Asn
1               5                   10
```

```
<210> SEQ ID NO 19
<211> LENGTH: 7
<212> TYPE: PRT
<213> ORGANISM: Homo sapiens

<400> SEQUENCE: 19

Gly Ala Thr Asn Leu Ala Asp
1               5

<210> SEQ ID NO 20
<211> LENGTH: 9
<212> TYPE: PRT
<213> ORGANISM: Homo sapiens

<400> SEQUENCE: 20

Gln Asn Val Leu Thr Thr Pro Trp Thr
1               5

<210> SEQ ID NO 21
<211> LENGTH: 117
<212> TYPE: PRT
<213> ORGANISM: Homo sapiens

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Glu Ile Asp Pro Glu Thr Gly Asp Thr Ala Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Phe Ser Ser Leu Arg Ser Glu Asp Thr Ala Val Tyr Tyr Cys
                85                  90                  95

Ser Arg Glu Thr Asp Tyr Phe Phe Asp Tyr Trp Gly Gln Gly Thr Leu
            100                 105                 110

Val Thr Val Ser Ser
        115

<210> SEQ ID NO 22
<211> LENGTH: 5
<212> TYPE: PRT
<213> ORGANISM: Homo sapiens

<400> SEQUENCE: 22

Asp Tyr Glu Met His
1               5

<210> SEQ ID NO 23
<211> LENGTH: 17
<212> TYPE: PRT
<213> ORGANISM: Homo sapiens

<400> SEQUENCE: 23

Glu Ile Asp Pro Glu Thr Gly Asp Thr Ala Tyr Ser Gln Lys Phe Gln
1               5                   10                  15

Gly

<210> SEQ ID NO 24
```

```
<211> LENGTH: 8
<212> TYPE: PRT
<213> ORGANISM: Homo sapiens

<400> SEQUENCE: 24

Glu Thr Asp Tyr Phe Phe Asp Tyr
1               5

<210> SEQ ID NO 25
<211> LENGTH: 108
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Gln Asn Val Leu Thr Thr Pro Trp
                85                  90                  95

Thr Phe Gly Gln Gly Thr Lys Leu Glu Ile Lys Arg
            100                 105

<210> SEQ ID NO 26
<211> LENGTH: 11
<212> TYPE: PRT
<213> ORGANISM: Homo sapiens

<400> SEQUENCE: 26

Gly Ala Ser Glu Asn Ile Tyr Gly Ala Leu Asn
1               5                   10

<210> SEQ ID NO 27
<211> LENGTH: 7
<212> TYPE: PRT
<213> ORGANISM: Homo sapiens

<400> SEQUENCE: 27

Gly Ala Thr Asn Leu Ala Asp
1               5

<210> SEQ ID NO 28
<211> LENGTH: 9
<212> TYPE: PRT
<213> ORGANISM: Homo sapiens

<400> SEQUENCE: 28

Gln Asn Val Leu Thr Thr Pro Trp Thr
1               5

<210> SEQ ID NO 29
<211> LENGTH: 117
<212> TYPE: PRT
<213> ORGANISM: Homo sapiens

<400> SEQUENCE: 29
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Glu Ile Asp Pro Glu Thr Gly Asp Thr Ala Tyr Ala Gln Lys Phe
50                  55                  60

Gln Gly Arg Val Thr Leu Thr Ala Asp Lys Ser Thr Ser Thr Ala Tyr
65                  70                  75                  80

Met Glu Phe Ser Ser Leu Arg Ser Glu Asp Thr Ala Val Tyr Tyr Cys
            85                  90                  95

Ser Arg Glu Thr Asp Tyr Phe Phe Asp Tyr Trp Gly Gln Gly Thr Leu
            100                 105                 110

Val Thr Val Ser Ser
            115

<210> SEQ ID NO 30
<211> LENGTH: 5
<212> TYPE: PRT
<213> ORGANISM: Homo sapiens

<400> SEQUENCE: 30

Asp Tyr Glu Met His
1               5

<210> SEQ ID NO 31
<211> LENGTH: 17
<212> TYPE: PRT
<213> ORGANISM: Homo sapiens

<400> SEQUENCE: 31

Glu Ile Asp Pro Glu Thr Gly Asp Thr Ala Tyr Ser Gln Lys Phe Gln
1               5                   10                  15

Gly

<210> SEQ ID NO 32
<211> LENGTH: 8
<212> TYPE: PRT
<213> ORGANISM: Homo sapiens

<400> SEQUENCE: 32

Glu Thr Asp Tyr Phe Phe Asp Tyr
1               5

<210> SEQ ID NO 33
<211> LENGTH: 108
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Glu Gly Val Pro Ser Arg Phe Ser Gly
50                  55                  60
```

```
Ser Gly Ser Gly Arg Asp Tyr Thr Leu Thr Ile Ser Ser Leu Gln Pro
 65                  70                  75                  80

Glu Asp Phe Ala Thr Tyr Tyr Cys Gln Asn Val Leu Thr Thr Pro Trp
                 85                  90                  95

Thr Phe Gly Gln Gly Thr Lys Leu Glu Ile Lys Arg
            100                 105
```

```
<210> SEQ ID NO 34
<211> LENGTH: 11
<212> TYPE: PRT
<213> ORGANISM: Homo sapiens

<400> SEQUENCE: 34

Arg Ala Ser Glu Asn Ile Tyr Gly Ala Leu Asn
 1               5                  10
```

```
<210> SEQ ID NO 35
<211> LENGTH: 7
<212> TYPE: PRT
<213> ORGANISM: Homo sapiens

<400> SEQUENCE: 35

Gly Ala Thr Asn Leu Ala Glu
 1               5
```

```
<210> SEQ ID NO 36
<211> LENGTH: 9
<212> TYPE: PRT
<213> ORGANISM: Homo sapiens

<400> SEQUENCE: 36

Gln Asn Val Leu Thr Thr Pro Trp Thr
 1               5
```

```
<210> SEQ ID NO 37
<211> LENGTH: 117
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Glu Met His Trp Val Arg Gln Ala Pro Gly Gln Gly Leu Glu Trp Met
             35                  40                  45

Gly Glu Ile Asp Pro Glu Thr Gly Asp Thr Ala Tyr Ala Gln Lys Phe
     50                  55                  60

Gln Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ser Arg Glu Thr Asp Tyr Phe Phe Asp Tyr Trp Gly Gln Gly Thr Leu
            100                 105                 110

Val Thr Val Ser Ser
        115
```

```
<210> SEQ ID NO 38
<211> LENGTH: 5
<212> TYPE: PRT
<213> ORGANISM: Homo sapiens
```

<400> SEQUENCE: 38

Asp Tyr Glu Met His
1               5

<210> SEQ ID NO 39
<211> LENGTH: 17
<212> TYPE: PRT
<213> ORGANISM: Homo sapiens

<400> SEQUENCE: 39

Glu Ile Asp Pro Glu Thr Gly Asp Thr Ala Tyr Ser Gln Lys Phe Gln
1               5                   10                  15

Gly

<210> SEQ ID NO 40
<211> LENGTH: 8
<212> TYPE: PRT
<213> ORGANISM: Homo sapiens

<400> SEQUENCE: 40

Glu Thr Asp Tyr Phe Phe Asp Tyr
1               5

<210> SEQ ID NO 41
<211> LENGTH: 108
<212> TYPE: PRT
<213> ORGANISM: Homo sapiens

<400> SEQUENCE: 41

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
                20                  25                  30

Leu Asn Trp Tyr Gln Arg Lys Gln Gly Lys Ser Pro Gln Leu Leu Ile
            35                  40                  45

Tyr Gly Ala Thr Asn Leu Ala Asp Gly Met Ser Ser Arg Phe Ser Gly
        50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Trp
                85                  90                  95

Thr Phe Gly Gly Gly Thr Lys Leu Glu Ile Lys Arg
            100                 105

<210> SEQ ID NO 42
<211> LENGTH: 11
<212> TYPE: PRT
<213> ORGANISM: Homo sapiens

<400> SEQUENCE: 42

Gly Ala Ser Glu Asn Ile Tyr Gly Ala Leu Asn
1               5                   10

<210> SEQ ID NO 43
<211> LENGTH: 7
<212> TYPE: PRT
<213> ORGANISM: Homo sapiens

<400> SEQUENCE: 43

Gly Ala Thr Asn Leu Ala Asp

<210> SEQ ID NO 44
<211> LENGTH: 9
<212> TYPE: PRT
<213> ORGANISM: Mus musculus

<400> SEQUENCE: 44

Gln Asn Val Leu Ser Thr Pro Trp Thr
1               5

<210> SEQ ID NO 45
<211> LENGTH: 117
<212> TYPE: PRT
<213> ORGANISM: Homo sapiens

<400> SEQUENCE: 45

Gln Val Gln Leu Gln Gln Pro Gly Ala Glu Leu Val Arg Pro Gly Ala
1               5                   10                  15

Ser Val Thr Leu Ser Cys Lys Ala Ser Asp Tyr Thr Phe Thr Asp Ser
            20                  25                  30

Glu Ile His Trp Val Lys Gln Thr Pro Val His Gly Leu Glu Trp Ile
        35                  40                  45

Gly Glu Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Arg Glu Thr Asp Tyr Phe Phe Asp Tyr Trp Gly Gln Gly Thr Thr
            100                 105                 110

Leu Thr Val Ser Ser
        115

<210> SEQ ID NO 46
<211> LENGTH: 5
<212> TYPE: PRT
<213> ORGANISM: Homo sapiens

<400> SEQUENCE: 46

Asp Ser Glu Ile His
1               5

<210> SEQ ID NO 47
<211> LENGTH: 17
<212> TYPE: PRT
<213> ORGANISM: Homo sapiens

<400> SEQUENCE: 47

Glu Ile Asp Pro Glu Thr Gly Gly Thr Ala Tyr Asn Gln Lys Phe Lys
1               5                   10                  15

Gly

<210> SEQ ID NO 48
<211> LENGTH: 8
<212> TYPE: PRT
<213> ORGANISM: Homo sapiens

<400> SEQUENCE: 48

Glu Thr Asp Tyr Phe Phe Asp Tyr
1               5

```
<210> SEQ ID NO 49
<211> LENGTH: 108
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Gln Gly Lys Ala Pro Gln Leu Leu Ile
        35                  40                  45

Tyr Gly Ala Thr Asn Leu Ala Asp Gly Val Ser Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Val Ala Thr Tyr Tyr Cys Gln Asn Val Leu Ser Thr Pro Trp
                85                  90                  95

Thr Phe Gly Gln Gly Thr Lys Leu Glu Ile Lys Arg
            100                 105

<210> SEQ ID NO 50
<211> LENGTH: 11
<212> TYPE: PRT
<213> ORGANISM: Homo sapiens

<400> SEQUENCE: 50

Gly Ala Ser Glu Asn Ile Tyr Gly Ala Leu Asn
1               5                   10

<210> SEQ ID NO 51
<211> LENGTH: 7
<212> TYPE: PRT
<213> ORGANISM: Homo sapiens

<400> SEQUENCE: 51

Gly Ala Thr Asn Leu Ala Asp
1               5

<210> SEQ ID NO 52
<211> LENGTH: 9
<212> TYPE: PRT
<213> ORGANISM: Homo sapiens

<400> SEQUENCE: 52

Gln Asn Val Leu Ser Thr Pro Trp Thr
1               5

<210> SEQ ID NO 53
<211> LENGTH: 117
<212> TYPE: PRT
<213> ORGANISM: Homo sapiens

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Asp Ser
            20                  25                  30

Glu Ile His Trp Val Arg Gln Ala Pro Gly Gln Gly Leu Glu Trp Ile
        35                  40                  45
```

```
Gly Glu Ile Asp Pro Glu Thr Gly Gly Thr Ala Tyr Asn Gln Lys Phe
        50                  55                  60

Lys Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ser Arg Glu Thr Asp Tyr Phe Phe Asp Tyr Trp Gly Gln Gly Thr Leu
                100                 105                 110

Val Thr Val Ser Ser
            115

<210> SEQ ID NO 54
<211> LENGTH: 5
<212> TYPE: PRT
<213> ORGANISM: Homo sapiens

<400> SEQUENCE: 54

Asp Ser Glu Ile His
 1               5

<210> SEQ ID NO 55
<211> LENGTH: 17
<212> TYPE: PRT
<213> ORGANISM: Homo sapiens

<400> SEQUENCE: 55

Glu Ile Asp Pro Glu Thr Gly Gly Thr Ala Tyr Asn Gln Lys Phe Lys
 1               5                  10                  15

Gly

<210> SEQ ID NO 56
<211> LENGTH: 8
<212> TYPE: PRT
<213> ORGANISM: Homo sapiens

<400> SEQUENCE: 56

Glu Thr Asp Tyr Phe Phe Asp Tyr
 1               5

<210> SEQ ID NO 57
<211> LENGTH: 108
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
                 20                  25                  30

Leu Asn Trp Tyr Gln Arg Lys Gln Gly Lys Ala Pro Lys Leu Leu Ile
                 35                  40                  45

Tyr Gly Ala Thr Asn Leu Ala Asp Gly Val Pro Ser Arg Phe Ser Gly
             50                  55                  60

Ser Gly Ser Gly Arg Asp Tyr Thr Leu Thr Ile Ser Ser Leu Gln Pro
 65                  70                  75                  80

Glu Asp Val Ala Thr Tyr Tyr Cys Gln Asn Val Leu Ser Thr Pro Trp
                 85                  90                  95

Thr Phe Gly Gln Gly Thr Lys Leu Glu Ile Lys Arg
                100                 105
```

```
<210> SEQ ID NO 58
<211> LENGTH: 11
<212> TYPE: PRT
<213> ORGANISM: Homo sapiens

<400> SEQUENCE: 58

Gly Ala Ser Glu Asn Ile Tyr Gly Ala Leu Asn
1               5                   10

<210> SEQ ID NO 59
<211> LENGTH: 7
<212> TYPE: PRT
<213> ORGANISM: Homo sapiens

<400> SEQUENCE: 59

Gly Ala Thr Asn Leu Ala Asp
1               5

<210> SEQ ID NO 60
<211> LENGTH: 9
<212> TYPE: PRT
<213> ORGANISM: Homo sapiens

<400> SEQUENCE: 60

Gln Asn Val Leu Ser Thr Pro Trp Thr
1               5

<210> SEQ ID NO 61
<211> LENGTH: 117
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Asp Ser
                20                  25                  30

Glu Ile His Trp Val Arg Gln Ala Pro Gly Gln Gly Leu Glu Trp Ile
            35                  40                  45

Gly Glu Ile Asp Pro Glu Thr Gly Gly Thr Ala Tyr Asn Gln Lys Phe
        50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Glu Thr Asp Tyr Phe Phe Asp Tyr Trp Gly Gln Gly Thr Leu
                100                 105                 110

Val Thr Val Ser Ser
            115

<210> SEQ ID NO 62
<211> LENGTH: 5
<212> TYPE: PRT
<213> ORGANISM: Homo sapiens

<400> SEQUENCE: 62

Asp Ser Glu Ile His
1               5

<210> SEQ ID NO 63
```

```
<211> LENGTH: 17
<212> TYPE: PRT
<213> ORGANISM: Homo sapiens

<400> SEQUENCE: 63

Glu Ile Asp Pro Glu Thr Gly Gly Thr Ala Tyr Asn Gln Lys Phe Gln
1               5                   10                  15

Gly

<210> SEQ ID NO 64
<211> LENGTH: 8
<212> TYPE: PRT
<213> ORGANISM: Homo sapiens

<400> SEQUENCE: 64

Glu Thr Asp Tyr Phe Phe Asp Tyr
1               5

<210> SEQ ID NO 65
<211> LENGTH: 108
<212> TYPE: PRT
<213> ORGANISM: Homo sapiens

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Leu Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Val Ala Thr Tyr Tyr Cys Gln Asn Val Leu Ser Thr Pro Trp
                85                  90                  95

Thr Phe Gly Gln Gly Thr Lys Leu Glu Ile Lys Arg
            100                 105

<210> SEQ ID NO 66
<211> LENGTH: 11
<212> TYPE: PRT
<213> ORGANISM: Homo sapiens

<400> SEQUENCE: 66

Gly Ala Ser Glu Asn Ile Tyr Gly Ala Leu Asn
1               5                   10

<210> SEQ ID NO 67
<211> LENGTH: 7
<212> TYPE: PRT
<213> ORGANISM: Homo sapiens

<400> SEQUENCE: 67

Gly Ala Thr Asn Leu Ala Asp
1               5

<210> SEQ ID NO 68
<211> LENGTH: 9
<212> TYPE: PRT
<213> ORGANISM: Homo sapiens
```

<400> SEQUENCE: 68

Gln Asn Val Leu Ser Thr Pro Trp Thr
1               5

<210> SEQ ID NO 69
<211> LENGTH: 117
<212> TYPE: PRT
<213> ORGANISM: Homo sapiens

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Asp Ser
            20                  25                  30

Glu Ile His Trp Val Arg Gln Ala Pro Gly Gln Gly Leu Glu Trp Met
        35                  40                  45

Gly Glu Ile Asp Pro Glu Thr Gly Gly Thr Ala Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Glu Thr Asp Tyr Phe Phe Asp Tyr Trp Gly Gln Gly Thr Leu
            100                 105                 110

Val Thr Val Ser Ser
        115

<210> SEQ ID NO 70
<211> LENGTH: 5
<212> TYPE: PRT
<213> ORGANISM: Homo sapiens

<400> SEQUENCE: 70

Asp Ser Glu Ile His
1               5

<210> SEQ ID NO 71
<211> LENGTH: 17
<212> TYPE: PRT
<213> ORGANISM: Homo sapiens

<400> SEQUENCE: 71

Glu Ile Asp Pro Glu Thr Gly Gly Thr Ala Tyr Ala Gln Lys Phe Gln
1               5                   10                  15

Gly

<210> SEQ ID NO 72
<211> LENGTH: 8
<212> TYPE: PRT
<213> ORGANISM: Homo sapiens

<400> SEQUENCE: 72

Glu Thr Asp Tyr Phe Phe Asp Tyr
1               5

<210> SEQ ID NO 73
<211> LENGTH: 108
<212> TYPE: PRT
<213> ORGANISM: Homo sapiens

<400> SEQUENCE: 73

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Glu Gly Val Pro Ser Arg Phe Ser Gly
    50                  55                  60

Ser Gly Ser Gly Arg Asp Tyr Thr Leu Thr Ile Ser Ser Leu Gln Pro
65              70                  75                  80

Glu Asp Val Ala Thr Tyr Tyr Cys Gln Asn Val Leu Ser Thr Pro Trp
                85                  90                  95

Thr Phe Gly Gln Gly Thr Lys Leu Glu Ile Lys Arg
            100                 105
```

<210> SEQ ID NO 74
<211> LENGTH: 11
<212> TYPE: PRT
<213> ORGANISM: Homo sapiens

<400> SEQUENCE: 74

```
Arg Ala Ser Glu Asn Ile Tyr Gly Ala Leu Asn
1               5                   10
```

<210> SEQ ID NO 75
<211> LENGTH: 7
<212> TYPE: PRT
<213> ORGANISM: Homo sapiens

<400> SEQUENCE: 75

```
Gly Ala Thr Asn Leu Ala Glu
1               5
```

<210> SEQ ID NO 76
<211> LENGTH: 9
<212> TYPE: PRT
<213> ORGANISM: Homo sapiens

<400> SEQUENCE: 76

```
Gln Asn Val Leu Ser Thr Pro Trp Thr
1               5
```

<210> SEQ ID NO 77
<211> LENGTH: 117
<212> TYPE: PRT
<213> ORGANISM: Homo sapiens

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met His Trp Val Arg Gln Ala Pro Gly Gln Gly Leu Glu Trp Met
        35                  40                  45

Gly Glu Ile Asp Pro Glu Thr Gly Gly Thr Ala Tyr Ala Gln Lys Phe
    50                  55                  60

Gln Gly Arg Val Thr Leu Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
```

```
                        85                  90                  95

Ser Arg Glu Thr Asp Tyr Phe Phe Asp Tyr Trp Gly Gln Gly Thr Leu
            100                 105                 110

Val Thr Val Ser Ser
            115

<210> SEQ ID NO 78
<211> LENGTH: 5
<212> TYPE: PRT
<213> ORGANISM: Homo sapiens

<400> SEQUENCE: 78

Asp Ser Glu Met His
1               5

<210> SEQ ID NO 79
<211> LENGTH: 17
<212> TYPE: PRT
<213> ORGANISM: Homo sapiens

<400> SEQUENCE: 79

Glu Ile Asp Pro Glu Thr Gly Gly Thr Ala Tyr Ala Gln Lys Phe Gln
1               5                   10                  15

Gly

<210> SEQ ID NO 80
<211> LENGTH: 8
<212> TYPE: PRT
<213> ORGANISM: Homo sapiens

<400> SEQUENCE: 80

Glu Thr Asp Tyr Phe Phe Asp Tyr
1               5

<210> SEQ ID NO 81
<211> LENGTH: 111
<212> TYPE: PRT
<213> ORGANISM: Homo sapiens

<400> SEQUENCE: 81

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Lys Leu Glu Leu Lys
            100                 105                 110

<210> SEQ ID NO 82
<211> LENGTH: 15
<212> TYPE: PRT
<213> ORGANISM: Homo sapiens

<400> SEQUENCE: 82
```

```
Lys Ala Ser Gln Ser Val Asp Tyr Asp Gly Asp Ser Tyr Met Asn
1               5                   10                  15
```

<210> SEQ ID NO 83
<211> LENGTH: 7
<212> TYPE: PRT
<213> ORGANISM: Homo sapiens

<400> SEQUENCE: 83

```
Ala Ala Ser Asn Leu Glu Ser
1               5
```

<210> SEQ ID NO 84
<211> LENGTH: 9
<212> TYPE: PRT
<213> ORGANISM: Homo sapiens

<400> SEQUENCE: 84

```
Gln Gln Ser Asn Glu Asp Pro Leu Thr
1               5
```

<210> SEQ ID NO 85
<211> LENGTH: 122
<212> TYPE: PRT
<213> ORGANISM: Homo sapiens

<400> SEQUENCE: 85

```
Gln Val Gln Met Lys Glu Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Ile His Trp Val Lys Gln Ser His Ala Lys Thr Leu Glu Trp Ile
        35                  40                  45

Gly Val Ile Ser Thr Tyr Tyr Gly Asp Ala Ser Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Asp Asp Ser Ala Ile Tyr Tyr Cys
                85                  90                  95

Ala Arg Ser Arg Gly Glu Tyr Gly Asn Tyr Asp Ala Met Asp Tyr Trp
            100                 105                 110

Gly Gln Gly Thr Ser Val Thr Val Ser Ser
        115                 120
```

<210> SEQ ID NO 86
<211> LENGTH: 5
<212> TYPE: PRT
<213> ORGANISM: Homo sapiens

<400> SEQUENCE: 86

```
Asp Tyr Ala Ile His
1               5
```

<210> SEQ ID NO 87
<211> LENGTH: 17
<212> TYPE: PRT
<213> ORGANISM: Homo sapiens

<400> SEQUENCE: 87

```
Val Ile Ser Thr Tyr Tyr Gly Asp Ala Ser Tyr Asn Gln Lys Phe Lys
1               5                   10                  15
```

Gly

<210> SEQ ID NO 88
<211> LENGTH: 13
<212> TYPE: PRT
<213> ORGANISM: Homo sapiens

<400> SEQUENCE: 88

Ser Arg Gly Glu Tyr Gly Asn Tyr Asp Ala Met Asp Tyr
1               5                   10

<210> SEQ ID NO 89
<211> LENGTH: 106
<212> TYPE: PRT
<213> ORGANISM: Homo sapiens

<400> SEQUENCE: 89

Asp Val Val Met Thr Gln Thr Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
            100                 105

<210> SEQ ID NO 90
<211> LENGTH: 10
<212> TYPE: PRT
<213> ORGANISM: Homo sapiens

<400> SEQUENCE: 90

Ser Ala Ser Ser Ser Val Ser Tyr Met Tyr
1               5                   10

<210> SEQ ID NO 91
<211> LENGTH: 7
<212> TYPE: PRT
<213> ORGANISM: Homo sapiens

<400> SEQUENCE: 91

Asp Thr Ser Asn Leu Ala Ser
1               5

<210> SEQ ID NO 92
<211> LENGTH: 9
<212> TYPE: PRT
<213> ORGANISM: Homo sapiens

<400> SEQUENCE: 92

Gln Gln Trp Ser Ser Tyr Pro Leu Thr
1               5

<210> SEQ ID NO 93
<211> LENGTH: 117

-continued

```
<212> TYPE: PRT
<213> ORGANISM: Homo sapiens

<400> SEQUENCE: 93

Glu Val Gln Leu Gln Gln Ser Gly Ala Glu Leu Val Arg Pro Gly Ala
1               5                   10                  15

Ser Val Thr Leu Ser Cys Lys Ala Ser Asp Tyr Thr Phe Thr Asp Ser
            20                  25                  30

Glu Ile His Trp Val Lys Gln Thr Pro Val His Gly Leu Glu Trp Ile
        35                  40                  45

Gly Glu Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Arg Glu Thr Asp Tyr Phe Phe Asp Tyr Trp Gly Gln Gly Thr Thr
            100                 105                 110

Leu Thr Val Ser Ser
        115

<210> SEQ ID NO 94
<211> LENGTH: 5
<212> TYPE: PRT
<213> ORGANISM: Homo sapiens

<400> SEQUENCE: 94

Asp Ser Glu Ile His
1               5

<210> SEQ ID NO 95
<211> LENGTH: 17
<212> TYPE: PRT
<213> ORGANISM: Homo sapiens

<400> SEQUENCE: 95

Glu Ile Asp Pro Glu Thr Gly Gly Thr Ala Tyr Asn Gln Lys Phe Lys
1               5                   10                  15

Gly

<210> SEQ ID NO 96
<211> LENGTH: 8
<212> TYPE: PRT
<213> ORGANISM: Homo sapiens

<400> SEQUENCE: 96

Glu Thr Asp Tyr Phe Phe Asp Tyr
1               5

<210> SEQ ID NO 97
<211> LENGTH: 106
<212> TYPE: PRT
<213> ORGANISM: Homo sapiens

<400> SEQUENCE: 97

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Arg Pro Gly Ser Ser Pro Arg Leu Leu Ile Tyr
```

```
            35                  40                  45
Asp Thr Ser Asn Leu Ala Ser Gly Val Pro Val Arg Phe Ser Gly Ser
        50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Trp Ser Ser Tyr Pro Leu Thr
                85                  90                  95
Phe Gly Ser Gly Thr Lys Leu Glu Ile Lys
            100                 105
```

<210> SEQ ID NO 98
<211> LENGTH: 10
<212> TYPE: PRT
<213> ORGANISM: Homo sapiens

<400> SEQUENCE: 98

```
Ser Ala Ser Ser Val Ser Tyr Met Tyr
1               5                   10
```

<210> SEQ ID NO 99
<211> LENGTH: 7
<212> TYPE: PRT
<213> ORGANISM: Homo sapiens

<400> SEQUENCE: 99

```
Asp Thr Ser Asn Leu Ala Ser
1               5
```

<210> SEQ ID NO 100
<211> LENGTH: 9
<212> TYPE: PRT
<213> ORGANISM: Homo sapiens

<400> SEQUENCE: 100

```
Gln Gln Trp Ser Ser Tyr Pro Leu Thr
1               5
```

<210> SEQ ID NO 101
<211> LENGTH: 117
<212> TYPE: PRT
<213> ORGANISM: Homo sapiens

<400> SEQUENCE: 101

```
Gln Val Gln Leu Gln Gln Ser Gly Ala Glu Leu Val Arg Pro Gly Ala
1               5                   10                  15
Pro Val Thr Leu Ser Cys Lys Ala Ser Asp Tyr Thr Phe Thr Asp Ser
            20                  25                  30
Glu Ile His Trp Val Lys Gln Thr Pro Val His Gly Leu Glu Trp Ile
        35                  40                  45
Gly Glu Ile Asp Pro Glu Thr Gly Gly Thr Ala Tyr Asn Gln Lys Phe
    50                  55                  60
Lys Gly Lys Ala Thr Leu Thr Ala Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ser Arg Glu Thr Asp Tyr Phe Phe Asp Tyr Trp Gly Gln Gly Thr Thr
            100                 105                 110
Leu Thr Val Ser Ser
            115
```

<210> SEQ ID NO 102
<211> LENGTH: 5
<212> TYPE: PRT
<213> ORGANISM: Homo sapiens

<400> SEQUENCE: 102

Asp Ser Glu Ile His
1               5

<210> SEQ ID NO 103
<211> LENGTH: 17
<212> TYPE: PRT
<213> ORGANISM: Homo sapiens

<400> SEQUENCE: 103

Glu Ile Asp Pro Glu Thr Gly Gly Thr Ala Tyr Asn Gln Lys Phe Lys
1               5                   10                  15

Gly

<210> SEQ ID NO 104
<211> LENGTH: 8
<212> TYPE: PRT
<213> ORGANISM: Homo sapiens

<400> SEQUENCE: 104

Glu Thr Asp Tyr Phe Phe Asp Tyr
1               5

<210> SEQ ID NO 105
<211> LENGTH: 111
<212> TYPE: PRT
<213> ORGANISM: Homo sapiens

<400> SEQUENCE: 105

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 106
<211> LENGTH: 15
<212> TYPE: PRT
<213> ORGANISM: Homo sapiens

<400> SEQUENCE: 106

Arg Ala Ser Glu Ser Val Asp Ser Tyr Gly Asn Ser Phe Met His
1               5                   10                  15

<210> SEQ ID NO 107
<211> LENGTH: 7
<212> TYPE: PRT

<213> ORGANISM: Homo sapiens

<400> SEQUENCE: 107

Leu Ala Ser Asn Leu Glu Ser
1               5

<210> SEQ ID NO 108
<211> LENGTH: 9
<212> TYPE: PRT
<213> ORGANISM: Homo sapiens

<400> SEQUENCE: 108

Gln Gln Asn Asn Glu Asp Pro Tyr Thr
1               5

<210> SEQ ID NO 109
<211> LENGTH: 116
<212> TYPE: PRT
<213> ORGANISM: Homo sapiens

<400> SEQUENCE: 109

Glu Val Gln Leu Val Glu Ser Gly Gly Gly Leu Val Lys Pro Gly Gly
1               5                   10                  15

Ser Leu Lys Leu Ser Cys Glu Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Ala Ile Gly Asp Gly Gly Ile Tyr Thr Tyr Tyr Ala Asp Thr Val
    50                  55                  60

Lys Gly Arg Phe Thr Ile Ser Arg Asp Asn Ala Lys Asn Ile Leu Tyr
65                  70                  75                  80

Leu Gln Met Ser Ser Leu Lys Ser Asn Asp Thr Ala Met Tyr Tyr Cys
                85                  90                  95

Ala Arg Gly Thr Gly Asp Gly Phe Ala Tyr Trp Gly Gln Gly Thr Leu
            100                 105                 110

Val Thr Val Ser
        115

<210> SEQ ID NO 110
<211> LENGTH: 5
<212> TYPE: PRT
<213> ORGANISM: Homo sapiens

<400> SEQUENCE: 110

Asp Tyr Tyr Met Tyr
1               5

<210> SEQ ID NO 111
<211> LENGTH: 17
<212> TYPE: PRT
<213> ORGANISM: Homo sapiens

<400> SEQUENCE: 111

Ala Ile Gly Asp Gly Gly Ile Tyr Thr Tyr Tyr Ala Asp Thr Val Lys
1               5                   10                  15

Gly

<210> SEQ ID NO 112
<211> LENGTH: 8
<212> TYPE: PRT
<213> ORGANISM: Homo sapiens

<400> SEQUENCE: 112

Gly Thr Gly Asp Gly Phe Ala Tyr
1               5

<210> SEQ ID NO 113
<211> LENGTH: 111
<212> TYPE: PRT
<213> ORGANISM: Homo sapiens

<400> SEQUENCE: 113

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 114
<211> LENGTH: 15
<212> TYPE: PRT
<213> ORGANISM: Homo sapiens

<400> SEQUENCE: 114

Arg Ala Ser Glu Ser Val Asp Ser Tyr Gly Asn Ser Phe Met His
1               5                   10                  15

<210> SEQ ID NO 115
<211> LENGTH: 7
<212> TYPE: PRT
<213> ORGANISM: Homo sapiens

<400> SEQUENCE: 115

Arg Ala Ser Asn Leu Glu Ser
1               5

<210> SEQ ID NO 116
<211> LENGTH: 9
<212> TYPE: PRT
<213> ORGANISM: Homo sapiens

<400> SEQUENCE: 116

Gln Gln Ser Asn Glu Asp Pro Tyr Thr
1               5

<210> SEQ ID NO 117
<211> LENGTH: 122
<212> TYPE: PRT
<213> ORGANISM: Homo sapiens

<400> SEQUENCE: 117

Glu Val Gln Leu Val Glu Ser Gly Ala Glu Leu Val Arg Pro Gly Val
1               5                   10                  15

```
Ser Val Lys Ile Ser Cys Lys Gly Ser Gly Tyr Thr Phe Thr Asp Tyr
            20                  25                  30

Ala Ile His Trp Val Lys Gln Ser His Ala Lys Ser Leu Glu Trp Ile
            35                  40                  45

Gly Val Ile Ser Thr Tyr Tyr Gly Asp Ala Ser Tyr Asn Gln Lys Phe
            50                  55                  60

Lys Gly Lys Ala Thr Met Thr Val Asp Lys Ser Ser Thr Ala Tyr
 65              70                  75                  80

Met Glu Leu Ala Arg Leu Thr Ser Glu Asp Ser Ala Ile Tyr Tyr Cys
                85                  90                  95

Ala Arg Ser Arg Gly Glu Tyr Gly Asn Tyr Asp Ala Met Asp Tyr Trp
            100                 105                 110

Gly Gln Gly Thr Ser Val Thr Val Ser Ser
            115                 120

<210> SEQ ID NO 118
<211> LENGTH: 5
<212> TYPE: PRT
<213> ORGANISM: Homo sapiens

<400> SEQUENCE: 118

Asp Tyr Ala Ile His
 1               5

<210> SEQ ID NO 119
<211> LENGTH: 17
<212> TYPE: PRT
<213> ORGANISM: Homo sapiens

<400> SEQUENCE: 119

Val Ile Ser Thr Tyr Tyr Gly Asp Ala Ser Tyr Asn Gln Lys Phe Lys
 1               5                  10                  15

Gly

<210> SEQ ID NO 120
<211> LENGTH: 13
<212> TYPE: PRT
<213> ORGANISM: Homo sapiens

<400> SEQUENCE: 120

Ser Arg Gly Glu Tyr Gly Asn Tyr Asp Ala Met Asp Tyr
 1               5                  10

<210> SEQ ID NO 121
<211> LENGTH: 240
<212> TYPE: PRT
<213> ORGANISM: Homo sapiens

<400> SEQUENCE: 121

Met Glu Glu Ser Val Val Arg Pro Ser Val Phe Val Val Asp Gly Gln
 1               5                  10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
            35                  40                  45

Ala Gly Leu Ala Val Gln Gly Trp Phe Leu Leu Gln Leu His Trp Arg
            50                  55                  60

Leu Gly Glu Met Val Thr Arg Leu Pro Asp Gly Pro Ala Gly Ser Trp
 65              70                  75                  80
```

```
Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 122
<211> LENGTH: 240
<212> TYPE: PRT
<213> ORGANISM: Homo sapiens

<400> SEQUENCE: 122

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220
```

```
Val Arg Leu Arg Asp Gly Thr Arg Ser Tyr Phe Gly Ala Phe Met Val
225                 230                 235                 240

<210> SEQ ID NO 123
<211> LENGTH: 240
<212> TYPE: PRT
<213> ORGANISM: Homo sapiens

<400> SEQUENCE: 123

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Leu
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 124
<211> LENGTH: 10
<212> TYPE: PRT
<213> ORGANISM: Homo sapiens

<400> SEQUENCE: 124

Gly Arg Ala Thr Ser Ser Ser Arg Val Trp
1               5                   10

<210> SEQ ID NO 125
<211> LENGTH: 7
<212> TYPE: PRT
<213> ORGANISM: Artificial sequence
<220> FEATURE:
<223> OTHER INFORMATION: Synthetic

<400> SEQUENCE: 125

Gly Tyr Thr Phe Thr Asp Tyr
1               5
```

```
1               5
```

<210> SEQ ID NO 126
<211> LENGTH: 8
<212> TYPE: PRT
<213> ORGANISM: Artificial sequence
<220> FEATURE:
<223> OTHER INFORMATION: Synthetic

<400> SEQUENCE: 126

```
Asp Pro Glu Thr Gly Asp Thr Ala
1               5
```

<210> SEQ ID NO 127
<211> LENGTH: 7
<212> TYPE: PRT
<213> ORGANISM: Artificial sequence
<220> FEATURE:
<223> OTHER INFORMATION: Synthetic

<400> SEQUENCE: 127

```
Asp Tyr Thr Phe Thr Asp Ser
1               5
```

<210> SEQ ID NO 128
<211> LENGTH: 8
<212> TYPE: PRT
<213> ORGANISM: Artificial sequence
<220> FEATURE:
<223> OTHER INFORMATION: Synthetic

<400> SEQUENCE: 128

```
Asp Pro Glu Thr Gly Gly Thr Ala
1               5
```

<210> SEQ ID NO 129
<211> LENGTH: 9
<212> TYPE: PRT
<213> ORGANISM: Artificial sequence
<220> FEATURE:
<223> OTHER INFORMATION: Synthetic

<400> SEQUENCE: 129

```
Ser Arg Val Trp Trp Asp Ser Ser Phe
1               5
```

<210> SEQ ID NO 130
<211> LENGTH: 8
<212> TYPE: PRT
<213> ORGANISM: Artificial sequence
<220> FEATURE:
<223> OTHER INFORMATION: Synthetic

<400> SEQUENCE: 130

```
Arg Val Trp Trp Asp Ser Ser Phe
1               5
```

<210> SEQ ID NO 131
<211> LENGTH: 6
<212> TYPE: PRT
<213> ORGANISM: Artificial sequence
<220> FEATURE:
<223> OTHER INFORMATION: Synthetic

<400> SEQUENCE: 131

```
Trp Trp Asp Ser Ser Phe
1               5
```

```
<210> SEQ ID NO 132
<211> LENGTH: 7
<212> TYPE: PRT
<213> ORGANISM: Artificial sequence
<220> FEATURE:
<223> OTHER INFORMATION: Synthetic

<400> SEQUENCE: 132

Leu Gly Gly Val Val His Leu
1               5

<210> SEQ ID NO 133
<211> LENGTH: 12
<212> TYPE: PRT
<213> ORGANISM: Artificial sequence
<220> FEATURE:
<223> OTHER INFORMATION: Synthetic

<400> SEQUENCE: 133

Leu Gly Gly Val Val His Leu Glu Ala Gly Glu Glu
1               5                   10

<210> SEQ ID NO 134
<211> LENGTH: 240
<212> TYPE: PRT
<213> ORGANISM: Homo sapiens

<400> SEQUENCE: 134

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 135
<211> LENGTH: 240
<212> TYPE: PRT
<213> ORGANISM: Artificial sequence
<220> FEATURE:
<223> OTHER INFORMATION: Synthetic

<400> SEQUENCE: 135

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Ala Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 136
<211> LENGTH: 240
<212> TYPE: PRT
<213> ORGANISM: Artificial sequence
<220> FEATURE:
<223> OTHER INFORMATION: Synthetic

<400> SEQUENCE: 136

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
50                  55                  60

Leu Gly Glu Met Val Thr Arg Leu Pro Asp Gly Pro Ala Gly Ser Trp
```

```
               65                  70                  75                  80
Glu Gln Leu Ile Gln Glu Arg Arg Ser His Glu Val Asn Pro Ala Ala
                    85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
                115                 120                 125

His Asp Gly Ala Leu Val Val Thr Lys Ala Gly Tyr Tyr Tyr Ile Tyr
                130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Ala Ala Thr Ser
                180                 185                 190

Ser Ser Arg Val Trp Trp Asp Ser Ser Phe Leu Gly Gly Val Val His
                195                 200                 205

Leu Glu Ala Gly Glu Lys Val Val Arg Val Leu Asp Glu Arg Leu
                210                 215                 220

Val Arg Leu Arg Asp Gly Thr Arg Ser Tyr Phe Gly Ala Phe Met Val
225                 230                 235                 240

<210> SEQ ID NO 137
<211> LENGTH: 240
<212> TYPE: PRT
<213> ORGANISM: Artificial sequence
<220> FEATURE:
<223> OTHER INFORMATION: Synthetic

<400> SEQUENCE: 137

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
                20                  25                  30

Cys Ser Val Ala Arg Val Gly Leu Gly Leu Leu Leu Leu Leu Met Gly
                35                  40                  45

Ala Gly Leu Ala Val Gln Gly Trp Phe Leu Leu Gln Leu His Trp Arg
            50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
                115                 120                 125

His Asp Gly Ala Leu Val Val Thr Lys Ala Gly Tyr Tyr Tyr Ile Tyr
                130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ser Thr Ser
                180                 185                 190

Ser Ser Arg Val Trp Trp Asp Ser Ser Phe Leu Gly Gly Val Val His
```

```
                195                 200                 205
Leu Glu Ala Gly Glu Lys Val Val Arg Val Leu Asp Glu Arg Leu
            210                 215                 220

Val Arg Leu Arg Asp Gly Thr Arg Ser Tyr Phe Gly Ala Phe Met Val
225                 230                 235                 240

<210> SEQ ID NO 138
<211> LENGTH: 240
<212> TYPE: PRT
<213> ORGANISM: Artificial sequence
<220> FEATURE:
<223> OTHER INFORMATION: Synthetic

<400> SEQUENCE: 138

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Ala Ser
            180                 185                 190

Ser Ser Arg Val Trp Trp Asp Ser Ser Phe Leu Gly Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 139
<211> LENGTH: 240
<212> TYPE: PRT
<213> ORGANISM: Artificial sequence
<220> FEATURE:
<223> OTHER INFORMATION: Synthetic

<400> SEQUENCE: 139

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30
```

```
Cys Ser Val Ala Arg Val Gly Leu Gly Leu Leu Leu Leu Met Gly
         35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Gly Pro Ala Gly Ser Trp
 65                  70                  75                  80

Glu Gln Leu Ile Gln Glu Arg Arg Ser His Glu Val Asn Pro Ala Ala
                 85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ala
            180                 185                 190

Ser Ser Arg Val Trp Trp Asp Ser Ser Phe Leu Gly Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 140
<211> LENGTH: 240
<212> TYPE: PRT
<213> ORGANISM: Artificial sequence
<220> FEATURE:
<223> OTHER INFORMATION: Synthetic

<400> SEQUENCE: 140

Met Glu Glu Ser Val Val Arg Pro Ser Val Phe Val Val Asp Gly Gln
 1               5                  10                  15

Thr Asp Ile Pro Phe Thr Arg Leu Gly Arg Ser His Arg Arg Gln Ser
                 20                  25                  30

Cys Ser Val Ala Arg Val Gly Leu Gly Leu Leu Leu Leu Met Gly
         35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Gly Pro Ala Gly Ser Trp
 65                  70                  75                  80

Glu Gln Leu Ile Gln Glu Arg Arg Ser His Glu Val Asn Pro Ala Ala
                 85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160
```

```
Thr Ile Thr His Gly Leu Tyr Lys Arg Thr Pro Arg Tyr Pro Glu Glu
            165                 170                 175

Leu Glu Leu Leu Val Ser Gln Gln Ser Pro Cys Gly Arg Ala Thr Ser
        180                 185                 190

Ala Ser Arg Val Trp Trp Asp Ser Ser Phe Leu Gly Val Val His
        195                 200                 205

Leu Glu Ala Gly Glu Lys Val Val Arg Val Leu Asp Glu Arg Leu
        210                 215                 220

Val Arg Leu Arg Asp Gly Thr Arg Ser Tyr Phe Gly Ala Phe Met Val
225                 230                 235                 240

<210> SEQ ID NO 141
<211> LENGTH: 240
<212> TYPE: PRT
<213> ORGANISM: Artificial sequence
<220> FEATURE:
<223> OTHER INFORMATION: Synthetic

<400> SEQUENCE: 141

Met Glu Glu Ser Val Arg Pro Ser Val Phe Val Asp Gly Gln
1               5                   10                  15

Thr Asp Ile Pro Phe Thr Arg Leu Gly Arg Ser His Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ala Arg Val Trp Trp Asp Ser Ser Phe Leu Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 142
<211> LENGTH: 240
<212> TYPE: PRT
<213> ORGANISM: Artificial sequence
<220> FEATURE:
<223> OTHER INFORMATION: Synthetic

<400> SEQUENCE: 142
```

Met Glu Glu Ser Val Val Arg Pro Ser Val Phe Val Asp Gly Gln
1               5                   10                  15

Thr Asp Ile Pro Phe Thr Arg Leu Gly Arg Ser His Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
        130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Ala Val Trp Trp Asp Ser Ser Phe Leu Gly Gly Val Val His
            195                 200                 205

Leu Glu Ala Gly Glu Lys Val Val Arg Val Leu Asp Glu Arg Leu
            210                 215                 220

Val Arg Leu Arg Asp Gly Thr Arg Ser Tyr Phe Gly Ala Phe Met Val
225                 230                 235                 240

<210> SEQ ID NO 143
<211> LENGTH: 240
<212> TYPE: PRT
<213> ORGANISM: Artificial sequence
<220> FEATURE:
<223> OTHER INFORMATION: Synthetic

<400> SEQUENCE: 143

Met Glu Glu Ser Val Val Arg Pro Ser Val Phe Val Asp Gly Gln
1               5                   10                  15

Thr Asp Ile Pro Phe Thr Arg Leu Gly Arg Ser His Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
        115                 120                 125

```
His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Ala Trp Trp Asp Ser Ser Phe Leu Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 144
<211> LENGTH: 240
<212> TYPE: PRT
<213> ORGANISM: Artificial sequence
<220> FEATURE:
<223> OTHER INFORMATION: Synthetic

<400> SEQUENCE: 144

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Ala Trp Asp Ser Ser Phe Leu Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 145
```

```
<211> LENGTH: 240
<212> TYPE: PRT
<213> ORGANISM: Artificial sequence
<220> FEATURE:
<223> OTHER INFORMATION: Synthetic

<400> SEQUENCE: 145

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
            35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Ala Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```